US009540438B2

(12) United States Patent
Barfield et al.

(10) Patent No.: US 9,540,438 B2
(45) Date of Patent: Jan. 10, 2017

(54) ALDEHYDE-TAGGED IMMUNOGLOBULIN POLYPEPTIDES AND METHODS OF USE THEREOF

(75) Inventors: Robyn M. Barfield, Berkeley, CA (US); Mark Alan Breidenbach, Oakland, CA (US); Gregory W. deHart, El Cerrito, CA (US); David Rabuka, Oakland, CA (US)

(73) Assignee: Redwood Bioscience, Inc., Emeryville, CA (US)

( * ) Notice: Subject to any disclaimer, the term of this patent is extended or adjusted under 35 U.S.C. 154(b) by 26 days.

(21) Appl. No.: 13/350,676

(22) Filed: Jan. 13, 2012

(65) Prior Publication Data

US 2012/0183566 A1 Jul. 19, 2012

Related U.S. Application Data

(60) Provisional application No. 61/433,042, filed on Jan. 14, 2011.

(51) Int. Cl.

| | |
|---|---|
| ***C07K 16/46*** | (2006.01) |
| ***A61K 39/395*** | (2006.01) |
| ***A61K 39/44*** | (2006.01) |
| ***A61K 39/39*** | (2006.01) |
| ***C07K 16/18*** | (2006.01) |
| ***C07K 16/08*** | (2006.01) |
| ***C07K 16/28*** | (2006.01) |
| ***A61K 47/48*** | (2006.01) |
| ***C07K 1/107*** | (2006.01) |
| ***C07K 1/13*** | (2006.01) |

(52) U.S. Cl.

CPC ..... *C07K 16/2803* (2013.01); *A61K 47/48384* (2013.01); *A61K 47/48561* (2013.01); *C07K 1/1077* (2013.01); *C07K 1/13* (2013.01); *C07K 2317/40* (2013.01)

(58) Field of Classification Search

None

See application file for complete search history.

(56) References Cited

U.S. PATENT DOCUMENTS

| | | | |
|---|---|---|---|
| 4,332,717 | A | 6/1982 | Kanaoka et al. |
| 4,342,832 | A | 8/1982 | Goeddel et al. |
| 4,671,958 | A | 6/1987 | Rodwell et al. |
| 4,952,394 | A | 8/1990 | Senter |
| 5,208,020 | A | 5/1993 | Chari et al. |
| 5,416,064 | A | 5/1995 | Chari et al. |
| 5,428,130 | A | 6/1995 | Capon et al. |
| 5,455,165 | A | 10/1995 | Capon et al. |
| 5,475,092 | A | 12/1995 | Chari et al. |
| 5,484,892 | A | 1/1996 | Tedder et al. |
| 5,514,582 | A | 5/1996 | Capon et al. |
| 5,585,499 | A | 12/1996 | Chari et al. |
| 5,624,821 | A | 4/1997 | Winter et al. |
| 5,681,566 | A | 10/1997 | Stevenson |
| 5,686,072 | A | 11/1997 | Uhr et al. |
| 5,698,672 | A | 12/1997 | Labroo et al. |
| 5,789,554 | A | 8/1998 | Leung et al. |
| 5,831,000 | A | 11/1998 | Murayama et al. |
| 5,846,545 | A | 12/1998 | Chari et al. |
| 5,885,573 | A | 3/1999 | Bluestone et al. |
| 5,980,895 | A | 11/1999 | Pastan et al. |
| 5,981,485 | A | 11/1999 | O'Connor et al. |
| 5,981,488 | A | 11/1999 | Hoffmann |
| 6,103,236 | A | 8/2000 | Suzawa et al. |
| 6,121,022 | A | 9/2000 | Presta et al. |
| 6,183,744 | B1 | 2/2001 | Goldenberg |
| 6,187,287 | B1 | 2/2001 | Leung et al. |
| 6,194,551 | B1 | 2/2001 | Idusogie et al. |
| 6,254,868 | B1 | 7/2001 | Leung et al. |
| 6,268,343 | B1 | 7/2001 | Knudsen et al. |
| 6,284,727 | B1 | 9/2001 | Kim et al. |
| 6,395,226 | B1 | 5/2002 | Plunkett |
| 6,441,163 | B1 | 8/2002 | Chari et al. |
| 6,528,624 | B1 | 3/2003 | Idusogie et al. |
| 6,538,124 | B1 | 3/2003 | Idusogie et al. |
| 6,548,644 | B1 | 4/2003 | Pettit |
| 6,570,040 | B2 | 5/2003 | Saxon et al. |
| 6,576,744 | B1 | 6/2003 | Presnell et al. |
| 6,608,183 | B1 | 8/2003 | Cox, III |
| 6,608,196 | B2 | 8/2003 | Wang et al. |

(Continued)

FOREIGN PATENT DOCUMENTS

| | | |
|---|---|---|
| WO | WO 9004413 | 5/1990 |
| WO | WO 9312812 | 7/1993 |

(Continued)

OTHER PUBLICATIONS

Rabuka, Nature Protocols, vol. 7, No. 6, p. 1052-1067, 2012.*
Montano, The Journal of Immunology, vol. 168, p. 224-231, 2002.*
Kubota, Cancer Science, vol. 100, No. 9, p. 1566-1572, 2009.*
Carter, Proceedings of the National Academy of Sciences, U.S.A., vol. 89, p. 4285-4289, 1992.*
Presta, Current Opinion in Immunology, vol. 20, p. 460-470, 2008.*
Connolly "Analytical molecular surface calculation" *J. Appl. Cryst.* (1983) 16:548-558.
GenBank Accession No. AAG00909 "recombinant IgG1 heavy chain [*Homo sapiens*]" dated May 11, 2001.
Kabsch & Sander (1983) "Dictionary of protein secondary structure: pattern recognition of hydrogen-bonded and geometrical features" *Biopolymers* 22: 2577-637.
Lee & Richards (1971) "The interpretation of protein structures: estimation of static accessibility" *J. Mol. Biol.* 55(3):379-400.

(Continued)

*Primary Examiner* — Michael D Allen
(74) *Attorney, Agent, or Firm* — Carol L. Francis; Bozicevic, Field & Francis LLP

(57) ABSTRACT

The present disclosure provides aldehyde-tagged immunoglobulin (Ig) polypeptides that can be converted by a formylglycine-generating enzyme to produce a 2-formylglycine (FGly)-modified Ig polypeptide. An FGly-modified Ig polypeptide can be covalently and site-specifically bound to a moiety of interest to provide an Ig conjugate. The disclosure also encompasses methods of production of such aldehyde-tagged Ig polypeptides, FGly-modified Ig polypeptides, and Ig conjugates, as well as methods of use of same.

44 Claims, 36 Drawing Sheets

(56) References Cited

U.S. PATENT DOCUMENTS 6,653,104 B2 11/2003 Goldenberg
6,660,843 B1 12/2003 Feige et al.
6,692,924 B2 2/2004 Presnell et al.
6,710,169 B2 3/2004 Capon et al.
6,716,821 B2 4/2004 Zhao et al.
6,737,056 B1 5/2004 Presta
6,756,480 B2 6/2004 Kostenuik et al.
6,770,625 B2 8/2004 Soltero et al.
6,777,539 B2 8/2004 Sprecher et al.
6,800,740 B1 10/2004 Cunningham et al.
6,803,451 B2 10/2004 Presnell et al.
6,825,166 B2 11/2004 McChesney et al.
6,875,845 B2 4/2005 Presnell et al.
6,884,869 B2 4/2005 Senter et al.
6,897,044 B1 5/2005 Braslawsky et al.
6,897,292 B2 5/2005 Presnell et al.
6,900,218 B2 5/2005 Wang et al.
6,913,748 B2 7/2005 Widdison
6,927,042 B2 8/2005 Schultz et al.
6,989,366 B2 1/2006 Beeley et al.
6,989,452 B2 1/2006 Ng et al.
6,998,253 B1 2/2006 Presta et al.
7,045,337 B2 5/2006 Schultz et al.
7,045,498 B2 5/2006 Kindsvogel et al.
7,045,605 B2 5/2006 Bander et al.
7,049,316 B2 5/2006 Zhao et al.
7,056,701 B2 6/2006 Fleer et al.
7,087,600 B2 8/2006 Ng et al.
7,091,186 B2 8/2006 Senter et al.
7,097,840 B2 8/2006 Erickson et al.
7,098,308 B2 8/2006 Senter et al.
7,112,439 B2 9/2006 Johnson et al.
7,115,573 B2 10/2006 Pickford et al.
7,122,637 B2 10/2006 Presta
7,138,371 B2 11/2006 DeFrees
7,141,547 B2 11/2006 Rosen et al.
7,176,278 B2 2/2007 Prior
7,183,387 B1 2/2007 Presta
7,189,811 B2 3/2007 Panda et al.
7,189,835 B2 3/2007 Raymond et al.
7,189,839 B2 3/2007 Presnell et al.
7,214,663 B2 5/2007 Bebbington et al.
7,214,685 B2 5/2007 Tietze et al.
7,226,990 B2 6/2007 Knudsen et al.
7,230,068 B2 6/2007 Wilson
7,255,012 B2 8/2007 Hedtke
7,256,257 B2 8/2007 Doronina et al.
7,265,203 B2 9/2007 Presnell et al.
7,271,149 B2 9/2007 Glaesner et al.
7,271,255 B2 9/2007 Raymond et al.
7,276,497 B2 10/2007 Chari et al.
7,276,585 B2 10/2007 Lazar et al.
7,276,947 B2 10/2007 Becker et al.
7,297,775 B2 11/2007 Idusogie et al.
7,317,091 B2 1/2008 Lazar et al.
7,321,026 B2 1/2008 Leung
7,332,571 B2 2/2008 Miao et al.
7,332,581 B2 2/2008 Presta
7,335,742 B2 2/2008 Presta
7,338,659 B2 3/2008 Leung
7,351,555 B2 4/2008 Presnell et al.
7,355,008 B2 4/2008 Stavenhagen et al.
7,355,011 B2 4/2008 Popplewell et al.
7,355,012 B2 4/2008 Pastan et al.
7,361,347 B2 4/2008 Adolf et al.
7,364,731 B2 4/2008 Idusogie et al.
7,368,565 B2 5/2008 Chari et al.
7,371,826 B2 5/2008 Presta
7,374,762 B2 5/2008 Amphlett
7,381,408 B2 6/2008 Mezo et al.
7,385,028 B2 6/2008 Miao et al.
7,388,026 B2 6/2008 Zhao et al.
7,404,956 B2 7/2008 Peters et al.
7,410,779 B2 8/2008 Fleer et al.
7,411,056 B2 8/2008 Presnell et al.
7,416,727 B2 8/2008 Presta
7,423,116 B2 9/2008 Doronina et al.
7,425,541 B2 9/2008 Dubois et al.
7,435,416 B2 10/2008 Devaux et al.
7,435,550 B2 10/2008 Novak et al.
7,442,778 B2 10/2008 Gegg et al.
7,445,764 B1 11/2008 Kratz
7,456,260 B2 11/2008 Rybak et al.
7,473,796 B2 1/2009 Chari et al.
7,488,590 B2 2/2009 Feige et al.
7,491,809 B2 2/2009 Presnell et al.
7,494,649 B2 2/2009 Amphlett et al.
7,498,298 B2 3/2009 Doronina et al.
7,498,302 B2 3/2009 Ng et al.
7,501,120 B2 3/2009 Amphlett et al.
7,501,497 B2 3/2009 Rixon et al.
7,507,420 B2 3/2009 Ng et al.
7,514,080 B2 4/2009 Amphlett et al.
7,517,903 B2 4/2009 Chen et al.
7,521,541 B2 4/2009 Eigenbrot et al.
7,521,542 B2 4/2009 Johnson et al.
7,534,427 B2 5/2009 Goldenberg et al.
7,541,034 B1 6/2009 Fitzgerald et al.
7,553,816 B2 6/2009 Senter et al.
7,572,456 B2 8/2009 Johnson et al.
7,572,892 B2 8/2009 Novak et al.
7,575,748 B1 8/2009 Erickson et al.
7,601,354 B2 10/2009 Chari
7,608,686 B2 10/2009 Gross et al.
7,618,628 B2 11/2009 Johnson et al.
7,622,116 B2 11/2009 Kuestner et al.
7,629,452 B2 12/2009 Sprecher et al.
7,632,497 B2 12/2009 Stavenhagen
7,635,767 B2 12/2009 Rixon et al.
7,642,228 B2 1/2010 Carter et al.
7,655,660 B2 2/2010 Zhao et al.
7,655,661 B2 2/2010 Zhao et al.
7,657,380 B2 2/2010 Lazar et al.
7,659,241 B2 2/2010 Senter et al.
7,662,387 B2 2/2010 Law et al.
7,662,925 B2 2/2010 Lazar et al.
7,662,936 B2 2/2010 Kadkhodayan et al.
7,691,962 B2 4/2010 Boyd et al.
7,722,865 B2 5/2010 Vellard et al.
7,723,485 B2 5/2010 Junutula et al.
7,745,394 B2 6/2010 Doronina et al.
7,750,116 B1 7/2010 Doronina et al.
7,754,681 B2 7/2010 Feng
7,771,727 B2 8/2010 Fuselier et al.
7,777,019 B2 8/2010 Pastan et al.
7,803,915 B2 9/2010 Cairns et al.
7,816,317 B2 10/2010 Bebbington et al.
7,829,086 B2 11/2010 Hilbert et al.
7,829,531 B2 11/2010 Senter et al.
7,837,980 B2 11/2010 Alley et al.
7,847,105 B2 12/2010 Gangwar et al.
7,851,432 B2 12/2010 Chari et al.
7,851,437 B2 12/2010 Senter et al.
7,855,275 B2 12/2010 Eigenbrot et al.
7,858,759 B2 12/2010 Brandt et al.
7,893,023 B2 2/2011 Tronet et al.
7,906,545 B2 3/2011 Zhao et al.
7,960,512 B2 6/2011 Stavenhagen et al.
7,964,195 B2 6/2011 Papkoff et al.
7,964,566 B2 6/2011 Doronina et al.
7,964,567 B2 6/2011 Doronina et al.
7,978,319 B2 7/2011 Okabe et al.
8,163,882 B2 4/2012 Presta
8,192,737 B2 6/2012 Stavenhagen et al.
2002/0103345 A1 8/2002 Zhu
2002/0128448 A1* 9/2002 Reff .......................... 530/387.3
2002/0177756 A1 11/2002 Pierre Godinot et al.
2003/0082575 A1 5/2003 Schultz et al.
2003/0108609 A1 6/2003 Berry et al.
2003/0109682 A1 6/2003 Santi et al.
2003/0124669 A1 7/2003 Pan et al.
2003/0157108 A1 8/2003 Presta
2003/0166868 A1 9/2003 Presta et al.
2003/0171285 A1 9/2003 Finn et al.

(56) References Cited

U.S. PATENT DOCUMENTS

| | | | |
|---|---|---|---|
| 2004/0010124 | A1 | 1/2004 | Johnson et al. |
| 2004/0048395 | A1 | 3/2004 | Lee et al. |
| 2004/0110226 | A1 | 6/2004 | Lazar et al. |
| 2004/0115774 | A1 | 6/2004 | Kochendoerfer et al. |
| 2004/0132101 | A1 | 7/2004 | Lazar et al. |
| 2004/0197866 | A1 | 10/2004 | Johnson et al. |
| 2004/0219156 | A1 | 11/2004 | Goldenberg et al. |
| 2004/0229250 | A1 | 11/2004 | Figura et al. |
| 2004/0265952 | A1 | 12/2004 | Deiters et al. |
| 2005/0037000 | A1 | 2/2005 | Stavenhagen et al. |
| 2005/0064514 | A1 | 3/2005 | Stavenhagen et al. |
| 2005/0084862 | A1 | 4/2005 | Lee et al. |
| 2005/0118174 | A1 | 6/2005 | Presta |
| 2005/0118182 | A1 | 6/2005 | Pastan et al. |
| 2005/0142133 | A1 | 6/2005 | Lazar |
| 2005/0147618 | A1 | 7/2005 | Rivera et al. |
| 2005/0170404 | A1 | 8/2005 | Cho et al. |
| 2005/0177878 | A1 | 8/2005 | Melo et al. |
| 2005/0220762 | A1 | 10/2005 | Cho et al. |
| 2005/0249723 | A1 | 11/2005 | Lazar |
| 2005/0260711 | A1 | 11/2005 | Datta et al. |
| 2005/0281829 | A1 | 12/2005 | Hehir et al. |
| 2006/0013810 | A1 | 1/2006 | Johnson et al. |
| 2006/0019347 | A1 | 1/2006 | Cho et al. |
| 2006/0024298 | A1 | 2/2006 | Lazar et al. |
| 2006/0057149 | A1 | 3/2006 | Johnson et al. |
| 2006/0121032 | A1 | 6/2006 | Dahiyat et al. |
| 2006/0134105 | A1 | 6/2006 | Lazar et al. |
| 2006/0134709 | A1 | 6/2006 | Stavehagen et al. |
| 2006/0135427 | A1 | 6/2006 | Hays et al. |
| 2006/0153860 | A1 | 7/2006 | Cho et al. |
| 2006/0173170 | A1 | 8/2006 | Chamberlain et al. |
| 2006/0182750 | A1 | 8/2006 | Chari et al. |
| 2006/0183198 | A1 | 8/2006 | Buechler et al. |
| 2006/0189529 | A1 | 8/2006 | Cho et al. |
| 2006/0194290 | A1 | 8/2006 | Presta |
| 2006/0194957 | A1 | 8/2006 | Presta |
| 2006/0217289 | A1 | 9/2006 | Miao et al. |
| 2006/0235208 | A1 | 10/2006 | Lazar et al. |
| 2006/0275254 | A1 | 12/2006 | Kim et al. |
| 2007/0004909 | A1 | 1/2007 | Johnson et al. |
| 2007/0009523 | A1 | 1/2007 | Presta |
| 2007/0020258 | A1 | 1/2007 | Jardieu et al. |
| 2007/0020260 | A1 | 1/2007 | Presta |
| 2007/0024389 | A1 | 2/2007 | Mizutani |
| 2007/0031922 | A1 | 2/2007 | Presta et al. |
| 2007/0036799 | A1 | 2/2007 | Stavehagen et al. |
| 2007/0037216 | A1 | 2/2007 | Johnson et al. |
| 2007/0053901 | A1 | 3/2007 | Lazar et al. |
| 2007/0077429 | A1 | 4/2007 | Mirkin et al. |
| 2007/0092940 | A1 | 4/2007 | Eigenbrot et al. |
| 2007/0122408 | A1 | 5/2007 | Barbas, III |
| 2007/0123691 | A1 | 5/2007 | Wilson |
| 2007/0123693 | A1 | 5/2007 | Wilson |
| 2007/0135620 | A1 | 6/2007 | Chamberlain et al. |
| 2007/0148170 | A1 | 6/2007 | Desjarlais et al. |
| 2007/0148171 | A1 | 6/2007 | Lazar et al. |
| 2007/0160597 | A1 | 7/2007 | Lazar et al. |
| 2007/0166309 | A1 | 7/2007 | Lazar et al. |
| 2007/0189962 | A1 | 8/2007 | Pastan et al. |
| 2007/0198996 | A1 | 8/2007 | Chiu et al. |
| 2007/0202098 | A1 | 8/2007 | Lazar et al. |
| 2007/0219133 | A1 | 9/2007 | Lazar et al. |
| 2007/0224189 | A1 | 9/2007 | Lazar et al. |
| 2007/0224192 | A1 | 9/2007 | Lazar et al. |
| 2007/0231329 | A1 | 10/2007 | Lazar et al. |
| 2007/0237765 | A1 | 10/2007 | Lazar et al. |
| 2007/0237766 | A1 | 10/2007 | Lazar et al. |
| 2007/0237767 | A1 | 10/2007 | Lazar et al. |
| 2007/0238665 | A1 | 10/2007 | Lazar et al. |
| 2007/0243188 | A1 | 10/2007 | Lazar et al. |
| 2007/0244303 | A1 | 10/2007 | Johnson et al. |
| 2007/0248602 | A1 | 10/2007 | Lazar et al. |
| 2007/0248603 | A1 | 10/2007 | Lazar et al. |
| 2007/0264260 | A1 | 11/2007 | Tuscano et al. |
| 2007/0269369 | A1 | 11/2007 | Gegg et al. |
| 2007/0275460 | A1 | 11/2007 | Desjarlais et al. |
| 2007/0286859 | A1 | 12/2007 | Lazar et al. |
| 2008/0044417 | A1 | 2/2008 | Johnson et al. |
| 2008/0044429 | A1 | 2/2008 | Johnson et al. |
| 2008/0050310 | A1 | 2/2008 | Ebens et al. |
| 2008/0050371 | A1 | 2/2008 | Johnson et al. |
| 2008/0050374 | A1 | 2/2008 | Cho et al. |
| 2008/0051563 | A1 | 2/2008 | Lazar et al. |
| 2008/0057056 | A1 | 3/2008 | Lazar et al. |
| 2008/0081038 | A1 | 4/2008 | Cho et al. |
| 2008/0085277 | A1 | 4/2008 | Cho et al. |
| 2008/0085538 | A1 | 4/2008 | Buechler et al. |
| 2008/0095762 | A1 | 4/2008 | Presta |
| 2008/0097083 | A1 | 4/2008 | Cho et al. |
| 2008/0102124 | A1 | 5/2008 | Cho et al. |
| 2008/0102125 | A1 | 5/2008 | Cho et al. |
| 2008/0103293 | A1 | 5/2008 | Cho et al. |
| 2008/0103294 | A1 | 5/2008 | Cho et al. |
| 2008/0108791 | A1 | 5/2008 | Cho et al. |
| 2008/0108792 | A1 | 5/2008 | Hays et al. |
| 2008/0108797 | A1 | 5/2008 | Cho et al. |
| 2008/0112943 | A1 | 5/2008 | Mariani et al. |
| 2008/0112961 | A1 | 5/2008 | Stavehagen et al. |
| 2008/0113408 | A1 | 5/2008 | Mariani et al. |
| 2008/0113411 | A1 | 5/2008 | Sheffer et al. |
| 2008/0113412 | A1 | 5/2008 | Sheffer et al. |
| 2008/0113457 | A1 | 5/2008 | Tsay et al. |
| 2008/0113912 | A1 | 5/2008 | Hays et al. |
| 2008/0113913 | A1 | 5/2008 | Hays et al. |
| 2008/0113914 | A1 | 5/2008 | Hays et al. |
| 2008/0114154 | A1 | 5/2008 | Cho et al. |
| 2008/0114155 | A1 | 5/2008 | Cho et al. |
| 2008/0118505 | A1 | 5/2008 | Tedder |
| 2008/0119640 | A1 | 5/2008 | Hays et al. |
| 2008/0125574 | A1 | 5/2008 | Sheffer et al. |
| 2008/0131435 | A1 | 6/2008 | Stavehagen et al. |
| 2008/0132681 | A1 | 6/2008 | Hays et al. |
| 2008/0138338 | A1 | 6/2008 | Idusogie et al. |
| 2008/0138344 | A1 | 6/2008 | Stavenhagen et al. |
| 2008/0138349 | A1 | 6/2008 | Stavenhagen et al. |
| 2008/0146781 | A1 | 6/2008 | Cho et al. |
| 2008/0152649 | A1 | 6/2008 | Chamberlain et al. |
| 2008/0154025 | A1 | 6/2008 | Lazar et al. |
| 2008/0161539 | A1 | 7/2008 | Cho et al. |
| 2008/0161541 | A1 | 7/2008 | Lazar et al. |
| 2008/0167452 | A1 | 7/2008 | Maiti et al. |
| 2008/0177027 | A1 | 7/2008 | Miao et al. |
| 2008/0177038 | A1 | 7/2008 | Miao et al. |
| 2008/0181890 | A1 | 7/2008 | Lazar et al. |
| 2008/0182968 | A1 | 7/2008 | Miao et al. |
| 2008/0182969 | A1 | 7/2008 | Miao et al. |
| 2008/0187491 | A1 | 8/2008 | Miao et al. |
| 2008/0187956 | A1 | 8/2008 | Carrico et al. |
| 2008/0194459 | A1 | 8/2008 | Miao et al. |
| 2008/0199471 | A1 | 8/2008 | Bernett et al. |
| 2008/0199909 | A1 | 8/2008 | Buechler et al. |
| 2008/0206242 | A1 | 8/2008 | Lawrence et al. |
| 2008/0206853 | A1 | 8/2008 | Lee et al. |
| 2008/0206867 | A1 | 8/2008 | Desjarlais et al. |
| 2008/0207877 | A1 | 8/2008 | Cho et al. |
| 2008/0213840 | A1 | 9/2008 | Miao et al. |
| 2008/0219974 | A1 | 9/2008 | Bernett et al. |
| 2008/0225287 | A1 | 9/2008 | Mirkin et al. |
| 2008/0227205 | A1 | 9/2008 | Cho |
| 2008/0242845 | A1 | 10/2008 | Lazar et al. |
| 2008/0244222 | A1 | 10/2008 | Supalov et al. |
| 2008/0248028 | A1 | 10/2008 | Lazar et al. |
| 2008/0249288 | A1 | 10/2008 | Mezo et al. |
| 2008/0254027 | A1 | 10/2008 | Bernett et al. |
| 2008/0255045 | A1 | 10/2008 | Cujec et al. |
| 2008/0260731 | A1 | 10/2008 | Bernett et al. |
| 2008/0268518 | A1 | 10/2008 | Miao et al. |
| 2008/0268519 | A1 | 10/2008 | Miao et al. |
| 2008/0274105 | A1 | 11/2008 | Presta |
| 2008/0274108 | A1 | 11/2008 | Presta |
| 2008/0274506 | A1 | 11/2008 | Presta |
| 2008/0292621 | A1 | 11/2008 | Lazar et al. |
| 2008/0317758 | A9 | 12/2008 | Presta |

(56) References Cited

U.S. PATENT DOCUMENTS

| | | | |
|---|---|---|---|
| 2009/0004734 | A1 | 1/2009 | Pastan et al. |
| 2009/0005312 | A1 | 1/2009 | Hansen et al. |
| 2009/0010920 | A1 | 1/2009 | Lazar et al. |
| 2009/0041758 | A1 | 2/2009 | Glaser et al. |
| 2009/0041770 | A1 | 2/2009 | Chamberlain et al. |
| 2009/0042291 | A1 | 2/2009 | Chu et al. |
| 2009/0053211 | A9 | 2/2009 | Lazar et al. |
| 2009/0053240 | A1 | 2/2009 | Lazar et al. |
| 2009/0060910 | A1 | 3/2009 | Johnson et al. |
| 2009/0068175 | A1 | 3/2009 | Lazar et al. |
| 2009/0068177 | A1 | 3/2009 | Lazar et al. |
| 2009/0081208 | A1 | 3/2009 | Lazar et al. |
| 2009/0092599 | A1 | 4/2009 | Lazar et al. |
| 2009/0098124 | A1 | 4/2009 | Stavehagen et al. |
| 2009/0136485 | A1 | 5/2009 | Chu et al. |
| 2009/0142340 | A1 | 6/2009 | Lazar et al. |
| 2009/0143246 | A1 | 6/2009 | Mirkin et al. |
| 2009/0155587 | A1 | 6/2009 | Mirkin et al. |
| 2009/0162353 | A1 | 6/2009 | Johnson et al. |
| 2009/0162382 | A1 | 6/2009 | Bernett et al. |
| 2009/0163699 | A1 | 6/2009 | Chamberlain et al. |
| 2009/0185290 | A1 | 7/2009 | Li et al. |
| 2009/0202536 | A1 | 8/2009 | Ebens et al. |
| 2009/0202537 | A1 | 8/2009 | Johnson et al. |
| 2009/0214526 | A1 | 8/2009 | Lazar et al. |
| 2009/0215991 | A1 | 8/2009 | Lazar et al. |
| 2009/0281286 | A1 | 11/2009 | Gregg et al. |
| 2009/0286964 | A1 | 11/2009 | Gregg et al. |
| 2009/0305411 | A1 | 12/2009 | FitzGerald et al. |
| 2009/0324593 | A1 | 12/2009 | Johnson et al. |
| 2010/0129908 | A1 | 5/2010 | Fang et al. |
| 2010/0143368 | A1 | 6/2010 | King et al. |
| 2010/0204454 | A1 | 8/2010 | Chamberlain et al. |
| 2010/0210543 | A1 | 8/2010 | Rabuka et al. |
| 2010/0234571 | A1 | 9/2010 | Chamberlain et al. |
| 2010/0234572 | A1 | 9/2010 | Chamberlain et al. |
| 2010/0234573 | A1 | 9/2010 | Chamberlain et al. |
| 2010/0234574 | A1 | 9/2010 | Chamberlain et al. |
| 2010/0234575 | A1 | 9/2010 | Chamberlain et al. |
| 2010/0311954 | A1 | 12/2010 | Chamberlain et al. |
| 2011/0020344 | A1 | 1/2011 | Dimitrov et al. |
| 2011/0065185 | A1 | 3/2011 | Pastan et al. |
| 2011/0142859 | A1 | 6/2011 | Ebens et al. |
| 2011/0293632 | A1 | 12/2011 | Presta |

FOREIGN PATENT DOCUMENTS

| | | |
|---|---|---|
| WO | WO 9426778 | 11/1994 |
| WO | WO 9604925 | 2/1996 |
| WO | WO 9958572 | 11/1999 |
| WO | WO 0042072 | 7/2000 |
| WO | WO 0181415 | 1/2001 |
| WO | WO 0160991 | 8/2001 |
| WO | WO 03027135 | 4/2003 |
| WO | WO 03105782 | 12/2003 |
| WO | WO 2004072275 | 8/2004 |
| WO | WO 2004082640 | 9/2004 |
| WO | WO 2004099249 | 11/2004 |
| WO | WO 2005000892 | 1/2005 |
| WO | WO 2005035727 | 4/2005 |
| WO | WO 2005047336 | 5/2005 |
| WO | WO 2005052006 | 6/2005 |
| WO | WO 2005074524 | 8/2005 |
| WO | WO 2005074546 | 8/2005 |
| WO | WO 2005074650 | 8/2005 |
| WO | WO 2006009901 | 1/2006 |
| WO | WO 2006068802 | 6/2006 |
| WO | WO 2006069220 | 6/2006 |
| WO | WO 2006071840 | 7/2006 |
| WO | WO 2006073846 | 7/2006 |
| WO | WO 2006091231 | 8/2006 |
| WO | WO 2006069246 | 9/2006 |
| WO | WO 2006132969 | 12/2006 |
| WO | WO 2006133089 | 12/2006 |
| WO | WO 2007021297 | 2/2007 |
| WO | WO 2007056083 | 5/2007 |
| WO | WO 2007056448 | 5/2007 |
| WO | WO 2007059312 | 5/2007 |
| WO | WO 2007070659 | 6/2007 |
| WO | WO 2007079130 | 7/2007 |
| WO | WO 2007094916 | 8/2007 |
| WO | WO 2007103470 | 9/2007 |
| WO | WO 2007140371 | 12/2007 |
| WO | WO 2008011446 | 1/2008 |
| WO | WO 2008030558 | 3/2008 |
| WO | WO 2008030612 | 3/2008 |
| WO | WO 2008030613 | 3/2008 |
| WO | WO 2008030614 | 3/2008 |
| WO | WO 2008036350 | 3/2008 |
| WO | WO 2008070569 | 6/2008 |
| WO | WO 2008077079 | 6/2008 |
| WO | WO 2008083346 | 7/2008 |
| WO | WO 2008121563 | 10/2008 |
| WO | WO 2008137471 | 11/2008 |
| WO | WO 2009058492 | 5/2009 |
| WO | WO 2009120611 | 10/2009 |
| WO | WO 2010096394 | 8/2010 |

OTHER PUBLICATIONS

Mahal et al. (1997) "Engineering chemical reactivity on cell surfaces through oligosaccharide biosynthesis" *Science* 276(5315):1125-1128.

Baenziger (2003) "A major step on the road to understanding a unique posttranslational modification and its role in a genetic disease" *Cell* 113(4):421-422.

Berteau et al. (2006) "A new type of bacterial sulfatase reveals a novel maturation pathway in prokaryotes" *J. Biol. Chem.* 281(32):22464-22470.

Cosma et al. (2003) "The multiple sulfatase deficiency gene encodes an essential and limiting factor for the activity of sulfatases" *Cell* 113(4):445-456.

Cosma et al. (2004) "Molecular and functional analysis of SUMF1 mutations in multiple sulfatase deficiency" *Hum. Mutat.* 23, 576-581.

Dierks et al. (1997) "Conversion of cysteine to formylglycine: a protein modification in the endoplasmic reticulum" *Proc Natl Acad Sci U S A* 94(22):11963-8.

Dierks et al. (1998) "Conversion of cysteine to formylglycine in eukaryotic sulfatases occurs by a common mechanism in the endoplasmic reticulum" *FEBS Lett.* 423(1):61-5.

Dierks et al. (1999) "Sequence determinants directing conversion of cysteine to formylglycine in eukaryotic sulfatases" *EMBO J* 18(8):2084-2091.

Dierks et al. (2003) "Multiple sulfatase deficiency is caused by mutations in the gene encoding the human Cα-formylglycine generating enzyme" *Cell* 113(4):435-444.

Dierks et al. (2005) "Molecular basis for multiple sulfatase deficiency and mechanism for formylglycine generation of the human formylglycine-generating enzyme" *Cell.* 121(4):541-552.

Fang et al. (2004) "Post-translational formylglycine modification of bacterial sulfatases by the radical S-adenosylmethionine protein AtsB" *J Biol Chem.* 79(15):14570-8.

GenBank Accession No. NM_182760 "*Homo sapiens* sulfatase modifying factor 1 (SUMF1), transcript variant 1, mRNA" dated Nov. 28, 2012.

Jefferis & Lefranc (2009) "Human Immunoglobulin Allotypes" *MAbs* 1(4):332-338.

Landgrebe et al. (2003) "The human SUMF1 gene, required for posttranslational sulfatase modification, defines a new gene family which is conserved from pro- to eukaryotes" *Gene.* 316:47-56.

Preusser-Kunze et al. (2005) "Molecular characterization of the human Cα-formylglycine-generating enzyme" *J. Biol. Chem.* 280(15):14900-10.

Roeser et al. (2006) "A general binding mechanism for all human sulfatases by the formylglycine-generating enzyme" *Proc Natl Acad Sci USA* 103(1):81-86.

Sardiello et al. (2005) "Sulfatases and sulfatase modifying factors: an exclusive and promiscuous relationship" *Hum Mol Genet.* 14(21):3203-3217.

(56) References Cited

OTHER PUBLICATIONS

Szameit et al. (1999) "The iron sulfur protein AtsB is required for posttranslational formation of formylglycine in the *Klebsiella* sulfatase" *J Biol Chem* 274(22):15375-15381.
Adams, et al. (2003) "Safety and Utilization of Blood Components as Therapeutic Delivery Systems" *Curr Pharm Biotechnol* 4(5):275-282.
Andreotti, et al. (2006) "Structural determinants of salmon calcitonin bioactivity: the role of the Leu-based amphipathic α-helix" *J. Biol. Chem.* 281(34):24193-24203.
Baggio, et al. (2008) "An albumin-exendin-4 conjugate engages central and peripheral circuits regulating murine energy and glucose homeostasis" *Gastroenterology* 134(4):1137-1147.
Baker (2002) "Albumin, steroid hormones and the origin of vertebrates" *J Endocrinol* 175(1):121-127.
Brubaker (2007) "Incretin-based therapies: mimetics versus protease inhibitors" *Trends Endoccrinol. Metab.*18(6):240-245.
Carter & Senter (2008) "Antibody-Drug Conjugates for Cancer Therapy" *Cancer J* 14(3):154-619.
Doronina, et al. (2008) "Novel peptide linkers for highly potent antibody-auristatin conjugate" *Bioconjugate Chem* 19(10):1960-1963.
Dou, et al. (2008) "Expression, purification, and characterization of recombinant human serum albumin fusion protein with two human glucagon-like peptide-1 mutants in *Pichia pastoris" Protein Expr Purif* 61(1):45-49.
Harohalli, et al. (2002) "Site-directed mutagenesis studies of human serum albumin define tryptophan at amino acid position 214 as the principal site for nitrosation" *J Biomed Sci* 9(1):47-58.
Junutula, et al. (2008) "Site-specific conjugation of a cytotoxic drug to an antibody improves the therapeutic index" *Nat Biotechnol* 26(8):925-932.
Komarova (2003) "Regulation of Osteoclasts by Calcitonin and Amphiphilic Calcitonin Conjugates: Role of Cytosolic Calcium" *Calcif Tissue Int* 73(3):265-273.
Kumar, et al. (2007) "Gene therapy of diabetes using a novel GLP-1/IgGl-Fc fusion construct normalizes glucose levels in db/db mice" *Gene Ther.* 14(2):162-172.
Léger, et al. (2004) "Identification of CJC-1131-albumin bioconjugate as a stable and bioactive GLP-1(7-36) analog" *Bioorg. Med. Chem. Lett.* 14(17):4395-4398.
Matthews, (2008) et al. "Pharmacodynamics, Pharmacokinetics, Safety, and Tolerability of Albiglutide, a Long-Acting Glucagon-Like Peptide-1 Mimetic, in Patients with Type 2 Diabetes" *J. Clin. Endocrinol. Metab.* 93(12):4810-4817.
McDonagh, et al. (2006) "Engineered antibody-drug conjugates with defined sites and stoichiometries of drug attachment" *Protein Eng Des Sel* 19(7):299-307.
Müller, et al. (2007) "Improved pharmacokinetics of recombinant bispecific antibody molecules by fusion to human serum albumin" *J Bio Chem* 282(17):12650-12660.
Peterson, et al. (2002) "Probing the structure of the warfarin-binding site on human serum albumin using site-directed mutagenesis" *Proteins* 47(2):116-125.
Picha, et al. (2008) "Protein Engineering Strategies for Sustained Glucagon-Like Peptide-1 Receptor-Dependent Control of Glucose Homeostasis" *Diabetes* 57(7):1926-1934.
Wu & Senter (2005) "Arming antibodies: prospects and challenges for immunoconjugates" *Nat Biotechnol* 23(9):1137-1146.
Youn, et al. (2007) "High-yield production of biologically active mono-PEGylated salmon calcitonin by site-specific PEGylation" *J. Control. Release* 117(3):371-379.
Advani et al. (2010) "Safety, pharmacokinetics, and preliminary clinical activity of inotuzumab ozogamicin, a novel immunoconjugate for the treatment of B-cell non-Hodgkin's lymphoma: results of a phase I study" *J Clin Oncol* 28(12):2085-2093.
Amlot et al. (1993) "A phase I study of an anti-CD22-deglycosylated ricin A chain immunotoxin in the treatment of B-cell lymphomas resistant to conventional therapy" *Blood* 82(9):2624-2633.
Asai et al. (1999) "Synthesis and antitumor activity of water-soluble duocarmycin B1 prodrugs" *Bioorg Med Chem Lett* 9(20):2995-2998.
Baird & Holowka (1985) "Structural mapping of Fc receptor bound immunoglobulin E: proximity to the membrane surface of the antibody combining site and another site in the Fab segments" *Biochem* 24(22):6252-6259.
Boghaert et al. (2008) "Determination of pharmacokinetic values of calicheamicin-antibody conjugates in mice by plasmon resonance analysis of small (5 microl) blood samples" *Cancer Chemother Pharmacol* 61(6):1027-1035.
Dijoseph et al. (2004) "Antibody-targeted chemotherapy with CMC-544: a CD22-targeted immunoconjugate of calicheamicin for the treatment of B-lymphoid malignancies" *Blood* 103(5):1807-1814.
Dijoseph et al. (2004) "Potent and specific antitumor efficacy of CMC-544, a CD22-targeted immunoconjugate of calicheamicin, against systemically disseminated B-cell lymphoma" *Clin Cancer Res* 10:8620-8629.
Dijoseph et al. (2006) "Antitumor efficacy of a combination of CMC-544 (inotuzumab ozogamicin), a CD22-targeted cytotoxic immunoconjugate of calicheamicin, and rituximab against non-Hodgkin's B-cell lymphoma" *Clin Cancer Res* 12(1):242-249.
Dijoseph et al. (2007) "Therapeutic potential of CD22-specific antibody-targeted chemotherapy using inotuzumab ozogamicin (CMC-544) for the treatment of acute lymphoblastic leukemia" *Leukemia* 21(11):2240-2245.
Fanslow et al. (1992) "Soluble forms of CD40 inhibit biologic responses of human B cells" *J Immunol* 149(2):655-660.
Ghetie et al. (1991) "Antitumor activity of Fab' and IgG-anti-CD22 immunotoxins in disseminated human B lymphoma grown in mice with severe combined immunodeficiency disease: effect on tumor cells in extranodal sites" *Cancer Res* 51(21):5876-5880.
Gilon et al. (1967) "Synthesis of ω-aminooxy acids by oxygen-alkyl fission of lactones: An improved synthesis of DL-canaline" *Tetrahedron* 23(11):4441-4447.
Idusogie et al. (2000) "Mapping of the C1q binding site on rituxan, a chimeric antibody with a human IgG1 Fc" *J Immunol* 164(8):4178-4184.
ImmunoGen, Inc. (2008) "ImmunoGen, Inc. Announces Clinical Findings Reported at ASCO with Targeted Anticancer Compounds IMGN242 and AVE1642" http://www.drugs.com/clinical_trials/immunogen-inc-announces-clinical-findings-reported-asco-targeted-anticancer-compounds-imgn242-4545.html#ixzz0r9nPlIXM.
Jeffrey et al. (2005) "Design, synthesis, and in vitro evaluation of dipeptide-based antibody minor groove binder conjugates" *J Med Chem* 48(5):1344-1358.
Johnson & Wu (2000) "Kabat database and its applications: 30 years after the first variability plot" *Nucl Acids Res* 28(1):214-218.
Jones et al. (2000) "A convenient synthesis of *N*-(*tert*-butyloxycarbonyl)aminooxy ethers" *Tetrahedron Lett* 41(10):1531-1533.
Kan (2001) "Thioether-bonded constructs of Fab'gamma and Fc gamma modules utilizing differential reduction of interchain disulfide bonds" *J Immunol* 166(2):1320-1326.
Ogura et al. (2010) "Phase I Study of Inotuzumab Ozogamicin (CMC-544) in Japanese Patients with Follicular Lymphoma Pretreated with Rituximab-Based Therapy" *Cancer Sci* 101(8):1840-1845. Epub Apr. 23, 2012 doi:10.1111/j. 1349-7006.2010.01601.x.
Pettit (1996) "Progress in the discovery of biosynthetic anticancer drugs" *J Nat Prod* 59(8):812-821.
Pleass (1999) "Identification of residues in the CH2/CH3 domain interface of IgA essential for interaction with the human fcalpha receptor (FcalphaR) CD89" *J Biol Chem* 274(33):23508-23514.
Presta (2002) "Engineering therapeutic antibodies for improved function" Biochem Soc Trans 30(4):487-490.
Rakestraw et al. (1990) "Preparation and characterization of immunoconjugates for antibody-targeted photolysis" *Bioconjugate Chem* 1(3):212-221.
Rutishauser et al. (1968) "Amino Acid Sequence of the Fc Region of a Human γ G-Immunoglobulin" *Proc Natl Acad Sci USA* 61(4)1414-1421.

(56) References Cited

OTHER PUBLICATIONS

Sayers et al. (1998) "Amino acid residues that influence Fc epsilon RI-mediated effector functions of human immunoglobulin E" *Biochemistry* 37(46):16152-16164.
Shields (2001) "High resolution mapping of the binding site on human IgG1 for Fc gamma RI, Fc gamma RII, Fc gamma RIII, and FcRn and design of IgG1 variants with improved binding to the Fc gamma R" *J Biol Chem* 276(9):6591-6604.
Singh & Francis (1978) "A direct binding assay for rheumatoid factor serum antiglobulins using fluorescein-labelled Fc fragment of human immunoglobulin-G" *J Clin Path* 31(10):963-973.
Singh et al. (2008) "Recent Trends in Targeted Anticancer Prodrug and Conjugate Design" *Curr Med Chem*15(18):1802-1826.
Sondermann & Oosthuizen (2002) "Mediation and Modulation of Antibody Function" Biochem Soc Trans 30(pt.4):481-486.
Stevenson et al. (1997) "Conjugation of human Fc gamma in closed-hinge or open-hinge configuration to Fab'gamma and analogous ligands" *J Immunol* 158(5):2242-2250.
Stevenson et al. (1999) "Preparation of fcgamma for addition to sulfhydryl-expressing ligands with minimal disturbance of the hinge" *J Immunol Meth* 231(1-2):169-175.
Stimmel et al. (2000) "Site-specific conjugation on serine → cysteine variant monoclonal antibodies" *J Biol Chem* 275(39):30445-30450.
Takeshita (2009) "CMC-544 (inotuzumab ozogamicin) shows less effect on multidrug resistant cells: analyses in cell lines and cells from patients with B-cell chronic lymphocytic leukaemia and lymphoma" *Br J Haematol* 146:34-43.
Taylor (2010) Mutations in an avian IgY-Fc fragment reveal the locations of monocyte Fc receptor binding sites *Dev Comp Immunol* 34(2):97-101.
Thrasher et al. (1975) "The effect of fluorescein conjugation on Fc-dependent properties of rabbit antibody" *J Immunol* 114(2 pt. 2):762-764.
Vitetta et al. (1991) "Phase I immunotoxin trial in patients with B-cell lymphoma" *Cancer Res* 51(15):4052-4058.
Wooley et al. (1993) "Influence of a recombinant human soluble tumor necrosis factor receptor Fc fusion protein on type II collagen-induced arthritis in mice" *J Immunol* 151(11):6602-6607.
Xu et al. (1999) "Bis(Hydroxamamide)-Based Bifunctional Chelating Agent $^{99m}$Tc Labeling of Polypeptides" *Bioconjug Chem* 10(1):9-17.
Bain et al. (1989) "Biosynthetic site-specific incorporation of a non-natural amino acid into a polypeptide" *J Am Chem Soc* 111(20):8013-8014.
Boer et al. (2003) "The genome-wide transcriptional responses of *Saccharomyces cerevisiae* grown on glucose in aerobic chemostat cultures limited for carbon, nitrogen, phosphorus, or sulfur" *J Biol Chem* 278(5):3265-3274.
Cornish et al. (1994) "Site-specific incorporation of biophysical probes into proteins" *Proc Natl Acad Sci USA* 91(8):2910-2914.
Cornish et al. (1995) "Probing Protein Structure and Function with an Expanded Genetic Code" *Angew Chem Int Ed Engl* 34:621-633.
Deiters et al. (2003) "Adding amino acids with novel reactivity to the genetic code of *Saccharomyces cerevisiae*" *J Am Chem Soc* 125(39):11782-11783.
Hall et al. (2005) "Contribution of horizontal gene transfer to the evolution of *Saccharomyces cerevisiae*" *Eukaryot Cell* 4(6):1102-1115.
Hecht (1992) "Probing the Synthetic Capabilities of a Center of Biochemical Catalysis" *Acc Chem Res* 25(12):545-552.
Hortin & Boime (1983) "Applications of amino acid analogs for studying co- and posttranslational modifications of proteins" *Meth Enzymol* 96:777-784.
Kirshenbaum et al. (2002) "Biosynthesis of proteins incorporating a versatile set of phenylalanine analogues" *Chembiochem* 3(2-3):235-237.
Takebe (1988) "SR alpha promoter: an efficient and versatile mammalian cDNA expression system composed of the simian virus 40 early promoter and the R-U5 segment of human T-cell leukemia virus type 1 long terminal repeat" *Mol Cell Biol* 8(1):466-472.
Extended European Search Report for European Application No. 12734663.3, dated Jul. 17, 2015, 10 pages.
Carrico et al. (2007) "Introducing genetically encoded aldehydes into proteins" Nature Chemical Biology, 3(6):321-322.
Prescher and Bertozzi (2005) "Chemistry in living systems" Nature Chemical Biology, 1(1):13-21.
Smith et al. (2014) "Chemoenzymatic Fc Glycosylation via Engineered Aldehyde Tags" Bioconjugate Chemistry, 25(4):788-795.
Wu et al., (2009) "Site-specific chemical modification of recombinant proteins produced in mammalian cells by using the genetically encoded aldehyde tag" Proc. Natl. Acad. Sci. 106(9):3000-3005.
Junutula, Jagath, R., et al. (2008) "Rapid identification of reactive cysteine residues for site-specific labeling of antibody-Fabs" Journal of Immunological Methods 332:41-52.

* cited by examiner

Figure 1A

IgG1
Light chain conserved region:

```
         140        150        160        170        180      189
RTVAAPSVFI FPPSDEQLKS GTASVVCLLN NFYPREAKVQ WKVDNALQSG NSQESVTEQD

         200        210        220        230   236
SKDSTYSLSS TLTLSKADYE KHKVYACEVT HQGLSSPVTK SFNRGEC
```

Heavy chain conserved region:

```
      130        140        150        160        170        180
ASTKGPSVFP LAPSSKSTSG GTAALGCLVK DYFPEPVTVS WNSGALTSGV HTFPAVLQSS

      190        200        210        220        230        240
GLYSLSSVVT VPSSSLGTQT YICNVNHKPS NTKVDKKVEP KSCDKTHTCP PCPAPELLGG

      250        260        270        280        290        300
PSVFLFPPKP KDTLMISRTP EVTCVVVDVS HEDPEVKFNW YVDGVEVHNA KTKPREEQYN

      310        320        330        340        350        360
STYRVVSVLT VLHQDWLNGK EYKCKVSNKA LPAPIEKTIS KAKGQPREPQ VYTLPPSREE

      370        380        390        400        410        420
MTKNQVSLTC LVKGFYPSDI AVEWESNGQP ENNYKTTPPV LDSDGSFFLY SKLTVDKSRW

      430        440        450
QQGNVFSCSV MHEALHNHYT QKSLSLSPGK
```

Figure 1B

Seq 1 = *Homo sapiens* IgG1 heavy chain constant region; GenBank P01857.1
Seq 2 = *Homo sapiens* IgG2 heavy chain constant region; GenBank P01859.2
Seq 3 = *Homo sapiens* IgG3 heavy chain constant region; GenBank P01860.2
Seq 4 = *Homo sapiens* IgG4 heavy chain constant region; GenBank AAB59394.1
Seq 5 = *Homo sapiens* IgA heavy chain constant region; GenBank AAAT74070

```
seq1    --ASTKGPSVFPLAPSSKSTSGGTAALGCLVKDYFP-EPVTVSWNSGALTSGVHTFPAVL 178
seq3    --ASTKGPSVFPLAPCSRSTSGGTAALGCLVKDYFP-EPVTVSWNSGALTSGVHTFPAVL
seq2    --ASTKGPSVFPLAPCSRSTSESTAALGCLVKDYFP-EPVTVSWNSGALTSGVHTFPAVL
seq4      STKGPSVFPLAPCSRSTSESTAALGCLVKDYFP-EPVTVSWNSGALTSGVHTFPAVL
seq5    --ASPTSPKVFPLSLCS-TQPDGNVVIACLVQGFFPQEPLSVTWSESGQGVTARNFPPSQ

seq1    QSSG-LYSLSSVVTVPS-SSLGTQTYICNVNHKPSNTKVDKKVE---------------- 220
seq3    QSSG-LYSLSSVVTVPS-SSLGTQTYTCNVNHKPSNTKVDKRVELKTPLGDTTHTCPRCP
seq2    QSSG-LYSLSSVVTVPS-SNFGTQTYTCNVDHKPSNTKVDKTVER---------------
seq4    QSSG-LYSLSSVVTVPS-SSLGTKTYTCNVDHKPSNTKVDKRVES---------------
seq5    DASGDLYTTSSQLTLPATQCLAGKSVTCHVKHY-TNPSQDVTVPCP--------------

seq1    ------------------------------PKSCDKTHTCPPCPAPELLGGPSVFLFPP 249
seq3    EPKSCDTPPPCPRCPEPKSCDTPPPCPRCPEPKSCDTPPPCPRCPAPELLGGPSVFLFPP
seq2    ------------------------------ERKCCVE---CPPCPAPPVAG-PSVFLFPP
seq4    --------------------------------ESKYGPPCPSCPAPEFLGGPSVFLFPP
seq5    ------------------------------VPSTPPTPSPSTPPTPSPSCCHPRLSLHR

seq1    KPKDTLMISRTPEVTCVVVDVSHEDPEVKFNWYVDGVEVHNAKTKPREEQYNSTYRVVSV 309
seq3    KPKDTLMISRTPEVTCVVVDVSHEDPEVQFKWYVDGVEVHNAKTKPREEQYNSTFRVVSV
seq2    KPKDTLMISRTPEVTCVVVDVSHEDPEVQFNWYVDGVEVHNAKTKPREEQFNSTFRVVSV
seq4    KPKDTLMISRTPEVTCVVVDVSQEDPEVQFNWYVDGVEVHNAKTKPREEQFNSTYRVVSV
seq5    PALEDLLLGSEANLTCTLTGLR-DASGVTFTWTPS--SGKSAVQGPPDRDLCGCYSVSSV
```

Figure 1C:
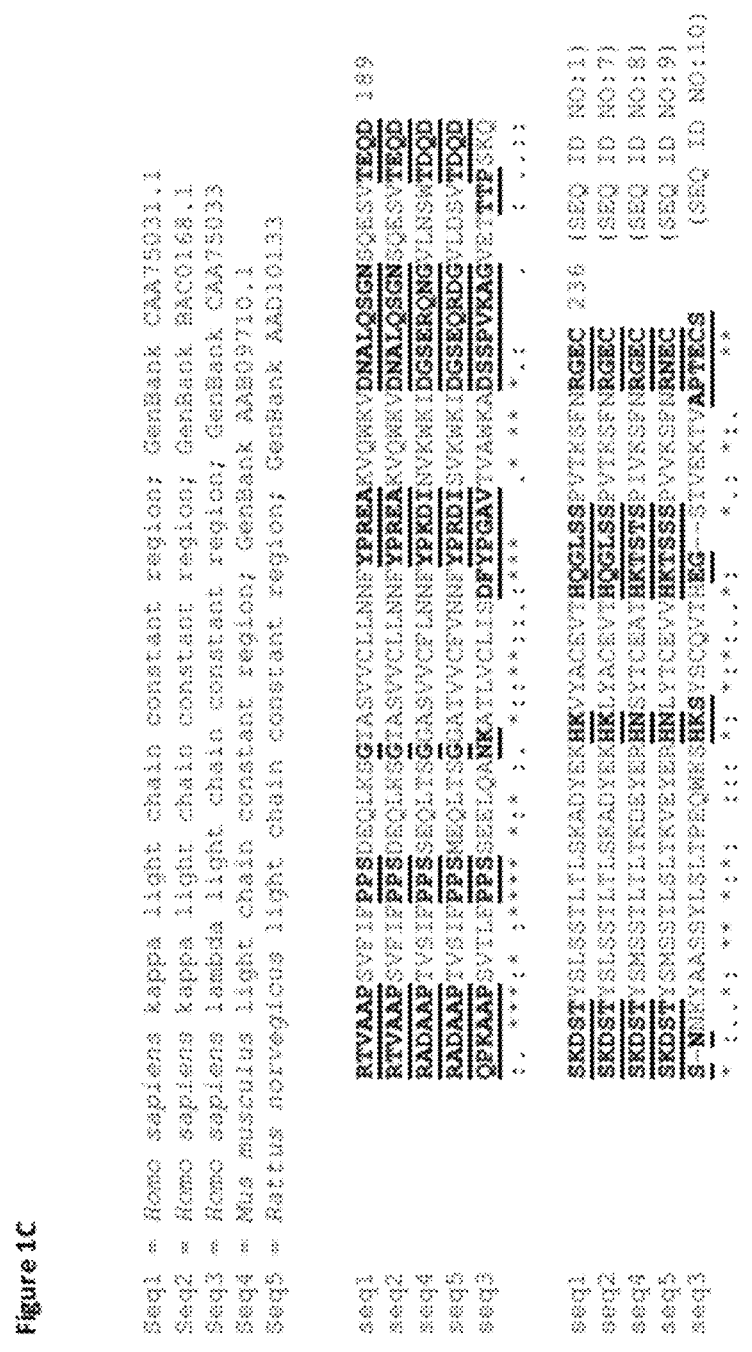

Seq1 = *Homo sapiens* kappa light chain constant region; GenBank CAA75031.1
Seq2 = *Homo sapiens* kappa light chain constant region; GenBank BAC0168.1
Seq3 = *Homo sapiens* lambda light chain constant region; GenBank CAA75033
Seq4 = *Mus musculus* light chain constant region; GenBank AAB09710.1
Seq5 = *Rattus norvegicous* light chain constant region; GenBank AAD10133

```
seq1    RTVAAPSVFIFPPSDEQLKSGTASVVCLLNNFYPREAKVQWKVDNALQSGNSQESVTEQD 189
seq2    RTVAAPSVFIFPPSDEQLKSGTASVVCLLNNFYPREAKVQWKVDNALQSGNSQESVTEQD
seq4    RADAAPTVSIFPPSSEQLTSGGASVVCFLNNFYPKDINVKWKIDGSERQNGVLNSWTDQD
seq5    RADAAPTVSIFPPSMEQLTSGGATVVCFVNNFYPRDISVKWKIDGSEQRDGVLDSVTDQD
seq3    QPKAAPSVTLFPPSSEELQANKATLVCLISDFYPGAVTVAWKADSSPVKAGVETTTPSKQ
        :. ***:* :**** *:* :. *::**::.:***   .* ** *.:     .    : ..::

seq1    SKDSTYSLSSTLTLSKADYEKHKVYACEVTHQGLSSPVTKSFNRGEC 236 (SEQ ID NO:1)
seq2    SKDSTYSLSSTLTLSKADYEKHKLYACEVTHQGLSSPVTKSFNRGEC     (SEQ ID NO:7)
seq4    SKDSTYSMSSTLTLTKDEYERHNSYTCEATHKTSTSPIVKSFNRGEC     (SEQ ID NO:8)
seq5    SKDSTYSMSSTLSLTKVEYERHNLYTCEVVHKTSSSPVVKSFNRNEC     (SEQ ID NO:9)
seq3    S-NNKYAASSYLSLTPEQWKSHKSYSCQVTHEG--STVEKTVAPTECS     (SEQ ID NO:10)
        * :..*: ** *:*:  ::: *: *:*:..*:   *.: *:.   **
```

Figure 3

Light chain:

mmssaqflgllllcfqgtrc/DILLTQTPASLAVSLGQRATISCKASQSVDYDGDSYLNWYQQIPGQPPKL
LIYDASNLVSGIPPRFSGSGSGTDFTLNIHPVEKVDAATYHCQQSTEDPWTFGGGTKLEIKRTVAAPSVF
IFPPSDEQLKSGTASVVCLLNNFYPREAKVQWKVDNALQSGNSQESVTEQDSKDSTYSLSSTLTLSKADYE
KHKVYACEVTHQGLSSPVTKSFNRGEC

Heavy chain:

mnfglsliflvlvlkgvqc/QVQLQQSGAELVRPGSSVKISCKASGYAFSSYWMNWVKQRPGQGLEWIGQI
WPGDGDTNYNGKFKGKATLTADESSSTAYMQLSSLASEDSAVYFCARREYYYGRYYYAMDYWGQGTSVTV
SSASTKGPSVFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCPPCPAPELLGGPSVFLFPPKPKDTLMISRTP
EVTCVVVDVSHEDPEVKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGSLCTPSRGS

Figure 5
A
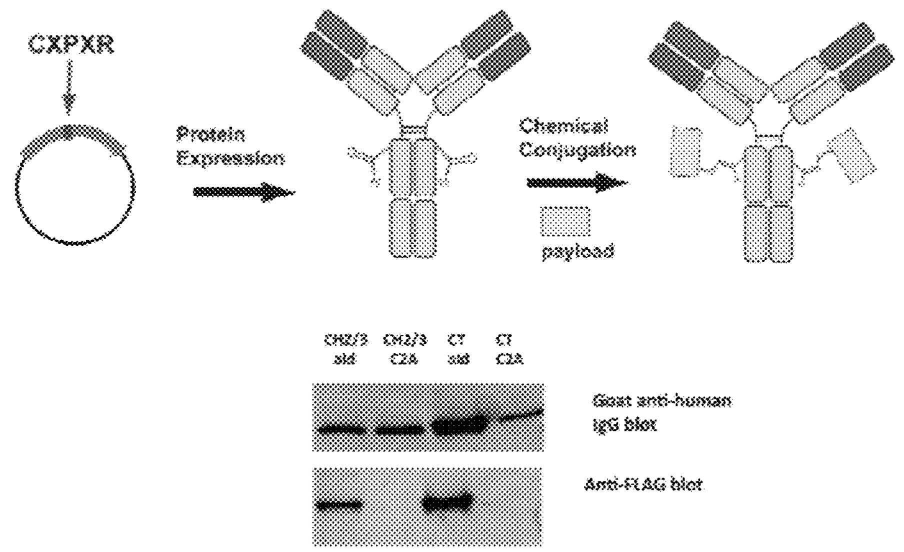
B
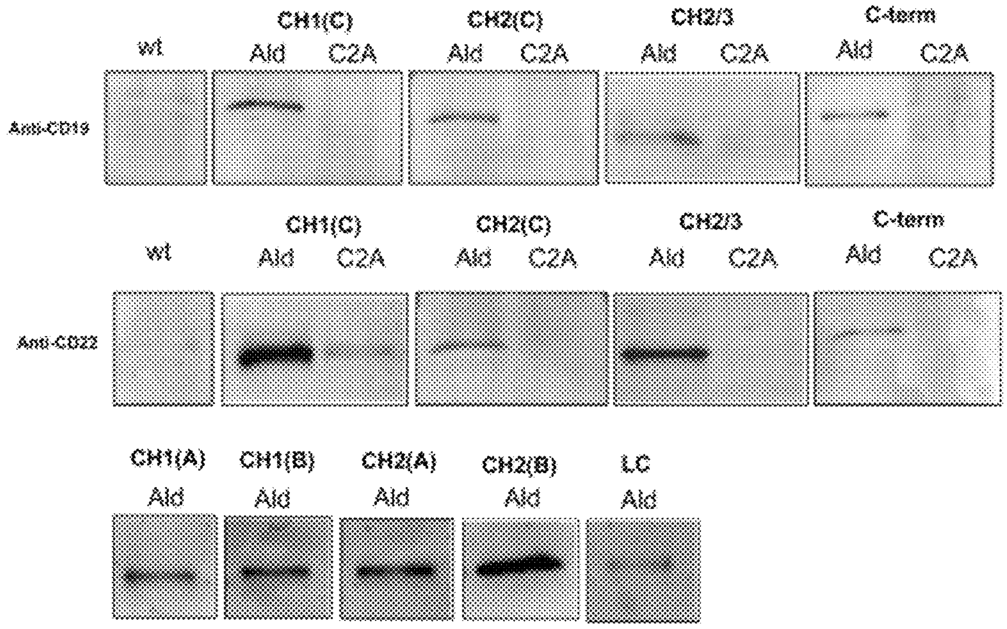

Figure 6A

CD22 specific anti-human IgG1 heavy chain - no aldehyde tag, wild-type

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAACCACAGGTGTACACCC
TGCCCCCATCCCGGGAGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCAC
GCCTCCCGTGCTGGACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGCACAACCACTACACG
CAGAAGAGCCTCTCCCTGTCTCCGGGTAAATGA

Figure 6B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALHN
HYTQKSLSLSPGK

Figure 7A

CD22 specific anti-human IgG1 heavy chain - CH1(A) LCTPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCctgtgtaccccttctagaGTCTTCCCCCTGGCACC
CTCCTCCAAGAGCACCTCTGGGGGCACAGCGGCCCTGGGCTGCCTGGTCAAGGACTACTTCCCCG
AACCGGTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTGGGCAC
CCAGACCTACATCTGCAACGTGAATCACAAGCCCAGCAACACCAAGGTGGACAAGAAAGTTGAGC
CCAAATCTTGTGACAAAACTCACACATGCCCACCGTGCCCAGCACCTGAACTCCTGGGGGGACCG
TCAGTCTTCCTCTTCCCCCCAAAACCCAAGGACACCCTCATGATCTCCCGGACCCCTGAGGTCAC
ATGCGTGGTGGTGGACGTGAGCCACGAAGACCCTGAGGTCAAGTTCAACTGGTACGTGGACGGCG
TGGAGGTGCATAATGCCAAGACAAAGCCGCGGGAGGAGCAGTACAACAGCACGTACCGTGTGGTC
AGCGTCCTCACCGTCCTGCACCAGGACTGGCTGAATGGCAAGGAGTACAAGTGCAAGGTCTCCAA
CAAAGCCCTCCCAGCCCCCATCGAGAAAACCATCTCCAAAGCCAAAGGGCAGCCCCGAGAACCAC
AGGTGTACACCCTGCCCCCATCCCGGGAGGAGATGACCAAGAACCAGGTCAGCCTGACCTGCCTG
GTCAAAGGCTTCTATCCCAGCGACATCGCCGTGGAGTGGGAGAGCAATGGGCAGCCGGAGAACAA
CTACAAGACCACGCCTCCCGTGCTGGACTCCGACGGCTCCTTCTTCCTCTACAGCAAGCTCACCG
TGGACAAGAGCAGGTGGCAGCAGGGGAACGTCTTCTCATGCTCCGTGATGCATGAGGCTCTGCAC
AACCACTACACGCAGAAGAGCCTCTCCCTGTCTCCGGGTAAATGA

Figure 7B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGLCTPSRVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSVMHE
ALHNHYTQKSLSLSPGK

Figure 8A

CD22 specific anti-human IgG1 heavy chain - CH1(B) LCTPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGTGTACCCCTTCTAGATC
CAAGAGCACCTCTGGGGGCACAGCGGCCCTGGGCTGCCTGGTCAAGGACTACTTCCCCGAACCGG
TGACGGTGTCGTGGAACTCAGGCGCCCTGACCAGCGGCGTGCACACCTTCCCGGCTGTCCTACAG
TCCTCAGGACTCTACTCCCTCAGCAGCGTGGTGACCGTGCCCTCCAGCAGCTTGGGCACCCAGAC
CTACATCTGCAACGTGAATCACAAGCCCAGCAACACCAAGGTGGACAAGAAAGTTGAGCCCAAAT
CTTGTGACAAAACTCACACATGCCCACCGTGCCCAGCACCTGAACTCCTGGGGGGACCGTCAGTC
TTCCTCTTCCCCCCAAAACCCAAGGACACCCTCATGATCTCCCGGACCCCTGAGGTCACATGCGT
GGTGGTGGACGTGAGCCACGAAGACCCTGAGGTCAAGTTCAACTGGTACGTGGACGGCGTGGAGG
TGCATAATGCCAAGACAAAGCCGCGGGAGGAGCAGTACAACAGCACGTACCGTGTGGTCAGCGTC
CTCACCGTCCTGCACCAGGACTGGCTGAATGGCAAGGAGTACAAGTGCAAGGTCTCCAACAAAGC
CCTCCCAGCCCCCATCGAGAAAACCATCTCCAAAGCCAAAGGGCAGCCCCGAGAACCACAGGTGT
ACACCCTGCCCCCATCCCGGGAGGAGATGACCAAGAACCAGGTCAGCCTGACCTGCCTGGTCAAA
GGCTTCTATCCCAGCGACATCGCCGTGGAGTGGGAGAGCAATGGGCAGCCGGAGAACAACTACAA
GACCACGCCTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTGCACAACCAC
TACACGCAGAAGAGCCTCTCCCTGTCTCCGGGTAAATGA

Figure 8B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLCTPSRSKSTSGGTAALGCLVKDYFPEPVTVSWNSGALTSGVHTFPA
VLQSSGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEAL
HNHYTQKSLSLSPGK

Figure 9A

CD22 specific anti-human IgG1 heavy chain - CH1(C) LCTPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGtgtaccccttctagaGGCGTGCACACCTTCCCGGCTGTCCTA
CAGTCCTCAGGACTCTACTCCCTCAGCAGCGTGGTGACCGTGCCCTCCAGCAGCTTGGGCACCCA
GACCTACATCTGCAACGTGAATCACAAGCCCAGCAACACCAAGGTGGACAAGAAAGTTGAGCCCA
AATCTTGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTCACATG
CGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGG
TGTACACCCTGCCCCCATCCCGGGAGGAGATGACCAAGAACCAGGTCAGCCTGACCTGCCTGGTC
AAAGGCTTCTATCCCAGCGACATCGCCGTGGAGTGGGAGAGCAATGGGCAGCCGGAGAACAACTA
CAAGACCACGCCTCCCGTGCTGGACTCCGACGGCTCCTTCTTCCTCTACAGCAAGCTCACCGTGG
ACAAGAGCAGGTGGCAGCAGGGGAACGTCTTCTCATGCTCCGTGATGCATGAGGCTCTGCACAAC
CACTACACGCAGAAGAGCCTCTCCCTGTCTCCGGGTAAATGA

Figure 9B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALCTPSRGVHTFP
AVLQSSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSVMHEA
LHNHYTQKSLSLSPGK

Figure 10A

CD22 specific anti-human IgG1 heavy chain - CH1(C) LATPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGgctaccccttctagaGGCGTGCACACCTTCCCGGCTGTCCTA
CAGTCCTCAGGACTCTACTCCCTCAGCAGCGTGGTGACCGTGCCCTCCAGCAGCTTGGGCACCCA
GACCTACATCTGCAACGTGAATCACAAGCCCAGCAACACCAAGGTGGACAAGAAAGTTGAGCCCA
AATCTTGTGACAAAACTCACACATGCCCACCGTGCCCAGCACCTGAACTCCTGGGGGGACCGTCA
GTCTTCCTCTTCCCCCCAAAACCCAAGGACACCCTCATGATCTCCCGGACCCCTGAGGTCACATG
CGTGGTGGTGGACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGG
TGTACACCCTGCCCCCATCCCGGGAGGAGATGACCAAGAACCAGGTCAGCCTGACCTGCCTGGTC
AAAGGCTTCTATCCCAGCGACATCGCCGTGGAGTGGGAGAGCAATGGGCAGCCGGAGAACAACTA
CAAGACCACGCCTCCCGTGCTGGACTCCGACGGCTCCTTCTTCCTCTACAGCAAGCTCACCGTGG
ACAAGAGCAGGTGGCAGCAGGGGAACGTCTTCTCATGCTCCGTGATGCATGAGGCTCTGCACAAC
CACTACACGCAGAAGAGCCTCTCCCTGTCTCCGGGTAAATGA

Figure 10B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALATPSRGVHTFP
AVLQSSGLYSLSSVVTVPSSSLGTQTYICNVNHKPSNTKVDKKVEPKSCDKTHTCPPCPAPELLG
GPSVFLFPPKPKDTLMISRTPEVTCVVVDVSHEDPEVKFNWYVDGVEVHNAKTKPREEQYNSTYR
VVSVLTVLHQDWLNGKEYKCKVSNKALPAPIEKTISKAKGQPREPQVYTLPPSREEMTKNQVSLT
CLVKGFYPSDIAVEWESNGQPENNYKTTPPVLDSDGSFFLYSKLTVDKSRWQQGNVFSCSVMHEA
LHNHYTQKSLSLSPGK

Figure 11A

CD22 specific anti-human IgG1 heavy chain - CH2(A) LCTPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCACTGTGTACCCCTTCTAGAGAACTCCT
GGGGGGACCGTCAGTCTTCCTCTTCCCCCCAAAACCCAAGGACACCCTCATGATCTCCCGGACCC
CTGAGGTCACATGCGTGGTGGTGGACGTGAGCCACGAAGACCCTGAGGTCAAGTTCAACTGGTAC
GTGGACGGCGTGGAGGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAAGGAGTACAAGTGCA
AGGTCTCCAACAAAGCCCTCCCAGCCCCCATCGAGAAAACCATCTCCAAAGCCAAAGGGCAGCCC
CGAGAACCACAGGTGTACACCCTGCCCCCATCCCGGGAGGAGATGACCAAGAACCAGGTCAGCCT
GACCTGCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCTACAGC
AAGCTCACCGTGGACAAGAGCAGGTGGCAGCAGGGGAACGTCTTCTCATGCTCCGTGATGCATGA
GGCTCTGCACAACCACTACACGCAGAAGAGCCTCTCCCTGTCTCCGGGTAAATGA

Figure 11B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPLCTPSRELL
GGPSVFLFPPKPKDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPSREEMTKNQVSL
TCLVKGFYPSDIAVEWESNGQPENNYKTTPPVLDSDGSFFLYSKLTVDKSRWQQGNVFSCSVMHE
ALHNHYTQKSLSLSPGK

Figure 12A

CD22 specific anti-human IgG1 heavy chain - CH2(B) LCTPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGT
GGACGTGAGCCACGAAGACCTGTGTACCCCTTCTAGAGAGGTCAAGTTCAACTGGTACGTGGACG
GCGTGGAGGTGCATAATGCCAAGACAAAGCCGCGGGAGGAGCAGTACAACAGCACGTACCGTGTG
GTCAGCGTCCTCACCGTCCTGCACCAGGACTGGCTGAATGGCAAGGAGTACAAGTGCAAGGTCTC
CAACAAAGCCCTCCCAGCCCCCATCGAGAAAACCATCTCCAAAGCCAAAGGGCAGCCCCGAGAAC
CACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTCA
CCGTGGACAAGAGCAGGTGGCAGCAGGGGAACGTCTTCTCATGCTCCGTGATGCATGAGGCTCTG
CACAACCACTACACGCAGAAGAGCCTCTCCCTGTCTCCGGGTAAATGA

Figure 12B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDLCTPSREVKFNWYVDGVEVHNAKTKPREEQYNST
YRVVSVLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFSCSVMH
EALHNHYTQKSLSLSPGK

Figure 13A

CD22 specific anti-human IgG1 heavy chain - CH2(C) LCTPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACttatgtacccc
ttctagaGCCCCCATCGAGAAAACCATCTCCAAAGCCAAAGGGCAGCCCCGAGAACCACAGGTGT
ACACCCTGCCCCCATCCCGGGAGGAGATGACCAAGAACCAGGTCAGCCTGACCTGCCTGGTCAAA
GGCTTCTATCCCAGCGACATCGCCGTGGAGTGGGAGAGCAATGGGCAGCCGGAGAACAACTACAA
GACCACGCCTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTGCACAACCAC
TACACGCAGAAGAGCCTCTCCCTGTCTCCGGGTAAATGA

Figure 13B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRVVS
VLTVLHQDWLNGKEYKCKVSNLCTPSRAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEAL
HNHYTQKSLSLSPGK

Figure 14A

CD22 specific anti-human IgG1 heavy chain ~ CH2(C) LATPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACttagctacccc
ttctagaGCCCCCATCGAGAAAACCATCTCCAAAGCCAAAGGGCAGCCCCGAGAACCACAGGTGT
ACACCCTGCCCCCATCCCGGGAGGAGATGACCAAGAACCAGGTCAGCCTGACCTGCCTGGTCAAA
GGCTTCTATCCCAGCGACATCGCCGTGGAGTGGGAGAGCAATGGGCAGCCGGAGAACAACTACAA
GACCACGCCTCCCGTGCTGGACTCCGACGGCTCCTTCTTCCTCTACAGCAAGCTCACCGTGGACA
AGAGCAGGTGGCAGCAGGGGAACGTCTTCTCATGCTCCGTGATGCATGAGGCTCTGCACAACCAC
TACACGCAGAAGAGCCTCTCCCTGTCTCCGGGTAAATGA

Figure 14B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRVVS
VLTVLHQDWLNGKEYKCKVSNLATPSRAPIEKTISKAKGQPREPQVYTLPPSREEMTKNQVSLTC
LVKGFYPSDIAVEWESNGQPENNYKTTPPVLDSDGSFFLYSKLTVDKSRWQQGNVFSCSVMHEAL
HNHYTQKSLSLSPGK

Figure 15A

CD22 specific anti-human IgG1 heavy chain - CH2/CH3 LCTPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACAAAGCCCTCCC
AGCCCCCATCGAGAAAACCATCTCCAAAGCCAAAGGGttatgtacccctctCGAGAACCACAGG
TGTACACCCTGCCCCCATCCCGGGAGGAGATGACCAAGAACCAGGTCAGCCTGACCTGCCTGGTC
AAAGGCTTCTATCCCAGCGACATCGCCGTGGAGTGGGAGAGCAATGGGCAGCCGGAGAACAACTA
CAAGACCACGCCTCCCGTGCTGGACTCCGACGGCTCCTTCTTCCTCTACAGCAAGCTCACCGTGG
ACAAGAGCAGGTGGCAGCAGGGGAACGTCTTCTCATGCTCCGTGATGCATGAGGCTCTGCACAAC
CACTACACGCAGAAGAGCCTCTCCCTGTCTCCGGGTAAATGA

Figure 15B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGLCTPSREPQVYTLPPSREEMTKNQVSLT
CLVKGFYPSDIAVEWESNGQPENNYKTTPPVLDSDGSFFLYSKLTVDKSRWQQGNVFSCSVMHEA
LHNHYTQKSLSLSPGK

Figure 16A

CD22 specific anti-human IgG1 heavy chain - CH2/CH3 LATPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACAAAGCCCTCCC
AGCCCCCATCGAGAAAACCATCTCCAAAGCCAAAGGGttagctacccttctCGAGAACCACAGG
TGTACACCCTGCCCCCATCCCGGGAGGAGATGACCAAGAACCAGGTCAGCCTGACCTGCCTGGTC
AAAGGCTTCTATCCCAGCGACATCGCCGTGGAGTGGGAGAGCAATGGGCAGCCGGAGAACAACTA
CAAGACCACGCCTCCCGTGCTGGACTCCGACGGCTCCTTCTTCCTCTACAGCAAGCTCACCGTGG
ACAAGAGCAGGTGGCAGCAGGGGAACGTCTTCTCATGCTCCGTGATGCATGAGGCTCTGCACAAC
CACTACACGCAGAAGAGCCTCTCCCTGTCTCCGGGTAAATGA

Figure 16B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGLATPSREPQVYTLPPSREEMTKNQVSLT
CLVKGFYPSDIAVEWESNGQPENNYKTTPPVLDSDGSFFLYSKLTVDKSRWQQGNVFSCSVMHEA
LHNHYTQKSLSLSPGK

Figure 17A

CD22 specific anti-human IgG1 heavy chain - C-terminal LCTPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAACCACAGGTGTACACCC
TGCCCCCATCCCGGGAGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCAC
GCCTCCCGTGCTGGACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGCACAACCACTACACG
CAGAAGAGCCTCTCCCTGTCTCCGGGATCCTTATGTACCCCTTCTAGAGGATCCTGA

Figure 17B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALHN
HYTQKSLSLSPGSLCTPSRGS

Figure 18A

CD22 specific anti-human IgG1 heavy chain - C-terminal LATPSR

ATGAACTTCGGGCTCAGCTTGATTTTCCTTGTCCTTGTTTTAAAAGGTGTCCAGTGTCAGGTCCA
GCTGCAGGAGTCAGGGGCTGAACTGTCAAAACCTGGGGCCTCAGTGAAGATGTCCTGCAAGGCTT
CTGGCTACACCTTTACTAGCTACTGGCTGCACTGGATAAAACAGAGGCCTGGACAGGGTCTGGAA
TGGATTGGATACATTAATCCTAGGAATGATTATACTGAGTACAATCAGAACTTCAAGGACAAGGC
CACATTGACTGCAGACAAATCCTCCAGCACAGCCTACATGCAACTGAGCAGCCTGACATCTGAGG
ACTCTGCAGTCTATTACTGTGCAAGAAGGGATATTACTACGTTCTACTGGGGCCAAGGCACCACT
CTCACAGTCTCCTCGGCTAGCACCAAGGGCCCATCGGTCTTCCCCCTGGCACCCTCCTCCAAGAG
CACCTCTGGGGGCACAGCGGCCCTGGGCTGCCTGGTCAAGGACTACTTCCCCGAACCGGTGACGG
TGTCGTGGAACTCAGGCGCCCTGACCAGCGGCGTGCACACCTTCCCGGCTGTCCTACAGTCCTCA
GGACTCTACTCCCTCAGCAGCGTGGTGACCGTGCCCTCCAGCAGCTTGGGCACCCAGACCTACAT
CTGCAACGTGAATCACAAGCCCAGCAACACCAAGGTGGACAAGAAAGTTGAGCCCAAATCTTGTG
ACAAAACTCACACATGCCCACCGTGCCCAGCACCTGAACTCCTGGGGGGACCGTCAGTCTTCCTC
TTCCCCCCAAAACCCAAGGACACCCTCATGATCTCCCGGACCCCTGAGGTCACATGCGTGGTGGT
GGACGTGAGCCACGAAGACCCTGAGGTCAAGTTCAACTGGTACGTGGACGGCGTGGAGGTGCATA
ATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACAAAGCCCTCCC
AGCCCCCATCGAGAAAACCATCTCCAAAGCCAAAGGGCAGCCCCGAGAACCACAGGTGTACACCC
TGCCCCCATCCCGGGAGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCAC
GCCTCCCGTGCTGGACTCCGACGGCTCCTTCTTCCTCTACAGCAAGCTCACCGTGGACAAGAGCA
GGTGGCAGCAGGGGAACGTCTTCTCATGCTCCGTGATGCATGAGGCTCTGCACAACCACTACACG
CAGAAGAGCCTCTCCCTGTCTCCGGGATCCTTAGCTACCCCTTCTAGAGGATCCTGA

Figure 18B

MNFGLSLIFLVLVLKGVQC/QVQLQESGAELSKPGASVKMSCKASGYTFTSYWLHWIKQRPGQGL
EWIGYINPRNDYTEYNQNFKDKATLTADKSSSTAYMQLSSLTSEDSAVYYCARRDITTFYWGQGT
TLTVSS//ASTKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSCDKTHTCPPCPAPELLGGPS
VFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLTCLV
KGFYPSDIAVEWESNGQPENNYKTTPPVLDSDGSFFLYSKLTVDKSRWQQGNVFSCSVMHEALHN
HYTQKSLSLSPGSLATPSRGS

Figure 19A

CD22 specific anti-human Ig kappa light chain - no aldehyde tag, wild-type

ATGATGTCCTCTGCTCAGTTCCTTGGTCTCCTGTTGCTCTGTTTTCAAGGTACCAGATGTGACAT
TCAGCTGACCCAGTCTCCATCATCTCTGGCTGTGTCTGCAGGAGAAAACGTCACTATGAGCTGTA
AGTCCAGTCAAAGTGTTTTATACAGTGCAAATCACAAGAACTACTTGGCCTGGTACCAGCAGAAA
CCAGGGCAGTCTCCTAAACTGCTGATCTACTGGGCATCCACTAGGGAATCTGGTGTCCCTGATCG
CTTCACAGGCAGCGGATCTGGGACAGATTTTACTCTTACCATCAGCAGAGTACAAGTTGAAGACC
TGGCAATTTATTATTGTCACCAATACCTCTCCTCGTGGACGTTCGGTGGAGGGACCAAGCTGGAG
ATCAAACGTCGTACGGTGGCTGCACCATCTGTCTTCATCTTCCCGCCATCTGATGAGCAGTTGAA
ATCTGGAACTGCCTCTGTTGTGTGCCTGCTGAATAACTTCTATCCCAGAGAGGCCAAAGTACAGT
GGAAGGTGGATAACGCCCTCCAATCGGGTAACTCCCAGGAGAGTGTCACAGAGCAGGACAGCAAG
GACAGCACCTACAGCCTCAGCAGCACCCTGACGCTGAGCAAAGCAGACTACGAGAAACACAAAGT
CTACGCCTGCGAAGTCACCCATCAGGGCCTGAGCTCGCCCGTCACAAAGAGCTTCAACAGGGGAG
AGTGTTAG

Figure 19B

MMSSAQFLGLLLLCFQGTRC/DIQLTQSPSSLAVSAGENVTMSCKSSQSVLYSANHKNYLA
WYQQKPGQSPKLLIYWASTRESGVPDRFTGSGSGTDFTLTISSVQVEDLAIYYCHQYLSS
WTFGGGTKLEIKR//RTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

Figure 20A

CD22 specific anti-human Ig kappa light chain -LCTPSR

ATGATGTCCTCTGCTCAGTTCCTTGGTCTCCTGTTGCTCTGTTTTCAAGGTACCAGATGTGACAT
TCAGCTGACCCAGTCTCCATCATCTCTGGCTGTGTCTGCAGGAGAAAACGTCACTATGAGCTGTA
AGTCCAGTCAAAGTGTTTTATACAGTGCAAATCACAAGAACTACTTGGCCTGGTACCAGCAGAAA
CCAGGGCAGTCTCCTAAACTGCTGATCTACTGGGCATCCACTAGGGAATCTGGTGTCCCTGATCG
CTTCACAGGCAGCGGATCTGGGACAGATTTTACTCTTACCATCAGCAGAGTACAAGTTGAAGACC
TGGCAATTTATTATTGTCACCAATACCTCTCCTCGTGGACGTTCGGTGGAGGGACCAAGCTGGAG
ATCAAACGTCGTACGGTGGCTGCACCATCTGTCTTCATCTTCCCGCCATCTGATGAGCAGTTGAA
ATCTGGAACTGCCTCTGTTGTGTGCCTGCTGAATAACTTCTATCCCAGAGAGGCCAAAGTACAGT
GGAAGGTGGATAACGCCCTCTGCACCCCCAGCCGGCAATCGGGTAACTCCCAGGAGAGTGTCACA
GAGCAGGACAGCAAGGACAGCACCTACAGCCTCAGCAGCACCCTGACGCTGAGCAAAGCAGACTA
CGAGAAACACAAAGTCTACGCCTGCGAAGTCACCCATCAGGGCCTGAGCTCGCCCGTCACAAAGA
GCTTCAACAGGGGAGAGTGTTAG

Figure 20B

MMSSAQFLGLLLLCFQGTRC/DIQLTQSPSSLAVSAGENVTMSCKSSQSVLYSANHKNYLAWYQQ
KPGQSPKLLIYWASTRESGVPDRFTGSGSGTDFTLTISRVQVEDLAIYYCHQYLSSWTFGGGTKL
EIKR//RTVAAPSVFIFPPSDEQLKSGTASVVCLLNNFYPREAKVQWKVDNA<u>LCTPSR</u>QSGNSQE
SVTEQDSKDSTYSLSSTLTLSKADYEKHKVYACEVTHQGLSSPVTKSFNRGEC

Figure 21A

CD22 specific anti-human Ig kappa light chain ~LATPSR

ATGATGTCCTCTGCTCAGTTCCTTGGTCTCCTGTTGCTCTGTTTTCAAGGTACCAGATGTGACAT
TCAGCTGACCCAGTCTCCATCATCTCTGGCTGTGTCTGCAGGAGAAAACGTCACTATGAGCTGTA
AGTCCAGTCAAAGTGTTTTATACAGTGCAAATCACAAGAACTACTTGGCCTGGTACCAGCAGAAA
CCAGGGCAGTCTCCTAAACTGCTGATCTACTGGGCATCCACTAGGGAATCTGGTGTCCCTGATCG
CTTCACAGGCAGCGGATCTGGGACAGATTTTACTCTTACCATCAGCAGAGTACAAGTTGAAGACC
TGGCAATTTATTATTGTCACCAATACCTCTCCTCGTGGACGTTCGGTGGAGGGACCAAGCTGGAG
ATCAAACGTCGTACGGTGGCTGCACCATCTGTCTTCATCTTCCCGCCATCTGATGAGCAGTTGAA
ATCTGGAACTGCCTCTGTTGTGTGCCTGCTGAATAACTTCTATCCCAGAGAGGCCAAAGTACAGT
GGAAGGTGGATAACGCCCTCGCCACCCCCAGCCGGCAATCGGGTAACTCCCAGGAGAGTGTCACA
GAGCAGGACAGCAAGGACAGCACCTACAGCCTCAGCAGCACCCTGACGCTGAGCAAAGCAGACTA
CGAGAAACACAAAGTCTACGCCTGCGAAGTCACCCATCAGGGCCTGAGCTCGCCCGTCACAAAGA
GCTTCAACAGGGGAGAGTGTTAG

Figure 21B

MMSSAQFLGLLLLCFQGTRC/DIQLTQSPSSLAVSAGENVTMSCKSSQSVLYSANHKNYLAWYQQ
KPGQSPKLLIYWASTRESGVPDRFTGSGSGTDFTLTISRVQVEDLAIYYCHQYLSSWTFGGGTKL
EIKR//RTVAAPSVFIFPPSDEQLKSGTASVVCLLNNFYPREAKVQWKVDNALATPSRQSGNSQE
SVTEQDSKDSTYSLSSTLTLSKADYEKHKVYACEVTHQGLSSPVTKSFNRGEC

Figure 22A

CD19 specific anti-human IgG1 heavy chain - no aldehyde tag, wild-type

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACACCAAGGTGGACA
AGAAAGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGGCAGC
CCCGAGAACCACAGGTGTACACCCTGCCCCCATCCCGGGAGGAGATGACCAAGAACCAGGTCAGC
CTGACCTGCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTCCTCTACA
GCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATGA

Figure 22B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSCS
VMHEALHNHYTQKSLSLSPGK

Figure 23A

CD19 specific anti-human IgG1 heavy chain ~ CH1 (C) LCTPSR

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGtgtaccccttctagaGGC
GTGCACACCTTCCCGGCTGTCCTACAGTCCTCAGGACTCTACTCCCTCAGCAGCGTGGTGACCGT
GCCCTCCAGCAGCTTGGGCACCCAGACCTACATCTGCAACGTGAATCACAAGCCCAGCAACACCA
AGGTGGACAAGAAAGTTGAGCCCAAATCTTGTGACAAAACTCACACATGCCCACCGTGCCCAGCA
CCTGAACTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGGTCAAGT
TCAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCA
AAGGGCAGCCCCGAGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGAG
CAATGGGCAGCCGGAGAACAACTACAAGACCACGCCTCCCGTGCTGGACTCCGACGGCTCCTTCT
TCCTCTACAGCAAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCTCCGGGTAAATG
A

Figure 23B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALCTP
SRGVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNVF
SCSVMHEALHNHYTQKSLSLSPGK

Figure 24A

CD19 specific anti-human IgG1 heavy chain - CH1 (C) LATPSR

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGgctacccctctagaGGC
GTGCACACCTTCCCGGCTGTCCTACAGTCCTCAGGACTCTACTCCCTCAGCAGCGTGGTGACCGT
GCCCTCCAGCAGCTTGGGCACCCAGACCTACATCTGCAACGTGAATCACAAGCCCAGCAACACCA
AGGTGGACAAGAAAGTTGAGCCCAAATCTTGTGACAAAACTCACACATGCCCACCGTGCCCAGCA
CCTGAACTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGGTCAAGT
TCAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCATCTCCAAAGCCA
AAGGGCAGCCCCGAGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGAG
CAATGGGCAGCCGGAGAACAACTACAAGACCACGCCTCCCGTGCTGGACTCCGACGGCTCCTTCT
TCCTCTACAGCAAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCTCCGGGTAAATG
A

Figure 24B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALATP
SRGVHTFPAVLQSSGLYSLSSVVTVPSSSLGTQTYICNVNHKPSNTKVDKKVEPKSCDKTHTCPP
CPAPELLGGPSVFLFPPKPKDTLMISRTPEVTCVVVDVSHEDPEVKFNWYVDGVEVHNAKTKPRE
EQYNSTYRVVSVLTVLHQDWLNGKEYKCKVSNKALPAPIEKTISKAKGQPREPQVYTLPPSREEM
TKNQVSLTCLVKGFYPSDIAVEWESNGQPENNYKTTPPVLDSDGSFFLYSKLTVDKSRWQQGNVF
SCSVMHEALHNHYTQKSLSLSPGK

Figure 25A

CD19 specific anti-human IgG1 heavy chain - CH2 (B) LCTPSR

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACACCAAGGTGGACA
AGAAAGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTACAAGTG
CAAGGTCTCCAACTTATGTACCCCTTCTAGAGCCCCCATCGAGAAAACCATCTCCAAAGCCAAAG
GGCAGCCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAGAGCAA
TGGGCAGCCGGAGAACAACTACAAGACCACGCCTCCCGTGCTGGACTCCGACGGCTCCTTCTTCC
TCTACAGCAAGCTCACCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTCTCCGGGTAAATGA

Figure 25B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNLCTPSRAPIEKTISKAKGQPREPQVYTLPPSREEMT
KNQVSLTCLVKGFYPSDIAVEWESNGQPENNYKTTPPVLDSDGSFFLYSKLTVDKSRWQQGNVFS
CSVMHEALHNHYTQKSLSLSPGK

Figure 26A

CD19 specific anti-human IgG1 heavy chain - CH2 (B) LATPSR

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACACCAAGGTGGACA
AGAAAGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTACAAGTG
CAAGGTCTCCAACttagctaccccttctagaGCCCCCATCGAGAAAACCATCTCCAAAGCCAAAG
GGCAGCCCCGAGAACCACAGGTGTACACCCTGCCCCCATCCCGGGAGGAGATGACCAAGAACCAG
GTCAGCCTGACCTGCCTGGTCAAAGGCTTCTATCCCAGCGACATCGCCGTGGAGTGGGAGAGCAA
TGGGCAGCCGGAGAACAACTACAAGACCACGCCTCCCGTGCTGGACTCCGACGGCTCCTTCTTCC
TCTACAGCAAGCTCACCGTGGACAAGAGCAGGTGGCAGCAGGGGAACGTCTTCTCATGCTCCGTG
ATGCATGAGGCTCTGCACAACCACTACACGCAGAAGAGCCTCTCCCTGTCTCCGGGTAAATGA

Figure 26B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNLATPSRAPIEKTISKAKGQPREPQVYTLPPSREEMT
KNQVSLTCLVKGFYPSDIAVEWESNGQPENNYKTTPPVLDSDGSFFLYSKLTVDKSRWQQGNVFS
CSVMHEALHNHYTQKSLSLSPGK

Figure 27A

CD19 specific anti-human IgG1 heavy chain - CH2/CH3 LCTPSR

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACACCAAGGTGGACA
AGAAAGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGGttat
gtacccctctCGAGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGAG
CAATGGGCAGCCGGAGAACAACTACAAGACCACGCCTCCCGTGCTGGACTCCGACGGCTCCTTCT
TCCTCTACAGCAAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCTCCGGGTAAATG
A

Figure 27B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGLCTPSREPQVYTLPPSREEM
TKNQVSLTCLVKGFYPSDIAVEWESNGQPENNYKTTPPVLDSDGSFFLYSKLTVDKSRWQQGNVF
SCSVMHEALHNHYTQKSLSLSPGK

Figure 28A

CD19 specific anti-human IgG1 heavy chain - CH2/CH3 LATPSR

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACACCAAGGTGGACA
AGAAAGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGGTTAG
CTACCCCTTCTCGAGAACCACAGGTGTACACCCTGCCCCCATCCCGGGAGGAGATGACCAAGAAC
CAGGTCAGCCTGACCTGCCTGGTCAAAGGCTTCTATCCCAGCGACATCGCCGTGGAGTGGGAGAG
CAATGGGCAGCCGGAGAACAACTACAAGACCACGCCTCCCGTGCTGGACTCCGACGGCTCCTTCT
TCCTCTACAGCAAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCTCCGGGTAAATG
A

Figure 28B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKG<u>LATPSR</u>EPQVYTLPPSREEM
TKNQVSLTCLVKGFYPSDIAVEWESNGQPENNYKTTPPVLDSDGSFFLYSKLTVDKSRWQQGNVF
SCSVMHEALHNHYTQKSLSLSPGK

Figure 29A

CD19 specific anti-human IgG1 heavy chain - C-terminal LCTPSR

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACACCAAGGTGGACA
AGAAAGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGGCAGC
CCCGAGAACCACAGGTGTACACCCTGCCCCCATCCCGGGAGGAGATGACCAAGAACCAGGTCAGC
CTGACCTGCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTCCTCTACA
GCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGATCCTTATGTACCCC
TTCTAGAGGATCCTGA

Figure 29B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSCS
VMHEALHNHYTQKSLSLSPGSLCTPSRGS

Figure 30A

CD19 specific anti-human IgG1 heavy chain - C-terminal LATPSR

ATGAACTTCGGGCTCAGCTTGATTTTCCTTGTCCTTGTTTTAAAAGGTGTCCAGTGTCAGGTGCA
GCTGCAGCAGTCTGGGGCTGAGCTGGTGAGGCCTGGGTCCTCAGTGAAGATTTCCTGCAAGGCTT
CTGGCTATGCATTCAGTAGCTACTGGATGAACTGGGTGAAGCAGAGGCCTGGACAGGGTCTTGAG
TGGATTGGACAGATTTGGCCTGGAGATGGTGATACTAACTACAATGGAAAGTTCAAGGGTAAAGC
CACTCTGACTGCAGACGAATCCTCCAGCACAGCCTACATGCAACTCAGCAGCCTAGCATCTGAGG
ACTCTGCGGTCTATTTCTGTGCAAGACGGGAGACTACGACGGTAGGCCGTTATTACTATGCTATG
GACTACTGGGGTCAAGGAACCTCAGTCACCGTCTCCTCAGCTAGCACCAAGGGCCCATCGGTCTT
CCCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCAG
CAGCTTGGGCACCCAGACCTACATCTGCAACGTGAATCACAAGCCCAGCAACACCAAGGTGGACA
AGAAAGTTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGAC
CCCTGAGGTCACATGCGTGGTGGTGGACGTGAGCCACGAAGACCCTGAGGTCAAGTTCAACTGGT
ACGTGGACGGCGTGGAGGTGCATAATGCCAAGACAAAGCCGCGGGAGGAGCAGTACAACAGCACG
TACCGTGTGGTCAGCGTCCTCACCGTCCTGCACCAGGACTGGCTGAATGGCAAGGAGTACAAGTG
CAAGGTCTCCAACAAAGCCCTCCCAGCCCCCATCGAGAAAACCATCTCCAAAGCCAAAGGGCAGC
CCCGAGAACCACAGGTGTACACCCTGCCCCCATCCCGGGAGGAGATGACCAAGAACCAGGTCAGC
CTGACCTGCCTGGTCAAAGGCTTCTATCCCAGCGACATCGCCGTGGAGTGGGAGAGCAATGGGCA
GCCGGAGAACAACTACAAGACCACGCCTCCCGTGCTGGACTCCGACGGCTCCTTCTTCCTCTACA
GCAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGATCCTTAGCTACCCC
TTCTAGAGGATCCTGA

Figure 30B

MNFGLSLIFLVLVLKGVQC/QVQLQQSGAELVRPGSSVKISCKASGYAFSSYWMNWVKQRPGQGL
EWIGQIWPGDGDTNYNGKFKGKATLTADESSSTAYMQLSSLASEDSAVYFCARRETTTVGRYYYA
MDYWGQGTSVTVSS//ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKVEPKSCDKTHTCPPCPA
PELLGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSCS
VMHEALHNHYTQKSLSLSPGSLATPSRGS

Figure 31A
CD19 specific anti-human Ig kappa light chain - no aldehyde tag, wild-type

ATGATGTCCTCTGCTCAGTTCCTTGGTCTCCTGTTGCTCTGTTTTCAAGGTACCAGATGTGATAT
CTTGCTCACCCAAACTCCAGCTTCTTTGGCTGTGTCTCTAGGGCAGAGGGCCACCATCTCCTGCA
AGGCCAGCCAAAGTGTTGATTATGATGGTGATAGTTATTTGAACTGGTACCAACAGATTCCAGGA
CAGCCACCCAAACTCCTCATCTATGATGCATCCAATCTAGTTTCTGGGATCCCACCCAGGTTTAG
TGGCAGTGGGTCTGGGACAGACTTCACCCTCAACATCCATCCTGTGGAGAAGGTGGATGCTGCAA
CCTATCACTGTCAGCAAAGTACTGAGGATCCGTGGACGTTCGGTGGAGGCACCAAGCTGGAAATC
AAACGGCGTACGGTGGCTGCACCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAGCAGGACAGCAAGGAC
AGCACCTACAGCCTCAGCAGCACCCTGACGCTGAGCAAAGCAGACTACGAGAAACACAAAGTCTA
CGCCTGCGAAGTCACCCATCAGGGCCTGAGCTCGCCCGTCACAAAGAGCTTCAACAGGGGAGAGT
GTTAG

Figure 31B

MMSSAQFLGLLLLCFQGTRC/DILLTQTPASLAVSLGQRATISCKASQSVDYDGDSYLNWY
QQIPGQPPKLLIYDASNLVSGIPPRFSGSGSGTDFTLNIHPVEKVDAATYHCQQSTEDPW
TFGGGTKLEIKR//RTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC

Figure 32A

CD19 specific anti-human Ig kappa light chain - LCTPSR

ATGATGTCCTCTGCTCAGTTCCTTGGTCTCCTGTTGCTCTGTTTTCAAGGTACCAGATGTGATAT
CTTGCTCACCCAAACTCCAGCTTCTTTGGCTGTGTCTCTAGGGCAGAGGGCCACCATCTCCTGCA
AGGCCAGCCAAAGTGTTGATTATGATGGTGATAGTTATTTGAACTGGTACCAACAGATTCCAGGA
CAGCCACCCAAACTCCTCATCTATGATGCATCCAATCTAGTTTCTGGGATCCCACCCAGGTTTAG
TGGCAGTGGGTCTGGGACAGACTTCACCCTCAACATCCATCCTGTGGAGAAGGTGGATGCTGCAA
CCTATCACTGTCAGCAAAGTACTGAGGATCCGTGGACGTTCGGTGGAGGCACCAAGCTGGAAATC
AAACGGCGTACGGTGGCTGCACCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTACAGTGGA
AGGTGGATAACGCCCTCTGCACCCCCAGCCGGCAATCGGGTAACTCCCAGGAGAGTGTCACAGAG
CAGGACAGCAAGGACAGCACCTACAGCCTCAGCAGCACCCTGACGCTGAGCAAAGCAGACTACGA
GAAACACAAAGTCTACGCCTGCGAAGTCACCCATCAGGGCCTGAGCTCGCCCGTCACAAAGAGCT
TCAACAGGGGAGAGTGTTAG

Figure 32B

MMSSAQFLGLLLLCFQGTRC/DILLTQTPASLAVSLGQRATISCKASQSVDYDGDSYLNWYQQIP
GQPPKLLIYDASNLVSGIPPRFSGSGSGTDFTLNIHPVEKVDAATYHCQQSTEDPWTFGGGTKLE
IKR//RTVAAPSVFIFPPSDEQLKSGTASVVCLLNNFYPREAKVQWKVDNALCTPSRQSGNSQES
VTEQDSKDSTYSLSSTLTLSKADYEKHKVYACEVTHQGLSSPVTKSFNRGEC

Figure 33A

CD19 specific anti-human Ig kappa light chain -LATPSR

ATGATGTCCTCTGCTCAGTTCCTTGGTCTCCTGTTGCTCTGTTTTCAAGGTACCAGATGTGATAT
CTTGCTCACCCAAACTCCAGCTTCTTTGGCTGTGTCTCTAGGGCAGAGGGCCACCATCTCCTGCA
AGGCCAGCCAAAGTGTTGATTATGATGGTGATAGTTATTTGAACTGGTACCAACAGATTCCAGGA
CAGCCACCCAAACTCCTCATCTATGATGCATCCAATCTAGTTTCTGGGATCCCACCCAGGTTTAG
TGGCAGTGGGTCTGGGACAGACTTCACCCTCAACATCCATCCTGTGGAGAAGGTGGATGCTGCAA
CCTATCACTGTCAGCAAAGTACTGAGGATCCGTGGACGTTCGGTGGAGGCACCAAGCTGGAAATC
AAACGGCGTACGGTGGCTGCACCATCTGTCTTCATCTTCCCGCCATCTGATGAGCAGTTGAAATC
TGGAACTGCCTCTGTTGTGTGCCTGCTGAATAACTTCTATCCCAGAGAGGCCAAAGTACAGTGGA
AGGTGGATAACGCCCTCGCCACCCCCAGCCGGCAATCGGGTAACTCCCAGGAGAGTGTCACAGAG
CAGGACAGCAAGGACAGCACCTACAGCCTCAGCAGCACCCTGACGCTGAGCAAAGCAGACTACGA
GAAACACAAAGTCTACGCCTGCGAAGTCACCCATCAGGGCCTGAGCTCGCCCGTCACAAAGAGCT
TCAACAGGGGAGAGTGTTAG

Figure 33B

MMSSAQFLGLLLLCFQGTRC/DILLTQTPASLAVSLGQRATISCKASQSVDYDGDSYLNWYQQIP
GQPPKLLIYDASNLVSGIPPRFSGSGSGTDFTLNIHPVEKVDAATYHCQQSTEDPWTFGGGTKLE
IKR//RTVAAPSVFIFPPSDEQLKSGTASVVCLLNNFYPREAKVQWKVDNALATPSRQSGNSQES
VTEQDSKDSTYSLSSTLTLSKADYEKHKVYACEVTHQGLSSPVTKSFNRGEC

SEQUENCE LISTING

```
<160> NUMBER OF SEQ ID NOS: 282

<210> SEQ ID NO 1
<211> LENGTH: 107
<212> TYPE: PRT
<213> ORGANISM: Homo sapiens

<400> SEQUENCE: 1

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

-continued

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 3
<211> LENGTH: 377
<212> TYPE: PRT
<213> ORGANISM: Homo sapiens

<400> SEQUENCE: 3

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175
```

Pro Lys Asp Thr Leu Met Ile Ser Arg Thr Pro Glu Val Thr Cys Val
180 185 190

Val Val Asp Val Ser His Glu Asp Pro Glu Val Gln Phe Lys Trp Tyr
195 200 205

Val Asp Gly Val Glu Val His Asn Ala Lys Thr Lys Pro Arg Glu Glu
210 215 220

Gln Tyr Asn Ser Thr Phe Arg Val Val Ser Val Leu Thr Val Leu His
225 230 235 240

Gln Asp Trp Leu Asn Gly Lys Glu Tyr Lys Cys Lys Val Ser Asn Lys
245 250 255

Ala Leu Pro Ala Pro Ile Glu Lys Thr Ile Ser Lys Thr Lys Gly Gln
260 265 270

Pro Arg Glu Pro Gln Val Tyr Thr Leu Pro Pro Ser Arg Glu Glu Met
275 280 285

Thr Lys Asn Gln Val Ser Leu Thr Cys Leu Val Lys Gly Phe Tyr Pro
290 295 300

Ser Asp Ile Ala Val Glu Trp Glu Ser Ser Gly Gln Pro Glu Asn Asn
305 310 315 320

Tyr Asn Thr Thr Pro Pro Met Leu Asp Ser Asp Gly Ser Phe Phe Leu
325 330 335

Tyr Ser Lys Leu Thr Val Asp Lys Ser Arg Trp Gln Gln Gly Asn Ile
340 345 350

Phe Ser Cys Ser Val Met His Glu Ala Leu His Asn Arg Phe Thr Gln
355 360 365

Lys Ser Leu Ser Leu Ser Pro Gly Lys
370 375

<210> SEQ ID NO 4
<211> LENGTH: 326
<212> TYPE: PRT
<213> ORGANISM: Homo sapiens

<400> SEQUENCE: 4

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn

-continued

```
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 5
<211> LENGTH: 326
<212> TYPE: PRT
<213> ORGANISM: Homo sapiens

<400> SEQUENCE: 5

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205
```

-continued

```
Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325


<210> SEQ ID NO 6
<211> LENGTH: 353
<212> TYPE: PRT
<213> ORGANISM: Homo sapiens

<400> SEQUENCE: 6

Ala Ser Pro Thr Ser Pro Lys Val Phe Pro Leu Ser Leu Cys Ser Thr
1               5                   10                  15

Gln Pro Asp Gly Asn Val Val Ile Ala Cys Leu Val Gln Gly Phe Phe
            20                  25                  30

Pro Gln Glu Pro Leu Ser Val Thr Trp Ser Glu Ser Gly Gln Gly Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Leu Ala Gly
65                  70                  75                  80

Lys Ser Val Thr Cys His Val Lys His Tyr Thr Asn Pro Ser Gln Asp
                85                  90                  95

Val Thr Val Pro Cys Pro Val Pro Ser Thr Pro Pro Thr Pro Ser Pro
            100                 105                 110

Ser Thr Pro Pro Thr Pro Ser Pro Ser Cys Cys His Pro Arg Leu Ser
        115                 120                 125

Leu His Arg Pro Ala Leu Glu Asp Leu Leu Leu Gly Ser Glu Ala Asn
    130                 135                 140

Leu Thr Cys Thr Leu Thr Gly Leu Arg Asp Ala Ser Gly Val Thr Phe
145                 150                 155                 160

Thr Trp Thr Pro Ser Ser Gly Lys Ser Ala Val Gln Gly Pro Pro Asp
                165                 170                 175

Arg Asp Leu Cys Gly Cys Tyr Ser Val Ser Ser Val Leu Ser Gly Cys
            180                 185                 190

Ala Glu Pro Trp Asn His Gly Lys Thr Phe Thr Cys Thr Ala Ala Tyr
        195                 200                 205

Pro Glu Ser Lys Thr Pro Leu Thr Ala Thr Leu Ser Lys Ser Gly Asn
    210                 215                 220

Thr Phe Arg Pro Glu Val His Leu Leu Pro Pro Pro Ser Glu Glu Leu
225                 230                 235                 240

Ala Leu Asn Glu Leu Val Thr Leu Thr Cys Leu Ala Arg Gly Phe Ser
                245                 250                 255
```

```
Pro Lys Asp Val Leu Val Arg Trp Leu Gln Gly Ser Gln Glu Leu Pro
            260                 265                 270

Arg Glu Lys Tyr Leu Thr Trp Ala Ser Arg Gln Glu Pro Ser Gln Gly
        275                 280                 285

Thr Thr Thr Phe Ala Val Thr Ser Ile Leu Arg Val Ala Ala Glu Asp
    290                 295                 300

Trp Lys Lys Gly Asp Thr Phe Ser Cys Met Val Gly His Glu Ala Leu
305                 310                 315                 320

Pro Leu Ala Phe Thr Gln Lys Thr Ile Asp Arg Leu Ala Gly Lys Pro
                325                 330                 335

Thr His Val Asn Val Ser Val Val Met Ala Glu Val Asp Gly Thr Cys
            340                 345                 350

Tyr


<210> SEQ ID NO 7
<211> LENGTH: 107
<212> TYPE: PRT
<213> ORGANISM: Homo sapiens

<400> SEQUENCE: 7

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 8
<211> LENGTH: 107
<212> TYPE: PRT
<213> ORGANISM: Mus musculus

<400> SEQUENCE: 8

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Gly Glu Cys
            100                 105
```

<210> SEQ ID NO 9
<211> LENGTH: 107
<212> TYPE: PRT
<213> ORGANISM: Rattus norvegicus

<400> SEQUENCE: 9

Arg Ala Asp Ala Ala Pro Thr Val Ser Ile Phe Pro Pro Ser Met Glu
1               5                   10                  15

Gln Leu Thr Ser Gly Gly Ala Thr Val Val Cys Phe Val Asn Asn Phe
            20                  25                  30

Tyr Pro Arg Asp Ile Ser Val Lys Trp Lys Ile Asp Gly Ser Glu Gln
        35                  40                  45

Arg Asp Gly Val Leu Asp Ser Val Thr Asp Gln Asp Ser Lys Asp Ser
    50                  55                  60

Thr Tyr Ser Met Ser Ser Thr Leu Ser Leu Thr Lys Val Glu Tyr Glu
65                  70                  75                  80

Arg His Asn Leu Tyr Thr Cys Glu Val Val His Lys Thr Ser Ser Ser
                85                  90                  95

Pro Val Val Lys Ser Phe Asn Arg Asn Glu Cys
            100                 105

<210> SEQ ID NO 10
<211> LENGTH: 105
<212> TYPE: PRT
<213> ORGANISM: Homo sapiens

<400> SEQUENCE: 10

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Lys Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 11
<211> LENGTH: 239
<212> TYPE: PRT
<213> ORGANISM: Artificial sequence
<220> FEATURE:
<223> OTHER INFORMATION: Synthetic polypeptide

<400> SEQUENCE: 11

Met Met Ser Ser Ala Gln Phe Leu Gly Leu Leu Leu Leu Cys Phe Gln
1               5                   10                  15

Gly Thr Arg Cys Asp Ile Leu Leu Thr Gln Thr Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Leu Asn Trp Tyr Gln Gln Ile Pro
    50                  55                  60

Gly Gln Pro Pro Lys Leu Leu Ile Tyr Asp Ala Ser Asn Leu Val Ser
65 70 75 80

Gly Ile Pro Pro Arg Phe Ser Gly Ser Gly Ser Gly Thr Asp Phe Thr
85 90 95

Leu Asn Ile His Pro Val Glu Lys Val Asp Ala Ala Thr Tyr His Cys
100 105 110

Gln Gln Ser Thr Glu Asp Pro Trp Thr Phe Gly Gly Gly Thr Lys Leu
115 120 125

Glu Ile Lys Arg Arg Thr Val Ala Ala Pro Ser Val Phe Ile Phe Pro
130 135 140

Pro Ser Asp Glu Gln Leu Lys Ser Gly Thr Ala Ser Val Val Cys Leu
145 150 155 160

Leu Asn Asn Phe Tyr Pro Arg Glu Ala Lys Val Gln Trp Lys Val Asp
165 170 175

Asn Ala Leu Gln Ser Gly Asn Ser Gln Glu Ser Val Thr Glu Gln Asp
180 185 190

Ser Lys Asp Ser Thr Tyr Ser Leu Ser Ser Thr Leu Thr Leu Ser Lys
195 200 205

Ala Asp Tyr Glu Lys His Lys Val Tyr Ala Cys Glu Val Thr His Gln
210 215 220

Gly Leu Ser Ser Pro Val Thr Lys Ser Phe Asn Arg Gly Glu Cys
225 230 235

<210> SEQ ID NO 12
<211> LENGTH: 481
<212> TYPE: PRT
<213> ORGANISM: Artificial sequence
<220> FEATURE:
<223> OTHER INFORMATION: Synthetic polypeptide

<400> SEQUENCE: 12

Met Asn Phe Gly Leu Ser Leu Ile Phe Leu Val Leu Val Leu Lys Gly
1 5 10 15

Val Gln Cys Gln Val Gln Leu Gln Gln Ser Gly Ala Glu Leu Val Arg
20 25 30

Pro Gly Ser Ser Val Lys Ile Ser Cys Lys Ala Ser Gly Tyr Ala Phe
35 40 45

Ser Ser Tyr Trp Met Asn Trp Val Lys Gln Arg Pro Gly Gln Gly Leu
50 55 60

Glu Trp Ile Gly Gln Ile Trp Pro Gly Asp Gly Asp Thr Asn Tyr Asn
65 70 75 80

Gly Lys Phe Lys Gly Lys Ala Thr Leu Thr Ala Asp Glu Ser Ser Ser
85 90 95

Thr Ala Tyr Met Gln Leu Ser Ser Leu Ala Ser Glu Asp Ser Ala Val
100 105 110

Tyr Phe Cys Ala Arg Arg Glu Thr Thr Thr Val Gly Arg Tyr Tyr Tyr
115 120 125

Ala Met Asp Tyr Trp Gly Gln Gly Thr Ser Val Thr Val Ser Ser Ala
130 135 140

Ser Thr Lys Gly Pro Ser Val Phe Pro Leu Ala Pro Ser Ser Lys Ser
145 150 155 160

Thr Ser Gly Gly Thr Ala Ala Leu Gly Cys Leu Val Lys Asp Tyr Phe
165 170 175

Pro Glu Pro Val Thr Val Ser Trp Asn Ser Gly Ala Leu Thr Ser Gly
180 185 190

```
Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Ser Leu Cys Thr Pro Ser Arg Gly
465                 470                 475                 480

Ser
```

<210> SEQ ID NO 13
<211> LENGTH: 1398
<212> TYPE: DNA
<213> ORGANISM: Artificial sequence
<220> FEATURE:
<223> OTHER INFORMATION: Synthetic polynucleotide

<400> SEQUENCE: 13

```
atgaacttcg ggctcagctt gattttcctt gtccttgttt taaaaggtgt ccagtgtcag     60

gtccagctgc aggagtcagg ggctgaactg tcaaaacctg gggcctcagt gaagatgtcc    120

tgcaaggctt ctggctacac ctttactagc tactggctgc actggataaa acagaggcct    180

ggacagggtc tggaatggat tggatacatt aatcctagga atgattatac tgagtacaat    240

cagaacttca aggacaaggc cacattgact gcagacaaat cctccagcac agcctacatg    300

caactgagca gcctgacatc tgaggactct gcagtctatt actgtgcaag aagggatatt    360
```

```
actacgttct actggggcca aggcaccact ctcacagtct cctcggctag caccaagggc    420

ccatcggtct tccccctggc accctcctcc aagagcacct ctgggggcac agcggccctg    480

ggctgcctgg tcaaggacta cttccccgaa ccggtgacgg tgtcgtggaa ctcaggcgcc    540

ctgaccagcg gcgtgcacac cttcccggct gtcctacagt cctcaggact ctactccctc    600

agcagcgtgg tgaccgtgcc ctccagcagc ttgggcaccc agacctacat ctgcaacgtg    660

aatcacaagc ccagcaacac caaggtggac aagaaagttg agcccaaatc ttgtgacaaa    720

actcacacat gcccaccgtg cccagcacct gaactcctgg ggggaccgtc agtcttcctc    780

ttccccccaa aacccaagga caccctcatg atctcccgga cccctgaggt cacatgcgtg    840

gtggtggacg tgagccacga agaccctgag gtcaagttca actggtacgt ggacggcgtg    900

gaggtgcata atgccaagac aaagccgcgg gaggagcagt acaacagcac gtaccgtgtg    960

gtcagcgtcc tcaccgtcct gcaccaggac tggctgaatg gcaaggagta caagtgcaag   1020

gtctccaaca aagccctccc agcccccatc gagaaaacca tctccaaagc caaagggcag   1080

ccccgagaac cacaggtgta caccctgccc ccatcccggg aggagatgac caagaaccag   1140

gtcagcctga cctgcctggt caaaggcttc tatcccagcg acatcgccgt ggagtgggag   1200

agcaatgggc agccggagaa caactacaag accacgcctc ccgtgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gtaaatga                                                 1398

<210> SEQ ID NO 14
<211> LENGTH: 465
<212> TYPE: PRT
<213> ORGANISM: Artificial sequence
<220> FEATURE:
<223> OTHER INFORMATION: Synthetic polypeptide

<400> SEQUENCE: 14

Met Asn Phe Gly Leu Ser Leu Ile Phe Leu Val Leu Val Leu Lys Gly
 1               5                  10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175
```

-continued

```
Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 15
<211> LENGTH: 1410
<212> TYPE: DNA
<213> ORGANISM: Artificial sequence
<220> FEATURE:
<223> OTHER INFORMATION: Synthetic polynucleotide

<400> SEQUENCE: 15

atgaacttcg ggctcagctt gattttcctt gtccttgttt taaaaggtgt ccagtgtcag     60

gtccagctgc aggagtcagg ggctgaactg tcaaaacctg gggcctcagt gaagatgtcc    120

tgcaaggctt ctggctacac ctttactagc tactggctgc actggataaa acagaggcct    180

ggacagggtc tggaatggat tggatacatt aatcctagga atgattatac tgagtacaat    240

cagaacttca aggacaaggc cacattgact gcagacaaat cctccagcac agcctacatg    300

caactgagca gcctgacatc tgaggactct gcagtctatt actgtgcaag aagggatatt    360
```

-continued

```
actacgttct actggggcca aggcaccact ctcacagtct cctcggctag caccaagggc    420

ctgtgtaccc cttctagagt cttccccctg gcaccctcct ccaagagcac ctctgggggc    480

acagcggccc tgggctgcct ggtcaaggac tacttccccg aaccggtgac ggtgtcgtgg    540

aactcaggcg ccctgaccag cggcgtgcac accttcccgg ctgtcctaca gtcctcagga    600

ctctactccc tcagcagcgt ggtgaccgtg ccctccagca gcttgggcac ccagacctac    660

atctgcaacg tgaatcacaa gcccagcaac accaaggtgg acaagaaagt tgagcccaaa    720

tcttgtgaca aaactcacac atgcccaccg tgcccagcac ctgaactcct ggggggaccg    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagccgc gggaggagca gtacaacagc    960

acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggaggagatg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260

gactccgacg gctccttctt cctctacagc aagctcaccg tggacaagag caggtggcag   1320

caggggaacg tcttctcatg ctccgtgatg catgaggctc tgcacaacca ctacacgcag   1380

aagagcctct ccctgtctcc gggtaaatga                                    1410
```

<210> SEQ ID NO 16
<211> LENGTH: 469
<212> TYPE: PRT
<213> ORGANISM: Artificial sequence
<220> FEATURE:
<223> OTHER INFORMATION: Synthetic polypeptide

<400> SEQUENCE: 16

```
Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Leu Cys Thr Pro
    130                 135                 140

Ser Arg Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175
```

Thr Val Ser Trp Asn Ser Gly Ala Leu Thr Ser Gly Val His Thr Phe
180 185 190

Pro Ala Val Leu Gln Ser Ser Gly Leu Tyr Ser Leu Ser Ser Val Val
195 200 205

Thr Val Pro Ser Ser Ser Leu Gly Thr Gln Thr Tyr Ile Cys Asn Val
210 215 220

Asn His Lys Pro Ser Asn Thr Lys Val Asp Lys Lys Val Glu Pro Lys
225 230 235 240

Ser Cys Asp Lys Thr His Thr Cys Pro Pro Cys Pro Ala Pro Glu Leu
245 250 255

Leu Gly Gly Pro Ser Val Phe Leu Phe Pro Pro Lys Pro Lys Asp Thr
260 265 270

Leu Met Ile Ser Arg Thr Pro Glu Val Thr Cys Val Val Val Asp Val
275 280 285

Ser His Glu Asp Pro Glu Val Lys Phe Asn Trp Tyr Val Asp Gly Val
290 295 300

Glu Val His Asn Ala Lys Thr Lys Pro Arg Glu Glu Gln Tyr Asn Ser
305 310 315 320

Thr Tyr Arg Val Val Ser Val Leu Thr Val Leu His Gln Asp Trp Leu
325 330 335

Asn Gly Lys Glu Tyr Lys Cys Lys Val Ser Asn Lys Ala Leu Pro Ala
340 345 350

Pro Ile Glu Lys Thr Ile Ser Lys Ala Lys Gly Gln Pro Arg Glu Pro
355 360 365

Gln Val Tyr Thr Leu Pro Pro Ser Arg Glu Glu Met Thr Lys Asn Gln
370 375 380

Val Ser Leu Thr Cys Leu Val Lys Gly Phe Tyr Pro Ser Asp Ile Ala
385 390 395 400

Val Glu Trp Glu Ser Asn Gly Gln Pro Glu Asn Asn Tyr Lys Thr Thr
405 410 415

Pro Pro Val Leu Asp Ser Asp Gly Ser Phe Phe Leu Tyr Ser Lys Leu
420 425 430

Thr Val Asp Lys Ser Arg Trp Gln Gln Gly Asn Val Phe Ser Cys Ser
435 440 445

Val Met His Glu Ala Leu His Asn His Tyr Thr Gln Lys Ser Leu Ser
450 455 460

Leu Ser Pro Gly Lys
465

<210> SEQ ID NO 17
<211> LENGTH: 6
<212> TYPE: PRT
<213> ORGANISM: Artificial sequence
<220> FEATURE:
<223> OTHER INFORMATION: Synthetic peptide

<400> SEQUENCE: 17

Leu Cys Thr Pro Ser Arg
1 5

<210> SEQ ID NO 18
<211> LENGTH: 1404
<212> TYPE: DNA
<213> ORGANISM: Artificial sequence
<220> FEATURE:
<223> OTHER INFORMATION: Synthetic polynucleotide

<400> SEQUENCE: 18

```
atgaacttcg ggctcagctt gattttcctt gtccttgttt taaaaggtgt ccagtgtcag     60

gtccagctgc aggagtcagg ggctgaactg tcaaaacctg gggcctcagt gaagatgtcc    120

tgcaaggctt ctggctacac ctttactagc tactggctgc actggataaa acagaggcct    180

ggacagggtc tggaatggat tggatacatt aatcctagga atgattatac tgagtacaat    240

cagaacttca aggacaaggc cacattgact gcagacaaat cctccagcac agcctacatg    300

caactgagca gcctgacatc tgaggactct gcagtctatt actgtgcaag aagggatatt    360

actacgttct actggggcca aggcaccact ctcacagtct cctcggctag caccaagggc    420

ccatcggtct tccccctgtg taccccttct agatccaaga gcacctctgg gggcacagcg    480

gccctgggct gcctggtcaa ggactacttc cccgaaccgg tgacggtgtc gtggaactca    540

ggcgccctga ccagcggcgt gcacaccttc ccggctgtcc tacagtcctc aggactctac    600

tccctcagca gcgtggtgac cgtgccctcc agcagcttgg gcacccagac ctacatctgc    660

aacgtgaatc acaagcccag caacaccaag gtggacaaga aagttgagcc caaatcttgt    720

gacaaaactc acacatgccc accgtgccca gcacctgaac tcctgggggg accgtcagtc    780

ttcctcttcc ccccaaaacc caaggacacc ctcatgatct cccggacccc tgaggtcaca    840

tgcgtggtgg tggacgtgag ccacgaagac cctgaggtca agttcaactg gtacgtggac    900

ggcgtggagg tgcataatgc caagacaaag ccgcgggagg agcagtacaa cagcacgtac    960

cgtgtggtca gcgtcctcac cgtcctgcac caggactggc tgaatggcaa ggagtacaag   1020

tgcaaggtct ccaacaaagc cctcccagcc cccatcgaga aaaccatctc caaagccaaa   1080

gggcagcccc gagaaccaca ggtgtacacc ctgcccccat cccgggagga gatgaccaag   1140

aaccaggtca gcctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcta cagcaagctc accgtggaca agagcaggtg gcagcagggg   1320

aacgtcttct catgctccgt gatgcatgag gctctgcaca accactacac gcagaagagc   1380

ctctccctgt ctccgggtaa atga                                          1404
```

<210> SEQ ID NO 19
<211> LENGTH: 467
<212> TYPE: PRT
<213> ORGANISM: Artificial sequence
<220> FEATURE:
<223> OTHER INFORMATION: Synthetic polypeptide

<400> SEQUENCE: 19

```
Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110
```

```
Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Cys Thr Pro Ser Arg Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465
```

<210> SEQ ID NO 20
<211> LENGTH: 1407
<212> TYPE: DNA
<213> ORGANISM: Artificial sequence
<220> FEATURE:
<223> OTHER INFORMATION: Synthetic polynucleotide

<400> SEQUENCE: 20

-continued

```
atgaacttcg ggctcagctt gattttcctt gtccttgttt taaaaggtgt ccagtgtcag      60
gtccagctgc aggagtcagg ggctgaactg tcaaaacctg gggcctcagt gaagatgtcc     120
tgcaaggctt ctggctacac ctttactagc tactggctgc actggataaa acagaggcct     180
ggacagggtc tggaatggat tggatacatt aatcctagga atgattatac tgagtacaat     240
cagaacttca aggacaaggc cacattgact gcagacaaat cctccagcac agcctacatg     300
caactgagca gcctgacatc tgaggactct gcagtctatt actgtgcaag aagggatatt     360
actacgttct actggggcca aggcaccact ctcacagtct cctcggctag caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgtgtaccc cttctagagg cgtgcacacc ttcccggctg tcctacagtc ctcaggactc     600
tactccctca gcagcgtggt gaccgtgccc tccagcagct tgggcaccca gacctacatc     660
tgcaacgtga atcacaagcc cagcaacacc aaggtggaca agaaagttga gcccaaatct     720
tgtgacaaaa ctcacacatg cccaccgtgc ccagcacctg aactcctggg gggaccgtca     780
gtcttcctct tccccccaaa acccaaggac accctcatga tctcccggac ccctgaggtc     840
acatgcgtgg tggtggacgt gagccacgaa gaccctgagg tcaagttcaa ctggtacgtg     900
gacggcgtgg aggtgcataa tgccaagaca aagccgcggg aggagcagta caacagcacg     960
taccgtgtgg tcagcgtcct caccgtcctg caccaggact ggctgaatgg caaggagtac    1020
aagtgcaagg tctccaacaa agccctccca gcccccatcg agaaaaccat ctccaaagcc    1080
aaagggcagc cccgagaacc acaggtgtac accctgcccc catcccggga ggagatgacc    1140
aagaaccagg tcagcctgac ctgcctggtc aaaggcttct atcccagcga catcgccgtg    1200
gagtgggaga gcaatgggca gccggagaac aactacaaga ccacgcctcc cgtgctggac    1260
tccgacggct ccttcttcct ctacagcaag ctcaccgtgg acaagagcag gtggcagcag    1320
gggaacgtct tctcatgctc cgtgatgcat gaggctctgc acaaccacta cacgcagaag    1380
agcctctccc tgtctccggg taaatga                                        1407
```

<210> SEQ ID NO 21
<211> LENGTH: 468
<212> TYPE: PRT
<213> ORGANISM: Artificial sequence
<220> FEATURE:
<223> OTHER INFORMATION: Synthetic polypeptide

<400> SEQUENCE: 21

```
Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110
```

```
Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Cys Thr Pro Ser Arg Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465
```

<210> SEQ ID NO 22
<211> LENGTH: 1407
<212> TYPE: DNA
<213> ORGANISM: Artificial sequence
<220> FEATURE:
<223> OTHER INFORMATION: Synthetic polynucleotide

<400> SEQUENCE: 22

```
atgaacttcg ggctcagctt gattttcctt gtccttgttt taaaaggtgt ccagtgtcag     60
gtccagctgc aggagtcagg ggctgaactg tcaaaacctg gggcctcagt gaagatgtcc    120
tgcaaggctt ctggctacac ctttactagc tactggctgc actggataaa acagaggcct    180
ggacagggtc tggaatggat tggatacatt aatcctagga atgattatac tgagtacaat    240
cagaacttca aggacaaggc cacattgact gcagacaaat cctccagcac agcctacatg    300
caactgagca gcctgacatc tgaggactct gcagtctatt actgtgcaag aagggatatt    360
actacgttct actggggcca aggcaccact ctcacagtct cctcggctag caccaagggc    420
ccatcggtct tccccctggc accctcctcc aagagcacct ctgggggcac agcggccctg    480
ggctgcctgg tcaaggacta cttccccgaa ccggtgacgg tgtcgtggaa ctcaggcgcc    540
ctggctaccc cttctagagg cgtgcacacc ttcccggctg tcctacagtc ctcaggactc    600
tactccctca gcagcgtggt gaccgtgccc tccagcagct tgggcaccca gacctacatc    660
tgcaacgtga atcacaagcc cagcaacacc aaggtggaca agaaagttga gcccaaatct    720
tgtgacaaaa ctcacacatg cccaccgtgc ccagcacctg aactcctggg gggaccgtca    780
gtcttcctct tccccccaaa acccaaggac accctcatga tctcccggac ccctgaggtc    840
acatgcgtgg tggtggacgt gagccacgaa gaccctgagg tcaagttcaa ctggtacgtg    900
gacggcgtgg aggtgcataa tgccaagaca aagccgcggg aggagcagta caacagcacg    960
taccgtgtgg tcagcgtcct caccgtcctg caccaggact ggctgaatgg caaggagtac   1020
aagtgcaagg tctccaacaa agccctccca gcccccatcg agaaaaccat ctccaaagcc   1080
aaagggcagc cccgagaacc acaggtgtac accctgcccc catcccggga ggagatgacc   1140
aagaaccagg tcagcctgac ctgcctggtc aaaggcttct atcccagcga catcgccgtg   1200
gagtgggaga gcaatgggca gccggagaac aactacaaga ccacgcctcc cgtgctggac   1260
tccgacggct ccttcttcct ctacagcaag ctcaccgtgg acaagagcag gtggcagcag   1320
gggaacgtct tctcatgctc cgtgatgcat gaggctctgc acaaccacta cacgcagaag   1380
agcctctccc tgtctccggg taaatga                                       1407
```

```
<210> SEQ ID NO 23
<211> LENGTH: 468
<212> TYPE: PRT
<213> ORGANISM: Artificial sequence
<220> FEATURE:
<223> OTHER INFORMATION: Synthetic polypeptide

<400> SEQUENCE: 23

Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110
```

```
Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Ala Thr Pro Ser Arg Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Lys Val Glu Pro Lys Ser
225                 230                 235                 240

Cys Asp Lys Thr His Thr Cys Pro Pro Cys Pro Ala Pro Glu Leu Leu
                245                 250                 255

Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
        275                 280                 285

His Glu Asp Pro Glu Val Lys Phe Asn Trp Tyr Val Asp Gly Val Glu
    290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460

Ser Pro Gly Lys
465
```

<210> SEQ ID NO 24
<211> LENGTH: 6
<212> TYPE: PRT
<213> ORGANISM: Artificial sequence
<220> FEATURE:
<223> OTHER INFORMATION: Synthetic peptide

<400> SEQUENCE: 24

```
Leu Ala Thr Pro Ser Arg
1               5


<210> SEQ ID NO 25
<211> LENGTH: 1410
<212> TYPE: DNA
<213> ORGANISM: Artificial sequence
<220> FEATURE:
<223> OTHER INFORMATION: Synthetic polynucleotide

<400> SEQUENCE: 25

atgaacttcg ggctcagctt gattttcctt gtccttgttt taaaaggtgt ccagtgtcag     60

gtccagctgc aggagtcagg ggctgaactg tcaaaacctg gggcctcagt gaagatgtcc    120

tgcaaggctt ctggctacac ctttactagc tactggctgc actggataaa acagaggcct    180

ggacagggtc tggaatggat tggatacatt aatcctagga atgattatac tgagtacaat    240

cagaacttca aggacaaggc cacattgact gcagacaaat cctccagcac agcctacatg    300

caactgagca gcctgacatc tgaggactct gcagtctatt actgtgcaag aagggatatt    360

actacgttct actggggcca aggcaccact ctcacagtct cctcggctag caccaagggc    420

ccatcggtct tccccctggc accctcctcc aagagcacct ctgggggcac agcggccctg    480

ggctgcctgg tcaaggacta cttccccgaa ccggtgacgg tgtcgtggaa ctcaggcgcc    540

ctgaccagcg gcgtgcacac cttcccggct gtcctacagt cctcaggact ctactccctc    600

agcagcgtgg tgaccgtgcc ctccagcagc ttgggcaccc agacctacat ctgcaacgtg    660

aatcacaagc ccagcaacac caaggtggac aagaaagttg agcccaaatc ttgtgacaaa    720

actcacacat gcccaccgtg cccactgtgt accccttcta gagaactcct gggggggaccg    780

tcagtcttcc tcttcccccc aaaacccaag gacaccctca tgatctcccg gacccctgag    840

gtcacatgcg tggtggtgga cgtgagccac gaagaccctg aggtcaagtt caactggtac    900

gtggacggcg tggaggtgca taatgccaag acaaagccgc gggaggagca gtacaacagc    960

acgtaccgtg tggtcagcgt cctcaccgtc ctgcaccagg actggctgaa tggcaaggag   1020

tacaagtgca aggtctccaa caaagccctc ccagccccca tcgagaaaac catctccaaa   1080

gccaaagggc agccccgaga accacaggtg tacaccctgc ccccatcccg ggaggagatg   1140

accaagaacc aggtcagcct gacctgcctg gtcaaaggct tctatcccag cgacatcgcc   1200

gtggagtggg agagcaatgg gcagccggag aacaactaca agaccacgcc tcccgtgctg   1260

gactccgacg gctccttctt cctctacagc aagctcaccg tggacaagag caggtggcag   1320

caggggaacg tcttctcatg ctccgtgatg catgaggctc tgcacaacca ctacacgcag   1380

aagagcctct ccctgtctcc gggtaaatga                                    1410


<210> SEQ ID NO 26
<211> LENGTH: 469
<212> TYPE: PRT
<213> ORGANISM: Artificial sequence
<220> FEATURE:
<223> OTHER INFORMATION: Synthetic polypeptide

<400> SEQUENCE: 26

Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
```

```
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Leu Cys Thr Pro Ser Arg Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460
```

Leu Ser Pro Gly Lys
465

<210> SEQ ID NO 27
<211> LENGTH: 1413
<212> TYPE: DNA
<213> ORGANISM: Artificial sequence
<220> FEATURE:
<223> OTHER INFORMATION: Synthetic polynucleotide

<400> SEQUENCE: 27

```
atgaacttcg ggctcagctt gattttcctt gtccttgttt taaaaggtgt ccagtgtcag     60

gtccagctgc aggagtcagg ggctgaactg tcaaaacctg gggcctcagt gaagatgtcc    120

tgcaaggctt ctggctacac ctttactagc tactggctgc actggataaa acagaggcct    180

ggacagggtc tggaatggat tggatacatt aatcctagga atgattatac tgagtacaat    240

cagaacttca aggacaaggc cacattgact gcagacaaat cctccagcac agcctacatg    300

caactgagca gcctgacatc tgaggactct gcagtctatt actgtgcaag aagggatatt    360

actacgttct actggggcca aggcaccact ctcacagtct cctcggctag caccaagggc    420

ccatcggtct tccccctggc accctcctcc aagagcacct ctgggggcac agcggccctg    480

ggctgcctgg tcaaggacta cttccccgaa ccggtgacgg tgtcgtggaa ctcaggcgcc    540

ctgaccagcg gcgtgcacac cttcccggct gtcctacagt cctcaggact ctactccctc    600

agcagcgtgg tgaccgtgcc ctccagcagc ttgggcaccc agacctacat ctgcaacgtg    660

aatcacaagc ccagcaacac caaggtggac aagaaagttg agcccaaatc ttgtgacaaa    720

actcacacat gcccaccgtg cccagcacct gaactcctgg ggggaccgtc agtcttcctc    780

ttccccccaa aacccaagga caccctcatg atctcccgga cccctgaggt cacatgcgtg    840

gtggtggacg tgagccacga agacctgtgt accccttcta gagaggtcaa gttcaactgg    900

tacgtggacg gcgtggaggt gcataatgcc aagacaaagc cgcgggagga gcagtacaac    960

agcacgtacc gtgtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag ggcagccccg agaaccacag gtgtacaccc tgcccccatc ccgggaggag   1140

atgaccaaga accaggtcag cctgacctgc ctggtcaaag gcttctatcc cagcgacatc   1200

gccgtggagt gggagagcaa tgggcagccg gagaacaact acaagaccac gcctcccgtg   1260

ctggactccg acggctcctt cttcctctac agcaagctca ccgtggacaa gagcaggtgg   1320

cagcagggga acgtcttctc atgctccgtg atgcatgagg ctctgcacaa ccactacacg   1380

cagaagagcc tctccctgtc tccgggtaaa tga                                1413
```

<210> SEQ ID NO 28
<211> LENGTH: 470
<212> TYPE: PRT
<213> ORGANISM: Artificial sequence
<220> FEATURE:
<223> OTHER INFORMATION: Synthetic polypeptide

<400> SEQUENCE: 28

```
Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
```

```
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Leu Cys Thr Pro Ser Arg Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460
```

```
Ser Leu Ser Pro Gly Lys
465                 470


<210> SEQ ID NO 29
<211> LENGTH: 1404
<212> TYPE: DNA
<213> ORGANISM: Artificial sequence
<220> FEATURE:
<223> OTHER INFORMATION: Synthetic polynucleotide

<400> SEQUENCE: 29

atgaacttcg ggctcagctt gattttcctt gtccttgttt taaaaggtgt ccagtgtcag     60

gtccagctgc aggagtcagg ggctgaactg tcaaaacctg gggcctcagt gaagatgtcc    120

tgcaaggctt ctggctacac ctttactagc tactggctgc actggataaa acagaggcct    180

ggacagggtc tggaatggat tggatacatt aatcctagga atgattatac tgagtacaat    240

cagaacttca aggacaaggc cacattgact gcagacaaat cctccagcac agcctacatg    300

caactgagca gcctgacatc tgaggactct gcagtctatt actgtgcaag aagggatatt    360

actacgttct actggggcca aggcaccact ctcacagtct cctcggctag caccaagggc    420

ccatcggtct tccccctggc accctcctcc aagagcacct ctgggggcac agcggccctg    480

ggctgcctgg tcaaggacta cttccccgaa ccggtgacgg tgtcgtggaa ctcaggcgcc    540

ctgaccagcg gcgtgcacac cttcccggct gtcctacagt cctcaggact ctactccctc    600

agcagcgtgg tgaccgtgcc ctccagcagc ttgggcaccc agacctacat ctgcaacgtg    660

aatcacaagc ccagcaacac caaggtggac aagaaagttg agcccaaatc ttgtgacaaa    720

actcacacat gcccaccgtg cccagcacct gaactcctgg ggggaccgtc agtcttcctc    780

ttccccccaa aacccaagga caccctcatg atctcccgga cccctgaggt cacatgcgtg    840

gtggtggacg tgagccacga agaccctgag gtcaagttca actggtacgt ggacggcgtg    900

gaggtgcata atgccaagac aaagccgcgg gaggagcagt acaacagcac gtaccgtgtg    960

gtcagcgtcc tcaccgtcct gcaccaggac tggctgaatg gcaaggagta caagtgcaag   1020

gtctccaact tatgtacccc ttctagagcc cccatcgaga aaaccatctc caaagccaaa   1080

gggcagcccc gagaaccaca ggtgtacacc ctgcccccat cccgggagga gatgaccaag   1140

aaccaggtca gcctgacctg cctggtcaaa ggcttctatc ccagcgacat cgccgtggag   1200

tgggagagca atgggcagcc ggagaacaac tacaagacca cgcctcccgt gctggactcc   1260

gacggctcct tcttcctcta cagcaagctc accgtggaca agagcaggtg gcagcagggg   1320

aacgtcttct catgctccgt gatgcatgag gctctgcaca accactacac gcagaagagc   1380

ctctccctgt ctccgggtaa atga                                          1404


<210> SEQ ID NO 30
<211> LENGTH: 467
<212> TYPE: PRT
<213> ORGANISM: Artificial sequence
<220> FEATURE:
<223> OTHER INFORMATION: Synthetic polypeptide

<400> SEQUENCE: 30

Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
```

-continued

```
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Leu Cys Thr Pro Ser Arg Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460
```

Pro Gly Lys
465

<210> SEQ ID NO 31
<211> LENGTH: 1404
<212> TYPE: DNA
<213> ORGANISM: Artificial sequence
<220> FEATURE:
<223> OTHER INFORMATION: Synthetic polynucleotide

<400> SEQUENCE: 31

```
atgaacttcg ggctcagctt gattttcctt gtccttgttt taaaaggtgt ccagtgtcag      60
gtccagctgc aggagtcagg ggctgaactg tcaaaacctg gggcctcagt gaagatgtcc     120
tgcaaggctt ctggctacac ctttactagc tactggctgc actggataaa acagaggcct     180
ggacagggtc tggaatggat tggatacatt aatcctagga atgattatac tgagtacaat     240
cagaacttca aggacaaggc cacattgact gcagacaaat cctccagcac agcctacatg     300
caactgagca gcctgacatc tgaggactct gcagtctatt actgtgcaag aagggatatt     360
actacgttct actggggcca aggcaccact ctcacagtct cctcggctag caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggct gtcctacagt cctcaggact ctactccctc     600
agcagcgtgg tgaccgtgcc ctccagcagc ttgggcaccc agacctacat ctgcaacgtg     660
aatcacaagc ccagcaacac caaggtggac aagaaagttg agcccaaatc ttgtgacaaa     720
actcacacat gcccaccgtg cccagcacct gaactcctgg ggggaccgtc agtcttcctc     780
ttccccccaa aacccaagga caccctcatg atctcccgga cccctgaggt cacatgcgtg     840
gtggtggacg tgagccacga agaccctgag gtcaagttca actggtacgt ggacggcgtg     900
gaggtgcata atgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaact tagctacccc ttctagagcc cccatcgaga aaaccatctc caaagccaaa    1080
gggcagcccc gagaaccaca ggtgtacacc ctgcccccat cccgggagga gatgaccaag    1140
aaccaggtca gcctgacctg cctggtcaaa ggcttctatc ccagcgacat cgccgtggag    1200
tgggagagca atgggcagcc ggagaacaac tacaagacca cgcctcccgt gctggactcc    1260
gacggctcct tcttcctcta cagcaagctc accgtggaca agagcaggtg gcagcagggg    1320
aacgtcttct catgctccgt gatgcatgag gctctgcaca accactacac gcagaagagc    1380
ctctccctgt ctccgggtaa atga                                           1404
```

<210> SEQ ID NO 32
<211> LENGTH: 467
<212> TYPE: PRT
<213> ORGANISM: Artificial sequence
<220> FEATURE:
<223> OTHER INFORMATION: Synthetic peptide

<400> SEQUENCE: 32

```
Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
```

```
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Leu Ala Thr Pro Ser Arg Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460
```

Pro Gly Lys
465

<210> SEQ ID NO 33
<211> LENGTH: 1407
<212> TYPE: DNA
<213> ORGANISM: Artificial sequence
<220> FEATURE:
<223> OTHER INFORMATION: Synthetic polynucleotide

<400> SEQUENCE: 33
atgaacttcg ggctcagctt gattttcctt gtccttgttt taaaaggtgt ccagtgtcag 60
gtccagctgc aggagtcagg ggctgaactg tcaaaacctg gggcctcagt gaagatgtcc 120
tgcaaggctt ctggctacac ctttactagc tactggctgc actggataaa acagaggcct 180
ggacagggtc tggaatggat tggatacatt aatcctagga atgattatac tgagtacaat 240
cagaacttca aggacaaggc cacattgact gcagacaaat cctccagcac agcctacatg 300
caactgagca gcctgacatc tgaggactct gcagtctatt actgtgcaag aagggatatt 360
actacgttct actggggcca aggcaccact ctcacagtct cctcggctag caccaagggc 420
ccatcggtct tccccctggc accctcctcc aagagcacct ctgggggcac agcggccctg 480
ggctgcctgg tcaaggacta cttccccgaa ccggtgacgg tgtcgtggaa ctcaggcgcc 540
ctgaccagcg gcgtgcacac cttcccggct gtcctacagt cctcaggact ctactccctc 600
agcagcgtgg tgaccgtgcc ctccagcagc ttgggcaccc agacctacat ctgcaacgtg 660
aatcacaagc ccagcaacac caaggtggac aagaaagttg agcccaaatc ttgtgacaaa 720
actcacacat gcccaccgtg cccagcacct gaactcctgg ggggaccgtc agtcttcctc 780
ttccccccaa aacccaagga caccctcatg atctcccgga cccctgaggt cacatgcgtg 840
gtggtggacg tgagccacga agaccctgag gtcaagttca actggtacgt ggacggcgtg 900
gaggtgcata atgccaagac aaagccgcgg gaggagcagt acaacagcac gtaccgtgtg 960
gtcagcgtcc tcaccgtcct gcaccaggac tggctgaatg gcaaggagta caagtgcaag 1020
gtctccaaca aagccctccc agcccccatc gagaaaacca tctccaaagc caaagggtta 1080
tgtacccctt ctcgagaacc acaggtgtac accctgcccc catcccggga ggagatgacc 1140
aagaaccagg tcagcctgac ctgcctggtc aaaggcttct atcccagcga catcgccgtg 1200
gagtgggaga gcaatgggca gccggagaac aactacaaga ccacgcctcc cgtgctggac 1260
tccgacggct ccttcttcct ctacagcaag ctcaccgtgg acaagagcag gtggcagcag 1320
gggaacgtct tctcatgctc cgtgatgcat gaggctctgc acaaccacta cacgcagaag 1380
agcctctccc tgtctccggg taaatga 1407

<210> SEQ ID NO 34
<211> LENGTH: 468
<212> TYPE: PRT
<213> ORGANISM: Artificial sequence
<220> FEATURE:
<223> OTHER INFORMATION: Synthetic polypeptide

<400> SEQUENCE: 34

Met Asn Phe Gly Leu Ser Leu Ile Phe Leu Val Leu Val Leu Lys Gly
1 5 10 15

Val Gln Cys Gln Val Gln Leu Gln Glu Ser Gly Ala Glu Leu Ser Lys
20 25 30

Pro Gly Ala Ser Val Lys Met Ser Cys Lys Ala Ser Gly Tyr Thr Phe

-continued

```
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Leu Cys Thr Pro Ser Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460
```

Ser Pro Gly Lys
465

<210> SEQ ID NO 35
<211> LENGTH: 1407
<212> TYPE: DNA
<213> ORGANISM: Artificial sequence
<220> FEATURE:
<223> OTHER INFORMATION: Synthetic polynucleotide

<400> SEQUENCE: 35
atgaacttcg ggctcagctt gattttcctt gtccttgttt taaaaggtgt ccagtgtcag 60
gtccagctgc aggagtcagg ggctgaactg tcaaaacctg gggcctcagt gaagatgtcc 120
tgcaaggctt ctggctacac ctttactagc tactggctgc actggataaa acagaggcct 180
ggacagggtc tggaatggat tggatacatt aatcctagga atgattatac tgagtacaat 240
cagaacttca aggacaaggc cacattgact gcagacaaat cctccagcac agcctacatg 300
caactgagca gcctgacatc tgaggactct gcagtctatt actgtgcaag aagggatatt 360
actacgttct actggggcca aggcaccact ctcacagtct cctcggctag caccaagggc 420
ccatcggtct tccccctggc accctcctcc aagagcacct ctgggggcac agcggccctg 480
ggctgcctgg tcaaggacta cttccccgaa ccggtgacgg tgtcgtggaa ctcaggcgcc 540
ctgaccagcg gcgtgcacac cttcccggct gtcctacagt cctcaggact ctactccctc 600
agcagcgtgg tgaccgtgcc ctccagcagc ttgggcaccc agacctacat ctgcaacgtg 660
aatcacaagc ccagcaacac caaggtggac aagaaagttg agcccaaatc ttgtgacaaa 720
actcacacat gcccaccgtg cccagcacct gaactcctgg ggggaccgtc agtcttcctc 780
ttccccccaa aacccaagga caccctcatg atctcccgga cccctgaggt cacatgcgtg 840
gtggtggacg tgagccacga agaccctgag gtcaagttca actggtacgt ggacggcgtg 900
gaggtgcata atgccaagac aaagccgcgg gaggagcagt acaacagcac gtaccgtgtg 960
gtcagcgtcc tcaccgtcct gcaccaggac tggctgaatg gcaaggagta caagtgcaag 1020
gtctccaaca aagccctccc agcccccatc gagaaaacca tctccaaagc caaagggtta 1080
gctacccctt ctcgagaacc acaggtgtac accctgcccc catcccggga ggagatgacc 1140
aagaaccagg tcagcctgac ctgcctggtc aaaggcttct atcccagcga catcgccgtg 1200
gagtgggaga gcaatgggca gccggagaac aactacaaga ccacgcctcc cgtgctggac 1260
tccgacggct ccttcttcct ctacagcaag ctcaccgtgg acaagagcag gtggcagcag 1320
gggaacgtct tctcatgctc cgtgatgcat gaggctctgc acaaccacta cacgcagaag 1380
agcctctccc tgtctccggg taaatga 1407

<210> SEQ ID NO 36
<211> LENGTH: 468
<212> TYPE: PRT
<213> ORGANISM: Artificial sequence
<220> FEATURE:
<223> OTHER INFORMATION: Synthetic polypeptide

<400> SEQUENCE: 36

Met Asn Phe Gly Leu Ser Leu Ile Phe Leu Val Leu Val Leu Lys Gly
1 5 10 15

Val Gln Cys Gln Val Gln Leu Gln Glu Ser Gly Ala Glu Leu Ser Lys
20 25 30

Pro Gly Ala Ser Val Lys Met Ser Cys Lys Ala Ser Gly Tyr Thr Phe

-continued

```
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Leu Ala Thr Pro Ser Arg Glu Pro Gln
        355                 360                 365

Val Tyr Thr Leu Pro Pro Ser Arg Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
        435                 440                 445

Met His Glu Ala Leu His Asn His Tyr Thr Gln Lys Ser Leu Ser Leu
    450                 455                 460
```

Ser Pro Gly Lys
465

<210> SEQ ID NO 37
<211> LENGTH: 1422
<212> TYPE: DNA
<213> ORGANISM: Artificial sequence
<220> FEATURE:
<223> OTHER INFORMATION: Synthetic polynucleotide

<400> SEQUENCE: 37
atgaacttcg ggctcagctt gattttcctt gtccttgttt taaaaggtgt ccagtgtcag 60
gtccagctgc aggagtcagg ggctgaactg tcaaaacctg gggcctcagt gaagatgtcc 120
tgcaaggctt ctggctacac ctttactagc tactggctgc actggataaa acagaggcct 180
ggacagggtc tggaatggat tggatacatt aatcctagga atgattatac tgagtacaat 240
cagaacttca aggacaaggc cacattgact gcagacaaat cctccagcac agcctacatg 300
caactgagca gcctgacatc tgaggactct gcagtctatt actgtgcaag aagggatatt 360
actacgttct actggggcca aggcaccact ctcacagtct cctcggctag caccaagggc 420
ccatcggtct tccccctggc accctcctcc aagagcacct ctgggggcac agcggccctg 480
ggctgcctgg tcaaggacta cttccccgaa ccggtgacgg tgtcgtggaa ctcaggcgcc 540
ctgaccagcg gcgtgcacac cttcccggct gtcctacagt cctcaggact ctactccctc 600
agcagcgtgg tgaccgtgcc ctccagcagc ttgggcaccc agacctacat ctgcaacgtg 660
aatcacaagc ccagcaacac caaggtggac aagaaagttg agcccaaatc ttgtgacaaa 720
actcacacat gcccaccgtg cccagcacct gaactcctgg ggggaccgtc agtcttcctc 780
ttccccccaa aacccaagga caccctcatg atctcccgga cccctgaggt cacatgcgtg 840
gtggtggacg tgagccacga agaccctgag gtcaagttca actggtacgt ggacggcgtg 900
gaggtgcata atgccaagac aaagccgcgg gaggagcagt acaacagcac gtaccgtgtg 960
gtcagcgtcc tcaccgtcct gcaccaggac tggctgaatg gcaaggagta caagtgcaag 1020
gtctccaaca aagccctccc agcccccatc gagaaaacca tctccaaagc caaagggcag 1080
ccccgagaac cacaggtgta caccctgccc ccatcccggg aggagatgac caagaaccag 1140
gtcagcctga cctgcctggt caaaggcttc tatcccagcg acatcgccgt ggagtgggag 1200
agcaatgggc agccggagaa caactacaag accacgcctc ccgtgctgga ctccgacggc 1260
tccttcttcc tctacagcaa gctcaccgtg gacaagagca ggtggcagca ggggaacgtc 1320
ttctcatgct ccgtgatgca tgaggctctg cacaaccact acacgcagaa gagcctctcc 1380
ctgtctccgg gatccttatg taccccttct agaggatcct ga 1422

<210> SEQ ID NO 38
<211> LENGTH: 473
<212> TYPE: PRT
<213> ORGANISM: Artificial sequence
<220> FEATURE:
<223> OTHER INFORMATION: Synthetic polypeptide

<400> SEQUENCE: 38

Met Asn Phe Gly Leu Ser Leu Ile Phe Leu Val Leu Val Leu Lys Gly
1 5 10 15

Val Gln Cys Gln Val Gln Leu Gln Glu Ser Gly Ala Glu Leu Ser Lys
20 25 30

Pro Gly Ala Ser Val Lys Met Ser Cys Lys Ala Ser Gly Tyr Thr Phe

-continued

```
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460
```

```
Ser Leu Cys Thr Pro Ser Arg Gly Ser
465                 470


<210> SEQ ID NO 39
<211> LENGTH: 1422
<212> TYPE: DNA
<213> ORGANISM: Artificial sequence
<220> FEATURE:
<223> OTHER INFORMATION: Synthetic polynucleotide

<400> SEQUENCE: 39

atgaacttcg ggctcagctt gattttcctt gtccttgttt taaaaggtgt ccagtgtcag     60

gtccagctgc aggagtcagg ggctgaactg tcaaaacctg gggcctcagt gaagatgtcc    120

tgcaaggctt ctggctacac ctttactagc tactggctgc actggataaa acagaggcct    180

ggacagggtc tggaatggat tggatacatt aatcctagga atgattatac tgagtacaat    240

cagaacttca aggacaaggc cacattgact gcagacaaat cctccagcac agcctacatg    300

caactgagca gcctgacatc tgaggactct gcagtctatt actgtgcaag aagggatatt    360

actacgttct actggggcca aggcaccact ctcacagtct cctcggctag caccaagggc    420

ccatcggtct tccccctggc accctcctcc aagagcacct ctgggggcac agcggccctg    480

ggctgcctgg tcaaggacta cttccccgaa ccggtgacgg tgtcgtggaa ctcaggcgcc    540

ctgaccagcg gcgtgcacac cttcccggct gtcctacagt cctcaggact ctactccctc    600

agcagcgtgg tgaccgtgcc ctccagcagc ttgggcaccc agacctacat ctgcaacgtg    660

aatcacaagc ccagcaacac caaggtggac aagaaagttg agcccaaatc ttgtgacaaa    720

actcacacat gcccaccgtg cccagcacct gaactcctgg ggggaccgtc agtcttcctc    780

ttccccccaa aacccaagga caccctcatg atctcccgga cccctgaggt cacatgcgtg    840

gtggtggacg tgagccacga agaccctgag gtcaagttca actggtacgt ggacggcgtg    900

gaggtgcata atgccaagac aaagccgcgg gaggagcagt acaacagcac gtaccgtgtg    960

gtcagcgtcc tcaccgtcct gcaccaggac tggctgaatg gcaaggagta caagtgcaag   1020

gtctccaaca aagccctccc agcccccatc gagaaaacca tctccaaagc caaagggcag   1080

ccccgagaac cacaggtgta caccctgccc ccatcccggg aggagatgac caagaaccag   1140

gtcagcctga cctgcctggt caaaggcttc tatcccagcg acatcgccgt ggagtgggag   1200

agcaatgggc agccggagaa caactacaag accacgcctc ccgtgctgga ctccgacggc   1260

tccttcttcc tctacagcaa gctcaccgtg gacaagagca ggtggcagca ggggaacgtc   1320

ttctcatgct ccgtgatgca tgaggctctg cacaaccact acacgcagaa gagcctctcc   1380

ctgtctccgg gatccttagc taccccttct agaggatcct ga                      1422


<210> SEQ ID NO 40
<211> LENGTH: 473
<212> TYPE: PRT
<213> ORGANISM: Artificial sequence
<220> FEATURE:
<223> OTHER INFORMATION: Synthetic polypeptide

<400> SEQUENCE: 40

Met Asn Phe Gly Leu Ser Leu Ile Phe Leu Val Leu Val Leu Lys Gly
1               5                   10                  15

Val Gln Cys Gln Val Gln Leu Gln Glu Ser Gly Ala Glu Leu Ser Lys
            20                  25                  30

Pro Gly Ala Ser Val Lys Met Ser Cys Lys Ala Ser Gly Tyr Thr Phe
```

-continued

```
        35                  40                  45

Thr Ser Tyr Trp Leu His Trp Ile Lys Gln Arg Pro Gly Gln Gly Leu
    50                  55                  60

Glu Trp Ile Gly Tyr Ile Asn Pro Arg Asn Asp Tyr Thr Glu Tyr Asn
65                  70                  75                  80

Gln Asn Phe Lys Asp Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Asp Ile Thr Thr Phe Tyr Trp Gly Gln Gly
        115                 120                 125

Thr Thr Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460
```

Ser Leu Ala Thr Pro Ser Arg Gly Ser
465 470

<210> SEQ ID NO 41
<211> LENGTH: 723
<212> TYPE: DNA
<213> ORGANISM: Artificial sequence
<220> FEATURE:
<223> OTHER INFORMATION: Synthetic polynucleotide

<400> SEQUENCE: 41
atgatgtcct ctgctcagtt ccttggtctc ctgttgctct gttttcaagg taccagatgt 60
gacattcagc tgacccagtc tccatcatct ctggctgtgt ctgcaggaga aaacgtcact 120
atgagctgta agtccagtca aagtgtttta tacagtgcaa atcacaagaa ctacttggcc 180
tggtaccagc agaaaccagg gcagtctcct aaactgctga tctactgggc atccactagg 240
gaatctggtg tccctgatcg cttcacaggc agcggatctg ggacagattt tactcttacc 300
atcagcagag tacaagttga agacctggca atttattatt gtcaccaata cctctcctcg 360
tggacgttcg gtggagggac caagctggag atcaaacgtc gtacggtggc tgcaccatct 420
gtcttcatct tcccgccatc tgatgagcag ttgaaatctg gaactgcctc tgttgtgtgc 480
ctgctgaata acttctatcc cagagaggcc aaagtacagt ggaaggtgga taacgccctc 540
caatcgggta actcccagga gagtgtcaca gagcaggaca gcaaggacag cacctacagc 600
ctcagcagca ccctgacgct gagcaaagca gactacgaga aacacaaagt ctacgcctgc 660
gaagtcaccc atcagggcct gagctcgccc gtcacaaaga gcttcaacag gggagagtgt 720
tag 723

<210> SEQ ID NO 42
<211> LENGTH: 240
<212> TYPE: PRT
<213> ORGANISM: Artificial sequence
<220> FEATURE:
<223> OTHER INFORMATION: Synthetic polypeptide

<400> SEQUENCE: 42

Met Met Ser Ser Ala Gln Phe Leu Gly Leu Leu Leu Leu Cys Phe Gln
1 5 10 15

Gly Thr Arg Cys Asp Ile Gln Leu Thr Gln Ser Pro Ser Ser Leu Ala
20 25 30

Val Ser Ala Gly Glu Asn Val Thr Met Ser Cys Lys Ser Ser Gln Ser
35 40 45

Val Leu Tyr Ser Ala Asn His Lys Asn Tyr Leu Ala Trp Tyr Gln Gln
50 55 60

Lys Pro Gly Gln Ser Pro Lys Leu Leu Ile Tyr Trp Ala Ser Thr Arg
65 70 75 80

Glu Ser Gly Val Pro Asp Arg Phe Thr Gly Ser Gly Ser Gly Thr Asp
85 90 95

Phe Thr Leu Thr Ile Ser Arg Val Gln Val Glu Asp Leu Ala Ile Tyr
100 105 110

Tyr Cys His Gln Tyr Leu Ser Ser Trp Thr Phe Gly Gly Gly Thr Lys
115 120 125

Leu Glu Ile Lys Arg Arg Thr Val Ala Ala Pro Ser Val Phe Ile Phe
130 135 140

Pro Pro Ser Asp Glu Gln Leu Lys Ser Gly Thr Ala Ser Val Val Cys
145 150 155 160

```
Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240


<210> SEQ ID NO 43
<211> LENGTH: 738
<212> TYPE: DNA
<213> ORGANISM: Artificial sequence
<220> FEATURE:
<223> OTHER INFORMATION: Synthetic polynucleotide

<400> SEQUENCE: 43

atgatgtcct ctgctcagtt ccttggtctc ctgttgctct gttttcaagg taccagatgt      60

gacattcagc tgacccagtc tccatcatct ctggctgtgt ctgcaggaga aaacgtcact     120

atgagctgta agtccagtca aagtgtttta tacagtgcaa atcacaagaa ctacttggcc     180

tggtaccagc agaaaccagg gcagtctcct aaactgctga tctactgggc atccactagg     240

gaatctggtg tccctgatcg cttcacaggc agcggatctg ggacagattt tactcttacc     300

atcagcagag tacaagttga agacctggca atttattatt gtcaccaata cctctcctcg     360

tggacgttcg gtggagggac caagctggag atcaaacgtc gtacggtggc tgcaccatct     420

gtcttcatct tcccgccatc tgatgagcag ttgaaatctg gaactgcctc tgttgtgtgc     480

ctgctgaata acttctatcc cagagaggcc aaagtacagt ggaaggtgga taacgccctc     540

tgcacccccca gccggcaatc gggtaactcc caggagagtg tcacagagca ggacagcaag     600

gacagcacct acagcctcag cagcaccctg acgctgagca aagcagacta cgagaaacac     660

aaagtctacg cctgcgaagt cacccatcag ggcctgagct cgcccgtcac aaagagcttc     720

aacaggggag agtgttag                                                   738


<210> SEQ ID NO 44
<211> LENGTH: 245
<212> TYPE: PRT
<213> ORGANISM: Artificial sequence
<220> FEATURE:
<223> OTHER INFORMATION: Synthetic polypeptide

<400> SEQUENCE: 44

Met Met Ser Ser Ala Gln Phe Leu Gly Leu Leu Leu Leu Cys Phe Gln
1               5                   10                  15

Gly Thr Arg Cys Asp Ile Gln Leu Thr Gln Ser Pro Ser Ser Leu Ala
            20                  25                  30

Val Ser Ala Gly Glu Asn Val Thr Met Ser Cys Lys Ser Ser Gln Ser
        35                  40                  45

Val Leu Tyr Ser Ala Asn His Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95
```

```
Phe Thr Leu Thr Ile Ser Arg Val Gln Val Glu Asp Leu Ala Ile Tyr
            100                 105                 110

Tyr Cys His Gln Tyr Leu Ser Ser Trp Thr Phe Gly Gly Gly Thr Lys
        115                 120                 125

Leu Glu Ile Lys Arg Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Cys Thr Pro Ser Arg Gln Ser Gly Asn Ser Gln Glu
            180                 185                 190

Ser Val Thr Glu Gln Asp Ser Lys Asp Ser Thr Tyr Ser Leu Ser Ser
        195                 200                 205

Thr Leu Thr Leu Ser Lys Ala Asp Tyr Glu Lys His Lys Val Tyr Ala
    210                 215                 220

Cys Glu Val Thr His Gln Gly Leu Ser Ser Pro Val Thr Lys Ser Phe
225                 230                 235                 240

Asn Arg Gly Glu Cys
                245
```

<210> SEQ ID NO 45
<211> LENGTH: 738
<212> TYPE: DNA
<213> ORGANISM: Artificial sequence
<220> FEATURE:
<223> OTHER INFORMATION: Synthetic polynucleotide

<400> SEQUENCE: 45

```
atgatgtcct ctgctcagtt ccttggtctc ctgttgctct gttttcaagg taccagatgt      60

gacattcagc tgacccagtc tccatcatct ctggctgtgt ctgcaggaga aaacgtcact     120

atgagctgta agtccagtca aagtgtttta tacagtgcaa atcacaagaa ctacttggcc     180

tggtaccagc agaaaccagg gcagtctcct aaactgctga tctactgggc atccactagg     240

gaatctggtg tccctgatcg cttcacaggc agcggatctg ggacagattt tactcttacc     300

atcagcagag tacaagttga agacctggca atttattatt gtcaccaata cctctcctcg     360

tggacgttcg gtggagggac caagctggag atcaaacgtc gtacggtggc tgcaccatct     420

gtcttcatct tcccgccatc tgatgagcag ttgaaatctg gaactgcctc tgttgtgtgc     480

ctgctgaata acttctatcc cagagaggcc aaagtacagt ggaaggtgga taacgccctc     540

gccacccccca gccggcaatc gggtaactcc caggagagtg tcacagagca ggacagcaag     600

gacagcacct acagcctcag cagcaccctg acgctgagca aagcagacta cgagaaacac     660

aaagtctacg cctgcgaagt cacccatcag ggcctgagct cgcccgtcac aaagagcttc     720

aacaggggag agtgttag                                                   738
```

<210> SEQ ID NO 46
<211> LENGTH: 245
<212> TYPE: PRT
<213> ORGANISM: Artificial sequence
<220> FEATURE:
<223> OTHER INFORMATION: Synthetic polypeptide

<400> SEQUENCE: 46

```
Met Met Ser Ser Ala Gln Phe Leu Gly Leu Leu Leu Leu Cys Phe Gln
1               5                   10                  15
```

-continued

```
Gly Thr Arg Cys Asp Ile Gln Leu Thr Gln Ser Pro Ser Ser Leu Ala
            20                  25                  30

Val Ser Ala Gly Glu Asn Val Thr Met Ser Cys Lys Ser Ser Gln Ser
        35                  40                  45

Val Leu Tyr Ser Ala Asn His Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Arg Val Gln Val Glu Asp Leu Ala Ile Tyr
            100                 105                 110

Tyr Cys His Gln Tyr Leu Ser Ser Trp Thr Phe Gly Gly Gly Thr Lys
        115                 120                 125

Leu Glu Ile Lys Arg Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Ala Thr Pro Ser Arg Gln Ser Gly Asn Ser Gln Glu
            180                 185                 190

Ser Val Thr Glu Gln Asp Ser Lys Asp Ser Thr Tyr Ser Leu Ser Ser
        195                 200                 205

Thr Leu Thr Leu Ser Lys Ala Asp Tyr Glu Lys His Lys Val Tyr Ala
    210                 215                 220

Cys Glu Val Thr His Gln Gly Leu Ser Ser Pro Val Thr Lys Ser Phe
225                 230                 235                 240

Asn Arg Gly Glu Cys
                245
```

<210> SEQ ID NO 47
<211> LENGTH: 1422
<212> TYPE: DNA
<213> ORGANISM: Artificial sequence
<220> FEATURE:
<223> OTHER INFORMATION: Synthetic polynucleotide

<400> SEQUENCE: 47

```
atgaacttcg ggctcagctt gattttcctt gtccttgttt taaaaggtgt ccagtgtcag      60

gtgcagctgc agcagtctgg ggctgagctg gtgaggcctg ggtcctcagt gaagatttcc     120

tgcaaggctt ctggctatgc attcagtagc tactggatga actgggtgaa gcagaggcct     180

ggacagggtc ttgagtggat tggacagatt tggcctggag atggtgatac taactacaat     240

ggaaagttca agggtaaagc cactctgact gcagacgaat cctccagcac agcctacatg     300

caactcagca gcctagcatc tgaggactct gcggtctatt tctgtgcaag acgggagact     360

acgacggtag gccgttatta ctatgctatg gactactggg gtcaaggaac ctcagtcacc     420

gtctcctcag ctagcaccaa gggcccatcg gtcttccccc tggcaccctc ctccaagagc     480

acctctgggg gcacagcggc cctgggctgc ctggtcaagg actacttccc cgaaccggtg     540

acggtgtcgt ggaactcagg cgccctgacc agcggcgtgc acaccttccc ggctgtccta     600

cagtcctcag gactctactc cctcagcagc gtggtgaccg tgccctccag cagcttgggc     660

acccagacct acatctgcaa cgtgaatcac aagcccagca acaccaaggt ggacaagaaa     720
```

```
gttgagccca aatcttgtga caaaactcac acatgcccac cgtgcccagc acctgaactc    780

ctgggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatcc   1140

cgggaggaga tgaccaagaa ccaggtcagc ctgacctgcc tggtcaaagg cttctatccc   1200

agcgacatcg ccgtggagtg ggagagcaat gggcagccgg agaacaacta caagaccacg   1260

cctcccgtgc tggactccga cggctccttc ttcctctaca gcaagctcac cgtggacaag   1320

agcaggtggc agcaggggaa cgtcttctca tgctccgtga tgcatgaggc tctgcacaac   1380

cactacacgc agaagagcct ctccctgtct ccgggtaaat ga                      1422


<210> SEQ ID NO 48
<211> LENGTH: 473
<212> TYPE: PRT
<213> ORGANISM: Artificial sequence
<220> FEATURE:
<223> OTHER INFORMATION: Synthetic polypeptide

<400> SEQUENCE: 48

Met Asn Phe Gly Leu Ser Leu Ile Phe Leu Val Leu Val Leu Lys Gly
1               5                   10                  15

Val Gln Cys Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240
```

```
Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 49
<211> LENGTH: 1431
<212> TYPE: DNA
<213> ORGANISM: Artificial sequence
<220> FEATURE:
<223> OTHER INFORMATION: Synthetic polynucleotide

<400> SEQUENCE: 49

```
atgaacttcg ggctcagctt gattttcctt gtccttgttt taaaaggtgt ccagtgtcag      60

gtgcagctgc agcagtctgg ggctgagctg gtgaggcctg ggtcctcagt gaagatttcc     120

tgcaaggctt ctggctatgc attcagtagc tactggatga actgggtgaa gcagaggcct     180

ggacagggtc ttgagtggat tggacagatt tggcctggag atggtgatac taactacaat     240

ggaaagttca agggtaaagc cactctgact gcagacgaat cctccagcac agcctacatg     300

caactcagca gcctagcatc tgaggactct gcggtctatt tctgtgcaag acgggagact     360

acgacggtag gccgttatta ctatgctatg gactactggg gtcaaggaac ctcagtcacc     420

gtctcctcag ctagcaccaa gggcccatcg gtcttccccc tggcaccctc ctccaagagc     480

acctctgggg gcacagcggc cctgggctgc ctggtcaagg actacttccc cgaaccggtg     540

acggtgtcgt ggaactcagg cgccctgtgt acccccttcta gaggcgtgca caccttcccg    600

gctgtcctac agtcctcagg actctactcc ctcagcagcg tggtgaccgt gccctccagc     660

agcttgggca cccagaccta catctgcaac gtgaatcaca agcccagcaa caccaaggtg     720
```

-continued

```
gacaagaaag ttgagcccaa atcttgtgac aaaactcaca catgcccacc gtgcccagca    780

cctgaactcc tggggggacc gtcagtcttc ctcttccccc caaaacccaa ggacaccctc    840

atgatctccc ggacccctga ggtcacatgc gtggtggtgg acgtgagcca cgaagaccct    900

gaggtcaagt tcaactggta cgtggacggc gtggaggtgc ataatgccaa gacaaagccg    960

cgggaggagc agtacaacag cacgtaccgt gtggtcagcg tcctcaccgt cctgcaccag   1020

gactggctga atggcaagga gtacaagtgc aaggtctcca acaaagccct cccagccccc   1080

atcgagaaaa ccatctccaa agccaaaggg cagccccgag aaccacaggt gtacaccctg   1140

cccccatccc gggaggagat gaccaagaac caggtcagcc tgacctgcct ggtcaaaggc   1200

ttctatccca gcgacatcgc cgtggagtgg gagagcaatg ggcagccgga gaacaactac   1260

aagaccacgc ctcccgtgct ggactccgac ggctccttct tcctctacag caagctcacc   1320

gtggacaaga gcaggtggca gcaggggaac gtcttctcat gctccgtgat gcatgaggct   1380

ctgcacaacc actacacgca gaagagcctc tccctgtctc cgggtaaatg a            1431
```

<210> SEQ ID NO 50
<211> LENGTH: 476
<212> TYPE: PRT
<213> ORGANISM: Artificial sequence
<220> FEATURE:
<223> OTHER INFORMATION: Synthetic polypeptide

<400> SEQUENCE: 50

```
Met Asn Phe Gly Leu Ser Leu Ile Phe Leu Val Leu Val Leu Lys Gly
1               5                   10                  15

Val Gln Cys Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Cys Thr Pro
            180                 185                 190

Ser Arg Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240
```

```
Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475
```

<210> SEQ ID NO 51
<211> LENGTH: 1431
<212> TYPE: DNA
<213> ORGANISM: Artificial sequence
<220> FEATURE:
<223> OTHER INFORMATION: Synthetic polynucleotide

<400> SEQUENCE: 51

```
atgaacttcg ggctcagctt gattttcctt gtccttgttt taaaaggtgt ccagtgtcag     60

gtgcagctgc agcagtctgg ggctgagctg gtgaggcctg ggtcctcagt gaagatttcc    120

tgcaaggctt ctggctatgc attcagtagc tactggatga actgggtgaa gcagaggcct    180

ggacagggtc ttgagtggat tggacagatt tggcctggag atggtgatac taactacaat    240

ggaaagttca agggtaaagc cactctgact gcagacgaat cctccagcac agcctacatg    300

caactcagca gcctagcatc tgaggactct gcggtctatt tctgtgcaag acgggagact    360

acgacggtag gccgttatta ctatgctatg gactactggg gtcaaggaac ctcagtcacc    420

gtctcctcag ctagcaccaa gggcccatcg gtcttccccc tggcaccctc ctccaagagc    480

acctctgggg gcacagcggc cctgggctgc ctggtcaagg actacttccc cgaaccggtg    540

acggtgtcgt ggaactcagg cgccctggct accccttcta gaggcgtgca caccttcccg    600

gctgtcctac agtcctcagg actctactcc ctcagcagcg tggtgaccgt gccctccagc    660

agcttgggca cccagaccta catctgcaac gtgaatcaca agcccagcaa caccaaggtg    720
```

```
gacaagaaag ttgagcccaa atcttgtgac aaaactcaca catgcccacc gtgcccagca    780

cctgaactcc tggggggacc gtcagtcttc ctcttccccc caaaacccaa ggacaccctc    840

atgatctccc ggacccctga ggtcacatgc gtggtggtgg acgtgagcca cgaagaccct    900

gaggtcaagt tcaactggta cgtggacggc gtggaggtgc ataatgccaa gacaaagccg    960

cgggaggagc agtacaacag cacgtaccgt gtggtcagcg tcctcaccgt cctgcaccag   1020

gactggctga atggcaagga gtacaagtgc aaggtctcca acaaagccct cccagccccc   1080

atcgagaaaa ccatctccaa agccaaaggg cagccccgag aaccacaggt gtacaccctg   1140

cccccatccc gggaggagat gaccaagaac caggtcagcc tgacctgcct ggtcaaaggc   1200

ttctatccca gcgacatcgc cgtggagtgg gagagcaatg ggcagccgga gaacaactac   1260

aagaccacgc ctcccgtgct ggactccgac ggctccttct tcctctacag caagctcacc   1320

gtggacaaga gcaggtggca gcaggggaac gtcttctcat gctccgtgat gcatgaggct   1380

ctgcacaacc actacacgca gaagagcctc tccctgtctc cgggtaaatg a            1431
```

```
<210> SEQ ID NO 52
<211> LENGTH: 476
<212> TYPE: PRT
<213> ORGANISM: Artificial sequence
<220> FEATURE:
<223> OTHER INFORMATION: Synthetic polypeptide

<400> SEQUENCE: 52

Met Asn Phe Gly Leu Ser Leu Ile Phe Leu Val Leu Val Leu Lys Gly
1               5                   10                  15

Val Gln Cys Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Ala Thr Pro
            180                 185                 190

Ser Arg Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240
```

```
Asp Lys Lys Val Glu Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
    290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475


<210> SEQ ID NO 53
<211> LENGTH: 1428
<212> TYPE: DNA
<213> ORGANISM: Artificial sequence
<220> FEATURE:
<223> OTHER INFORMATION: Synthetic polynucleotide

<400> SEQUENCE: 53

atgaacttcg ggctcagctt gattttcctt gtccttgttt taaaaggtgt ccagtgtcag     60

gtgcagctgc agcagtctgg ggctgagctg gtgaggcctg ggtcctcagt gaagatttcc    120

tgcaaggctt ctggctatgc attcagtagc tactggatga actgggtgaa gcagaggcct    180

ggacagggtc ttgagtggat tggacagatt tggcctggag atggtgatac taactacaat    240

ggaaagttca agggtaaagc cactctgact gcagacgaat cctccagcac agcctacatg    300

caactcagca gcctagcatc tgaggactct gcggtctatt tctgtgcaag acgggagact    360

acgacggtag gccgttatta ctatgctatg gactactggg gtcaaggaac ctcagtcacc    420

gtctcctcag ctagcaccaa gggcccatcg gtcttccccc tggcaccctc ctccaagagc    480

acctctgggg gcacagcggc cctgggctgc ctggtcaagg actacttccc cgaaccggtg    540

acggtgtcgt ggaactcagg cgccctgacc agcggcgtgc acaccttccc ggctgtccta    600

cagtcctcag gactctactc cctcagcagc gtggtgaccg tgccctccag cagcttgggc    660

acccagacct acatctgcaa cgtgaatcac aagcccagca acaccaaggt ggacaagaaa    720
```

```
gttgagccca aatcttgtga caaaactcac acatgcccac cgtgcccagc acctgaactc    780

ctgggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacttatgta ccccttctag agccccccatc  1080

gagaaaacca tctccaaagc caaagggcag ccccgagaac cacaggtgta caccctgccc   1140

ccatcccggg aggagatgac caagaaccag gtcagcctga cctgcctggt caaaggcttc   1200

tatcccagcg acatcgccgt ggagtgggag agcaatgggc agccggagaa caactacaag   1260

accacgcctc ccgtgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccgg gtaaatga                1428
```

<210> SEQ ID NO 54
<211> LENGTH: 475
<212> TYPE: PRT
<213> ORGANISM: Artificial sequence
<220> FEATURE:
<223> OTHER INFORMATION: Synthetic polypeptide

<400> SEQUENCE: 54

```
Met Asn Phe Gly Leu Ser Leu Ile Phe Leu Val Leu Val Leu Lys Gly
1               5                   10                  15

Val Gln Cys Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240
```

```
Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Leu
            340                 345                 350

Cys Thr Pro Ser Arg Ala Pro Ile Glu Lys Thr Ile Ser Lys Ala Lys
        355                 360                 365

Gly Gln Pro Arg Glu Pro Gln Val Tyr Thr Leu Pro Pro Ser Arg Glu
    370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475
```

<210> SEQ ID NO 55
<211> LENGTH: 1428
<212> TYPE: DNA
<213> ORGANISM: Artificial sequence
<220> FEATURE:
<223> OTHER INFORMATION: Synthetic polynucleotide

<400> SEQUENCE: 55

```
atgaacttcg ggctcagctt gattttcctt gtccttgttt taaaaggtgt ccagtgtcag     60

gtgcagctgc agcagtctgg ggctgagctg gtgaggcctg ggtcctcagt gaagatttcc    120

tgcaaggctt ctggctatgc attcagtagc tactggatga actgggtgaa gcagaggcct    180

ggacagggtc ttgagtggat tggacagatt tggcctggag atggtgatac taactacaat    240

ggaaagttca agggtaaagc cactctgact gcagacgaat cctccagcac agcctacatg    300

caactcagca gcctagcatc tgaggactct gcggtctatt tctgtgcaag acgggagact    360

acgacggtag gccgttatta ctatgctatg gactactggg gtcaaggaac ctcagtcacc    420

gtctcctcag ctagcaccaa gggcccatcg gtcttccccc tggcaccctc ctccaagagc    480

acctctgggg gcacagcggc cctgggctgc ctggtcaagg actacttccc cgaaccggtg    540

acggtgtcgt ggaactcagg cgccctgacc agcggcgtgc acaccttccc ggctgtccta    600

cagtcctcag gactctactc cctcagcagc gtggtgaccg tgccctccag cagcttgggc    660

acccagacct acatctgcaa cgtgaatcac aagcccagca acaccaaggt ggacaagaaa    720
```

```
gttgagccca aatcttgtga caaaactcac acatgcccac cgtgcccagc acctgaactc    780

ctgggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacttagcta ccccttctag agcccccatc   1080

gagaaaacca tctccaaagc caaagggcag ccccgagaac cacaggtgta caccctgccc   1140

ccatcccggg aggagatgac caagaaccag gtcagcctga cctgcctggt caaaggcttc   1200

tatcccagcg acatcgccgt ggagtgggag agcaatgggc agccggagaa caactacaag   1260

accacgcctc ccgtgctgga ctccgacggc tccttcttcc tctacagcaa gctcaccgtg   1320

gacaagagca ggtggcagca ggggaacgtc ttctcatgct ccgtgatgca tgaggctctg   1380

cacaaccact acacgcagaa gagcctctcc ctgtctccgg gtaaatga                1428
```

<210> SEQ ID NO 56
<211> LENGTH: 475
<212> TYPE: PRT
<213> ORGANISM: Artificial sequence
<220> FEATURE:
<223> OTHER INFORMATION: Synthetic polypeptide

<400> SEQUENCE: 56

```
Met Asn Phe Gly Leu Ser Leu Ile Phe Leu Val Leu Val Leu Lys Gly
1               5                   10                  15

Val Gln Cys Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240
```

Val Glu Pro Lys Ser Cys Asp Lys Thr His Thr Cys Pro Pro Cys Pro
245 250 255

Ala Pro Glu Leu Leu Gly Gly Pro Ser Val Phe Leu Phe Pro Pro Lys
260 265 270

Pro Lys Asp Thr Leu Met Ile Ser Arg Thr Pro Glu Val Thr Cys Val
275 280 285

Val Val Asp Val Ser His Glu Asp Pro Glu Val Lys Phe Asn Trp Tyr
290 295 300

Val Asp Gly Val Glu Val His Asn Ala Lys Thr Lys Pro Arg Glu Glu
305 310 315 320

Gln Tyr Asn Ser Thr Tyr Arg Val Val Ser Val Leu Thr Val Leu His
325 330 335

Gln Asp Trp Leu Asn Gly Lys Glu Tyr Lys Cys Lys Val Ser Asn Leu
340 345 350

Ala Thr Pro Ser Arg Ala Pro Ile Glu Lys Thr Ile Ser Lys Ala Lys
355 360 365

Gly Gln Pro Arg Glu Pro Gln Val Tyr Thr Leu Pro Pro Ser Arg Glu
370 375 380

Glu Met Thr Lys Asn Gln Val Ser Leu Thr Cys Leu Val Lys Gly Phe
385 390 395 400

Tyr Pro Ser Asp Ile Ala Val Glu Trp Glu Ser Asn Gly Gln Pro Glu
405 410 415

Asn Asn Tyr Lys Thr Thr Pro Pro Val Leu Asp Ser Asp Gly Ser Phe
420 425 430

Phe Leu Tyr Ser Lys Leu Thr Val Asp Lys Ser Arg Trp Gln Gln Gly
435 440 445

Asn Val Phe Ser Cys Ser Val Met His Glu Ala Leu His Asn His Tyr
450 455 460

Thr Gln Lys Ser Leu Ser Leu Ser Pro Gly Lys
465 470 475

<210> SEQ ID NO 57
<211> LENGTH: 1431
<212> TYPE: DNA
<213> ORGANISM: Artificial sequence
<220> FEATURE:
<223> OTHER INFORMATION: Synthetic polynucleotide

<400> SEQUENCE: 57
atgaacttcg ggctcagctt gattttcctt gtccttgttt taaaaggtgt ccagtgtcag 60
gtgcagctgc agcagtctgg ggctgagctg gtgaggcctg ggtcctcagt gaagatttcc 120
tgcaaggctt ctggctatgc attcagtagc tactggatga actgggtgaa gcagaggcct 180
ggacagggtc ttgagtggat tggacagatt tggcctggag atggtgatac taactacaat 240
ggaaagttca agggtaaagc cactctgact gcagacgaat cctccagcac agcctacatg 300
caactcagca gcctagcatc tgaggactct gcggtctatt tctgtgcaag acgggagact 360
acgacggtag gccgttatta ctatgctatg gactactggg gtcaaggaac ctcagtcacc 420
gtctcctcag ctagcaccaa gggcccatcg gtcttccccc tggcaccctc ctccaagagc 480
acctctgggg gcacagcggc cctgggctgc ctggtcaagg actacttccc cgaaccggtg 540
acggtgtcgt ggaactcagg cgccctgacc agcggcgtgc acaccttccc ggctgtccta 600
cagtcctcag gactctactc cctcagcagc gtggtgaccg tgccctccag cagcttgggc 660
acccagacct acatctgcaa cgtgaatcac aagcccagca acaccaaggt ggacaagaaa 720

```
gttgagccca aatcttgtga caaaactcac acatgcccac cgtgcccagc acctgaactc    780

ctgggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gttatgtacc ccttctcgag aaccacaggt gtacaccctg   1140

cccccatccc gggaggagat gaccaagaac caggtcagcc tgacctgcct ggtcaaaggc   1200

ttctatccca gcgacatcgc cgtggagtgg gagagcaatg ggcagccgga gaacaactac   1260

aagaccacgc ctcccgtgct ggactccgac ggctccttct tcctctacag caagctcacc   1320

gtggacaaga gcaggtggca gcaggggaac gtcttctcat gctccgtgat gcatgaggct   1380

ctgcacaacc actacacgca gaagagcctc tccctgtctc cgggtaaatg a            1431
```

<210> SEQ ID NO 58
<211> LENGTH: 476
<212> TYPE: PRT
<213> ORGANISM: Artificial sequence
<220> FEATURE:
<223> OTHER INFORMATION: Synthetic polypeptide

<400> SEQUENCE: 58

```
Met Asn Phe Gly Leu Ser Leu Ile Phe Leu Val Leu Val Leu Lys Gly
1               5                   10                  15

Val Gln Cys Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240
```

```
Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Leu
        355                 360                 365

Cys Thr Pro Ser Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475
```

<210> SEQ ID NO 59
<211> LENGTH: 1431
<212> TYPE: DNA
<213> ORGANISM: Artificial sequence
<220> FEATURE:
<223> OTHER INFORMATION: Synthetic polynucleotide

<400> SEQUENCE: 59

```
atgaacttcg ggctcagctt gattttcctt gtccttgttt taaaaggtgt ccagtgtcag     60

gtgcagctgc agcagtctgg ggctgagctg gtgaggcctg ggtcctcagt gaagatttcc    120

tgcaaggctt ctggctatgc attcagtagc tactggatga actgggtgaa gcagaggcct    180

ggacagggtc ttgagtggat tggacagatt tggcctggag atggtgatac taactacaat    240

ggaaagttca agggtaaagc cactctgact gcagacgaat cctccagcac agcctacatg    300

caactcagca gcctagcatc tgaggactct gcggtctatt tctgtgcaag acgggagact    360

acgacggtag gccgttatta ctatgctatg gactactggg gtcaaggaac ctcagtcacc    420

gtctcctcag ctagcaccaa gggcccatcg gtcttccccc tggcaccctc ctccaagagc    480

acctctgggg gcacagcggc cctgggctgc ctggtcaagg actacttccc cgaaccggtg    540

acggtgtcgt ggaactcagg cgccctgacc agcggcgtgc acaccttccc ggctgtccta    600

cagtcctcag gactctactc cctcagcagc gtggtgaccg tgccctccag cagcttgggc    660

acccagacct acatctgcaa cgtgaatcac aagcccagca acaccaaggt ggacaagaaa    720
```

gttgagccca aatcttgtga caaaactcac acatgcccac cgtgcccagc acctgaactc 780
ctggggggac cgtcagtctt cctcttcccc ccaaaaccca aggacaccct catgatctcc 840
cggacccctg aggtcacatg cgtggtggtg gacgtgagcc acgaagaccc tgaggtcaag 900
ttcaactggt acgtggacgg cgtggaggtg cataatgcca agacaaagcc gcgggaggag 960
cagtacaaca gcacgtaccg tgtggtcagc gtcctcaccg tcctgcacca ggactggctg 1020
aatggcaagg agtacaagtg caaggtctcc aacaaagccc tcccagcccc catcgagaaa 1080
accatctcca aagccaaagg gttagctacc ccttctcgag aaccacaggt gtacaccctg 1140
cccccatccc gggaggagat gaccaagaac caggtcagcc tgacctgcct ggtcaaaggc 1200
ttctatccca gcgacatcgc cgtggagtgg gagagcaatg ggcagccgga gaacaactac 1260
aagaccacgc ctcccgtgct ggactccgac ggctccttct tcctctacag caagctcacc 1320
gtggacaaga gcaggtggca gcaggggaac gtcttctcat gctccgtgat gcatgaggct 1380
ctgcacaacc actacacgca gaagagcctc tccctgtctc cgggtaaatg a 1431

<210> SEQ ID NO 60
<211> LENGTH: 476
<212> TYPE: PRT
<213> ORGANISM: Artificial sequence
<220> FEATURE:
<223> OTHER INFORMATION: Synthetic polypeptide

<400> SEQUENCE: 60

Met Asn Phe Gly Leu Ser Leu Ile Phe Leu Val Leu Val Leu Lys Gly
1 5 10 15

Val Gln Cys Gln Val Gln Leu Gln Gln Ser Gly Ala Glu Leu Val Arg
20 25 30

Pro Gly Ser Ser Val Lys Ile Ser Cys Lys Ala Ser Gly Tyr Ala Phe
35 40 45

Ser Ser Tyr Trp Met Asn Trp Val Lys Gln Arg Pro Gly Gln Gly Leu
50 55 60

Glu Trp Ile Gly Gln Ile Trp Pro Gly Asp Gly Asp Thr Asn Tyr Asn
65 70 75 80

Gly Lys Phe Lys Gly Lys Ala Thr Leu Thr Ala Asp Glu Ser Ser Ser
85 90 95

Thr Ala Tyr Met Gln Leu Ser Ser Leu Ala Ser Glu Asp Ser Ala Val
100 105 110

Tyr Phe Cys Ala Arg Arg Glu Thr Thr Thr Val Gly Arg Tyr Tyr Tyr
115 120 125

Ala Met Asp Tyr Trp Gly Gln Gly Thr Ser Val Thr Val Ser Ser Ala
130 135 140

Ser Thr Lys Gly Pro Ser Val Phe Pro Leu Ala Pro Ser Ser Lys Ser
145 150 155 160

Thr Ser Gly Gly Thr Ala Ala Leu Gly Cys Leu Val Lys Asp Tyr Phe
165 170 175

Pro Glu Pro Val Thr Val Ser Trp Asn Ser Gly Ala Leu Thr Ser Gly
180 185 190

Val His Thr Phe Pro Ala Val Leu Gln Ser Ser Gly Leu Tyr Ser Leu
195 200 205

Ser Ser Val Val Thr Val Pro Ser Ser Ser Leu Gly Thr Gln Thr Tyr
210 215 220

Ile Cys Asn Val Asn His Lys Pro Ser Asn Thr Lys Val Asp Lys Lys
225 230 235 240

```
Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Leu
        355                 360                 365

Ala Thr Pro Ser Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475


<210> SEQ ID NO 61
<211> LENGTH: 1446
<212> TYPE: DNA
<213> ORGANISM: Artificial sequence
<220> FEATURE:
<223> OTHER INFORMATION: Synthetic polynucleotide

<400> SEQUENCE: 61

atgaacttcg ggctcagctt gattttcctt gtccttgttt taaaaggtgt ccagtgtcag     60

gtgcagctgc agcagtctgg ggctgagctg gtgaggcctg ggtcctcagt gaagatttcc    120

tgcaaggctt ctggctatgc attcagtagc tactggatga actgggtgaa gcagaggcct    180

ggacagggtc ttgagtggat tggacagatt tggcctggag atggtgatac taactacaat    240

ggaaagttca agggtaaagc cactctgact gcagacgaat cctccagcac agcctacatg    300

caactcagca gcctagcatc tgaggactct gcggtctatt tctgtgcaag acgggagact    360

acgacggtag gccgttatta ctatgctatg gactactggg gtcaaggaac ctcagtcacc    420

gtctcctcag ctagcaccaa gggcccatcg gtcttccccc tggcaccctc ctccaagagc    480

acctctgggg gcacagcggc cctgggctgc ctggtcaagg actacttccc cgaaccggtg    540

acggtgtcgt ggaactcagg cgccctgacc agcggcgtgc acaccttccc ggctgtccta    600

cagtcctcag gactctactc cctcagcagc gtggtgaccg tgccctccag cagcttgggc    660

acccagacct acatctgcaa cgtgaatcac aagcccagca acaccaaggt ggacaagaaa    720
```

```
gttgagccca aatcttgtga caaaactcac acatgcccac cgtgcccagc acctgaactc    780

ctgggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatcc   1140

cgggaggaga tgaccaagaa ccaggtcagc ctgacctgcc tggtcaaagg cttctatccc   1200

agcgacatcg ccgtggagtg ggagagcaat gggcagccgg agaacaacta caagaccacg   1260

cctcccgtgc tggactccga cggctccttc ttcctctaca gcaagctcac cgtggacaag   1320

agcaggtggc agcaggggaa cgtcttctca tgctccgtga tgcatgaggc tctgcacaac   1380

cactacacgc agaagagcct ctccctgtct ccgggatcct tatgtacccc ttctagagga   1440

tcctga                                                              1446
```

<210> SEQ ID NO 62
<211> LENGTH: 481
<212> TYPE: PRT
<213> ORGANISM: Artificial sequence
<220> FEATURE:
<223> OTHER INFORMATION: Synthetic polypeptide

<400> SEQUENCE: 62

```
Met Asn Phe Gly Leu Ser Leu Ile Phe Leu Val Leu Val Leu Lys Gly
1               5                   10                  15

Val Gln Cys Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220
```

-continued

```
Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Ser Leu Cys Thr Pro Ser Arg Gly
465                 470                 475                 480

Ser
```

<210> SEQ ID NO 63
<211> LENGTH: 1446
<212> TYPE: DNA
<213> ORGANISM: Artificial sequence
<220> FEATURE:
<223> OTHER INFORMATION: Synthetic polynucleotide

<400> SEQUENCE: 63

```
atgaacttcg ggctcagctt gattttcctt gtccttgttt taaaaggtgt ccagtgtcag     60

gtgcagctgc agcagtctgg ggctgagctg gtgaggcctg ggtcctcagt gaagatttcc    120

tgcaaggctt ctggctatgc attcagtagc tactggatga actgggtgaa gcagaggcct    180

ggacagggtc ttgagtggat tggacagatt tggcctggag atggtgatac taactacaat    240

ggaaagttca agggtaaagc cactctgact gcagacgaat cctccagcac agcctacatg    300

caactcagca gcctagcatc tgaggactct gcggtctatt tctgtgcaag acgggagact    360

acgacggtag gccgttatta ctatgctatg gactactggg gtcaaggaac ctcagtcacc    420

gtctcctcag ctagcaccaa gggcccatcg gtcttccccc tggcaccctc ctccaagagc    480

acctctgggg gcacagcggc cctgggctgc ctggtcaagg actacttccc cgaaccggtg    540

acggtgtcgt ggaactcagg cgccctgacc agcggcgtgc acaccttccc ggctgtccta    600
```

-continued

```
cagtcctcag gactctactc cctcagcagc gtggtgaccg tgccctccag cagcttgggc    660

acccagacct acatctgcaa cgtgaatcac aagcccagca acaccaaggt ggacaagaaa    720

gttgagccca aatcttgtga caaaactcac acatgcccac cgtgcccagc acctgaactc    780

ctggggggac cgtcagtctt cctcttcccc ccaaaaccca aggacaccct catgatctcc    840

cggacccctg aggtcacatg cgtggtggtg gacgtgagcc acgaagaccc tgaggtcaag    900

ttcaactggt acgtggacgg cgtggaggtg cataatgcca agacaaagcc gcgggaggag    960

cagtacaaca gcacgtaccg tgtggtcagc gtcctcaccg tcctgcacca ggactggctg   1020

aatggcaagg agtacaagtg caaggtctcc aacaaagccc tcccagcccc catcgagaaa   1080

accatctcca aagccaaagg gcagccccga gaaccacagg tgtacaccct gcccccatcc   1140

cgggaggaga tgaccaagaa ccaggtcagc ctgacctgcc tggtcaaagg cttctatccc   1200

agcgacatcg ccgtggagtg ggagagcaat gggcagccgg agaacaacta caagaccacg   1260

cctcccgtgc tggactccga cggctccttc ttcctctaca gcaagctcac cgtggacaag   1320

agcaggtggc agcaggggaa cgtcttctca tgctccgtga tgcatgaggc tctgcacaac   1380

cactacacgc agaagagcct ctccctgtct ccgggatcct tagctacccc ttctagagga   1440

tcctga                                                              1446
```

<210> SEQ ID NO 64
<211> LENGTH: 481
<212> TYPE: PRT
<213> ORGANISM: Artificial sequence
<220> FEATURE:
<223> OTHER INFORMATION: Synthetic polypeptide

<400> SEQUENCE: 64

```
Met Asn Phe Gly Leu Ser Leu Ile Phe Leu Val Leu Val Leu Lys Gly
1               5                   10                  15

Val Gln Cys Gln Val Gln Leu Gln Gln Ser Gly Ala Glu Leu Val Arg
            20                  25                  30

Pro Gly Ser Ser Val Lys Ile Ser Cys Lys Ala Ser Gly Tyr Ala Phe
        35                  40                  45

Ser Ser Tyr Trp Met Asn Trp Val Lys Gln Arg Pro Gly Gln Gly Leu
    50                  55                  60

Glu Trp Ile Gly Gln Ile Trp Pro Gly Asp Gly Asp Thr Asn Tyr Asn
65                  70                  75                  80

Gly Lys Phe Lys Gly Lys Ala Thr Leu Thr Ala Asp Glu Ser Ser Ser
                85                  90                  95

Thr Ala Tyr Met Gln Leu Ser Ser Leu Ala Ser Glu Asp Ser Ala Val
            100                 105                 110

Tyr Phe Cys Ala Arg Arg Glu Thr Thr Thr Val Gly Arg Tyr Tyr Tyr
        115                 120                 125

Ala Met Asp Tyr Trp Gly Gln Gly Thr Ser Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205
```

```
Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Glu Glu Met
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
    450                 455                 460

Lys Ser Leu Ser Leu Ser Pro Gly Ser Leu Ala Thr Pro Ser Arg Gly
465                 470                 475                 480

Ser


<210> SEQ ID NO 65
<211> LENGTH: 720
<212> TYPE: DNA
<213> ORGANISM: Artificial sequence
<220> FEATURE:
<223> OTHER INFORMATION: Synthetic polynucleotide

<400> SEQUENCE: 65

atgatgtcct ctgctcagtt ccttggtctc ctgttgctct gttttcaagg taccagatgt     60

gatatcttgc tcacccaaac tccagcttct ttggctgtgt ctctagggca gagggccacc    120

atctcctgca aggccagcca aagtgttgat tatgatggtg atagttattt gaactggtac    180

caacagattc caggacagcc acccaaactc ctcatctatg atgcatccaa tctagtttct    240

gggatcccac ccaggtttag tggcagtggg tctgggacag acttcaccct caacatccat    300

cctgtggaga aggtggatgc tgcaacctat cactgtcagc aaagtactga ggatccgtgg    360

acgttcggtg gaggcaccaa gctggaaatc aaacggcgta cggtggctgc accatctgtc    420

ttcatcttcc cgccatctga tgagcagttg aaatctggaa ctgcctctgt tgtgtgcctg    480
```

ctgaataact tctatcccag agaggccaaa gtacagtgga aggtggataa cgccctccaa 540
tcgggtaact cccaggagag tgtcacagag caggacagca aggacagcac ctacagcctc 600
agcagcaccc tgacgctgag caaagcagac tacgagaaac acaaagtcta cgcctgcgaa 660
gtcacccatc agggcctgag ctcgcccgtc acaaagagct tcaacagggg agagtgttag 720

<210> SEQ ID NO 66
<211> LENGTH: 239
<212> TYPE: PRT
<213> ORGANISM: Artificial sequence
<220> FEATURE:
<223> OTHER INFORMATION: Synthetic polypeptide

<400> SEQUENCE: 66

Met Met Ser Ser Ala Gln Phe Leu Gly Leu Leu Leu Leu Cys Phe Gln
1 5 10 15

Gly Thr Arg Cys Asp Ile Leu Leu Thr Gln Thr Pro Ala Ser Leu Ala
20 25 30

Val Ser Leu Gly Gln Arg Ala Thr Ile Ser Cys Lys Ala Ser Gln Ser
35 40 45

Val Asp Tyr Asp Gly Asp Ser Tyr Leu Asn Trp Tyr Gln Gln Ile Pro
50 55 60

Gly Gln Pro Pro Lys Leu Leu Ile Tyr Asp Ala Ser Asn Leu Val Ser
65 70 75 80

Gly Ile Pro Pro Arg Phe Ser Gly Ser Gly Ser Gly Thr Asp Phe Thr
85 90 95

Leu Asn Ile His Pro Val Glu Lys Val Asp Ala Ala Thr Tyr His Cys
100 105 110

Gln Gln Ser Thr Glu Asp Pro Trp Thr Phe Gly Gly Gly Thr Lys Leu
115 120 125

Glu Ile Lys Arg Arg Thr Val Ala Ala Pro Ser Val Phe Ile Phe Pro
130 135 140

Pro Ser Asp Glu Gln Leu Lys Ser Gly Thr Ala Ser Val Val Cys Leu
145 150 155 160

Leu Asn Asn Phe Tyr Pro Arg Glu Ala Lys Val Gln Trp Lys Val Asp
165 170 175

Asn Ala Leu Gln Ser Gly Asn Ser Gln Glu Ser Val Thr Glu Gln Asp
180 185 190

Ser Lys Asp Ser Thr Tyr Ser Leu Ser Ser Thr Leu Thr Leu Ser Lys
195 200 205

Ala Asp Tyr Glu Lys His Lys Val Tyr Ala Cys Glu Val Thr His Gln
210 215 220

Gly Leu Ser Ser Pro Val Thr Lys Ser Phe Asn Arg Gly Glu Cys
225 230 235

<210> SEQ ID NO 67
<211> LENGTH: 735
<212> TYPE: DNA
<213> ORGANISM: Artificial sequence
<220> FEATURE:
<223> OTHER INFORMATION: Synthetic polynucleotide

<400> SEQUENCE: 67
atgatgtcct ctgctcagtt ccttggtctc ctgttgctct gttttcaagg taccagatgt 60
gatatcttgc tcacccaaac tccagcttct ttggctgtgt ctctagggca gagggccacc 120
atctcctgca aggccagcca aagtgttgat tatgatggtg atagttattt gaactggtac 180

```
caacagattc caggacagcc acccaaactc ctcatctatg atgcatccaa tctagtttct    240

gggatcccac ccaggtttag tggcagtggg tctgggacag acttcaccct caacatccat    300

cctgtggaga aggtggatgc tgcaacctat cactgtcagc aaagtactga ggatccgtgg    360

acgttcggtg gaggcaccaa gctggaaatc aaacggcgta cggtggctgc accatctgtc    420

ttcatcttcc cgccatctga tgagcagttg aaatctggaa ctgcctctgt tgtgtgcctg    480

ctgaataact tctatcccag agaggccaaa gtacagtgga aggtggataa cgccctctgc    540

acccccagcc ggcaatcggg taactcccag gagagtgtca cagagcagga cagcaaggac    600

agcacctaca gcctcagcag caccctgacg ctgagcaaag cagactacga gaaacacaaa    660

gtctacgcct gcgaagtcac ccatcagggc ctgagctcgc ccgtcacaaa gagcttcaac    720

aggggagagt gttag                                                     735
```

```
<210> SEQ ID NO 68
<211> LENGTH: 244
<212> TYPE: PRT
<213> ORGANISM: Artificial sequence
<220> FEATURE:
<223> OTHER INFORMATION: Synthetic polypeptide

<400> SEQUENCE: 68

Met Met Ser Ser Ala Gln Phe Leu Gly Leu Leu Leu Leu Cys Phe Gln
1               5                   10                  15

Gly Thr Arg Cys Asp Ile Leu Leu Thr Gln Thr Pro Ala Ser Leu Ala
            20                  25                  30

Val Ser Leu Gly Gln Arg Ala Thr Ile Ser Cys Lys Ala Ser Gln Ser
        35                  40                  45

Val Asp Tyr Asp Gly Asp Ser Tyr Leu Asn Trp Tyr Gln Gln Ile Pro
    50                  55                  60

Gly Gln Pro Pro Lys Leu Leu Ile Tyr Asp Ala Ser Asn Leu Val Ser
65                  70                  75                  80

Gly Ile Pro Pro Arg Phe Ser Gly Ser Gly Ser Gly Thr Asp Phe Thr
                85                  90                  95

Leu Asn Ile His Pro Val Glu Lys Val Asp Ala Ala Thr Tyr His Cys
            100                 105                 110

Gln Gln Ser Thr Glu Asp Pro Trp Thr Phe Gly Gly Gly Thr Lys Leu
        115                 120                 125

Glu Ile Lys Arg Arg Thr Val Ala Ala Pro Ser Val Phe Ile Phe Pro
    130                 135                 140

Pro Ser Asp Glu Gln Leu Lys Ser Gly Thr Ala Ser Val Val Cys Leu
145                 150                 155                 160

Leu Asn Asn Phe Tyr Pro Arg Glu Ala Lys Val Gln Trp Lys Val Asp
                165                 170                 175

Asn Ala Leu Cys Thr Pro Ser Arg Gln Ser Gly Asn Ser Gln Glu Ser
            180                 185                 190

Val Thr Glu Gln Asp Ser Lys Asp Ser Thr Tyr Ser Leu Ser Ser Thr
        195                 200                 205

Leu Thr Leu Ser Lys Ala Asp Tyr Glu Lys His Lys Val Tyr Ala Cys
    210                 215                 220

Glu Val Thr His Gln Gly Leu Ser Ser Pro Val Thr Lys Ser Phe Asn
225                 230                 235                 240

Arg Gly Glu Cys
```

<210> SEQ ID NO 69
<211> LENGTH: 735
<212> TYPE: DNA
<213> ORGANISM: Artificial sequence
<220> FEATURE:
<223> OTHER INFORMATION: Synthetic polynucleotide

<400> SEQUENCE: 69
atgatgtcct ctgctcagtt ccttggtctc ctgttgctct gttttcaagg taccagatgt 60
gatatcttgc tcacccaaac tccagcttct ttggctgtgt ctctagggca gagggccacc 120
atctcctgca aggccagcca aagtgttgat tatgatggtg atagttattt gaactggtac 180
caacagattc caggacagcc acccaaactc ctcatctatg atgcatccaa tctagtttct 240
gggatcccac ccaggtttag tggcagtggg tctgggacag acttcaccct caacatccat 300
cctgtggaga aggtggatgc tgcaacctat cactgtcagc aaagtactga ggatccgtgg 360
acgttcggtg gaggcaccaa gctggaaatc aaacggcgta cggtggctgc accatctgtc 420
ttcatcttcc cgccatctga tgagcagttg aaatctggaa ctgcctctgt tgtgtgcctg 480
ctgaataact tctatcccag agaggccaaa gtacagtgga aggtggataa cgccctcgcc 540
acccccagcc ggcaatcggg taactcccag gagagtgtca cagagcagga cagcaaggac 600
agcacctaca gcctcagcag caccctgacg ctgagcaaag cagactacga gaaacacaaa 660
gtctacgcct gcgaagtcac ccatcagggc ctgagctcgc ccgtcacaaa gagcttcaac 720
aggggagagt gttag 735

<210> SEQ ID NO 70
<211> LENGTH: 244
<212> TYPE: PRT
<213> ORGANISM: Artificial sequence
<220> FEATURE:
<223> OTHER INFORMATION: Synthetic polypeptide

<400> SEQUENCE: 70

Met Met Ser Ser Ala Gln Phe Leu Gly Leu Leu Leu Leu Cys Phe Gln
1 5 10 15

Gly Thr Arg Cys Asp Ile Leu Leu Thr Gln Thr Pro Ala Ser Leu Ala
20 25 30

Val Ser Leu Gly Gln Arg Ala Thr Ile Ser Cys Lys Ala Ser Gln Ser
35 40 45

Val Asp Tyr Asp Gly Asp Ser Tyr Leu Asn Trp Tyr Gln Gln Ile Pro
50 55 60

Gly Gln Pro Pro Lys Leu Leu Ile Tyr Asp Ala Ser Asn Leu Val Ser
65 70 75 80

Gly Ile Pro Pro Arg Phe Ser Gly Ser Gly Ser Gly Thr Asp Phe Thr
85 90 95

Leu Asn Ile His Pro Val Glu Lys Val Asp Ala Ala Thr Tyr His Cys
100 105 110

Gln Gln Ser Thr Glu Asp Pro Trp Thr Phe Gly Gly Gly Thr Lys Leu
115 120 125

Glu Ile Lys Arg Arg Thr Val Ala Ala Pro Ser Val Phe Ile Phe Pro
130 135 140

Pro Ser Asp Glu Gln Leu Lys Ser Gly Thr Ala Ser Val Val Cys Leu
145 150 155 160

Leu Asn Asn Phe Tyr Pro Arg Glu Ala Lys Val Gln Trp Lys Val Asp
165 170 175

Asn Ala Leu Ala Thr Pro Ser Arg Gln Ser Gly Asn Ser Gln Glu Ser

-continued

```
            180                 185                 190

Val Thr Glu Gln Asp Ser Lys Asp Ser Thr Tyr Ser Leu Ser Ser Thr
        195                 200                 205

Leu Thr Leu Ser Lys Ala Asp Tyr Glu Lys His Lys Val Tyr Ala Cys
    210                 215                 220

Glu Val Thr His Gln Gly Leu Ser Ser Pro Val Thr Lys Ser Phe Asn
225                 230                 235                 240

Arg Gly Glu Cys


<210> SEQ ID NO 71
<211> LENGTH: 6
<212> TYPE: PRT
<213> ORGANISM: Artificial sequence
<220> FEATURE:
<223> OTHER INFORMATION: Synthetic peptide

<400> SEQUENCE: 71

Ala Ser Thr Lys Gly Pro
1               5


<210> SEQ ID NO 72
<211> LENGTH: 7
<212> TYPE: PRT
<213> ORGANISM: Artificial sequence
<220> FEATURE:
<223> OTHER INFORMATION: Synthetic peptide

<400> SEQUENCE: 72

Lys Ser Thr Ser Gly Gly Thr
1               5


<210> SEQ ID NO 73
<211> LENGTH: 4
<212> TYPE: PRT
<213> ORGANISM: Artificial sequence
<220> FEATURE:
<223> OTHER INFORMATION: Synthetic peptide

<400> SEQUENCE: 73

Pro Glu Pro Val
1


<210> SEQ ID NO 74
<211> LENGTH: 21
<212> TYPE: PRT
<213> ORGANISM: Artificial sequence
<220> FEATURE:
<223> OTHER INFORMATION: Synthetic peptide

<400> SEQUENCE: 74

Asn Ser Gly Ala Leu Thr Ser Gly Val His Thr Phe Pro Ala Val Leu
1               5                   10                  15

Gln Ser Ser Gly Leu
            20


<210> SEQ ID NO 75
<211> LENGTH: 4
<212> TYPE: PRT
<213> ORGANISM: Artificial sequence
<220> FEATURE:
<223> OTHER INFORMATION: Synthetic peptide

<400> SEQUENCE: 75

Thr Gln Thr Tyr
```

1

<210> SEQ ID NO 76
<211> LENGTH: 5
<212> TYPE: PRT
<213> ORGANISM: Artificial sequence
<220> FEATURE:
<223> OTHER INFORMATION: Synthetic peptide

<400> SEQUENCE: 76

His Lys Pro Ser Asn
1 5

<210> SEQ ID NO 77
<211> LENGTH: 22
<212> TYPE: PRT
<213> ORGANISM: Artificial sequence
<220> FEATURE:
<223> OTHER INFORMATION: Synthetic peptide

<400> SEQUENCE: 77

Glu Pro Lys Ser Cys Asp Lys Thr His Thr Cys Pro Pro Cys Pro Ala
1 5 10 15

Pro Glu Leu Leu Gly Gly
20

<210> SEQ ID NO 78
<211> LENGTH: 5
<212> TYPE: PRT
<213> ORGANISM: Artificial sequence
<220> FEATURE:
<223> OTHER INFORMATION: Synthetic peptide

<400> SEQUENCE: 78

Phe Pro Pro Lys Pro
1 5

<210> SEQ ID NO 79
<211> LENGTH: 5
<212> TYPE: PRT
<213> ORGANISM: Artificial sequence
<220> FEATURE:
<223> OTHER INFORMATION: Synthetic peptide

<400> SEQUENCE: 79

Ile Ser Arg Thr Pro
1 5

<210> SEQ ID NO 80
<211> LENGTH: 9
<212> TYPE: PRT
<213> ORGANISM: Artificial sequence
<220> FEATURE:
<223> OTHER INFORMATION: Synthetic peptide

<400> SEQUENCE: 80

Asp Val Ser His Glu Asp Pro Glu Val
1 5

<210> SEQ ID NO 81
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 81

Asp Gly Val Glu Val His Asn Ala Lys
1               5

<210> SEQ ID NO 82
<211> LENGTH: 5
<212> TYPE: PRT
<213> ORGANISM: Artificial sequence
<220> FEATURE:
<223> OTHER INFORMATION: Synthetic peptide

<400> SEQUENCE: 82

Gln Tyr Asn Ser Thr
1               5

<210> SEQ ID NO 83
<211> LENGTH: 5
<212> TYPE: PRT
<213> ORGANISM: Artificial sequence
<220> FEATURE:
<223> OTHER INFORMATION: Synthetic peptide

<400> SEQUENCE: 83

Val Leu Thr Val Leu
1               5

<210> SEQ ID NO 84
<211> LENGTH: 7
<212> TYPE: PRT
<213> ORGANISM: Artificial sequence
<220> FEATURE:
<223> OTHER INFORMATION: Synthetic peptide

<400> SEQUENCE: 84

Asn Lys Ala Leu Pro Ala Pro
1               5

<210> SEQ ID NO 85
<211> LENGTH: 9
<212> TYPE: PRT
<213> ORGANISM: Artificial sequence
<220> FEATURE:
<223> OTHER INFORMATION: Synthetic peptide

<400> SEQUENCE: 85

Ser Lys Ala Lys Gly Gln Pro Arg Glu
1               5

<210> SEQ ID NO 86
<211> LENGTH: 10
<212> TYPE: PRT
<213> ORGANISM: Artificial sequence
<220> FEATURE:
<223> OTHER INFORMATION: Synthetic peptide

<400> SEQUENCE: 86

Pro Pro Ser Arg Lys Glu Leu Thr Lys Asn
1               5                   10

<210> SEQ ID NO 87
<211> LENGTH: 5
<212> TYPE: PRT
<213> ORGANISM: Artificial sequence
<220> FEATURE:
<223> OTHER INFORMATION: Synthetic peptide

<400> SEQUENCE: 87

Tyr Pro Ser Asp Ile
1 5

<210> SEQ ID NO 88
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 88

Asn Gly Gln Pro Glu Asn Asn
1 5

<210> SEQ ID NO 89
<211> LENGTH: 10
<212> TYPE: PRT
<213> ORGANISM: Artificial sequence
<220> FEATURE:
<223> OTHER INFORMATION: Synthetic peptide

<400> SEQUENCE: 89

Thr Pro Pro Val Leu Asp Ser Asp Gly Ser
1 5 10

<210> SEQ ID NO 90
<211> LENGTH: 19
<212> TYPE: PRT
<213> ORGANISM: Artificial sequence
<220> FEATURE:
<223> OTHER INFORMATION: Synthetic peptide

<400> SEQUENCE: 90

His Glu Ala Leu His Asn His Tyr Thr Gln Lys Ser Leu Ser Leu Ser
1 5 10 15

Pro Gly Lys

<210> SEQ ID NO 91
<211> LENGTH: 12
<212> TYPE: PRT
<213> ORGANISM: Artificial sequence
<220> FEATURE:
<223> OTHER INFORMATION: Synthetic peptide

<400> SEQUENCE: 91

Pro Cys Ser Arg Ser Thr Ser Glu Ser Thr Ala Ala
1 5 10

<210> SEQ ID NO 92
<211> LENGTH: 7
<212> TYPE: PRT
<213> ORGANISM: Artificial sequence
<220> FEATURE:
<223> OTHER INFORMATION: Synthetic peptide

<400> SEQUENCE: 92

Ala Ala Leu Leu Thr Gly Arg
1 5

<210> SEQ ID NO 93
<211> LENGTH: 7
<212> TYPE: PRT
<213> ORGANISM: Artificial sequence
<220> FEATURE:
<223> OTHER INFORMATION: Synthetic peptide

<400> SEQUENCE: 93

Ser Gln Leu Leu Thr Gly Arg
1 5

<210> SEQ ID NO 94
<211> LENGTH: 7
<212> TYPE: PRT
<213> ORGANISM: Artificial sequence
<220> FEATURE:
<223> OTHER INFORMATION: Synthetic peptide

<400> SEQUENCE: 94

Ala Ala Phe Met Thr Gly Arg
1 5

<210> SEQ ID NO 95
<211> LENGTH: 7
<212> TYPE: PRT
<213> ORGANISM: Artificial sequence
<220> FEATURE:
<223> OTHER INFORMATION: Synthetic peptide

<400> SEQUENCE: 95

Ala Ala Phe Leu Thr Gly Arg
1 5

<210> SEQ ID NO 96
<211> LENGTH: 7
<212> TYPE: PRT
<213> ORGANISM: Artificial sequence
<220> FEATURE:
<223> OTHER INFORMATION: Synthetic peptide

<400> SEQUENCE: 96

Ser Ala Phe Leu Thr Gly Arg
1 5

<210> SEQ ID NO 97
<211> LENGTH: 7
<212> TYPE: PRT
<213> ORGANISM: Artificial sequence
<220> FEATURE:
<223> OTHER INFORMATION: Synthetic peptide

<400> SEQUENCE: 97

Ala Ser Ile Leu Thr Gly Lys
1 5

<210> SEQ ID NO 98
<211> LENGTH: 7
<212> TYPE: PRT
<213> ORGANISM: Artificial sequence
<220> FEATURE:
<223> OTHER INFORMATION: Synthetic peptide

<400> SEQUENCE: 98

Val Ser Phe Leu Thr Gly Arg
1 5

<210> SEQ ID NO 99
<211> LENGTH: 7
<212> TYPE: PRT
<213> ORGANISM: Artificial sequence
<220> FEATURE:
<223> OTHER INFORMATION: Synthetic peptide

<400> SEQUENCE: 99

Ala Ser Leu Leu Thr Gly Leu
1 5

<210> SEQ ID NO 100
<211> LENGTH: 7
<212> TYPE: PRT
<213> ORGANISM: Artificial sequence
<220> FEATURE:
<223> OTHER INFORMATION: Synthetic peptide

<400> SEQUENCE: 100

Ala Ser Ile Leu Ile Thr Gly
1 5

<210> SEQ ID NO 101
<211> LENGTH: 7
<212> TYPE: PRT
<213> ORGANISM: Artificial sequence
<220> FEATURE:
<223> OTHER INFORMATION: Synthetic peptide

<400> SEQUENCE: 101

Val Ser Phe Leu Thr Gly Arg
1 5

<210> SEQ ID NO 102
<211> LENGTH: 7
<212> TYPE: PRT
<213> ORGANISM: Artificial sequence
<220> FEATURE:
<223> OTHER INFORMATION: Synthetic peptide

<400> SEQUENCE: 102

Ser Ala Ile Met Thr Gly Arg
1 5

<210> SEQ ID NO 103
<211> LENGTH: 7
<212> TYPE: PRT
<213> ORGANISM: Artificial sequence
<220> FEATURE:
<223> OTHER INFORMATION: Synthetic peptide

<400> SEQUENCE: 103

Ser Ala Ile Val Thr Gly Arg
1 5

<210> SEQ ID NO 104
<211> LENGTH: 6
<212> TYPE: PRT
<213> ORGANISM: Artificial sequence
<220> FEATURE:
<223> OTHER INFORMATION: Synthetic peptide

<400> SEQUENCE: 104

Thr Asn Leu Trp Arg Gly
1 5

<210> SEQ ID NO 105
<211> LENGTH: 7
<212> TYPE: PRT
<213> ORGANISM: Artificial sequence
<220> FEATURE:
<223> OTHER INFORMATION: Synthetic peptide

<400> SEQUENCE: 105

Thr Asn Leu Trp Arg Gly Gln 1 5

<210> SEQ ID NO 106
<211> LENGTH: 7
<212> TYPE: PRT
<213> ORGANISM: Artificial sequence
<220> FEATURE:
<223> OTHER INFORMATION: Synthetic peptide

<400> SEQUENCE: 106

Thr Asn Leu Cys Ala Ala Ser
1 5

<210> SEQ ID NO 107
<211> LENGTH: 7
<212> TYPE: PRT
<213> ORGANISM: Artificial sequence
<220> FEATURE:
<223> OTHER INFORMATION: Synthetic peptide

<400> SEQUENCE: 107

Val Ser Leu Trp Thr Gly Lys
1 5

<210> SEQ ID NO 108
<211> LENGTH: 6
<212> TYPE: PRT
<213> ORGANISM: Artificial sequence
<220> FEATURE:
<223> OTHER INFORMATION: Synthetic peptide

<400> SEQUENCE: 108

Ser Met Leu Leu Thr Gly
1 5

<210> SEQ ID NO 109
<211> LENGTH: 7
<212> TYPE: PRT
<213> ORGANISM: Artificial sequence
<220> FEATURE:
<223> OTHER INFORMATION: Synthetic peptide

<400> SEQUENCE: 109

Ser Met Leu Leu Thr Gly Asn
1 5

<210> SEQ ID NO 110
<211> LENGTH: 7
<212> TYPE: PRT
<213> ORGANISM: Artificial sequence
<220> FEATURE:
<223> OTHER INFORMATION: Synthetic peptide

<400> SEQUENCE: 110

Ser Met Leu Leu Thr Gly Thr
1 5

<210> SEQ ID NO 111
<211> LENGTH: 7
<212> TYPE: PRT
<213> ORGANISM: Artificial sequence
<220> FEATURE:
<223> OTHER INFORMATION: Synthetic polypeptide

<400> SEQUENCE: 111

Ala Ser Phe Met Ala Gly Gln
1 5

<210> SEQ ID NO 112
<211> LENGTH: 7
<212> TYPE: PRT
<213> ORGANISM: Artificial sequence
<220> FEATURE:
<223> OTHER INFORMATION: Synthetic peptide

<400> SEQUENCE: 112

Ala Ser Leu Leu Thr Gly Leu
1 5

<210> SEQ ID NO 113
<211> LENGTH: 7
<212> TYPE: PRT
<213> ORGANISM: Artificial sequence
<220> FEATURE:
<223> OTHER INFORMATION: Synthetic peptide

<400> SEQUENCE: 113

Gly Ser Leu Phe Thr Gly Arg
1 5

<210> SEQ ID NO 114
<211> LENGTH: 6
<212> TYPE: PRT
<213> ORGANISM: Artificial sequence
<220> FEATURE:
<223> OTHER INFORMATION: Synthetic peptide

<400> SEQUENCE: 114

Cys Gly Pro Ser Arg Ser
1 5

<210> SEQ ID NO 115
<211> LENGTH: 5
<212> TYPE: PRT
<213> ORGANISM: Artificial sequence
<220> FEATURE:
<223> OTHER INFORMATION: Synthetic peptide

<400> SEQUENCE: 115

Cys Gly Pro Ser Arg
1 5

<210> SEQ ID NO 116
<211> LENGTH: 6
<212> TYPE: PRT
<213> ORGANISM: Artificial sequence
<220> FEATURE:
<223> OTHER INFORMATION: Synthetic peptide

<400> SEQUENCE: 116

Met Cys Thr Pro Ser Arg
1 5

<210> SEQ ID NO 117
<211> LENGTH: 6
<212> TYPE: PRT
<213> ORGANISM: Artificial sequence
<220> FEATURE:
<223> OTHER INFORMATION: Synthetic peptide

<400> SEQUENCE: 117

Val Cys Thr Pro Ser Arg
1 5

<210> SEQ ID NO 118
<211> LENGTH: 6
<212> TYPE: PRT
<213> ORGANISM: Artificial sequence
<220> FEATURE:
<223> OTHER INFORMATION: Synthetic peptide

<400> SEQUENCE: 118

Leu Cys Ser Pro Ser Arg
1               5

<210> SEQ ID NO 119
<211> LENGTH: 6
<212> TYPE: PRT
<213> ORGANISM: Artificial sequence
<220> FEATURE:
<223> OTHER INFORMATION: Synthetic peptide

<400> SEQUENCE: 119

Leu Cys Ala Pro Ser Arg
1               5

<210> SEQ ID NO 120
<211> LENGTH: 6
<212> TYPE: PRT
<213> ORGANISM: Artificial sequence
<220> FEATURE:
<223> OTHER INFORMATION: Synthetic peptide

<400> SEQUENCE: 120

Leu Cys Val Pro Ser Arg
1               5

<210> SEQ ID NO 121
<211> LENGTH: 6
<212> TYPE: PRT
<213> ORGANISM: Artificial sequence
<220> FEATURE:
<223> OTHER INFORMATION: Synthetic peptide

<400> SEQUENCE: 121

Leu Cys Gly Pro Ser Arg
1               5

<210> SEQ ID NO 122
<211> LENGTH: 6
<212> TYPE: PRT
<213> ORGANISM: Artificial sequence
<220> FEATURE:
<223> OTHER INFORMATION: Synthetic peptide

<400> SEQUENCE: 122

Ile Cys Thr Pro Ala Arg
1               5

<210> SEQ ID NO 123
<211> LENGTH: 6
<212> TYPE: PRT
<213> ORGANISM: Artificial sequence
<220> FEATURE:
<223> OTHER INFORMATION: Synthetic peptide

<400> SEQUENCE: 123

Leu Cys Thr Pro Ser Lys
1               5

<210> SEQ ID NO 124
<211> LENGTH: 6
<212> TYPE: PRT
<213> ORGANISM: Artificial sequence
<220> FEATURE:
<223> OTHER INFORMATION: Synthetic peptide

<400> SEQUENCE: 124

Met Cys Thr Pro Ser Lys
1 5

<210> SEQ ID NO 125
<211> LENGTH: 6
<212> TYPE: PRT
<213> ORGANISM: Artificial sequence
<220> FEATURE:
<223> OTHER INFORMATION: Synthetic peptide

<400> SEQUENCE: 125

Val Cys Thr Pro Ser Lys
1 5

<210> SEQ ID NO 126
<211> LENGTH: 6
<212> TYPE: PRT
<213> ORGANISM: Artificial sequence
<220> FEATURE:
<223> OTHER INFORMATION: Synthetic peptide

<400> SEQUENCE: 126

Leu Cys Ser Pro Ser Lys
1 5

<210> SEQ ID NO 127
<211> LENGTH: 6
<212> TYPE: PRT
<213> ORGANISM: Artificial sequence
<220> FEATURE:
<223> OTHER INFORMATION: Synthetic peptide

<400> SEQUENCE: 127

Leu Cys Ala Pro Ser Lys
1 5

<210> SEQ ID NO 128
<211> LENGTH: 6
<212> TYPE: PRT
<213> ORGANISM: Artificial sequence
<220> FEATURE:
<223> OTHER INFORMATION: Synthetic peptide

<400> SEQUENCE: 128

Leu Cys Val Pro Ser Lys
1 5

<210> SEQ ID NO 129
<211> LENGTH: 6
<212> TYPE: PRT
<213> ORGANISM: Artificial sequence
<220> FEATURE:
<223> OTHER INFORMATION: Synthetic peptide

<400> SEQUENCE: 129

Leu Cys Gly Pro Ser Lys
1 5

<210> SEQ ID NO 130

-continued

<211> LENGTH: 6
<212> TYPE: PRT
<213> ORGANISM: Artificial sequence
<220> FEATURE:
<223> OTHER INFORMATION: Synthetic peptide

<400> SEQUENCE: 130

Leu Cys Thr Pro Ser Ala
1 5

<210> SEQ ID NO 131
<211> LENGTH: 6
<212> TYPE: PRT
<213> ORGANISM: Artificial sequence
<220> FEATURE:
<223> OTHER INFORMATION: Synthetic peptide

<400> SEQUENCE: 131

Ile Cys Thr Pro Ala Ala
1 5

<210> SEQ ID NO 132
<211> LENGTH: 6
<212> TYPE: PRT
<213> ORGANISM: Artificial sequence
<220> FEATURE:
<223> OTHER INFORMATION: Synthetic peptide

<400> SEQUENCE: 132

Met Cys Thr Pro Ser Ala
1 5

<210> SEQ ID NO 133
<211> LENGTH: 6
<212> TYPE: PRT
<213> ORGANISM: Artificial sequence
<220> FEATURE:
<223> OTHER INFORMATION: Synthetic peptide

<400> SEQUENCE: 133

Val Cys Thr Pro Ser Ala
1 5

<210> SEQ ID NO 134
<211> LENGTH: 6
<212> TYPE: PRT
<213> ORGANISM: Artificial sequence
<220> FEATURE:
<223> OTHER INFORMATION: Synthetic peptide

<400> SEQUENCE: 134

Leu Cys Ser Pro Ser Ala
1 5

<210> SEQ ID NO 135
<211> LENGTH: 6
<212> TYPE: PRT
<213> ORGANISM: Artificial sequence
<220> FEATURE:
<223> OTHER INFORMATION: Synthetic peptide

<400> SEQUENCE: 135

Leu Cys Ala Pro Ser Ala
1 5

<210> SEQ ID NO 136
<211> LENGTH: 6

<212> TYPE: PRT
<213> ORGANISM: Artificial sequence
<220> FEATURE:
<223> OTHER INFORMATION: Synthetic peptide

<400> SEQUENCE: 136

Leu Cys Val Pro Ser Ala
1               5

<210> SEQ ID NO 137
<211> LENGTH: 6
<212> TYPE: PRT
<213> ORGANISM: Artificial sequence
<220> FEATURE:
<223> OTHER INFORMATION: Synthetic peptide

<400> SEQUENCE: 137

Leu Cys Gly Pro Ser Ala
1               5

<210> SEQ ID NO 138
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 138

Leu Gly Thr Pro Ser Arg
1               5

<210> SEQ ID NO 139
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 139

Met Gly Thr Pro Ser Arg
1               5

<210> SEQ ID NO 140
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 140

Val Gly Thr Pro Ser Arg
1               5

<210> SEQ ID NO 141
<211> LENGTH: 5
<212> TYPE: PRT
<213> ORGANISM: Artificial sequence
<220> FEATURE:
<223> OTHER INFORMATION: Synthetic peptide
<220> FEATURE:

<221> NAME/KEY: FORMYLATION
<222> LOCATION: (2)..(2)

<400> SEQUENCE: 141

Leu Gly Pro Ser Arg
1               5

<210> SEQ ID NO 142
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 142

Leu Gly Ala Pro Ser Arg
1               5

<210> SEQ ID NO 143
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 143

Leu Gly Val Pro Ser Arg
1               5

<210> SEQ ID NO 144
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 144

Leu Gly Gly Pro Ser Arg
1               5

<210> SEQ ID NO 145
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 145

Ile Gly Thr Pro Ala Arg
1               5

<210> SEQ ID NO 146
<211> LENGTH: 6
<212> TYPE: PRT
<213> ORGANISM: Artificial sequence
<220> FEATURE:
<223> OTHER INFORMATION: Synthetic peptide

<220> FEATURE:
<221> NAME/KEY: FORMYLATION
<222> LOCATION: (2)..(2)

<400> SEQUENCE: 146

Leu Gly Thr Pro Ser Lys
1 5

<210> SEQ ID NO 147
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 147

Met Gly Thr Pro Ser Lys
1 5

<210> SEQ ID NO 148
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 148

Val Gly Thr Pro Ser Lys
1 5

<210> SEQ ID NO 149
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 149

Leu Gly Ser Pro Ser Lys
1 5

<210> SEQ ID NO 150
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 150

Leu Gly Ala Pro Ser Lys
1 5

<210> SEQ ID NO 151
<211> LENGTH: 6
<212> TYPE: PRT
<213> ORGANISM: Artificial sequence
<220> FEATURE:

<223> OTHER INFORMATION: Synthetic peptide
<220> FEATURE:
<221> NAME/KEY: FORMYLATION
<222> LOCATION: (2)..(2)

<400> SEQUENCE: 151

Leu Gly Val Pro Ser Lys
1               5

<210> SEQ ID NO 152
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 152

Leu Gly Gly Pro Ser Lys
1               5

<210> SEQ ID NO 153
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 153

Leu Gly Thr Pro Ser Ala
1               5

<210> SEQ ID NO 154
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 154

Met Gly Thr Pro Ser Ala
1               5

<210> SEQ ID NO 155
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 155

Val Gly Thr Pro Ser Ala
1               5

<210> SEQ ID NO 156
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 156

Leu Gly Ser Pro Ser Ala
1 5

<210> SEQ ID NO 157
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 157

Leu Gly Ala Pro Ser Ala
1 5

<210> SEQ ID NO 158
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: FORMYLATION
<222> LOCATION: (2)..(2)

<400> SEQUENCE: 158

Leu Gly Val Pro Ser Ala
1 5

<210> SEQ ID NO 159
<211> LENGTH: 6
<212> TYPE: PRT
<213> ORGANISM: Artificial sequence
<220> FEATURE:
<223> OTHER INFORMATION: Synthetic peptide

<400> SEQUENCE: 159

Leu Gly Gly Pro Ser Ala
1 5

<210> SEQ ID NO 160
<211> LENGTH: 12
<212> TYPE: PRT
<213> ORGANISM: Artificial sequence
<220> FEATURE:
<223> OTHER INFORMATION: Synthetic peptide

<400> SEQUENCE: 160

Ser Gly Ala Leu Thr Ser Gly Val His Thr Phe Pro
1 5 10

<210> SEQ ID NO 161
<211> LENGTH: 6
<212> TYPE: PRT
<213> ORGANISM: Artificial sequence
<220> FEATURE:
<223> OTHER INFORMATION: Synthetic peptide

<400> SEQUENCE: 161

Gln Ser Ser Gly Leu Tyr
1 5

<210> SEQ ID NO 162
<211> LENGTH: 5
<212> TYPE: PRT
<213> ORGANISM: Artificial sequence
<220> FEATURE:
<223> OTHER INFORMATION: Synthetic peptide

<400> SEQUENCE: 162

Val Ala Gly Pro Ser
1 5

<210> SEQ ID NO 163
<211> LENGTH: 5
<212> TYPE: PRT
<213> ORGANISM: Artificial sequence
<220> FEATURE:
<223> OTHER INFORMATION: Synthetic peptide

<400> SEQUENCE: 163

Val Leu Thr Val Val
1 5

<210> SEQ ID NO 164
<211> LENGTH: 7
<212> TYPE: PRT
<213> ORGANISM: Artificial sequence
<220> FEATURE:
<223> OTHER INFORMATION: Synthetic peptide

<400> SEQUENCE: 164

Asn Lys Gly Leu Pro Ala Pro
1 5

<210> SEQ ID NO 165
<211> LENGTH: 9
<212> TYPE: PRT
<213> ORGANISM: Artificial sequence
<220> FEATURE:
<223> OTHER INFORMATION: Synthetic peptide

<400> SEQUENCE: 165

Ser Lys Thr Lys Gly Gln Pro Arg Glu
1 5

<210> SEQ ID NO 166
<211> LENGTH: 5
<212> TYPE: PRT
<213> ORGANISM: Artificial sequence
<220> FEATURE:
<223> OTHER INFORMATION: Synthetic peptide

<400> SEQUENCE: 166

Met Thr Lys Asn Gln
1 5

<210> SEQ ID NO 167
<211> LENGTH: 10
<212> TYPE: PRT
<213> ORGANISM: Artificial sequence
<220> FEATURE:
<223> OTHER INFORMATION: Synthetic peptide

<400> SEQUENCE: 167

Thr Pro Pro Met Leu Asp Ser Asp Gly Ser 1 5 10

<210> SEQ ID NO 168
<211> LENGTH: 10
<212> TYPE: PRT
<213> ORGANISM: Artificial sequence
<220> FEATURE:
<223> OTHER INFORMATION: Synthetic peptide

<400> SEQUENCE: 168

Pro Cys Ser Arg Ser Thr Ser Gly Gly Thr
1 5 10

<210> SEQ ID NO 169
<211> LENGTH: 5
<212> TYPE: PRT
<213> ORGANISM: Artificial sequence
<220> FEATURE:
<223> OTHER INFORMATION: Synthetic peptide

<400> SEQUENCE: 169

Phe Pro Glu Pro Val
1 5

<210> SEQ ID NO 170
<211> LENGTH: 19
<212> TYPE: PRT
<213> ORGANISM: Artificial sequence
<220> FEATURE:
<223> OTHER INFORMATION: Synthetic peptide

<400> SEQUENCE: 170

Ser Gly Ala Leu Thr Ser Gly Val His Thr Phe Pro Ala Val Leu Gln
1 5 10 15

Ser Ser Gly

<210> SEQ ID NO 171
<211> LENGTH: 10
<212> TYPE: PRT
<213> ORGANISM: Artificial sequence
<220> FEATURE:
<223> OTHER INFORMATION: Synthetic peptide

<400> SEQUENCE: 171

Arg Val Glu Leu Lys Thr Pro Leu Gly Asp
1 5 10

<210> SEQ ID NO 172
<211> LENGTH: 7
<212> TYPE: PRT
<213> ORGANISM: Artificial sequence
<220> FEATURE:
<223> OTHER INFORMATION: Synthetic peptide

<400> SEQUENCE: 172

Cys Pro Arg Cys Pro Lys Pro
1 5

<210> SEQ ID NO 173
<211> LENGTH: 10
<212> TYPE: PRT
<213> ORGANISM: Artificial sequence
<220> FEATURE:
<223> OTHER INFORMATION: Synthetic peptide

<400> SEQUENCE: 173

```
Pro Pro Ser Arg Glu Glu Met Thr Lys Asn
1               5                   10


<210> SEQ ID NO 174
<211> LENGTH: 8
<212> TYPE: PRT
<213> ORGANISM: Artificial sequence
<220> FEATURE:
<223> OTHER INFORMATION: Synthetic peptide

<400> SEQUENCE: 174

Ser Ser Gly Gln Pro Glu Asn Asn
1               5


<210> SEQ ID NO 175
<211> LENGTH: 7
<212> TYPE: PRT
<213> ORGANISM: Artificial sequence
<220> FEATURE:
<223> OTHER INFORMATION: Synthetic peptide

<400> SEQUENCE: 175

His Glu Ala Leu His Asn Arg
1               5


<210> SEQ ID NO 176
<211> LENGTH: 6
<212> TYPE: PRT
<213> ORGANISM: Artificial sequence
<220> FEATURE:
<223> OTHER INFORMATION: Synthetic peptide

<400> SEQUENCE: 176

Ser Leu Ser Pro Gly Lys
1               5


<210> SEQ ID NO 177
<211> LENGTH: 5
<212> TYPE: PRT
<213> ORGANISM: Artificial sequence
<220> FEATURE:
<223> OTHER INFORMATION: Synthetic peptide

<400> SEQUENCE: 177

Ser Thr Lys Gly Pro
1               5


<210> SEQ ID NO 178
<211> LENGTH: 11
<212> TYPE: PRT
<213> ORGANISM: Artificial sequence
<220> FEATURE:
<223> OTHER INFORMATION: Synthetic peptide

<400> SEQUENCE: 178

Cys Pro Ala Pro Glu Phe Leu Gly Gly Pro Ser
1               5                   10


<210> SEQ ID NO 179
<211> LENGTH: 9
<212> TYPE: PRT
<213> ORGANISM: Artificial sequence
<220> FEATURE:
<223> OTHER INFORMATION: Synthetic peptide

<400> SEQUENCE: 179

Asp Val Ser Gln Glu Asp Pro Glu Val
```

1 5

<210> SEQ ID NO 180
<211> LENGTH: 7
<212> TYPE: PRT
<213> ORGANISM: Artificial sequence
<220> FEATURE:
<223> OTHER INFORMATION: Synthetic peptide

<400> SEQUENCE: 180

Asn Lys Gly Leu Pro Ser Ser
1 5

<210> SEQ ID NO 181
<211> LENGTH: 10
<212> TYPE: PRT
<213> ORGANISM: Artificial sequence
<220> FEATURE:
<223> OTHER INFORMATION: Synthetic peptide

<400> SEQUENCE: 181

Ser Lys Ala Lys Gly Gln Pro Arg Glu Pro
1 5 10

<210> SEQ ID NO 182
<211> LENGTH: 10
<212> TYPE: PRT
<213> ORGANISM: Artificial sequence
<220> FEATURE:
<223> OTHER INFORMATION: Synthetic peptide

<400> SEQUENCE: 182

Pro Pro Ser Gln Glu Glu Met Thr Lys Asn
1 5 10

<210> SEQ ID NO 183
<211> LENGTH: 4
<212> TYPE: PRT
<213> ORGANISM: Artificial sequence
<220> FEATURE:
<223> OTHER INFORMATION: Synthetic peptide

<400> SEQUENCE: 183

Gly Asn Val Phe
1

<210> SEQ ID NO 184
<211> LENGTH: 19
<212> TYPE: PRT
<213> ORGANISM: Artificial sequence
<220> FEATURE:
<223> OTHER INFORMATION: Synthetic peptide

<400> SEQUENCE: 184

His Glu Ala Leu His Asn His Tyr Thr Gln Lys Ser Leu Ser Leu Ser
1 5 10 15

Leu Gly Lys

<210> SEQ ID NO 185
<211> LENGTH: 13
<212> TYPE: PRT
<213> ORGANISM: Artificial sequence
<220> FEATURE:
<223> OTHER INFORMATION: Synthetic peptide

<400> SEQUENCE: 185

Ala Ser Pro Thr Ser Pro Lys Val Phe Pro Leu Ser Leu
1 5 10

<210> SEQ ID NO 186
<211> LENGTH: 5
<212> TYPE: PRT
<213> ORGANISM: Artificial sequence
<220> FEATURE:
<223> OTHER INFORMATION: Synthetic peptide

<400> SEQUENCE: 186

Gln Pro Asp Gly Asn
1 5

<210> SEQ ID NO 187
<211> LENGTH: 10
<212> TYPE: PRT
<213> ORGANISM: Artificial sequence
<220> FEATURE:
<223> OTHER INFORMATION: Synthetic peptide

<400> SEQUENCE: 187

Val Gln Gly Phe Phe Pro Gln Glu Pro Leu
1 5 10

<210> SEQ ID NO 188
<211> LENGTH: 11
<212> TYPE: PRT
<213> ORGANISM: Artificial sequence
<220> FEATURE:
<223> OTHER INFORMATION: Synthetic peptide

<400> SEQUENCE: 188

Ser Gly Gln Gly Val Thr Ala Arg Asn Phe Pro
1 5 10

<210> SEQ ID NO 189
<211> LENGTH: 7
<212> TYPE: PRT
<213> ORGANISM: Artificial sequence
<220> FEATURE:
<223> OTHER INFORMATION: Synthetic peptide

<400> SEQUENCE: 189

Ser Gly Asp Leu Tyr Thr Thr
1 5

<210> SEQ ID NO 190
<211> LENGTH: 4
<212> TYPE: PRT
<213> ORGANISM: Artificial sequence
<220> FEATURE:
<223> OTHER INFORMATION: Synthetic peptide

<400> SEQUENCE: 190

Pro Ala Thr Gln
1

<210> SEQ ID NO 191
<211> LENGTH: 4
<212> TYPE: PRT
<213> ORGANISM: Artificial sequence
<220> FEATURE:
<223> OTHER INFORMATION: Synthetic peptide

<400> SEQUENCE: 191

His Arg Pro Ala

-continued

1

<210> SEQ ID NO 192
<211> LENGTH: 5
<212> TYPE: PRT
<213> ORGANISM: Artificial sequence
<220> FEATURE:
<223> OTHER INFORMATION: Synthetic peptide

<400> SEQUENCE: 192

Leu Leu Gly Ser Glu
1               5

<210> SEQ ID NO 193
<211> LENGTH: 8
<212> TYPE: PRT
<213> ORGANISM: Artificial sequence
<220> FEATURE:
<223> OTHER INFORMATION: Synthetic peptide

<400> SEQUENCE: 193

Gly Leu Arg Asp Ala Ser Gly Val
1               5

<210> SEQ ID NO 194
<211> LENGTH: 10
<212> TYPE: PRT
<213> ORGANISM: Artificial sequence
<220> FEATURE:
<223> OTHER INFORMATION: Synthetic peptide

<400> SEQUENCE: 194

Ser Ser Gly Lys Ser Ala Val Gln Gly Pro
1               5                   10

<210> SEQ ID NO 195
<211> LENGTH: 4
<212> TYPE: PRT
<213> ORGANISM: Artificial sequence
<220> FEATURE:
<223> OTHER INFORMATION: Synthetic peptide

<400> SEQUENCE: 195

Gly Cys Tyr Ser
1

<210> SEQ ID NO 196
<211> LENGTH: 4
<212> TYPE: PRT
<213> ORGANISM: Artificial sequence
<220> FEATURE:
<223> OTHER INFORMATION: Synthetic peptide

<400> SEQUENCE: 196

Cys Ala Glu Pro
1

<210> SEQ ID NO 197
<211> LENGTH: 24
<212> TYPE: PRT
<213> ORGANISM: Artificial sequence
<220> FEATURE:
<223> OTHER INFORMATION: Synthetic peptide

<400> SEQUENCE: 197

Ser Gly Asn Thr Phe Arg Pro Glu Val His Leu Leu Pro Pro Pro Ser
1               5                   10                  15

Glu Glu Leu Ala Leu Asn Glu Leu
20

<210> SEQ ID NO 198
<211> LENGTH: 5
<212> TYPE: PRT
<213> ORGANISM: Artificial sequence
<220> FEATURE:
<223> OTHER INFORMATION: Synthetic peptide

<400> SEQUENCE: 198

Ala Arg Gly Phe Ser
1 5

<210> SEQ ID NO 199
<211> LENGTH: 11
<212> TYPE: PRT
<213> ORGANISM: Artificial sequence
<220> FEATURE:
<223> OTHER INFORMATION: Synthetic peptide

<400> SEQUENCE: 199

Gln Gly Ser Gln Glu Leu Pro Arg Glu Lys Tyr
1 5 10

<210> SEQ ID NO 200
<211> LENGTH: 4
<212> TYPE: PRT
<213> ORGANISM: Artificial sequence
<220> FEATURE:
<223> OTHER INFORMATION: Synthetic peptide

<400> SEQUENCE: 200

Ala Ala Glu Asp
1

<210> SEQ ID NO 201
<211> LENGTH: 4
<212> TYPE: PRT
<213> ORGANISM: Artificial sequence
<220> FEATURE:
<223> OTHER INFORMATION: Synthetic peptide

<400> SEQUENCE: 201

His Glu Ala Leu
1

<210> SEQ ID NO 202
<211> LENGTH: 25
<212> TYPE: PRT
<213> ORGANISM: Artificial sequence
<220> FEATURE:
<223> OTHER INFORMATION: Synthetic peptide

<400> SEQUENCE: 202

Ile Asp Arg Leu Ala Gly Lys Pro Thr His Val Asn Val Ser Val Val
1 5 10 15

Met Ala Glu Val Asp Gly Thr Cys Tyr
20 25

<210> SEQ ID NO 203
<211> LENGTH: 8
<212> TYPE: PRT
<213> ORGANISM: Artificial sequence
<220> FEATURE:
<223> OTHER INFORMATION: Synthetic peptide

<400> SEQUENCE: 203

Asn Ser Gly Ala Leu Thr Ser Gly
1 5

<210> SEQ ID NO 204
<211> LENGTH: 11
<212> TYPE: PRT
<213> ORGANISM: Artificial sequence
<220> FEATURE:
<223> OTHER INFORMATION: Synthetic peptide

<400> SEQUENCE: 204

Asn Ser Gly Ala Leu Cys Thr Pro Ser Arg Gly
1 5 10

<210> SEQ ID NO 205
<211> LENGTH: 5
<212> TYPE: PRT
<213> ORGANISM: Artificial sequence
<220> FEATURE:
<223> OTHER INFORMATION: Synthetic peptide

<400> SEQUENCE: 205

Cys Thr Pro Ser Arg
1 5

<210> SEQ ID NO 206
<211> LENGTH: 9
<212> TYPE: PRT
<213> ORGANISM: Artificial sequence
<220> FEATURE:
<223> OTHER INFORMATION: Synthetic peptide

<400> SEQUENCE: 206

Asn Leu Cys Thr Pro Ser Arg Ala Pro
1 5

<210> SEQ ID NO 207
<211> LENGTH: 7
<212> TYPE: PRT
<213> ORGANISM: Artificial sequence
<220> FEATURE:
<223> OTHER INFORMATION: Synthetic peptide

<400> SEQUENCE: 207

Lys Ala Lys Gly Gln Pro Arg
1 5

<210> SEQ ID NO 208
<211> LENGTH: 10
<212> TYPE: PRT
<213> ORGANISM: Artificial sequence
<220> FEATURE:
<223> OTHER INFORMATION: Synthetic peptide

<400> SEQUENCE: 208

Lys Ala Lys Gly Leu Cys Thr Pro Ser Arg
1 5 10

<210> SEQ ID NO 209
<211> LENGTH: 5
<212> TYPE: PRT
<213> ORGANISM: Artificial sequence
<220> FEATURE:
<223> OTHER INFORMATION: Synthetic peptide

<400> SEQUENCE: 209

Leu Cys Thr Pro Ser
1 5

<210> SEQ ID NO 210
<211> LENGTH: 6
<212> TYPE: PRT
<213> ORGANISM: Artificial sequence
<220> FEATURE:
<223> OTHER INFORMATION: Synthetic peptide

<400> SEQUENCE: 210

Arg Thr Val Ala Ala Pro
1 5

<210> SEQ ID NO 211
<211> LENGTH: 5
<212> TYPE: PRT
<213> ORGANISM: Artificial sequence
<220> FEATURE:
<223> OTHER INFORMATION: Synthetic peptide

<400> SEQUENCE: 211

Tyr Pro Arg Glu Ala
1 5

<210> SEQ ID NO 212
<211> LENGTH: 8
<212> TYPE: PRT
<213> ORGANISM: Artificial sequence
<220> FEATURE:
<223> OTHER INFORMATION: Synthetic peptide

<400> SEQUENCE: 212

Asp Asn Ala Leu Gln Ser Gly Asn
1 5

<210> SEQ ID NO 213
<211> LENGTH: 9
<212> TYPE: PRT
<213> ORGANISM: Artificial sequence
<220> FEATURE:
<223> OTHER INFORMATION: Synthetic peptide

<400> SEQUENCE: 213

Thr Glu Gln Asp Ser Lys Asp Ser Thr
1 5

<210> SEQ ID NO 214
<211> LENGTH: 6
<212> TYPE: PRT
<213> ORGANISM: Artificial sequence
<220> FEATURE:
<223> OTHER INFORMATION: Synthetic peptide

<400> SEQUENCE: 214

His Gln Gly Leu Ser Ser
1 5

<210> SEQ ID NO 215
<211> LENGTH: 4
<212> TYPE: PRT
<213> ORGANISM: Artificial sequence
<220> FEATURE:
<223> OTHER INFORMATION: Synthetic peptide

<400> SEQUENCE: 215

Arg Gly Glu Cys
1

<210> SEQ ID NO 216
<211> LENGTH: 6
<212> TYPE: PRT
<213> ORGANISM: Artificial sequence
<220> FEATURE:
<223> OTHER INFORMATION: Synthetic peptide

<400> SEQUENCE: 216

Gln Pro Lys Ala Ala Pro
1 5

<210> SEQ ID NO 217
<211> LENGTH: 7
<212> TYPE: PRT
<213> ORGANISM: Artificial sequence
<220> FEATURE:
<223> OTHER INFORMATION: Synthetic peptide

<400> SEQUENCE: 217

Asp Phe Tyr Pro Gly Ala Val
1 5

<210> SEQ ID NO 218
<211> LENGTH: 8
<212> TYPE: PRT
<213> ORGANISM: Artificial sequence
<220> FEATURE:
<223> OTHER INFORMATION: Synthetic peptide

<400> SEQUENCE: 218

Asp Ser Ser Pro Val Lys Ala Gly
1 5

<210> SEQ ID NO 219
<211> LENGTH: 6
<212> TYPE: PRT
<213> ORGANISM: Artificial sequence
<220> FEATURE:
<223> OTHER INFORMATION: Synthetic peptide

<400> SEQUENCE: 219

Ala Pro Thr Glu Cys Ser
1 5

<210> SEQ ID NO 220
<211> LENGTH: 13
<212> TYPE: PRT
<213> ORGANISM: Artificial sequence
<220> FEATURE:
<223> OTHER INFORMATION: Synthetic peptide

<400> SEQUENCE: 220

Asp Asn Ala Leu Cys Thr Pro Ser Arg Gln Ser Gly Asn
1 5 10

<210> SEQ ID NO 221
<211> LENGTH: 4
<212> TYPE: PRT
<213> ORGANISM: Artificial sequence
<220> FEATURE:
<223> OTHER INFORMATION: Synthetic peptide

<400> SEQUENCE: 221

Asp Asn Ala Leu
1

<210> SEQ ID NO 222
<211> LENGTH: 4
<212> TYPE: PRT
<213> ORGANISM: Artificial sequence
<220> FEATURE:
<223> OTHER INFORMATION: Synthetic peptide

<400> SEQUENCE: 222

Gln Ser Gly Asn
1

<210> SEQ ID NO 223
<211> LENGTH: 8
<212> TYPE: PRT
<213> ORGANISM: Artificial sequence
<220> FEATURE:
<223> OTHER INFORMATION: Synthetic peptide

<400> SEQUENCE: 223

Asp Tyr Lys Asp Asp Asp Asp Lys
1 5

<210> SEQ ID NO 224
<211> LENGTH: 7
<212> TYPE: PRT
<213> ORGANISM: Artificial sequence
<220> FEATURE:
<223> OTHER INFORMATION: Synthetic peptide

<400> SEQUENCE: 224

Ser His Glu Asp Pro Glu Val
1 5

<210> SEQ ID NO 225
<211> LENGTH: 5
<212> TYPE: PRT
<213> ORGANISM: Artificial sequence
<220> FEATURE:
<223> OTHER INFORMATION: Synthetic peptide

<400> SEQUENCE: 225

Asp Ser Asp Gly Ser
1 5

<210> SEQ ID NO 226
<211> LENGTH: 14
<212> TYPE: PRT
<213> ORGANISM: Artificial sequence
<220> FEATURE:
<223> OTHER INFORMATION: Synthetic peptide

<400> SEQUENCE: 226

Ser Leu Ser Pro Gly Ser Leu Cys Thr Pro Ser Arg Gly Ser
1 5 10

<210> SEQ ID NO 227
<211> LENGTH: 4
<212> TYPE: PRT
<213> ORGANISM: Artificial sequence
<220> FEATURE:
<223> OTHER INFORMATION: Synthetic peptide

<400> SEQUENCE: 227

Pro Arg Glu Ala

-continued

1

<210> SEQ ID NO 228
<211> LENGTH: 5
<212> TYPE: PRT
<213> ORGANISM: Artificial sequence
<220> FEATURE:
<223> OTHER INFORMATION: Synthetic peptide

<400> SEQUENCE: 228

Gln Ser Ser Gly Leu
1               5

<210> SEQ ID NO 229
<211> LENGTH: 330
<212> TYPE: PRT
<213> ORGANISM: Homo sapiens

<400> SEQUENCE: 229

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

```
Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 230
<211> LENGTH: 21
<212> TYPE: PRT
<213> ORGANISM: Artificial sequence
<220> FEATURE:
<223> OTHER INFORMATION: Synthetic peptide

<400> SEQUENCE: 230

```
Pro Lys Ser Cys Asp Thr Pro Pro Pro Cys Pro Arg Cys Pro Ala Pro
1               5                   10                  15

Glu Leu Leu Gly Gly
            20
```

<210> SEQ ID NO 231
<211> LENGTH: 12
<212> TYPE: PRT
<213> ORGANISM: Artificial Sequence
<220> FEATURE:
<223> OTHER INFORMATION: Synthetic peptide

<400> SEQUENCE: 231

```
Ala Ser Thr Lys Gly Leu Cys Thr Pro Ser Arg Val
1               5                   10
```

<210> SEQ ID NO 232
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: FORMYLATION

<400> SEQUENCE: 232

```
Ala Ser Thr Lys Gly Leu Gly Thr Pro Ser Arg Val
1               5                   10
```

<210> SEQ ID NO 233
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: FORMYLATION, conjugated to a covalently bound moiety

<400> SEQUENCE: 233

```
Ala Ser Thr Lys Gly Leu Gly Thr Pro Ser Arg Val
1               5                   10
```

<210> SEQ ID NO 234
<211> LENGTH: 14
<212> TYPE: PRT
<213> ORGANISM: Artificial sequence
<220> FEATURE:
<223> OTHER INFORMATION: Synthetic peptide

<400> SEQUENCE: 234

Leu Cys Thr Pro Ser Arg Ser Lys Ser Thr Ser Gly Gly Thr
1 5 10

<210> SEQ ID NO 235
<211> LENGTH: 24
<212> TYPE: PRT
<213> ORGANISM: Artificial sequence
<220> FEATURE:
<223> OTHER INFORMATION: Synthetic peptide

<400> SEQUENCE: 235

Asn Ser Gly Ala Leu Cys Thr Pro Ser Arg Gly Val His Thr Phe Pro
1 5 10 15

Ala Val Leu Gln Ser Ser Gly Leu
20

<210> SEQ ID NO 236
<211> LENGTH: 26
<212> TYPE: PRT
<213> ORGANISM: Artificial sequence
<220> FEATURE:
<223> OTHER INFORMATION: Synthetic peptide

<400> SEQUENCE: 236

Glu Pro Lys Ser Cys Asp Lys Thr His Thr Cys Pro Pro Cys Pro Leu
1 5 10 15

Cys Thr Pro Ser Arg Glu Leu Leu Gly Gly
20 25

<210> SEQ ID NO 237
<211> LENGTH: 12
<212> TYPE: PRT
<213> ORGANISM: Artificial sequence
<220> FEATURE:
<223> OTHER INFORMATION: Synthetic peptide

<400> SEQUENCE: 237

Ser Lys Ala Lys Gly Leu Cys Thr Pro Ser Arg Glu
1 5 10

<210> SEQ ID NO 238
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: FORMYLATION

<400> SEQUENCE: 238

Leu Gly Thr Pro Ser Arg Ser Lys Ser Thr Ser Gly Gly Thr
1 5 10

<210> SEQ ID NO 239
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: FORMYLATION

<400> SEQUENCE: 239

Asn Ser Gly Ala Leu Gly Thr Pro Ser Arg Gly Val His Thr Phe Pro
1 5 10 15

Ala Val Leu Gln Ser Ser Gly Leu
20

<210> SEQ ID NO 240
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (17)..(17)
<223> OTHER INFORMATION: FORMYLATION

<400> SEQUENCE: 240

Glu Pro Lys Ser Cys Asp Lys Thr His Thr Cys Pro Pro Cys Pro Leu
1 5 10 15

Gly Thr Pro Ser Arg Glu Leu Leu Gly Gly
20 25

<210> SEQ ID NO 241
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: FORMYLATION

<400> SEQUENCE: 241

Asn Leu Gly Thr Pro Ser Arg Ala Pro
1 5

<210> SEQ ID NO 242
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: FORMYLATION

<400> SEQUENCE: 242

Ser Lys Ala Lys Gly Leu Gly Thr Pro Ser Arg Glu
1 5 10

<210> SEQ ID NO 243
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (2)..(2)
<223> OTHER INFORMATION: FORMYLATION, conjugated to a covalently bound moiety

<400> SEQUENCE: 243

Leu Gly Thr Pro Ser Arg Ser Lys Ser Thr Ser Gly Gly Thr
1 5 10

<210> SEQ ID NO 244
<211> LENGTH: 24
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (6)..(6)
<223> OTHER INFORMATION: FORMYLATION, conjugated to a covalently bound moiety

<400> SEQUENCE: 244

```
Asn Ser Gly Ala Leu Gly Thr Pro Ser Arg Gly Val His Thr Phe Pro
1               5                   10                  15

Ala Val Leu Gly Ser Ser Gly Leu
            20
```

<210> SEQ ID NO 245
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (17)..(17)
<223> OTHER INFORMATION: FORMYLATION, conjugated to a covalently bound moiety

<400> SEQUENCE: 245

```
Glu Pro Lys Ser Cys Asp Lys Thr His Thr Cys Pro Pro Cys Pro Leu
1               5                   10                  15

Gly Thr Pro Ser Arg Glu Leu Leu Gly Gly
            20                  25
```

<210> SEQ ID NO 246
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (3)..(3)
<223> OTHER INFORMATION: FORMYLATION, conjugated to a covalently bound moiety

<400> SEQUENCE: 246

```
Asn Leu Gly Thr Pro Ser Arg Ala Pro
1               5
```

<210> SEQ ID NO 247
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: FORMYLATION, conjugated to a covalently bound moiety

<400> SEQUENCE: 247

```
Ser Lys Ala Lys Gly Leu Gly Thr Pro Ser Arg Glu
1               5                   10
```

<210> SEQ ID NO 248
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: FORMYLATION

<400> SEQUENCE: 248

Asp Asn Ala Leu Gly Thr Pro Ser Arg Gln Ser Gly Asn
1               5                   10

<210> SEQ ID NO 249
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: FORMYLATION, conjugated to a covalently bound
      moiety

<400> SEQUENCE: 249

Asp Asn Ala Leu Gly Thr Pro Ser Arg Gln Ser Gly Asn
1               5                   10

<210> SEQ ID NO 250
<211> LENGTH: 14
<212> TYPE: PRT
<213> ORGANISM: Artificial Sequence
<220> FEATURE:
<223> OTHER INFORMATION: Synthetic peptide

<400> SEQUENCE: 250

Asp Val Ser His Glu Asp Leu Cys Thr Pro Ser Arg Glu Val
1               5                   10

<210> SEQ ID NO 251
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: FORMYLATION

<400> SEQUENCE: 251

Asp Val Ser His Glu Asp Leu Gly Thr Pro Ser Arg Glu Val
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (8)..(8)
<223> OTHER INFORMATION: FORMYLATION, conjugated to a covalently bound
      moiety

<400> SEQUENCE: 252

Asp Val Ser His Glu Asp Leu Gly Thr Pro Ser Arg Glu Val
1               5                   10

<210> SEQ ID NO 253
<211> LENGTH: 334
<212> TYPE: PRT
<213> ORGANISM: Artificial sequence
<220> FEATURE:
<223> OTHER INFORMATION: synthetic polypeptide

<400> SEQUENCE: 253

Ala Ser Thr Lys Gly Leu Cys Thr Pro Ser Arg Val Phe Pro Leu Ala
1               5                   10                  15

Pro Ser Ser Lys Ser Thr Ser Gly Gly Thr Ala Ala Leu Gly Cys Leu
            20                  25                  30

Val Lys Asp Tyr Phe Pro Glu Pro Val Thr Val Ser Trp Asn Ser Gly
        35                  40                  45

Ala Leu Thr Ser Gly Val His Thr Phe Pro Ala Val Leu Gln Ser Ser
    50                  55                  60

Gly Leu Tyr Ser Leu Ser Ser Val Val Thr Val Pro Ser Ser Ser Leu
65                  70                  75                  80

Gly Thr Gln Thr Tyr Ile Cys Asn Val Asn His Lys Pro Ser Asn Thr
                85                  90                  95

Lys Val Asp Lys Lys Val Glu Pro Lys Ser Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330

<210> SEQ ID NO 254

<211> LENGTH: 334
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (7)..(7)
<223> OTHER INFORMATION: FORMYLATION

<400> SEQUENCE: 254

```
Ala Ser Thr Lys Gly Leu Gly Thr Pro Ser Arg Val Phe Pro Leu Ala
1               5                   10                  15

Pro Ser Ser Lys Ser Thr Ser Gly Gly Thr Ala Ala Leu Gly Cys Leu
            20                  25                  30

Val Lys Asp Tyr Phe Pro Glu Pro Val Thr Val Ser Trp Asn Ser Gly
        35                  40                  45

Ala Leu Thr Ser Gly Val His Thr Phe Pro Ala Val Leu Gln Ser Ser
    50                  55                  60

Gly Leu Tyr Ser Leu Ser Ser Val Val Thr Val Pro Ser Ser Ser Leu
65                  70                  75                  80

Gly Thr Gln Thr Tyr Ile Cys Asn Val Asn His Lys Pro Ser Asn Thr
                85                  90                  95

Lys Val Asp Lys Lys Val Glu Pro Lys Ser Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330
```

<210> SEQ ID NO 255
<211> LENGTH: 334
<212> TYPE: PRT

```
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (7)..(7)
<223> OTHER INFORMATION: FORMYLATION, conjugated to a covalently bound
      moiety

<400> SEQUENCE: 255

Ala Ser Thr Lys Gly Leu Gly Thr Pro Ser Arg Val Phe Pro Leu Ala
1               5                   10                  15

Pro Ser Ser Lys Ser Thr Ser Gly Gly Thr Ala Ala Leu Gly Cys Leu
            20                  25                  30

Val Lys Asp Tyr Phe Pro Glu Pro Val Thr Val Ser Trp Asn Ser Gly
        35                  40                  45

Ala Leu Thr Ser Gly Val His Thr Phe Pro Ala Val Leu Gln Ser Ser
    50                  55                  60

Gly Leu Tyr Ser Leu Ser Ser Val Val Thr Val Pro Ser Ser Ser Leu
65                  70                  75                  80

Gly Thr Gln Thr Tyr Ile Cys Asn Val Asn His Lys Pro Ser Asn Thr
                85                  90                  95

Lys Val Asp Lys Lys Val Glu Pro Lys Ser Cys Asp Lys Thr His Thr
            100                 105                 110

Cys Pro Pro Cys Pro Ala Pro Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330


<210> SEQ ID NO 256
<211> LENGTH: 332
<212> TYPE: PRT
<213> ORGANISM: Artificial sequence
```

<220> FEATURE:
<223> OTHER INFORMATION: synthetic polypeptide

<400> SEQUENCE: 256

Ala Ser Thr Lys Gly Pro Ser Val Phe Pro Leu Cys Thr Pro Ser Arg
1 5 10 15

Ser Lys Ser Thr Ser Gly Gly Thr Ala Ala Leu Gly Cys Leu Val Lys
20 25 30

Asp Tyr Phe Pro Glu Pro Val Thr Val Ser Trp Asn Ser Gly Ala Leu
35 40 45

Thr Ser Gly Val His Thr Phe Pro Ala Val Leu Gln Ser Ser Gly Leu
50 55 60

Tyr Ser Leu Ser Ser Val Val Thr Val Pro Ser Ser Ser Leu Gly Thr
65 70 75 80

Gln Thr Tyr Ile Cys Asn Val Asn His Lys Pro Ser Asn Thr Lys Val
85 90 95

Asp Lys Lys Val Glu Pro Lys Ser Cys Asp Lys Thr His Thr Cys Pro
100 105 110

Pro Cys Pro Ala Pro Glu Leu Leu Gly Gly Pro Ser Val Phe Leu Phe
115 120 125

Pro Pro Lys Pro Lys Asp Thr Leu Met Ile Ser Arg Thr Pro Glu Val
130 135 140

Thr Cys Val Val Val Asp Val Ser His Glu Asp Pro Glu Val Lys Phe
145 150 155 160

Asn Trp Tyr Val Asp Gly Val Glu Val His Asn Ala Lys Thr Lys Pro
165 170 175

Arg Glu Glu Gln Tyr Asn Ser Thr Tyr Arg Val Val Ser Val Leu Thr
180 185 190

Val Leu His Gln Asp Trp Leu Asn Gly Lys Glu Tyr Lys Cys Lys Val
195 200 205

Ser Asn Lys Ala Leu Pro Ala Pro Ile Glu Lys Thr Ile Ser Lys Ala
210 215 220

Lys Gly Gln Pro Arg Glu Pro Gln Val Tyr Thr Leu Pro Pro Ser Arg
225 230 235 240

Glu Glu Met Thr Lys Asn Gln Val Ser Leu Thr Cys Leu Val Lys Gly
245 250 255

Phe Tyr Pro Ser Asp Ile Ala Val Glu Trp Glu Ser Asn Gly Gln Pro
260 265 270

Glu Asn Asn Tyr Lys Thr Thr Pro Pro Val Leu Asp Ser Asp Gly Ser
275 280 285

Phe Phe Leu Tyr Ser Lys Leu Thr Val Asp Lys Ser Arg Trp Gln Gln
290 295 300

Gly Asn Val Phe Ser Cys Ser Val Met His Glu Ala Leu His Asn His
305 310 315 320

Tyr Thr Gln Lys Ser Leu Ser Leu Ser Pro Gly Lys
325 330

<210> SEQ ID NO 257
<211> LENGTH: 332
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (12)..(12)
<223> OTHER INFORMATION: FORMYLATION

<400> SEQUENCE: 257

Ala Ser Thr Lys Gly Pro Ser Val Phe Pro Leu Gly Thr Pro Ser Arg
1 5 10 15

Ser Lys Ser Thr Ser Gly Gly Thr Ala Ala Leu Gly Cys Leu Val Lys
20 25 30

Asp Tyr Phe Pro Glu Pro Val Thr Val Ser Trp Asn Ser Gly Ala Leu
35 40 45

Thr Ser Gly Val His Thr Phe Pro Ala Val Leu Gln Ser Ser Gly Leu
50 55 60

Tyr Ser Leu Ser Ser Val Val Thr Val Pro Ser Ser Ser Leu Gly Thr
65 70 75 80

Gln Thr Tyr Ile Cys Asn Val Asn His Lys Pro Ser Asn Thr Lys Val
85 90 95

Asp Lys Lys Val Glu Pro Lys Ser Cys Asp Lys Thr His Thr Cys Pro
100 105 110

Pro Cys Pro Ala Pro Glu Leu Leu Gly Gly Pro Ser Val Phe Leu Phe
115 120 125

Pro Pro Lys Pro Lys Asp Thr Leu Met Ile Ser Arg Thr Pro Glu Val
130 135 140

Thr Cys Val Val Val Asp Val Ser His Glu Asp Pro Glu Val Lys Phe
145 150 155 160

Asn Trp Tyr Val Asp Gly Val Glu Val His Asn Ala Lys Thr Lys Pro
165 170 175

Arg Glu Glu Gln Tyr Asn Ser Thr Tyr Arg Val Val Ser Val Leu Thr
180 185 190

Val Leu His Gln Asp Trp Leu Asn Gly Lys Glu Tyr Lys Cys Lys Val
195 200 205

Ser Asn Lys Ala Leu Pro Ala Pro Ile Glu Lys Thr Ile Ser Lys Ala
210 215 220

Lys Gly Gln Pro Arg Glu Pro Gln Val Tyr Thr Leu Pro Pro Ser Arg
225 230 235 240

Glu Glu Met Thr Lys Asn Gln Val Ser Leu Thr Cys Leu Val Lys Gly
245 250 255

Phe Tyr Pro Ser Asp Ile Ala Val Glu Trp Glu Ser Asn Gly Gln Pro
260 265 270

Glu Asn Asn Tyr Lys Thr Thr Pro Pro Val Leu Asp Ser Asp Gly Ser
275 280 285

Phe Phe Leu Tyr Ser Lys Leu Thr Val Asp Lys Ser Arg Trp Gln Gln
290 295 300

Gly Asn Val Phe Ser Cys Ser Val Met His Glu Ala Leu His Asn His
305 310 315 320

Tyr Thr Gln Lys Ser Leu Ser Leu Ser Pro Gly Lys
325 330

<210> SEQ ID NO 258
<211> LENGTH: 332
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (12)..(12)
<223> OTHER INFORMATION: FORMYLATION, conjugated to a covalently bound moiety

<400> SEQUENCE: 258

Ala Ser Thr Lys Gly Pro Ser Val Phe Pro Leu Gly Thr Pro Ser Arg
1 5 10 15

Ser Lys Ser Thr Ser Gly Gly Thr Ala Ala Leu Gly Cys Leu Val Lys
20 25 30

Asp Tyr Phe Pro Glu Pro Val Thr Val Ser Trp Asn Ser Gly Ala Leu
35 40 45

Thr Ser Gly Val His Thr Phe Pro Ala Val Leu Gln Ser Ser Gly Leu
50 55 60

Tyr Ser Leu Ser Ser Val Val Thr Val Pro Ser Ser Ser Leu Gly Thr
65 70 75 80

Gln Thr Tyr Ile Cys Asn Val Asn His Lys Pro Ser Asn Thr Lys Val
85 90 95

Asp Lys Lys Val Glu Pro Lys Ser Cys Asp Lys Thr His Thr Cys Pro
100 105 110

Pro Cys Pro Ala Pro Glu Leu Leu Gly Gly Pro Ser Val Phe Leu Phe
115 120 125

Pro Pro Lys Pro Lys Asp Thr Leu Met Ile Ser Arg Thr Pro Glu Val
130 135 140

Thr Cys Val Val Val Asp Val Ser His Glu Asp Pro Glu Val Lys Phe
145 150 155 160

Asn Trp Tyr Val Asp Gly Val Glu Val His Asn Ala Lys Thr Lys Pro
165 170 175

Arg Glu Glu Gln Tyr Asn Ser Thr Tyr Arg Val Val Ser Val Leu Thr
180 185 190

Val Leu His Gln Asp Trp Leu Asn Gly Lys Glu Tyr Lys Cys Lys Val
195 200 205

Ser Asn Lys Ala Leu Pro Ala Pro Ile Glu Lys Thr Ile Ser Lys Ala
210 215 220

Lys Gly Gln Pro Arg Glu Pro Gln Val Tyr Thr Leu Pro Pro Ser Arg
225 230 235 240

Glu Glu Met Thr Lys Asn Gln Val Ser Leu Thr Cys Leu Val Lys Gly
245 250 255

Phe Tyr Pro Ser Asp Ile Ala Val Glu Trp Glu Ser Asn Gly Gln Pro
260 265 270

Glu Asn Asn Tyr Lys Thr Thr Pro Pro Val Leu Asp Ser Asp Gly Ser
275 280 285

Phe Phe Leu Tyr Ser Lys Leu Thr Val Asp Lys Ser Arg Trp Gln Gln
290 295 300

Gly Asn Val Phe Ser Cys Ser Val Met His Glu Ala Leu His Asn His
305 310 315 320

Tyr Thr Gln Lys Ser Leu Ser Leu Ser Pro Gly Lys
325 330

<210> SEQ ID NO 259
<211> LENGTH: 333
<212> TYPE: PRT
<213> ORGANISM: Artificial sequence
<220> FEATURE:
<223> OTHER INFORMATION: synthetic polypeptide

<400> SEQUENCE: 259

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr

```
            20                  25                  30

Phe Pro Glu Pro Val Thr Val Ser Trp Asn Ser Gly Ala Leu Cys Thr
        35                  40                  45

Pro Ser Arg Gly Val His Thr Phe Pro Ala Val Leu Gln Ser Ser Gly
    50                  55                  60

Leu Tyr Ser Leu Ser Ser Val Val Thr Val Pro Ser Ser Ser Leu Gly
65                  70                  75                  80

Thr Gln Thr Tyr Ile Cys Asn Val Asn His Lys Pro Ser Asn Thr Lys
                85                  90                  95

Val Asp Lys Lys Val Glu Pro Lys Ser Cys Asp Lys Thr His Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
    210                 215                 220

Ala Lys Gly Gln Pro Arg Glu Pro Gln Val Tyr Thr Leu Pro Pro Ser
225                 230                 235                 240

Arg Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330


<210> SEQ ID NO 260
<211> LENGTH: 333
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (47)..(47)
<223> OTHER INFORMATION: FORMYLATION

<400> SEQUENCE: 260

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Gly Thr
        35                  40                  45

Pro Ser Arg Gly Val His Thr Phe Pro Ala Val Leu Gln Ser Ser Gly
    50                  55                  60

Leu Tyr Ser Leu Ser Ser Val Val Thr Val Pro Ser Ser Ser Leu Gly
65                  70                  75                  80

Thr Gln Thr Tyr Ile Cys Asn Val Asn His Lys Pro Ser Asn Thr Lys
                85                  90                  95

Val Asp Lys Lys Val Glu Pro Lys Ser Cys Asp Lys Thr His Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
    210                 215                 220

Ala Lys Gly Gln Pro Arg Glu Pro Gln Val Tyr Thr Leu Pro Pro Ser
225                 230                 235                 240

Arg Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330


<210> SEQ ID NO 261
<211> LENGTH: 333
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (47)..(47)
<223> OTHER INFORMATION: FORMYLATION, conjugated to a covalently bound
      moiety

<400> SEQUENCE: 261

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Gly Thr
```

```
        35                  40                  45

Pro Ser Arg Gly Val His Thr Phe Pro Ala Val Leu Gln Ser Ser Gly
    50                  55                  60

Leu Tyr Ser Leu Ser Ser Val Val Thr Val Pro Ser Ser Ser Leu Gly
65                  70                  75                  80

Thr Gln Thr Tyr Ile Cys Asn Val Asn His Lys Pro Ser Asn Thr Lys
                85                  90                  95

Val Asp Lys Lys Val Glu Pro Lys Ser Cys Asp Lys Thr His Thr Cys
            100                 105                 110

Pro Pro Cys Pro Ala Pro Glu Leu Leu Gly Gly Pro Ser Val Phe Leu
        115                 120                 125

Phe Pro Pro Lys Pro Lys Asp Thr Leu Met Ile Ser Arg Thr Pro Glu
    130                 135                 140

Val Thr Cys Val Val Val Asp Val Ser His Glu Asp Pro Glu Val Lys
145                 150                 155                 160

Phe Asn Trp Tyr Val Asp Gly Val Glu Val His Asn Ala Lys Thr Lys
                165                 170                 175

Pro Arg Glu Glu Gln Tyr Asn Ser Thr Tyr Arg Val Val Ser Val Leu
            180                 185                 190

Thr Val Leu His Gln Asp Trp Leu Asn Gly Lys Glu Tyr Lys Cys Lys
        195                 200                 205

Val Ser Asn Lys Ala Leu Pro Ala Pro Ile Glu Lys Thr Ile Ser Lys
    210                 215                 220

Ala Lys Gly Gln Pro Arg Glu Pro Gln Val Tyr Thr Leu Pro Pro Ser
225                 230                 235                 240

Arg Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330


<210> SEQ ID NO 262
<211> LENGTH: 334
<212> TYPE: PRT
<213> ORGANISM: Artificial sequence
<220> FEATURE:
<223> OTHER INFORMATION: synthetic polypeptide

<400> SEQUENCE: 262

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Leu Cys Thr Pro Ser Arg Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330


<210> SEQ ID NO 263
<211> LENGTH: 334
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (115)..(115)
<223> OTHER INFORMATION: FORMYLATION

<400> SEQUENCE: 263

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Leu Gly Thr Pro Ser Arg Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330


<210> SEQ ID NO 264
<211> LENGTH: 334
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (115)..(115)
<223> OTHER INFORMATION: FORMYLATION, conjugated to a covalently bound
      moiety

<400> SEQUENCE: 264

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
```

```
                85                  90                  95

Lys Val Glu Pro Lys Ser Cys Asp Lys Thr His Thr Cys Pro Pro Cys
            100                 105                 110

Pro Leu Gly Thr Pro Ser Arg Glu Leu Leu Gly Gly Pro Ser Val Phe
        115                 120                 125

Leu Phe Pro Pro Lys Pro Lys Asp Thr Leu Met Ile Ser Arg Thr Pro
    130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Glu Glu Met Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
    290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330


<210> SEQ ID NO 265
<211> LENGTH: 332
<212> TYPE: PRT
<213> ORGANISM: Artificial sequence
<220> FEATURE:
<223> OTHER INFORMATION: synthetic polypeptide

<400> SEQUENCE: 265

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Leu Cys Thr Pro Ser Arg Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330


<210> SEQ ID NO 266
<211> LENGTH: 332
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (210)..(210)
<223> OTHER INFORMATION: FORMYLATION

<400> SEQUENCE: 266

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Leu Gly Thr Pro Ser Arg Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330


<210> SEQ ID NO 267
<211> LENGTH: 332
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (210)..(210)
<223> OTHER INFORMATION: FORMYLATION, conjugated to a covalently bound
      moiety

<400> SEQUENCE: 267

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

```
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Leu Gly Thr Pro Ser Arg Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Glu Glu Met Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330


<210> SEQ ID NO 268
<211> LENGTH: 333
<212> TYPE: PRT
<213> ORGANISM: Artificial sequence
<220> FEATURE:
<223> OTHER INFORMATION: synthetic polypeptide

<400> SEQUENCE: 268

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Leu Cys Thr Pro Ser Arg Glu Pro Gln Val Tyr Thr Leu Pro Pro Ser
225                 230                 235                 240

Arg Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330


<210> SEQ ID NO 269
<211> LENGTH: 333
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (226)..(226)
<223> OTHER INFORMATION: FORMYLATION

<400> SEQUENCE: 269

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Leu Gly Thr Pro Ser Arg Glu Pro Gln Val Tyr Thr Leu Pro Pro Ser
225                 230                 235                 240

Arg Glu Glu Met Thr Lys Asn Gln Val Ser Leu Thr Cys Leu Val Lys
                245                 250                 255

Gly Phe Tyr Pro Ser Asp Ile Ala Val Glu Trp Glu Ser Asn Gly Gln
            260                 265                 270

Pro Glu Asn Asn Tyr Lys Thr Thr Pro Pro Val Leu Asp Ser Asp Gly
        275                 280                 285

Ser Phe Phe Leu Tyr Ser Lys Leu Thr Val Asp Lys Ser Arg Trp Gln
    290                 295                 300

Gln Gly Asn Val Phe Ser Cys Ser Val Met His Glu Ala Leu His Asn
305                 310                 315                 320

His Tyr Thr Gln Lys Ser Leu Ser Leu Ser Pro Gly Lys
                325                 330


<210> SEQ ID NO 270
<211> LENGTH: 333
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (226)..(226)
<223> OTHER INFORMATION: FORMYLATION, conjugated to a covalently bound
      moiety

<400> SEQUENCE: 270

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Leu Gly Thr Pro Ser Arg Glu Pro Gln Val Tyr Thr Leu Pro Pro Ser
225 230 235 240

Arg Glu Glu Met Thr Lys Asn Gln Val Ser Leu Thr Cys Leu Val Lys
245 250 255

Gly Phe Tyr Pro Ser Asp Ile Ala Val Glu Trp Glu Ser Asn Gly Gln
260 265 270

Pro Glu Asn Asn Tyr Lys Thr Thr Pro Pro Val Leu Asp Ser Asp Gly
275 280 285

Ser Phe Phe Leu Tyr Ser Lys Leu Thr Val Asp Lys Ser Arg Trp Gln
290 295 300

Gln Gly Asn Val Phe Ser Cys Ser Val Met His Glu Ala Leu His Asn
305 310 315 320

His Tyr Thr Gln Lys Ser Leu Ser Leu Ser Pro Gly Lys
325 330

<210> SEQ ID NO 271
<211> LENGTH: 335
<212> TYPE: PRT
<213> ORGANISM: Artificial sequence
<220> FEATURE:
<223> OTHER INFORMATION: synthetic polypeptide

<400> SEQUENCE: 271

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Leu Cys Thr Pro Ser Arg Glu
145 150 155 160

Val Lys Phe Asn Trp Tyr Val Asp Gly Val Glu Val His Asn Ala Lys
165 170 175

Thr Lys Pro Arg Glu Glu Gln Tyr Asn Ser Thr Tyr Arg Val Val Ser
180 185 190

Val Leu Thr Val Leu His Gln Asp Trp Leu Asn Gly Lys Glu Tyr Lys
195 200 205

Cys Lys Val Ser Asn Lys Ala Leu Pro Ala Pro Ile Glu Lys Thr Ile

```
    210                 215                 220

Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335


<210> SEQ ID NO 272
<211> LENGTH: 335
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (155)..(155)
<223> OTHER INFORMATION: FORMYLATION

<400> SEQUENCE: 272

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Leu Gly Thr Pro Ser Arg Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220
```

```
Ser Lys Ala Lys Gly Gln Pro Arg Glu Pro Gln Val Tyr Thr Leu Pro
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335


<210> SEQ ID NO 273
<211> LENGTH: 335
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (155)..(155)
<223> OTHER INFORMATION: FORMYLATION, conjugated to a covalently bound
      moiety

<400> SEQUENCE: 273

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Leu Gly Thr Pro Ser Arg Glu
145                 150                 155                 160

Val Lys Phe Asn Trp Tyr Val Asp Gly Val Glu Val His Asn Ala Lys
                165                 170                 175

Thr Lys Pro Arg Glu Glu Gln Tyr Asn Ser Thr Tyr Arg Val Val Ser
            180                 185                 190

Val Leu Thr Val Leu His Gln Asp Trp Leu Asn Gly Lys Glu Tyr Lys
        195                 200                 205

Cys Lys Val Ser Asn Lys Ala Leu Pro Ala Pro Ile Glu Lys Thr Ile
    210                 215                 220

Ser Lys Ala Lys Gly Gln Pro Arg Glu Pro Gln Val Tyr Thr Leu Pro
```

```
225                 230                 235                 240

Pro Ser Arg Glu Glu Met Thr Lys Asn Gln Val Ser Leu Thr Cys Leu
                245                 250                 255

Val Lys Gly Phe Tyr Pro Ser Asp Ile Ala Val Glu Trp Glu Ser Asn
            260                 265                 270

Gly Gln Pro Glu Asn Asn Tyr Lys Thr Thr Pro Pro Val Leu Asp Ser
        275                 280                 285

Asp Gly Ser Phe Phe Leu Tyr Ser Lys Leu Thr Val Asp Lys Ser Arg
    290                 295                 300

Trp Gln Gln Gly Asn Val Phe Ser Cys Ser Val Met His Glu Ala Leu
305                 310                 315                 320

His Asn His Tyr Thr Gln Lys Ser Leu Ser Leu Ser Pro Gly Lys
                325                 330                 335


<210> SEQ ID NO 274
<211> LENGTH: 112
<212> TYPE: PRT
<213> ORGANISM: Artificial sequence
<220> FEATURE:
<223> OTHER INFORMATION: synthetic polypeptide

<400> SEQUENCE: 274

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Cys
        35                  40                  45

Thr Pro Ser Arg Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110


<210> SEQ ID NO 275
<211> LENGTH: 112
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (48)..(48)
<223> OTHER INFORMATION: FORMYLATION

<400> SEQUENCE: 275

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gly
        35                  40                  45

Thr Pro Ser Arg Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80
```

```
Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110
```

<210> SEQ ID NO 276
<211> LENGTH: 112
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (48)..(48)
<223> OTHER INFORMATION: FORMYLATION, conjugated to a covalently bound moiety

<400> SEQUENCE: 276

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gly
        35                  40                  45

Thr Pro Ser Arg Gln Ser Gly Asn Ser Gln Glu Ser Val Thr Glu Gln
    50                  55                  60

Asp Ser Lys Asp Ser Thr Tyr Ser Leu Ser Ser Thr Leu Thr Leu Ser
65                  70                  75                  80

Lys Ala Asp Tyr Glu Lys His Lys Val Tyr Ala Cys Glu Val Thr His
                85                  90                  95

Gln Gly Leu Ser Ser Pro Val Thr Lys Ser Phe Asn Arg Gly Glu Cys
            100                 105                 110
```

<210> SEQ ID NO 277
<211> LENGTH: 329
<212> TYPE: PRT
<213> ORGANISM: Artificial sequence
<220> FEATURE:
<223> OTHER INFORMATION: synthetic polypeptide

<400> SEQUENCE: 277

```
Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Cys Thr Pro
        35                  40                  45

Ser Arg Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Lys Thr Tyr Thr Cys Asn Val Asp His Lys Pro Ser Asn Thr Lys Val
                85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140
```

```
Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325


<210> SEQ ID NO 278
<211> LENGTH: 329
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (46)..(46)
<223> OTHER INFORMATION: FORMYLATION

<400> SEQUENCE: 278

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Gly Thr Pro
        35                  40                  45

Ser Arg Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Lys Thr Tyr Thr Cys Asn Val Asp His Lys Pro Ser Asn Thr Lys Val
                85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
```

```
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325


<210> SEQ ID NO 279
<211> LENGTH: 329
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (46)..(46)
<223> OTHER INFORMATION: FORMYLATION, conjugated to a covalently bound
      moiety

<400> SEQUENCE: 279

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Gly Thr Pro
        35                  40                  45

Ser Arg Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Lys Thr Tyr Thr Cys Asn Val Asp His Lys Pro Ser Asn Thr Lys Val
                85                  90                  95

Asp Lys Arg Val Glu Ser Lys Tyr Gly Pro Pro Cys Pro Ser Cys Pro
            100                 105                 110

Ala Pro Glu Phe Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser Gln Glu Asp Pro Glu Val Gln Phe Asn Trp Tyr
145                 150                 155                 160
```

```
Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325


<210> SEQ ID NO 280
<211> LENGTH: 329
<212> TYPE: PRT
<213> ORGANISM: Artificial sequence
<220> FEATURE:
<223> OTHER INFORMATION: synthetic polypeptide

<400> SEQUENCE: 280

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190
```

```
Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Leu Cys Thr Pro
    210                 215                 220

Ser Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325
```

<210> SEQ ID NO 281
<211> LENGTH: 329
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (222)..(222)
<223> OTHER INFORMATION: FORMYLATION

<400> SEQUENCE: 281

```
Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
```

-continued

```
        195                 200                 205

Ser Ser Ile Glu Lys Thr Ile Ser Lys Ala Lys Gly Leu Gly Thr Pro
    210                 215                 220

Ser Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325


<210> SEQ ID NO 282
<211> LENGTH: 329
<212> TYPE: PRT
<213> ORGANISM: Artificial sequence
<220> FEATURE:
<223> OTHER INFORMATION: synthetic polypeptide
<220> FEATURE:
<221> NAME/KEY: MOD_RES
<222> LOCATION: (222)..(222)
<223> OTHER INFORMATION: FORMYLATION, conjugated to a covalently bound
      moiety

<400> SEQUENCE: 282

Ser Thr Lys Gly Pro Ser Val Phe Pro Leu Ala Pro Cys Ser Arg Ser
1               5                   10                  15

Thr Ser Glu Ser Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Ser Leu Gly Thr Lys Thr Tyr
65                  70                  75                  80

Thr Cys Asn Val Asp His Lys Pro Ser Asn Thr Lys Val Asp Lys Arg
                85                  90                  95

Val Glu Ser Lys Tyr Gly Pro Pro Cys Pro Ser Cys Pro Ala Pro Glu
            100                 105                 110

Phe Leu Gly Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205
```

-continued

```
Ser Ser Ile Glu Lys Thr Ile Ser Lys Ala Lys Gly Leu Gly Thr Pro
    210                 215                 220

Ser Arg Glu Pro Gln Val Tyr Thr Leu Pro Pro Ser Gln Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Arg Leu Thr Val Asp Lys Ser Arg Trp Gln Glu Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Leu Gly Lys
                325
```

ALDEHYDE-TAGGED IMMUNOGLOBULIN POLYPEPTIDES AND METHODS OF USE THEREOF

CROSS-REFERENCE TO RELATED APPLICATIONS

This application claims priority benefit of U.S. provisional application Ser. No. 61/433,042, filed Jan. 14, 2011, which application is incorporated herein by reference in its entirety.

INTRODUCTION

Antibodies find use in various diagnostic and therapeutic applications. Antibodies can also be used to deliver drugs. However, conjugation of a drug to an antibody can be difficult to control, resulting in a heterogeneous mixture of conjugates that differ in the number of drug molecules attached. This can make controlling the amount administered to a patient difficult.

LITERATURE

U.S. Patent Publication No. 2010/0210543; WO 2010/096394; U.S. Patent Publication No. 2008/0187956; WO 2009/120611.

SUMMARY

The present disclosure provides aldehyde-tagged immunoglobulin (Ig) polypeptides that can be converted by a formylglycine-generating enzyme to produce a formylglycine (FGly)-modified Ig polypeptide. An FGly-modified Ig polypeptide can be covalently and site-specifically bound to a moiety of interest to provide an Ig conjugate. The disclosure also encompasses methods of production of such aldehyde-tagged Ig polypeptides, FGly-modified Ig polypeptides, and Ig conjugates, as well as methods of use of same.

BRIEF DESCRIPTION OF THE DRAWINGS

FIG. 3 depicts solvent-accessible loop regions in anti-CD19 light chain (upper sequence (SEQ ID NO:11)) and heavy chain (lower sequence (SEQ ID NO:12)) constant regions, with an LCTPSR sulfatase motif in the heavy chain constant region. The signal peptide is shown in lower-case letters; the variable region is underlined; solvent-accessible loop regions in the constant regions are shown in bold and underlined. The LCTPSR sequence is shown in bold and double underlining.

FIG. 5 depicts Western blot analysis of a) aldehyde-tagged anti-CD22 antibodies chemically conjugated with aminooxy-FLAG (Panel A); and b) Western blot analysis of aldehyde-tagged anti-CD19 antibodies and aldehyde-tagged anti-CD22 antibodies chemically conjugated with aminooxy-FLAG.

FIGS. 6A and 6B depict a nucleotide sequence (FIG. 6A; (SEQ ID NO:13)) encoding the heavy chain of a CD22-specific IgG1 antibody, and the encoded amino acid sequence (FIG. 6B; (SEQ ID NO:14)). The end of the signal sequence is denoted by "/". The end of the variable region and the beginning of the constant region is denoted "//".

FIGS. 7A and 7B depict a nucleotide sequence (FIG. 7A; (SEQ ID NO:15)) encoding an aldehyde-tagged anti-CD22 immunoglobulin (Ig) heavy chain ("CH1 (A) LCTPSR"), and the encoded amino acid sequence (FIG. 7B; (SEQ ID NO:16)). The LCTPSR (SEQ ID NO:17) sulfatase motif sequence in CH1 is underlined. The end of the signal sequence is denoted by "/". The end of the variable region and the beginning of the constant region is denoted "//".

FIGS. 8A and 8B depict a nucleotide sequence (FIG. 8A; (SEQ ID NO:18)) encoding an aldehyde-tagged anti-CD22 immunoglobulin (Ig) heavy chain ("CH1 (B) LCTPSR"), and the encoded amino acid sequence (FIG. 8B; (SEQ ID NO:19)). The LCTPSR (SEQ ID NO:17) sulfatase motif sequence in CH1 is underlined. The end of the signal sequence is denoted by "/". The end of the variable region and the beginning of the constant region is denoted "//".

FIGS. 9A and 9B depict a nucleotide sequence (FIG. 9A; (SEQ ID NO:20)) encoding an aldehyde-tagged anti-CD22 immunoglobulin (Ig) heavy chain ("CH1 (C) LCTPSR"), and the encoded amino acid sequence (FIG. 9B; (SEQ ID NO:21)). The LCTPSR (SEQ ID NO:17) sulfatase motif sequence in CH1 is underlined. The end of the signal sequence is denoted by "/". The end of the variable region and the beginning of the constant region is denoted "//".

FIGS. 10A and 10B depict a nucleotide sequence (FIG. 10A; (SEQ ID NO:22)) encoding an aldehyde-tagged anti-CD221 g heavy chain ("CH1 (C) LATPSR"), and the encoded amino acid sequence (FIG. 10B; (SEQ ID NO:23)). The LATPSR (SEQ ID NO:24) sulfatase motif sequence in CH1 is underlined. The end of the signal sequence is denoted by "/". The end of the variable region and the beginning of the constant region is denoted "//".

FIGS. 11A and 11B depict a nucleotide sequence (FIG. 11A; (SEQ ID NO:25)) encoding an aldehyde-tagged anti-CD221 g heavy chain ("CH2 (A) LCTPSR"), and the encoded amino acid sequence (FIG. 11B; (SEQ ID NO:26)). The LCTPSR (SEQ ID NO:17) sulfatase motif sequence in CH2 is underlined. The end of the signal sequence is denoted by "/". The end of the variable region and the beginning of the constant region is denoted "//".

FIGS. 12A and 12B depict a nucleotide sequence (FIG. 12A; (SEQ ID NO:27)) encoding an aldehyde-tagged anti-CD221 g heavy chain ("CH2 (B) LCTPSR"), and the encoded amino acid sequence (FIG. 12B; (SEQ ID NO:28)). The LCTPSR (SEQ ID NO:17) sulfatase motif sequence in CH2 is underlined. The end of the signal sequence is denoted by "/". The end of the variable region and the beginning of the constant region is denoted "//".

FIGS. 13A and 13B depict a nucleotide sequence (FIG. 13A; (SEQ ID NO:29)) encoding an aldehyde-tagged anti-CD221 g heavy chain ("CH2 (C) LCTPSR"), and the encoded amino acid sequence (FIG. 13B; (SEQ ID NO:30)). The LCTPSR (SEQ ID NO:17) sulfatase motif sequence in CH2 is underlined. The end of the signal sequence is denoted by "/". The end of the variable region and the beginning of the constant region is denoted "//".

FIGS. 14A and 14B depict a nucleotide sequence (FIG. 14A; (SEQ ID NO:31)) encoding an aldehyde-tagged anti-CD221 g heavy chain ("CH2 (C)"), and the encoded amino acid sequences (FIG. 14B; (SEQ ID NO:32)). The LATPSR (SEQ ID NO:24) sulfatase motif sequence in CH2 is underlined.

FIGS. 15A and 15B depict a nucleotide sequence (FIG. 15A; (SEQ ID NO:33)) encoding an aldehyde-tagged anti-CD221 g heavy chain ("CH2/CH3 LCTPSR"), and the encoded amino acid sequences (FIG. 15B; (SEQ ID NO:34)). The LCTPSR (SEQ ID NO:17) sulfatase motif sequence in CH2/CH3 is underlined. The end of the signal sequence is denoted by "/". The end of the variable region and the beginning of the constant region is denoted "//".

FIGS. 16A and 16B depict a nucleotide sequence (FIG. 16A; (SEQ ID NO:35)) encoding an aldehyde-tagged anti-CD221 g heavy chain ("CH2/CH3 LATPSR"), and the encoded amino acid sequences (FIG. 16B; (SEQ ID NO:36)). The LATPSR (SEQ ID NO:24) sulfatase motif sequence in CH2/CH3 is underlined. The end of the signal sequence is denoted by "/". The end of the variable region and the beginning of the constant region is denoted "//".

FIGS. 17A and 17B depict a nucleotide sequence (FIG. 17A; (SEQ ID NO:37)) encoding an aldehyde-tagged anti-CD221 g heavy chain ("C-terminal LCTPSR"), and the encoded amino acid sequences (FIG. 17B; (SEQ ID NO:38)). The LCTPSR (SEQ ID NO:17) sulfatase motif sequence in the C-terminal region is underlined. The end of the signal sequence is denoted by "/". The end of the variable region and the beginning of the constant region is denoted "//".

FIGS. 18A and 18B depict a nucleotide sequence (FIG. 18A; (SEQ ID NO:39)) encoding an aldehyde-tagged anti-CD221 g heavy chain ("C-terminal LATPSR") . . . , and the encoded amino acid sequences (FIG. 18B; (SEQ ID NO:40)) The LATPSR (SEQ ID NO:24) sulfatase motif sequence in the C-terminal region is underlined. The end of the signal sequence is denoted by "/". The end of the variable region and the beginning of the constant region is denoted "//".

FIGS. 19A and 19B depict a nucleotide sequence (FIG. 19A; (SEQ ID NO:41)) encoding a CD22-specific human Ig kappa light chain, and the encoded amino acid sequence (FIG. 19B; (SEQ ID NO:42)). The end of the signal sequence is denoted by "/". The end of the variable region and the beginning of the constant region is denoted "//".

FIGS. 20A and 20B depict a nucleotide sequence (FIG. 20A; (SEQ ID NO:43)) encoding an aldehyde-tagged anti-CD22 Ig kappa light chain, and the encoded amino acid sequences (FIG. 20B; (SEQ ID NO:44)). The LCTPSR (SEQ ID NO:17) sulfatase motif sequence is underlined. The end of the signal sequence is denoted by "/". The end of the variable region and the beginning of the constant region is denoted "//".

FIGS. 21A and 21B depict a nucleotide sequence (FIG. 21A; (SEQ ID NO:45)) encoding an aldehyde-tagged anti-CD221 g kappa light chain, and the encoded amino acid sequences (FIG. 21B; (SEQ ID NO:46)). The LATPSR (SEQ ID NO:24) sulfatase motif sequence is underlined. The end of the signal sequence is denoted by "/". The end of the variable region and the beginning of the constant region is denoted "//".

FIGS. 22A and 22B depict a nucleotide sequence (FIG. 22A; (SEQ ID NO:47)) encoding the heavy chain of a CD19-specific IgG1 antibody, and the encoded amino acid sequence (FIG. 22B; (SEQ ID NO:48)). The end of the signal sequence is denoted by "/". The end of the variable region and the beginning of the constant region is denoted "//".

FIGS. 23A and 23B depict a nucleotide sequence (FIG. 23A; (SEQ ID NO:49)) encoding an aldehyde-tagged anti-CD191 g heavy chain ("CH1 (C) LCTPSR"), and the encoded amino acid sequences (FIG. 23B; (SEQ ID NO:50)) (CHI (C)). The LCTPSR (SEQ ID NO:17) sulfatase motif sequence in the CH1 region is underlined. The end of the signal sequence is denoted by "/". The end of the variable region and the beginning of the constant region is denoted "//".

FIGS. 24A and 24B depict a nucleotide sequence (FIG. 24A; (SEQ ID NO:51)) encoding an aldehyde-tagged anti-CD191 g heavy chain ("CH1 (C) LATPSR"), and the encoded amino acid sequences (FIG. 24B; (SEQ ID NO:52)). The LATPSR (SEQ ID NO:24) sulfatase motif sequence in the CH1 region is underlined. The end of the signal sequence is denoted by "/". The end of the variable region and the beginning of the constant region is denoted "//".

FIGS. 25A and 25B depict a nucleotide sequence (FIG. 25A; (SEQ ID NO:53)) encoding an aldehyde-tagged anti-CD191 g heavy chain ("CH2 (B) LCTPSR"), and the encoded amino acid sequences (FIG. 25B; (SEQ ID NO:54)). The LCTPSR (SEQ ID NO:17) sulfatase motif sequence in the CH2 region is underlined. The end of the signal sequence is denoted by "/". The end of the variable region and the beginning of the constant region is denoted "//".

FIGS. 26A and 26B depict a nucleotide sequence (FIG. 26A; (SEQ ID NO:55)) encoding an aldehyde-tagged anti-CD191 g heavy chain ("CH2 (B) LATPSR"), and the encoded amino acid sequences (FIG. 26B; (SEQ ID NO:56)). The LATPSR (SEQ ID NO:24) sulfatase motif sequence in the CH2 region is underlined. The end of the signal sequence is denoted by "/". The end of the variable region and the beginning of the constant region is denoted "//".

FIGS. 27A and 27B depict a nucleotide sequence (FIG. 27A; (SEQ ID NO:57)) encoding an aldehyde-tagged anti-CD191 g heavy chain ("CH2/CH3 LCTPSR"), and the encoded amino acid sequences (FIG. 27B; (SEQ ID NO:58)). The LCTPSR (SEQ ID NO:17) sulfatase motif sequence in the CH2/CH3 region is underlined. The end of the signal sequence is denoted by "/". The end of the variable region and the beginning of the constant region is denoted "//".

FIGS. 28A and 28B depict a nucleotide sequence (FIG. 28A; (SEQ ID NO:59)) encoding an aldehyde-tagged anti-CD191 g heavy chain ("CH2/CH3 LATPSR"), and the encoded amino acid sequences (FIG. 28B; (SEQ ID NO:60)). The LATPSR (SEQ ID NO:24) sulfatase motif sequence in the CH2/CH3 region is underlined. The end of the signal sequence is denoted by "/". The end of the variable region and the beginning of the constant region is denoted "//".

FIGS. 29A and 29B depict a nucleotide sequence (FIG. 29A; (SEQ ID NO:61)) encoding an aldehyde-tagged anti-CD191 g heavy chain ("C-terminal LCTPSR"), and the encoded amino acid sequences (FIG. 29B; (SEQ ID NO:62)). The LCTPSR (SEQ ID NO:17) sulfatase motif sequence in the C-terminal region is underlined. The end of the signal sequence is denoted by "/". The end of the variable region and the beginning of the constant region is denoted "//".

FIGS. 30A and 30B depict a nucleotide sequence (FIG. 30A; (SEQ ID NO:63)) encoding an aldehyde-tagged anti-CD191 g heavy chain ("C-terminal LATPSR"), and the encoded amino acid sequences (FIG. 30B; (SEQ ID NO:64)). The LATPSR (SEQ ID NO:24) sulfatase motif sequence in the C-terminal region is underlined. The end of the signal sequence is denoted by "/". The end of the variable region and the beginning of the constant region is denoted "//".

FIGS. 31A and 31B depict a nucleotide sequence (FIG. 31A; (SEQ ID NO:65)) encoding a CD19-specific human Ig kappa light chain, and the encoded amino acid sequence (FIG. 31B; (SEQ ID NO:66)). The end of the signal sequence is denoted by "/". The end of the variable region and the beginning of the constant region is denoted "//".

FIGS. 32A and 32B depict a nucleotide sequence (FIG. 32A; (SEQ ID NO:67)) encoding an aldehyde-tagged anti-CD191 g kappa light chain, and the encoded amino acid sequences (FIG. 32B; (SEQ ID NO:68)). The LCTPSR (SEQ ID NO:17) sulfatase motif sequence is underlined. The end of the signal sequence is denoted by "/". The end of the variable region and the beginning of the constant region is denoted "//".

FIGS. 33A and 33B depict a nucleotide sequence (FIG. 33A; (SEQ ID NO:69)) encoding an aldehyde-tagged anti-CD191 g kappa light chain, and the encoded amino acid sequences (FIG. 33B; (SEQ ID NO:70)). The LATPSR (SEQ ID NO:24) sulfatase motif sequence is underlined. The end of the signal sequence is denoted by "/". The end of the variable region and the beginning of the constant region is denoted "//".

DEFINITIONS

Figure 1:
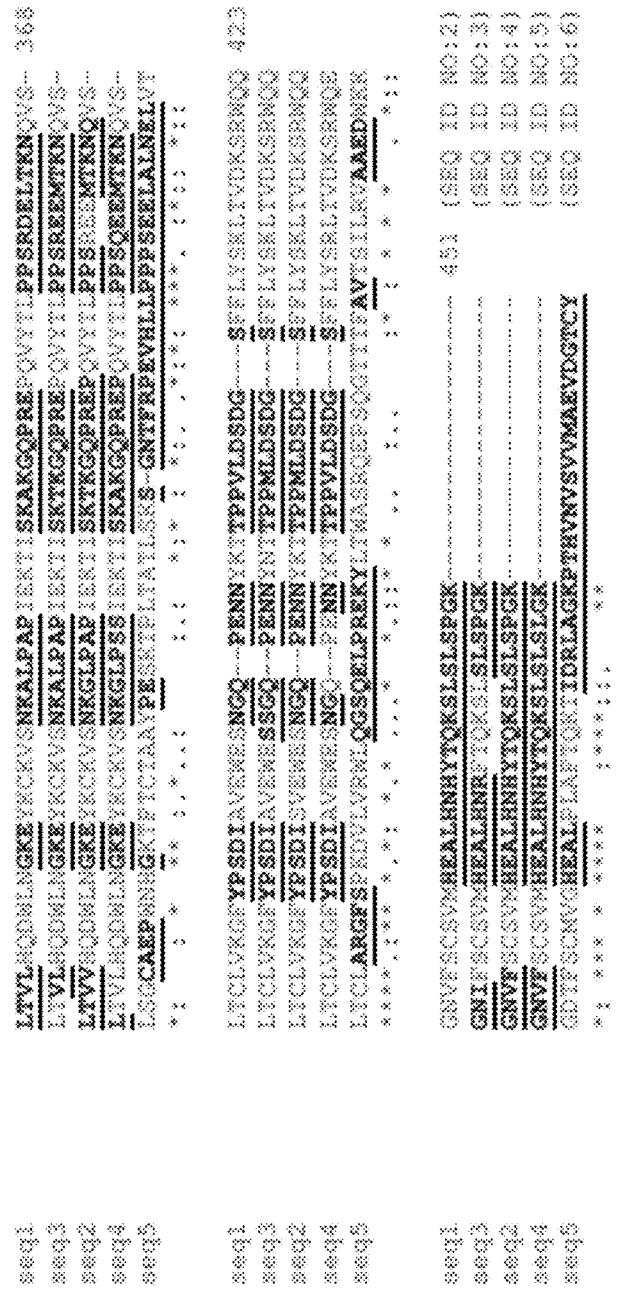
FIG. 1A depicts a site map showing possible modification sites for generation of an aldehyde tagged Ig polypeptide. The upper sequence is the amino acid sequence of the conserved region of an IgG1 light chain polypeptide (SEQ ID NO:1) and shows possible modification sites in an Ig light chain; the lower sequence is the amino acid sequence of the conserved region of an Ig heavy chain polypeptide (SEQ ID NO:228; GenBank Accession No. AAG00909) and shows possible modification sites in an Ig heavy chain. The heavy and light chain numbering is based on the full-length heavy and light chains.
FIG. 1B depicts an alignment of immunoglobulin heavy chain constant regions for IgG1 (SEQ ID NO:2), IgG2 (SEQ ID NO:4), IgG3 (SEQ ID NO:3), IgG4 (SEQ ID NO:5), and IgA (SEQ ID NO:6), showing modification sites at which aldehyde tags can be provided in an immunoglobulin heavy chain. The heavy and light chain numbering is based on the full-heavy and light chains.
FIG. 1C depicts an alignment of immunoglobulin light chain constant regions (SEQ ID NOS:1 and 7-10), showing modification sites at which aldehyde tags can be provided in an immuoglobulin immunoglobulin light chain.

The terms "polypeptide," "peptide," and "protein" are used interchangeably herein to refer to a polymeric form of amino acids of any length. Unless specifically indicated otherwise, "polypeptide," "peptide," and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein in the context of an immunoglobulin to refer to the amino acid sequence of the immunoglobulin prior to modification to include a heterologous aldehyde tag.

The term "antibody" is used in the broadest sense and includes monoclonal antibodies (including full length monoclonal antibodies), polyclonal antibodies, and multispecific antibodies (e.g., bispecific antibodies), humanized antibodies, single-chain antibodies, chimeric antibodies, antibody fragments (e.g., Fab fragments), and the like. An antibody is capable of binding a target antigen. (Janeway, C., Travers, P., Walport, M., Shlomchik (2001) Immuno Biology, 5th Ed., Garland Publishing, New York). A target antigen can have one or more binding sites, also called epitopes, recognized by complementarity determining regions (CDRs) formed by one or more variable regions of an antibody.

"Immunoglobulin polypeptide" as used herein refers to a polypeptide comprising at least a constant region of a light chain polypeptide or at least a constant region of a heavy chain polypeptide.

An immunoglobulin polypeptide immunoglobulin light or heavy chain variable region is composed of a framework region (FR) interrupted by three hypervariable regions, also called "complementarity determining regions" or "CDRs". The extent of the framework region and CDRs have been defined (see, "Sequences of Proteins of Immunological Interest," E. Kabat et al., U.S. Department of Health and Human Services, 1991). The framework region of an antibody, that is the combined framework regions of the constituent light and heavy chains, serves to position and align the CDRs. The CDRs are primarily responsible for binding to an epitope of an antigen.

The term "natural antibody" refers to an antibody in which the heavy and light chains of the antibody have been made and paired by the immune system of a multi-cellular organism. Spleen, lymph nodes, bone marrow and serum are examples of tissues that produce natural antibodies. For example, the antibodies produced by the antibody producing cells isolated from a first animal immunized with an antigen are natural antibodies.

Throughout the present disclosure, the numbering of the residues in an immunoglobulin heavy chain and in an immunoglobulin light chain is that as in Kabat et al., Sequences of Proteins of Immunological Interest, 5th Ed. Public Health Service, National Institutes of Health, Bethesda, Md. (1991), expressly incorporated herein by reference.

A "parent Ig polypeptide" is a polypeptide comprising an amino acid sequence which lacks an aldehyde-tagged constant region as described herein. The parent polypeptide may comprise a native sequence constant region, or may comprise a constant region with pre-existing amino acid sequence modifications (such as additions, deletions and/or substitutions).

In the context of an Ig polypeptide, the term "constant region" is well understood in the art, and refers to a C-terminal region of an Ig heavy chain, or an Ig light chain. An Ig heavy chain constant region includes CH1, CH2, and CH3 domains (and CH4 domains, where the heavy chain is a μ or an ϵ heavy chain). In a native Ig heavy chain, the CH1, CH2, CH3 (and, if present, CH4) domains begin immediately after (C-terminal to) the heavy chain variable (VH) region, and are each from about 100 amino acids to about 130 amino acids in length. In a native Ig light chain, the constant region begins begin immediately after (C-terminal to) the light chain variable (VL) region, and is about 100 amino acids to 120 amino acids in length.

In some embodiments, a "functional Fc region" possesses an "effector function" of a native sequence Fc region. Exemplary "effector functions" include C1q binding; complement dependent cytotoxicity; Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays that are well known in the art.

Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII.

The terms "Fc receptor" or "FcR" are used to describe a receptor that binds to the Fc region of an antibody. FcRs are reviewed in Ravetch and Kinet, Annu. Rev. Immunol 9:457 92 (1991); Capel et al., Immunomethods 4:25 34 (1994); and de Haas et al., J. Lab. Clin. Med. 126:330 41 (1995).

The term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28 (4/5):489-498 (1991); Studnicka et al., Protein Engineering 7(6):805-814 (1994); Roguska. et al., PNAS 91:969-973 (1994)), and chain shuffling (U.S. Pat. No. 5,565,332). In certain embodiments, framework substitutions are identified by modeling of the interactions of the CDR and framework residues to identify framework residues important for antigen binding and sequence comparison to identify unusual framework residues at particular positions (see, e.g., U.S. Pat. No. 5,585,089; Riechmann et al., Nature 332:323 (1988)). Additional methods for humanizing antibodies contemplated for use in the present invention are described in U.S. Pat. Nos. 5,750,078; 5,502,167; 5,705,154; 5,770,403; 5,698,417; 5,693,493; 5,558,864; 4,935,496; and 4,816,567, and PCT publications WO 98/45331 and WO 98/45332. In particular embodiments, a subject rabbit antibody may be humanized according to the methods set forth in US20040086979 and US20050033031. Accordingly, the antibodies described above may be humanized using methods that are well known in the art.

The term "chimeric antibodies" refer to antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a mouse antibody and the constant or effector domain from a human antibody, although domains from other mammalian species may be used.

By "aldehyde tag" or "ald-tag" is meant an amino acid sequence that contains an amino acid sequence derived from a sulfatase motif which is capable of being converted, or which has been converted, by action of a formylglycine generating enzyme (FGE) to contain a 2-formylglycine residue (referred to herein as "FGly"). The FGly residue generated by an FGE is often referred to in the literature as a "formylglycine". Stated differently, the term "aldehyde tag" is used herein to refer to an amino acid sequence comprising an "unconverted" sulfatase motif (i.e., a sulfatase motif in which the cysteine or serine residues has not been converted to FGly by an FGE, but is capable of being converted) as well as to an amino acid sequence comprising a "converted" sulfatase motif (i.e., a sulfatase motif in which the cysteine or the serine residue has been converted to FGly by action of an FGE).

By "conversion" as used in the context of action of a formylglycine generating enzyme (FGE) on a sulfatase motif refers to biochemical modification of a cysteine or serine residue in a sulfatase motif to a formylglycine (FGly) residue (e.g., Cys to FGly, or Ser to FGly).

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences that facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest (e.g., an aldehyde tagged-Ig protein), and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, at least 75% free, at least 80% free, at least 85% free, at least 90% free, at least 95% free, at least 98% free, or more than 98% free, from other components with which it is naturally associated.

The term "physiological conditions" is meant to encompass those conditions compatible with living cells, e.g., predominantly aqueous conditions of a temperature, pH, salinity, etc. that are compatible with living cells.

By "reactive partner" is meant a molecule or molecular moiety that specifically reacts with another reactive partner to produce a reaction product. Exemplary reactive partners include a cysteine or serine of sulfatase motif and an FGE, which react to form a reaction product of a converted aldehyde tag containing an FGly in lieu of cysteine or serine in the motif. Other exemplary reactive partners include an aldehyde of a formylglycine (FGly) residue of a converted aldehyde tag and an "aldehyde-reactive reactive partner", which comprises an aldehyde-reactive group and a moiety of interest, and which reacts to form a reaction product of a modified aldehyde tagged polypeptide having the moiety of interest conjugated to the modified polypeptide through a modified FGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "internal site" as used in referenced to a polypeptide or an amino acid sequence of a polypeptide means a region of the polypeptide that is not at the N-terminus or at the C-terminus.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "an aldehyde-tagged Ig polypeptide" includes a plurality of such polypeptides and reference to "the drug-conjugated Ig polypeptide" includes reference to one or more drug-conjugated Ig polypeptide and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides aldehyde-tagged immunoglobulin (Ig) polypeptides that can be converted by a formylglycine-generating enzyme (FGE) to produce a formylglycine (FGly)-modified Ig polypeptide. An FGly-modified Ig polypeptide can be covalently and site-specifically bound to a moiety of interest via reaction with an aldehyde-reactive reactive partner to provide an Ig conjugate. The disclosure also encompasses methods of production of such aldehyde-tagged Ig polypeptides, FGly-modified Ig polypeptides, and Ig conjugates, as well as methods of use of same.

Aldehyde-tagged Ig polypeptides may also be referred to herein as "ald-tagged Ig polypeptides", "ald-tagged Ig heavy chains" or "ald-tagged Ig light chains". Such Ald-tagged Ig polypeptides can be site-specifically decorated with a covalently bound molecule of interest, such as a drug (e.g., a peptide drug, a small molecule drug, and the like), a water-soluble polymer, a detectable label, a synthetic peptide, etc.

The compositions and methods of the present disclosure exploit a naturally-occurring, genetically-encodable sulfatase motif for use as a tag, referred to herein as an "aldehyde tag" or "ald tag", to direct site-specific modification of the Ig polypeptide. The sulfatase motif of the aldehyde tag, which is based on a motif found in active sites of sulfatases, contains a serine or cysteine residue that is capable of being converted (oxidized) to a 2-formylglycine (FGly) residue by action of a formylglycine generating enzyme (FGE) either in vivo (e.g., at the time of translation of an ald tag-containing protein in a cell) or in vitro (e.g., by contacting an ald tag-containing protein with an FGE in a cell-free system). The aldehyde moiety of the resulting FGly residue can be used as a "chemical handle" to facilitate site-specific chemical modification of the Ig polypeptide, and thus site-specific attachment of a moiety of interest. For example, a peptide modified to contain an α-nucleophile-containing moiety (e.g., an aminooxy or hydrazide moiety) can be reacted with the FGly-containing Ig polypeptide to yield a conjugate in which the Ig polypeptide and the peptide are linked by a hydrazone or oxime bond, respectively, or via alternative aldehyde-specific chemistries such as reductive amination. The reactivity of the aldehyde thus allows for bioorthogonal and chemoselective modification of the Ig polypeptide, and thus provides a site-specific means for chemical modification that in turn can be exploited to provide for site-specific attachment of a moiety of interest in the final conjugate.

Aldehyde Tagged Immunoglobulin Polypeptides

The present disclosure provides isolated aldehyde-tagged Ig polypeptides, including aldehyde-tagged Ig heavy chains and aldehyde-tagged Ig light chains, where the aldehyde-tagged Ig polypeptides, where the aldehyde tag is within or adjacent a solvent-accessible loop region of the Ig constant region, and where the aldehyde tag is not at the C-terminus of the Ig polypeptide.

In general, an aldehyde tag can be based on any amino acid sequence derived from a sulfatase motif (also referred to as a "sulfatase domain") which is capable of being converted by action of a formylglycine generating enzyme (FGE) to contain a formylglycine (FGly). Such sulfatase motifs may also be referred to herein as an FGE-modification site. Action of FGE is directed in a sequence-specific manner in that the FGE acts at a sulfatase motif positioned within the immunoglobulin polypeptide.

The present disclosure also provides a library of aldehyde-tagged Ig polypeptides, where the library comprises a plurality (a population) of members, and where each member Ig polypeptide comprises an aldehyde tag at a different location(s) from the other members.

The present disclosure provides an aldehyde-tagged antibody, where an aldehyde-tagged antibody can include: 1) an aldehyde-tagged Ig heavy chain constant region; and an aldehyde-tagged Ig light chain constant region; 2) an aldehyde-tagged Ig heavy chain constant region; and an Ig light chain constant region that is not aldehyde tagged; or 3) an Ig heavy chain constant region that is not aldehyde tagged; and an aldehyde-tagged Ig light chain constant region. A subject aldehyde-tagged antibody also includes VH and/or VL domains and can bind antigen.

Exemplary Aldehyde Tags

A minimal sulfatase motif of an aldehyde tag is usually 5 or 6 amino acid residues in length, usually no more than 6 amino acid residues in length. Sulfatase motifs provided in an Ig polypeptide are at least 5 or 6 amino acid residues, and can be, for example, from 5 to 16, 6-16, 5-15, 6-15, 5-14, 6-14, 5-13, 6-13, 5-12, 6-12, 5-11, 6-11, 5-10, 6-10, 5-9, 6-9, 5-8, or 6-8 amino acid residues in length, so as to define a sulfatase motif of less than 16, 15, 14, 13, 12, 11, 10, 9, 8 or 7 amino acid residues in length.

In general, it is normally desirable to minimize the extent of modification of the native amino acid sequence of the target Ig polypeptide, so as to minimize the number of amino acid residues that are inserted, deleted, substituted (replaced), or added (e.g., to the N- or C-terminus). Minimizing the extent of amino acid sequence modification of the target Ig polypeptide is usually desirable so as to minimize the impact such modifications may have upon Ig function and/or structure. Thus, aldehyde tags of particular interest include those that require modification (insertion, addition, deletion, substitution/replacement) of less than 16, 15, 14, 13, 12, 11, 10, 9, 8, 7, 6, 5, 4, 3 or 2 amino acid residues of the amino acid sequence of the target polypeptide. Where an amino acid sequence native to the Ig polypeptide contains one or more residues of the desired sulfatase motif, the total number of modifications of residues can be reduced, e.g., by site-specification modification of amino acid residues flanking native amino acid residues to provides a sequence of a sulfatase motif.

It should be noted that while aldehyde tags of particular interest are those comprising at least a minimal sulfatase motif (also referred to a "consensus sulfatase motif"), it will be readily appreciated that longer aldehyde tags are both contemplated and encompassed by the present disclosure and can find use in the compositions and methods of the invention. Aldehyde tags can thus comprise a minimal sulfatase motif of 5 or 6 residues, or can be longer and comprise a minimal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

In certain embodiments, the sulfatase motif used may be described by the formula:

$$X_1Z_1X_2Z_2X_3Z_3 \quad \text{(I)}$$

where $Z_1$ is cysteine or serine (which can also be represented by (C/S));

$Z_2$ is either a proline or alanine residue (which can also be represented by (P/A));

$Z_3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I;

$X_1$ is present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M, S or V, with the proviso that when the sulfatase motif is at the N-terminus of the target polypeptide, $X_1$ is present; and $X_2$ and $X_3$ independently can be any amino acid, though usually an aliphatic amino acid, a polar, uncharged amino acid, or a sulfur containing amino acid (i.e., other than a aromatic amino acid or a charged amino acid), usually S, T, A, V, G or C, more usually S, T, A, V or G.

Thus, the present disclosure provides isolated aldehyde-tagged Ig polypeptides, including aldehyde-tagged Ig heavy chains and aldehyde-tagged Ig light chains, where the aldehyde-tagged Ig polypeptides comprise an Ig constant region amino acid sequence modified to provide a sequence of at least 5 amino acids of the formula $X_1Z_1X_2Z_2X_3Z_3$, where $Z_1$ is cysteine or serine;

$Z_2$ is a proline or alanine residue;

$Z_3$ is an aliphatic amino acid or a basic amino acid;

$X_1$ is present or absent and, when present, is any amino acid, with the proviso that when the heterologous sulfatase motif is at an N-terminus of the polypeptide, $X_1$ is present;

$X_2$ and $X_3$ are each independently any amino acid, where the sequence is within or adjacent a solvent-accessible loop region of the Ig constant region, and wherein the sequence is not at the C-terminus of the Ig heavy chain.

It should be noted that, following action of an FGE on the sulfatase motif, $Z_1$ is oxidized to generate a formylglycine (FGly) residue. Furthermore, following both FGE-mediated conversion and reaction with a reactive partner comprising a moiety of interest, FGly position at $Z_1$ in the formula above is covalently bound to the moiety of interest (e.g., detectable label, water soluble polymer, polypeptide, drug, etc).

Where the aldehyde tag is present at a location other than the N-terminus of the target polypeptide, $X_1$ of the formula above can be provided by an amino acid residue of the native amino acid sequence of the target polypeptide. Therefore, in some embodiments, and when present at a location other than the N-terminus of a target polypeptide, sulfatase motifs are of the formula:

$$(C/S)X_1(P/A)X_2Z_3 \quad (II)$$

where $X_1$ and $X_2$ independently can be any amino acid, though usually an aliphatic amino acid, a polar, uncharged amino acid, or a sulfur-containing amino acid (i.e., other than an aromatic amino acid or a charged amino acid), usually S, T, A, V, or C, more usually S, T, A, or V; and $Z_3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I.

As noted above, the sulfatase motif can contain additional residues at one or both of the N- and C-terminus of the sequence, e.g., such that the aldehyde tag includes both a sulfatase motif and an "auxiliary motif". In one embodiment, the sulfatase motif includes an auxiliary motif at the C-terminus (i.e., following the arginine residue in the formula above) 1, 2, 3, 4, 5, 6, or all 7 of the contiguous residues of an amino acid sequence of AALLTGR (SEQ ID NO:92), SQLLTGR (SEQ ID NO:93), AAFMTGR (SEQ ID NO:94), AAFLTGR (SEQ ID NO:95), SAFLTGR (SEQ ID NO:96), ASILTGK (SEQ ID NO:97), VSFLTGR (SEQ ID NO:98), ASLLTGL (SEQ ID NO:99), ASILITG (SEQ ID NO:100), VSFLTGR (SEQ ID NO:101), SAIMTGR (SEQ ID NO:102), SAIVTGR (SEQ ID NO:103), TNLWRG (SEQ ID NO:104), TNLWRGQ (SEQ ID NO:105), TNLCAAS (SEQ ID NO:106), VSLWTGK (SEQ ID NO:107), SMLLTG (SEQ ID NO:108), SMLLTGN (SEQ ID NO:109), SMLLTGT (SEQ ID NO:110), ASFMAGQ (SEQ ID NO:111), or ASLLTGL (SEQ ID NO:112), (see, e.g., Dierks et al. (1999) EMBO J. 18(8): 2084-2091), or of GSLFTGR (SEQ ID NO:113). However, such additional C-terminal amino acid residues are not required for FGE-mediated conversion of the sulfatase motif of the aldehyde tag, and thus are only optional and may be specifically excluded from the aldehyde tags described herein. In some embodiments the aldehyde tag does not contain an amino acid sequence CGPSR(M/A)S (SEQ ID NO:114) or CGPSR (M/A) (SEQ ID NO:115), which may be present as a native amino acid sequence in phosphonate monoester hydrolases.

The sulfatase motif of the aldehyde tag is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

Selection of aldehyde tags and an FGE that provide for suitable reactive partners to provide for generation of an FGly in the aldehyde tagged target Ig polypeptide can be readily accomplished in light of information available in the art. In general, sulfatase motifs susceptible to conversion by a eukaryotic FGE contain a cysteine and a proline (i.e., a cysteine and proline at $Z_1$ and $Z_2$, respectively, in Formula I above (e.g., $X_1CX_2PX_3Z_3$); $CX_1PX_2Z_3$ in Formula II above) and are modified by the "SUMF1-type" FGE (Cosma et al. Cell 2003, 113, (4), 445-56; Dierks et al. Cell 2003, 113, (4), 435-44). Sulfatase motifs susceptible to conversion by a prokaryotic FGE contain either a cysteine or a serine, and a proline in the sulfatase motif (i.e., a cysteine or serine at $Z_1$, and a proline at $Z_2$, respectively, in Formula I above (e.g., $X_1(C/S)X_2PX_3Z_3$); $(C/S)X_1PX_2Z_3$ in Formula II above) are modified either by the "SUMF1-type" FGE or the "AtsB-type" FGE, respectively (Szameit et al. J Biol Chem 1999, 274, (22), 15375-81). Other sulfatase motifs susceptible to conversion by a prokaryotic FGE contain either a cysteine or a serine, and either a proline or an alanine in the sulfatase motif (i.e., a cysteine or serine at $Z_1$, and a proline or alanine at $Z_2$, respectively, in Formula I or II above (e.g., $X_1CX_2PX_3R$; $X_1SX_2PX_2R$; $X_1CX_2AX_3R$; $X_1SX_2AX_3R$; $CX_1PX_2R$; $SX_1PX_2R$; $CX_1AX_2R$; $SX_1AX_2R$, $X_1CX_2PX_3Z_3$; $X_1SX_2PX_2$ $Z_3$; $X_1CX_2AX_3Z_3$; $X_1SX_2AX_3Z_3$; $CX_1PX_2Z_3$; $SX_1PX_2Z_3$; $CX_1AX_2Z_3$; $SX_1AX_2Z_3$), and are susceptible to modification by, for example, can be modified by an FGE of a Firmicutes (e.g., *Clostridium perfringens*) (see Berteau et al. *J. Biol. Chem.* 2006; 281:22464-22470) or an FGE of *Mycobacterium tuberculosis*.

Therefore, for example, where the FGE is a eukaryotic FGE (e.g., a mammalian FGE, including a human FGE), the sulfatase motif is usually of the formula:

$$X_1CX_2PX_3Z_3$$

where $X_1$ may be present or absent and, when present, can be any amino acid, though usually an aliphatic amino acid, a sulfur-containing amino acid, or a polar, uncharged amino acid, (i.e., other than a aromatic amino acid or a charged amino acid), usually L, M, S or V, with the proviso that when the sulfatase motif is at the N-terminus of the target polypeptide, $X_1$ is present;

$X_2$ and $X_3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G, or C, more usually S, T, A, V or G; and $Z_3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I.

Specific examples of sulfatase motifs include LCTPSR (SEQ ID NO:17), MCTPSR (SEQ ID NO:116), VCTPSR (SEQ ID NO:117), LCSPSR (SEQ ID NO:118), LCAPSR (SEQ ID NO:119), LCVPSR (SEQ ID NO:120), LCGPSR (SEQ ID NO:121), ICTPAR (SEQ ID NO:122), LCTPSK (SEQ ID NO:123), MCTPSK (SEQ ID NO:124), VCTPSK (SEQ ID NO:125), LCSPSK (SEQ ID NO:126), LCAPSK (SEQ ID NO:127), LCVPSK (SEQ ID NO:128), LCGPSK (SEQ ID NO:129), LCTPSA (SEQ ID NO:130), ICTPAA (SEQ ID NO:131), MCTPSA (SEQ ID NO:132), VCTPSA (SEQ ID NO:133), LCSPSA (SEQ ID NO:134), LCAPSA (SEQ ID NO:135), LCVPSA (SEQ ID NO:136), and LCGPSA (SEQ ID NO:137). Other specific sulfatase motifs are readily apparent from the disclosure provided herein.

Formylglycine-Modified Ig Polypeptides

As described in more detail below, a converted aldehyde tagged Ig polypeptide is reacted with a reactive partner containing a moiety of interest to provide for conjugation of the moiety of interest to the FGly residue of the converted aldehyde tagged Ig polypeptide, and production of a modified polypeptide. Modified Ig polypeptides having a modified aldehyde tag are generally described by comprising a modified sulfatase motif of the formula:

$$X_1(FGly')X_2Z_2X_3Z_3 \quad (I')$$

where

FGly' is the formylglycine residue having a covalently attached moiety;

$Z_2$ is either a proline or alanine residue (which can also be represented by (P/A)); $Z_3$ is a basic amino acid (e.g., arginine (R), and may be lysine (K) or histidine (H), usually lysine), or an aliphatic amino acid (alanine (A), glycine (G), leucine (L), valine (V), isoleucine (I), or proline (P), usually A, G, L, V, or I;

$X_1$ may be present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M or V, with the proviso that when the sulfatase motif is at the N-terminus of the target polypeptide, $X_1$ is present; and $X_2$ and $X_3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G or C, more usually S, T, A, V or G.

Thus, the present disclosure provides an Ig polypeptide modified to comprise formylglycine moiety, wherein the Ig polypeptide comprises an FGly-converted sulfatase motif of the formula:

$$X_1(FGly)X_2Z_2X_3Z_3$$

wherein:

$X_1$ is present or absent and, when present, is any amino acid, with the proviso that when the sulfatase motif is at an N-terminus of the polypeptide, $X_1$ is present;

$X_2$ and $X_3$ are each independently any amino acid; and $Z^3$ is a basic amino acid; and where the FGly-modified Ig polypeptide presents the FGly group on a solvent-accessible surface when in a folded state.

Figure 2:
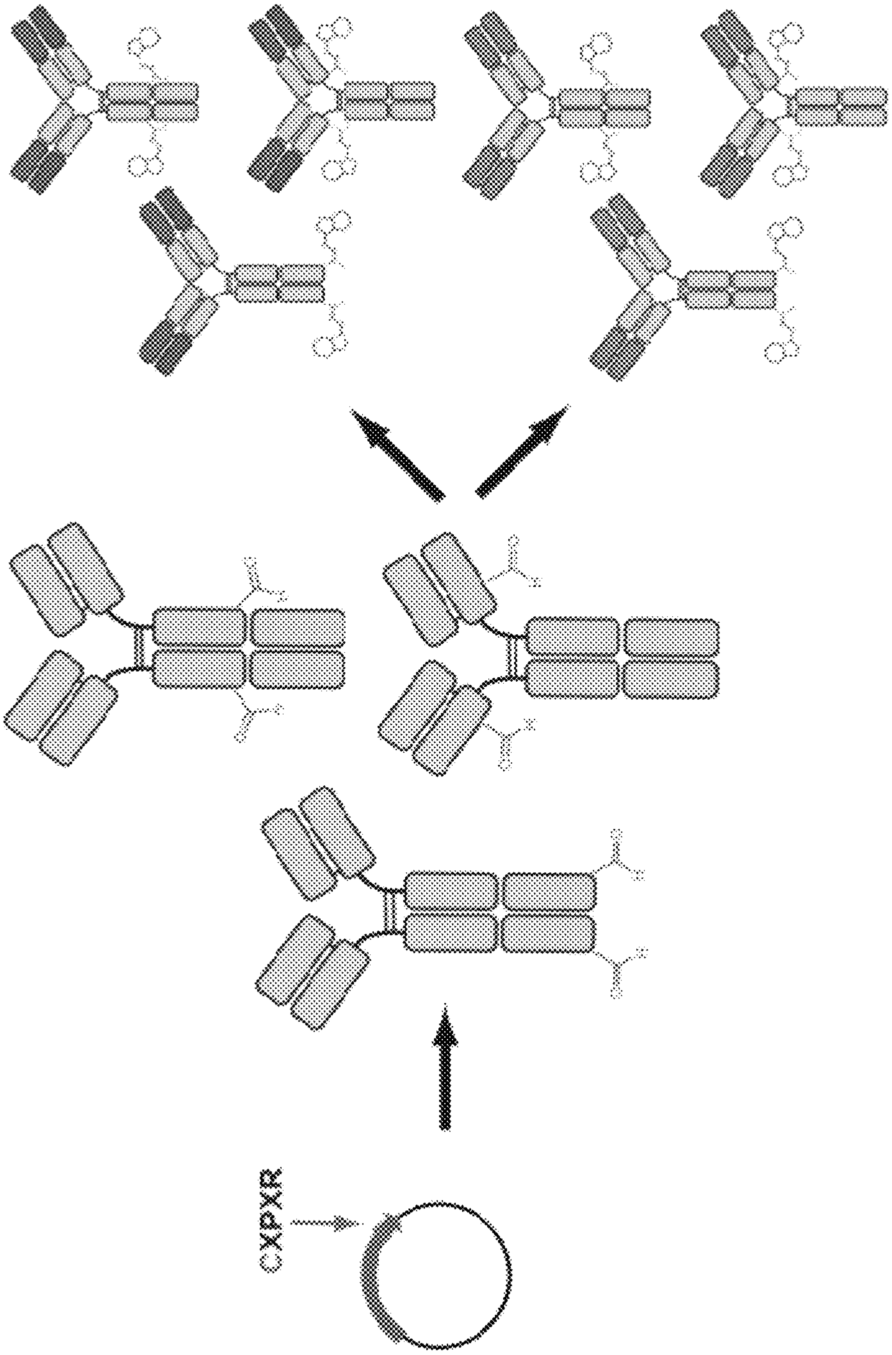
FIG. 2 presents a scheme for expression of aldehyde-tagged antibodies and their subsequent chemical conjugation.

The present disclosure also provides a library of FGly-modified Ig polypeptides, where the library comprises a plurality (a population) of members, where each member FGly-modified Ig polypeptide comprises an FGly-modified aldehyde tag, and where each member FGly-modified Ig polypeptide comprises an aldehyde tag at a different location(s) from the other members. FIG. 2 depicts an example of a scheme for generating a library of FGly-modified Ig polypeptides, in which each member Ig polypeptide comprises an aldehyde tag at a different location from the other members. FIG. 2 depicts attachment of drug to the FGly-modified polypeptides.

The present disclosure provides an FGly-modified antibody, where an FGly-modified antibody can include: 1) an FGly-modified Ig heavy chain constant region; and an FGly-modified Ig light chain constant region; 2) an FGly-modified Ig heavy chain constant region; and an Ig light chain constant region that is not FGly-modified; or 3) an Ig heavy chain constant region that is not FGly-modified; and an FGly-modified Ig light chain constant region. A subject FGly-modified antibody also includes VH and/or VL domains and can bind antigen.

Specific examples of converted sulfatase motifs include L(FGly)TPSR (SEQ ID NO:138), M(FGly)TPSR (SEQ ID NO:139), V(FGly)TPSR (SEQ ID NO:140), L(FGly)SPSR (SEQ ID NO:141), L(FGly)APSR (SEQ ID NO:142), L(FGly)VPSR (SEQ ID NO:143), and L(FGly)GPSR (SEQ ID NO:144), I(FGly)TPAR (SEQ ID NO:145), L(FGly)TPSK (SEQ ID NO:146), M(FGly)TPSK (SEQ ID NO:147), V(FGly)TPSK (SEQ ID NO:148), L(FGly)SPSK (SEQ ID NO:149), L(FGly)APSK (SEQ ID NO:150), L(FGly)VPSK (SEQ ID NO:151), L(FGly)GPSK (SEQ ID NO:152), L(FGly)TPSA (SEQ ID NO:152), M(FGly)TPSA (SEQ ID NO:153), V(FGly)TPSA (SEQ ID NO:154), L(FGly)SPSA (SEQ ID NO:155), L(FGly)APSA (SEQ ID NO:156), L(FGly)VPSA (SEQ ID NO:157), and L(FGly)GPSA (SEQ ID NO:158).

As described in more detail below, the moiety of interest can be any of a variety of moieties such as a water-soluble polymer, a detectable label, a drug, or a moiety for immobilization of the Ig polypeptide in a membrane or on a surface. As is evident from the above discussion of aldehyde tagged Ig polypeptides, the modified sulfatase motif of the modified polypeptide can be positioned at any desired site of the polypeptide. Thus, the present disclosure provides, for example, a modified polypeptide having a modified sulfatase motif positioned at a site of post-translational modification of a parent of the modified polypeptide (i.e., if the target polypeptide is modified to provide an aldehyde tag at a site of post-translational modification, the later-produced modified polypeptide will contain a moiety at a position corresponding to this site of post-translational modification in the parent polypeptide). For example, then, a modified polypeptide can be produced so as to have a covalently bound, water-soluble polymer at a site corresponding to a site at which glycosylation would normally occur in the parent target polypeptide. Thus, for example, a PEGylated polypeptide can be produced having the PEG moiety positioned at the same or nearly the same location as sugar residues would be positioned in the naturally-occurring parent polypeptide. Similarly, where the parent target polypeptide is engineered to include one or more non-native sites of post-translational modification, the modified polypeptide can contain covalently attached water-soluble polymers at one or more sites of the modified polypeptide corresponding to these non-native sites of post-translational modification in the parent polypeptide.

Modification of a Target Ig Polypeptide to Include an Aldehyde Tag

Modification of a target Ig polypeptide to include one or more aldehyde tags can be accomplished using recombinant molecular genetic techniques, so as produce nucleic acid encoding the desired aldehyde tagged Ig polypeptide. Such methods are well known in the art, and include cloning methods, site-specific mutation methods, and the like (see, e.g., Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements).

Target Immunoglobulin Heavy and Light Chains

As discussed above, the present disclosure provides aldehyde-tagged Ig polypeptides, FGly-modified aldehyde-tagged Ig polypeptides, and Ig conjugates. The Ig polypeptides used to generate an aldehyde-tagged Ig polypeptide, an FGly-modified aldehyde-tagged Ig polypeptide, or an Ig conjugate, of the present disclosure, include at least an Ig constant region, e.g., an Ig heavy chain constant region (e.g., at least a CH1 domain; at least a CH1 and a CH2 domain; a CH1, a CH2, and a CH3 domain; or a CH1, a CH2, a CH3, and a CH4 domain), or an Ig light chain constant region. Such Ig polypeptides are referred to herein as "target Ig polypeptides."

A target Ig polypeptide can comprise an amino acid sequence having 90%, 91%, 92%, 93%, 94%, 95%, 96%, 97%, 98%, 99%, or 100%, amino acid sequence identity to a contiguous stretch of from about 300 amino acids to about 330 amino acids of an amino acid sequence of a heavy chain constant region depicted in FIG. 1B. For example, a target Ig polypeptide can comprise an amino acid sequence having 90%, 91%, 92%, 93%, 94%, 95%, 96%, 97%, 98%, 99%, or 100%, amino acid sequence identity to a contiguous stretch of from about 300 amino acids to about 330 amino acids of the amino acid sequence set forth in SEQ ID NO:2.

A target Ig polypeptide can comprise an amino acid sequence having 90%, 91%, 92%, 93%, 94%, 95%, 96%, 97%, 98%, 99%, or 100%, amino acid sequence identity to a contiguous stretch of from about 200 amino acids to about 233 amino acids, or from about 200 amino acids to about 236 amino acids, of an amino acid sequence of a light chain constant region depicted in FIG. 1C. For example, a target Ig polypeptide can comprise an amino acid sequence having 90%, 91%, 92%, 93%, 94%, 95%, 96%, 97%, 98%, 99%, or 100%, amino acid sequence identity to a contiguous stretch of from about 200 amino acids to about 236 amino acids of the amino acid sequence set forth in SEQ ID NO:1.

As noted above, a target Ig polypeptide generally includes at least an Ig heavy chain constant region or an Ig light chain constant region, and can further include an Ig variable region (e.g., a $V_L$ region and/or a $V_H$ region). Ig heavy chain constant regions include Ig constant regions of any heavy chain isotype, non-naturally occurring Ig heavy chain constant regions (including consensus Ig heavy chain constant regions). An Ig constant region can be modified to include an aldehyde tag, where the aldehyde tag is present in or adjacent a solvent-accessible loop region of the Ig constant region.

An Ig constant region can be modified by insertion and/or substitution of 1, 2, 3, 4, 5, 6, 7, 8, 9, 10, 11, 12, 13, 14, 15, or 16 amino acids, or more than 16 amino acids, to provide an amino acid sequence of a sulfatase motif as described above.

In some cases, an aldehyde-tagged Ig polypeptide of the present disclosure comprises an aldehyde-tagged Ig heavy chain constant region (e.g., at least a CH1 domain; at least a CH1 and a CH2 domain; a CH1, a CH2, and a CH3 domain; or a CH1, a CH2, a CH3, and a CH4 domain). The aldehyde-tagged Ig heavy chain constant region can include heavy chain constant region sequences of an IgA, IgM, IgD, IgE, IgG1, IgG2, IgG3, or IgG4 isotype heavy chain or any allotypic variant of same, e.g., human heavy chain constant region sequences or mouse heavy chain constant region sequences, a hybrid heavy chain constant region, a synthetic heavy chain constant region, or a consensus heavy chain constant region sequence, etc., modified to include at least one sulfatase motif that can be modified by an FGE to generate an FGly-modified Ig polypeptide. Allotypic variants of Ig heavy chains are known in the art. See, e.g., Jefferis and Lefranc (2009) *MAbs* 1:4.

In some cases, an aldehyde-tagged Ig polypeptide of the present disclosure comprises an aldehyde-tagged Ig light chain constant region. The aldehyde-tagged Ig light chain constant region can include constant region sequences of a kappa light chain, a lambda light chain, e.g., human kappa or lambda light chain constant regions, a hybrid light chain constant region, a synthetic light chain constant region, or a consensus light chain constant region sequence, etc., modified to include at least one sulfatase motif that can be modified by an FGE to generate an FGly-modified Ig polypeptide. Exemplary constant regions include human gamma 1 and gamma 3 regions. With the exception of the sufatase motif, a modified constant region may have a wild-type amino acid sequence, or it may have an amino acid sequence that is at least 70% identical (e.g., at least 80%, at least 90% or at least 95% identical) to a wild type amino acid sequence.

As noted above, an isolated aldehyde-tagged Ig polypeptide of the present disclosure comprises an Ig constant region amino acid sequence modified to provide a sulfatase motif sequence of at least 5 amino acids of the formula described above, where the sequence is within or adjacent a solvent-accessible loop region of the Ig polypeptide constant region. In some embodiments the sulfatase motif is at a position other than, or in addition to, the C-terminus of the Ig polypeptide heavy chain.

Solvent accessible loop of an antibody can be identified by molecular modeling, or by comparison to a known antibody structure. The relative accessibility of amino acid residues can also be calculated using a method of DSSP (Dictionary of Secondary Structure in Proteins; Kabsch and Sander 1983 Biopolymers 22: 2577-637) and solvent accessible surface area of an amino acid may be calculated based on a 3-dimensional model of an antibody, using algorithms known in the art (e.g., Connolly, J. Appl. Cryst. 16, 548 (1983) and Lee and Richards, J. Mol. Biol. 55, 379 (1971), both of which are incorporated herein by reference).

As noted above, an isolated aldehyde-tagged Ig polypeptide can comprise a heavy chain constant region modified to include a sulfatase motif as described above, where the sulfatase motif is in or adjacent a surface-accessible loop region of the Ig polypeptide heavy chain constant region. Illustrative examples of surface-accessible loop regions of a heavy chain constant region are presented in FIGS. 1A and 1B.

In some instances, a target immunoglobulin is modified to include a sulfatase motif as described above, where the sulfatase motif is within, or adjacent to, a region of an IgG1 heavy chain constant region corresponding to one or more of: 1) amino acids 122-127; 2) amino acids 137-143; 3) amino acids 155-158; 4) amino acids 163-170; 5) amino acids 163-183; 6) amino acids 179-183; 7) amino acids 190-192; 8) amino acids 200-202; 9) amino acids 199-202; 10) amino acids 208-212; 11) amino acids 220-241; 12) amino acids 247-251; 13) amino acids 257-261; 14) amino acid 269-277; 15) amino acids 271-277; 16) amino acids 284-285; 17) amino acids 284-292; 18) amino acids 289-291; 19) amino acids 299-303; 20) amino acids 309-313; 21)

amino acids 320-322; 22) amino acids 329-335; 23) amino acids 341-349; 24) amino acids 342-348; 25) amino acids 356-365; 26) amino acids 377-381; 27) amino acids 388-394; 28) amino acids 398-407; 29) amino acids 433-451; and 30) amino acids 446-451; wherein the amino acid numbering is based on the amino acid numbering of human IgG1 as depicted in FIG. 1B.

Exemplary surface-accessible loop regions of an IgG1 heavy chain include: 1) ASTKGP (SEQ ID NO:71); 2) KSTSGGT (SEQ ID NO:72); 3) PEPV (SEQ ID NO:73); 4) NSGALTSG (SEQ ID NO:202); 5) NSGALTSGVHTFPAVLQSSGL (SEQ ID NO:74); 6) QSSGL (SEQ ID NO:227); 7) VTV; 8) QTY; 9) TQTY (SEQ ID NO:75); 10) HKPSN (SEQ ID NO:76); 11) EPKSCDKTHTCPPCPAPELLGG (SEQ ID NO:77); 12) FPPKP (SEQ ID NO:78); 13) ISRTP (SEQ ID NO:79); 14) DVSHEDPEV (SEQ ID NO:80); 15) SHEDPEV (SEQ ID NO:223; 16) DG; 17) DGVEVHNAK (SEQ ID NO:81); 18) HNA; 19) QYNST (SEQ ID NO:82); 20) VLTVL (SEQ ID NO:83); 21) GKE; 22) NKALPAP (SEQ ID NO:84); 23) SKAKGQPRE (SEQ ID NO:85); 24) KAKGQPR (SEQ ID NO:206); 25) PPSRKELTKN (SEQ ID NO:86); 26) YPSDI (SEQ ID NO:87); 27) NGQPENN (SEQ ID NO:88); 28) TPPVLDSDGS (SEQ ID NO:89); 29) HEALHNHYTQKSLSLSPGK (SEQ ID NO:90); and 30) SLSPGK (SEQ ID NO:175), as shown in FIGS. 1A and 1B.

In some instances, a target immunoglobulin is modified to include a sulfatase motif as described above, where the sulfatase motif is within, or adjacent to, a region of an IgG2 heavy chain constant region corresponding to one or more of: 1) amino acids 1-6; 2) amino acids 13-24; 3) amino acids 33-37; 4) amino acids 43-54; 5) amino acids 58-63; 6) amino acids 69-71; 7) amino acids 78-80; 8) 87-89; 9) amino acids 95-96; 10) 114-118; 11) 122-126; 12) 134-136; 13) 144-152; 14) 159-167; 15) 175-176; 16) 184-188; 17) 195-197; 18) 204-210; 19) 216-224; 20) 231-233; 21) 237-241; 22) 252-256; 23) 263-269; 24) 273-282; 25) amino acids 299-302; where the amino acid numbering is based on the numbering of the amino acid sequence set forth in SEQ ID NO:4 (human IgG2; also depicted in FIG. 1B).

Exemplary surface-accessible loop regions of an IgG2 heavy chain include 1) ASTKGP (SEQ ID NO:71); 2) PCSRSTSESTAA (SEQ ID NO:91); 3) FPEPV (SEQ ID NO:168); 4) SGALTSGVHTFP (SEQ ID NO:159); 5) QSSGLY (SEQ ID NO:160); 6) VTV; 7) TQT; 8) HKP; 9) DK; 10) VAGPS (SEQ ID NO:161); 11) FPPKP (SEQ ID NO:78); 12) RTP; 13) DVSHEDPEV (SEQ ID NO:80); 14) DGVEVHNAK (SEQ ID NO:81); 15) FN; 16) VLTVV (SEQ ID NO:162); 17) GKE; 18) NKGLPAP (SEQ ID NO:163); 19) SKTKGQPRE (SEQ ID NO:164); 20) PPS; 21) MTKNQ (SEQ ID NO:165); 22) YPSDI (SEQ ID NO:87); 23) NGQPENN (SEQ ID NO:88); 24) TPPMLDSDGS (SEQ ID NO:166); 25) GNVF (SEQ ID NO:182); and 26) HEALHNHYTQKSLSLSPGK (SEQ ID NO:90), as shown in FIG. 1B.

In some instances, a target immunoglobulin is modified to include a sulfatase motif as described above, where the sulfatase motif is within, or adjacent to, a region of an IgG3 heavy chain constant region corresponding to one or more of: 1) amino acids 1-6; 2) amino acids 13-22; 3) amino acids 33-37; 4) amino acids 43-61; 5) amino acid 71; 6) amino acids 78-80; 7) 87-91; 8) amino acids 97-106; 9) 111-115; 10) 147-167; 11) 173-177; 16) 185-187; 13) 195-203; 14) 210-218; 15) 226-227; 16) 238-239; 17) 246-248; 18) 255-261; 19) 267-275; 20) 282-291; 21) amino acids 303-307; 22) amino acids 313-320; 23) amino acids 324-333; 24) amino acids 350-352; 25) amino acids 359-365; and 26) amino acids 372-377; where the amino acid numbering is based on the numbering of the amino acid sequence set forth in SEQ ID NO:3 (human IgG3; also depicted in FIG. 1B).

Exemplary surface-accessible loop regions of an IgG3 heavy chain include 1) ASTKGP (SEQ ID NO:71); 2) PCSRSTSGGT (SEQ ID NO:167); 3) FPEPV (SEQ ID NO:168); 4) SGALTSGVHTFPAVLQSSG (SEQ ID NO:169); 5) V; 6) TQT; 7) HKPSN (SEQ ID NO:76); 8) RVELKTPLGD (SEQ ID NO:170); 9) CPRCPKP (SEQ ID NO:171); 10) PKSCDTPPPCPRCPAPELLGG (SEQ ID NO:229); 11) FPPKP (SEQ ID NO:78); 12) RTP; 13) DVSHEDPEV (SEQ ID NO:80); 14) DGVEVHNAK (SEQ ID NO:81); 15) YN; 16) VL; 17) GKE; 18) NKALPAP (SEQ ID NO:84); 19) SKTKGQPRE (SEQ ID NO:164); 20) PPSREEMTKN (SEQ ID NO:172); 21) YPSDI (SEQ ID NO:87); 22) SSGQPENN (SEQ ID NO:173); 23) TPPMLDSDGS (SEQ ID NO:166); 24) GNI; 25) HEALHNR (SEQ ID NO:174); and 26) SLSPGK (SEQ ID NO:175), as shown in FIG. 1B.

In some instances, a target immunoglobulin is modified to include a sulfatase motif as described above, where the sulfatase motif is within, or adjacent to, a region of an IgG4 heavy chain constant region corresponding to one or more of: 1) amino acids 1-5; 2) amino acids 12-23; 3) amino acids 32-36; 4) amino acids 42-53; 5) amino acids 57-62; 6) amino acids 68-70; 7) amino acids 77-79; 8) amino acids 86-88; 9) amino acids 94-95; 10) amino acids 101-102; 11) amino acids 108-118; 12) amino acids 122-126; 13) amino acids 134-136; 14) amino acids 144-152; 15) amino acids 159-167; 16) amino acids 175-176; 17) amino acids 185-186; 18) amino acids 196-198; 19) amino acids 205-211; 20) amino acids 217-226; 21) amino acids 232-241; 22) amino acids 253-257; 23) amino acids 264-265; 24) 269-270; 25) amino acids 274-283; 26) amino acids 300-303; 27) amino acids 399-417; where the amino acid numbering is based on the numbering of the amino acid sequence set forth in SEQ ID NO:5 (human IgG4; also depicted in FIG. 1B).

Exemplary surface-accessible loop regions of an IgG4 heavy chain include 1) STKGP (SEQ ID NO:176); 2) PCSRSTSESTAA (SEQ ID NO:91); 3) FPEPV (SEQ ID NO:168); 4) SGALTSGVHTFP (SEQ ID NO:159); 5) QSSGLY (SEQ ID NO:160); 6) VTV; 7) TKT; 8) HKP; 9) DK; 10) YG; 11) CPAPEFLGGPS (SEQ ID NO:177); 12) FPPKP (SEQ ID NO:78); 13) RTP; 14) DVSQEDPEV (SEQ ID NO:178); 15) DGVEVHNAK (SEQ ID NO:81); 16) FN; 17) VL; 18) GKE; 19) NKGLPSS (SEQ ID NO:179); 20) SKAKGQPREP (SEQ ID NO:180); 21) PPSQEEMTKN (SEQ ID NO:181); 22) YPSDI (SEQ ID NO:87); 23) NG; 24) NN; 25) TPPVLDSDGS (SEQ ID NO:89); 26) GNVF (SEQ ID NO:182); and 27) HEALHNHYTQKSLSLSLGK (SEQ ID NO:183), as shown in FIG. 1B.

In some instances, a target immunoglobulin is modified to include a sulfatase motif as described above, where the sulfatase motif is within, or adjacent to, a region of an IgA heavy chain constant region corresponding to one or more of: 1) amino acids 1-13; 2) amino acids 17-21; 3) amino acids 28-32; 4) amino acids 44-54; 5) amino acids 60-66; 6) amino acids 73-76; 7) amino acids 80-82; 8) amino acids 90-91; 9) amino acids 123-125; 10) amino acids 130-133; 11) amino acids 138-142; 12) amino acids 151-158; 13) amino acids 165-174; 14) amino acids 181-184; 15) amino acids 192-195; 16) amino acid 199; 17) amino acids 209-210; 18) amino acids 222-245; 19) amino acids 252-256; 20) amino acids 266-276; 21) amino acids 293-294; 22) amino acids 301-304; 23) amino acids 317-320; 24) amino acids 329-353; where the amino acid numbering is based on the numbering of the amino acid sequence set forth in SEQ ID NO:6 (human IgA; also depicted in FIG. 1B).

Exemplary surface-accessible loop regions of an IgA heavy chain include 1) ASPTSPKVFPLSL (SEQ ID NO:184); 2) QPDGN (SEQ ID NO:185); 3) VQGFFPQEPL (SEQ ID NO:186); 4) SGQGVTARNFP (SEQ ID NO:187); 5) SGDLYTT (SEQ ID NO:188); 6) PATQ (SEQ ID NO:189); 7) GKS; 8) YT; 9) CHP; 10) HRPA (SEQ ID NO:190); 11) LLGSE (SEQ ID NO:191); 12) GLRDASGV (SEQ ID NO:192); 13) SSGKSAVQGP (SEQ ID NO:193); 14) GCYS (SEQ ID NO:194); 15) CAEP (SEQ ID NO:195); 16) PE; 17) SGNTFRPEVHLLPPPSEELALNEL (SEQ ID NO:196); 18) ARGFS (SEQ ID NO:197); 19) QGSQEL-PREKY (SEQ ID NO:198); 20) AV; 21) AAED (SEQ ID NO:199); 22) HEAL (SEQ ID NO:200); and 23) IDRLAG-KPTHVNVSVVMAEVDGTCY (SEQ ID NO:201), as shown in FIG. 1B.

A sulfatase motif can be provided within or adjacent one or more of these amino acid sequences of such modification sites of an Ig heavy chain. For example, an Ig heavy chain polypeptide can be modified at one or more of these amino acid sequences to provide a sulfatase motif adjacent and N-terminal and/or adjacent and C-terminal to these modification sites. Alternatively or in addition, an Ig heavy chain polypeptide can be modified at one or more of these amino acid sequences to provide a sulfatase motif insertion between any two residues of the Ig heavy chain modifications sites. In some embodiments, an Ig heavy chain polypeptide may be modified to include two motifs, which may be adjacent to one another, or which may be separated by one, two, three, four or more (e.g., from about 1 to about 25, from about 25 to about 50, or from about 50 to about 100, or more, amino acids. Alternatively or in addition, where a native amino acid sequence provides for one or more amino acid residues of a sulfatase motif sequence, selected amino acid residues of the modification sites of an Ig heavy chain polypeptide amino acid sequence can be modified so as to provide a sulfatase motif at the modification site.

The amino acid sequence of a surface-accessible loop region can thus be modified to provide a sulfatase motif, where the modifications can include substitution and/or insertion. For example, where the modification is in a CH1 domain, the surface-accessible loop region can have the amino acid sequence NSGALTSG (SEQ ID NO:202), and the aldehyde-tagged sequence can be, e.g., NSGAL-CTPSRG (SEQ ID NO:203), e.g., where the "TS" residues of the NSGALTSG (SEQ ID NO:202) sequence are replaced with "CTPSR," (SEQ ID NO:204) such that the sulfatase motif has the sequence LCTPSR (SEQ ID NO:17). As another example, where the modification is in a CH2 domain, the surface-accessible loop region can have the amino acid sequence NKALPAP (SEQ ID NO:84), and the aldehyde-tagged sequence can be, e.g., NLCTPSRAP (SEQ ID NO:206), e.g., where the "KAL" residues of the NKA-LPAP (SEQ ID NO:84) sequence are replaced with "LCTPSR," (SEQ ID NO:17) such that the sulfatase motif has the sequence LCTPSR (SEQ ID NO:17). As another example, where the modification is in a CH2/CH3 domain, the surface-accessible loop region can have the amino acid sequence KAKGQPR (SEQ ID NO:207), and the aldehyde-tagged sequence can be, e.g., KAKGLCTPSR (SEQ ID NO:208), e.g., where the "GQP" residues of the KAKGQPR (SEQ ID NO:207) sequence are replaced with "LCTPS," (SEQ ID NO:209) such that the sulfatase motif has the sequence LCTPSR (SEQ ID NO:17).

As noted above, an isolated aldehyde-tagged Ig polypeptide can comprise a light chain constant region modified to include a sulfatase motif as described above, where the sulfatase motif is in or adjacent a surface-accessible loop region of the Ig polypeptide light chain constant region. Illustrative examples of surface-accessible loop regions of a light chain constant region are presented in FIGS. 1A and 1C.

In some instances, a target immunoglobulin is modified to include a sulfatase motif as described above, where the sulfatase motif is within, or adjacent to, a region of an Ig light chain constant region corresponding to one or more of: 1) amino acids 130-135; 2) amino acids 141-143; 3) amino acid 150; 4) amino acids 162-166; 5) amino acids 163-166; 6) amino acids 173-180; 7) amino acids 186-194; 8) amino acids 211-212; 9) amino acids 220-225; 10) amino acids 233-236; wherein the amino acid numbering is based on the amino acid numbering of human kappa light chain as depicted in FIG. 1C.

Exemplary surface-accessible loop regions of an Ig light chain (e.g., a human kappa light chain) include: 1) RTVAAP (SEQ ID NO:209); 2) PPS; 3) Gly (see, e.g., Gly at position 150 of the human kappa light chain sequence depicted in FIG. 1C); 4) YPREA (SEQ ID NO:210); 5) PREA (SEQ ID NO:226); 6) DNALQSGN (SEQ ID NO:211); 7) TEQD-SKDST (SEQ ID NO:212); 8) HK; 9) HQGLSS (SEQ ID NO:213); and 10) RGEC (SEQ ID NO:214), as shown in FIGS. 1A and 1C.

Exemplary surface-accessible loop regions of an Ig lambda light chain include QPKAAP (SEQ ID NO:215), PPS, NK, DFYPGAV (SEQ ID NO:216), DSSPVKAG (SEQ ID NO:217), TTP, SN, HKS, EG, and APTECS (SEQ ID NO:218), as shown in FIG. 1C.

In some instances, a target immunoglobulin is modified to include a sulfatase motif as described above, where the sulfatase motif is within, or adjacent to, a region of a rat Ig light chain constant region corresponding to one or more of: 1) amino acids 1-6; 2) amino acids 12-14; 3) amino acids 121-22; 4) amino acids 31-37; 5) amino acids 44-51; 6) amino acids 55-57; 7) amino acids 61-62; 8) amino acids 81-83; 9) amino acids 91-92; 10) amino acids 102-105; wherein the amino acid numbering is based on the amino acid numbering of rat light chain as set forth in SEQ ID NO:10 (and depicted in FIG. 1C).

Non-limiting examples of amino acid sequences of aldehyde-tagged IgG1 heavy chain polypeptides are shown in FIGS. 7B, 8B, 9B, 11B, 12B, 14B, 15B, 17B, 23B, 25B, 27B, and 29B, with the LCTPSR (SEQ ID NO:17) sulfatase motif in the CH1 domain (see, e.g., FIGS. 7B, 8B, 9B, and 23B), CH2 domain (FIGS. 11B, 12B, 14B, and 25B), CH2/CH3 domain (FIGS. 15B, and 27B), and near the C-terminus (FIGS. 17B, and 29B).

Non-limiting examples of amino acid sequences of aldehyde-tagged kappa light chain polypeptides are shown in FIGS. 20B and 32B.

A sulfatase motif can be provided within or adjacent one or more of these amino acid sequences of such modification sites of an Ig light chain. For example, an Ig light chain polypeptide can be modified at one or more of these amino acid sequences to provide a sulfatase motif adjacent and N-terminal and/or adjacent and C-terminal these modification sites. Alternatively or in addition, an Ig light chain polypeptide can be modified at one or more of these amino acid sequences to provide a sulfatase motif insertion between any two residues of the Ig light chain modifications sites. Alternatively or in addition, where a native amino acid sequence provides for one or more amino acid residues of a sulfatase motif sequence, selected amino acid residues of the modification sites of an Ig light chain polypeptide amino acid sequence can be modified so as to provide a sulfatase motif at the modification site.

The amino acid sequence of a surface-accessible loop region is modified to provide a sulfatase motif, where the modifications can include substitution and/or insertion. For example, where the modification is in a CL region, the surface-accessible loop region can have the amino acid sequence DNALQSGN (SEQ ID NO:211), and the aldehyde-tagged sequence can be, e.g., DNALCTPSRQSGN (SEQ ID NO:220), e.g., where the sequence "CTPSR" (SEQ ID NO:204) is inserted between the "DNAL" (SEQ ID NO:221) and the "QSGN" (SEQ ID NO:222) sequences of the surface-accessible loop region, such that the sulfatase motif is LCTPSR (SEQ ID NO:17).

In one embodiment, modification of an Ig constant region does not substantially alter functionality of the heavy chain constant region. For example, the Fc portion (e.g., CH2 and CH3 domains of IgA or IgG antibodies; and CH2, CH3, and CH4 domains of IgM or IgE antibodies) can have various binding and effector functions. Non limiting examples, of Fc binding and effector functions include, e.g., Fc receptor (FcR) binding, C1q binding, and antibody-dependent cell-mediated cytotoxicity (ADCC) activity. Modification of an Ig constant region to provide an aldehyde tag, as described herein, does not substantially increase or decrease one or more of Fc binding, and any effector function of the heavy chain, e.g., the modification does not increase or decrease the FcR binding and/or an effector function by more than about 1%, about 2%, about 5%, or about 10%, compared to a parent Ig polypeptide.

Modification of an Ig constant region to provide an aldehyde tag, as described herein, does not substantially reduce antigen binding affinity of an antibody comprising the aldehyde-tagged Ig constant region.

Modification of an Ig constant region to provide an aldehyde tag, as described herein, does not substantially reduce production of the Ig polypeptide, e.g., the aldehyde-tagged Ig polypeptide can be expressed in a host cell and can be folded properly so as to result in a functional polypeptide.

An aldehyde-tagged Ig heavy chain can include an Ig variable region, or can lack an Ig variable region. Similarly, an aldehyde-tagged Ig light chain can include an Ig variable region, or can lack an Ig variable region. Ig variable regions are well known in the art, and can provide antigen-binding specificity to an Ig polypeptide.

An aldehyde-tagged Ig heavy chain can include, in addition to an aldehyde tag, one or more additional modifications, e.g., glycosylation, and the like.

The present disclosure provides an aldehyde-tagged antibody comprising an Ig heavy chain and an Ig light chain, where the Ig heavy chain and/or the Ig light chain comprises an aldehyde tag. An aldehyde-tagged antibody can include an Ig heavy chain with one, two, three, or more aldehyde tags; and an Ig light chain with no aldehyde tags. An aldehyde-tagged antibody can include an Ig heavy chain with no aldehyde tags; and an Ig light chain with one, two, three, or more aldehyde tags. An aldehyde-tagged antibody can include an Ig heavy chain with one, two, three, or more aldehyde tags; and an Ig light chain with one, two, three, or more aldehyde tags.

An aldehyde-tagged antibody of the present disclosure can have any of a variety of antigen-binding specificities. An aldehyde-tagged antibody can bind any of a variety of antigens, including, e.g., an antigen present on a cancer cell; an antigen present on an autoimmune cell; an antigen present on a pathogenic microorganism; an antigen present on a virus-infected cell (e.g., a human immunodeficiency virus-infected cell), e.g., CD4 or gp120; an antigen present on a diseased cell; and the like. For example, an aldehyde-tagged antibody can bind an antigen, as noted above, where the antigen is present on the surface of the cell.

For example, an aldehyde-tagged antibody can specifically bind an antigen present on a cancer cell. Non-limiting examples of cancer antigens that can be recognized and bound (e.g., specifically bound) by an aldhehyde-tagged antibody of the present disclosure include antigens present on carcinomas, prostate cancer cells, breast cancer cells, colorectal cancer cells, melanoma cells, T-cell leukemia cells, T-cell lymphoma cells, B-cell lymphoma cells, non-Hodgkin's lymphoma cells, and the like.

Non-limiting examples of antigens present on particular cancer cells include, e.g., CA125, CA15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti-transferrin receptor, p97, MUC1-KLH, HER2, CEA, gp100, MART1, prostate-specific antigen, human chorionic gonadotropin, IL-2 receptor, EphB2, CD19, CD20, CD22, CD52, CD33, CD38, CD40, mucin, P21, MPG, and Neu oncogene product. In some embodiments, the antigen is CD19. In other embodiments, the antigen is CD22.

Non-limiting examples of antibodies that can be modified to include an aldehyde tag, as described herein, include, but are not limited to, an anti-CD19 antibody, and an anti-CD22 antibody.

Formylglycine Generating Enzymes (FGEs)

The enzyme that oxidizes cysteine or serine in a sulfatase motif to FGly is referred to herein as a formylglycine generating enzyme (FGE). As discussed above, "FGE" is used herein to refer to FGly-generating enzymes that mediate conversion of a cysteine (C) of a sulfatase motif to FGly as well as FGly-generating enzymes that mediate conversion of serine (S) of a sulfatase motif to FGly. It should be noted that in general, the literature refers to FGly-generating enzymes that convert a C to FGly in a sulfatase motif as FGEs, and refers to enzymes that convert S to FGly in a sulfatase motif as Ats-B-like. However, for purposes of the present disclosure "FGE" is used generically to refer to both types of FGly-generating enzymes, with the understanding that an appropriate FGE will be selected according to the target reactive partner containing the appropriate sulfatase motif (i.e., C-containing or S-containing).

As evidenced by the ubiquitous presence of sulfatases having an FGly at the active site, FGEs are found in a wide variety of cell types, including both eukaryotes and prokaryotes. There are at least two forms of FGEs. Eukaryotic sulfatases contain a cysteine in their sulfatase motif and are modified by the "SUMF1-type" FGE (Cosma et al. Cell 2003, 113, (4), 445-56; Dierks et al. Cell 2003, 113, (4), 435-44). The FGly-generating enzyme (FGE) is encoded by the SUMF1 gene. Prokaryotic sulfatases can contain either a cysteine or a serine in their sulfatase motif and are modified either by the "SUMF1-type" FGE or the "AtsB-type" FGE, respectively (Szameit et al. J Biol Chem 1999, 274, (22), 15375-81). In eukaryotes, it is believed that this modification happens co-translationally or shortly after translation in the endoplasmic reticulum (ER) (Dierks et al. Proc Natl Acad Sci USA 1997, 94(22):11963-8). Without being held to theory, in prokaryotes it is thought that SUMF1-type FGE functions in the cytosol and AtsB-type FGE functions near or at the cell membrane. A SUMF2 FGE has also been described in deuterostomia, including vertebrates and echinodermata (see, e.g., Pepe et al. (2003) Cell 113, 445-456, Dierks et al. (2003) Cell 113, 435-444; Cosma et al. (2004) Hum. Mutat. 23, 576-581).

In general, the FGE used to facilitate conversion of cysteine or serine to FGly in a sulfatase motif of an aldehyde tag of a target polypeptide is selected according to the sulfatase motif present in the aldehyde tag. The FGE can be native to the host cell in which the aldehyde tagged polypeptide is expressed, or the host cell can be genetically modified to express an appropriate FGE. In some embodiments it may be desired to use a sulfatase motif compatible with a human FGE (e.g., the SUMF1-type FGE, see, e.g., Cosma et al. Cell 113, 445-56 (2003); Dierks et al. Cell 113, 435-44 (2003)), and express the aldehyde tagged protein in a human cell that expresses the FGE or in a host cell, usually a mammalian cell, genetically modified to express a human FGE.

In general, an FGE for use in the methods disclosed herein can be obtained from naturally occurring sources or synthetically produced. For example, an appropriate FGE can be derived from biological sources which naturally produce an FGE or which are genetically modified to express a recombinant gene encoding an FGE. Nucleic acids encoding a number of FGEs are known in the art and readily available (see, e.g., Preusser et al. 2005 J. Biol. Chem. 280(15):14900-10 (Epub 2005 Jan. 18); Fang et al. 2004 J Biol. Chem. 79(15):14570-8 (Epub 2004 Jan. 28); Landgrebe et al. Gene. 2003 Oct. 16; 316:47-56; Dierks et al. 1998 FEBS Lett. 423(1):61-5; Dierks et al. Cell. 2003 May 16; 113(4):435-44; Cosma et al. (2003 May 16) Cell 113(4):445-56; Baenziger (2003 May 16) Cell 113(4):421-2 (review); Dierks et al. Cell. 2005 May 20; 121(4):541-52; Roeser et al. (2006 Jan. 3)Proc Natl Acad Sci USA 103(1):81-6; Sardiello et al. (2005 Nov. 1) Hum Mol. Genet. 14(21):3203-17; WO 2004/072275; WO 2008/036350; U.S. Patent Publication No. 2008/0187956; and GenBank Accession No. NM_182760. Accordingly, the disclosure here provides for recombinant host cells genetically modified to express an FGE that is compatible for use with an aldehyde tag of a tagged target polypeptide. In certain embodiments, the FGE used may be a naturally occurring enzyme (may have a wild type amino acid sequence). In other embodiments, the FGE used may be non-naturally occurring, in which case it may, in certain cases, have an amino acid sequence that is at least 80% identical, at least 90% identical or at least 95% identical to that of a wild type enzyme. Because FGEs have been studied structurally and functionally and the amino acid sequences of several examples of such enzymes are available, variants that retain enzymatic activity should be readily designable.

Where a cell-free method is used to convert a sulfatase motif-containing polypeptide, an isolated FGE can be used. Any convenient protein purification procedures may be used to isolate an FGE, see, e.g., Guide to Protein Purification, (Deuthser ed.) (Academic Press, 1990). For example, a lysate may be prepared from a cell that produces a desired FGE, and purified using HPLC, exclusion chromatography, gel electrophoresis, affinity chromatography, and the like.

Expression Vectors and Genetically Modified Host Cells

The present disclosure provides nucleic acid encoding ald-tagged Ig polypeptides, as well as constructs and host cells containing nucleic acid. Such nucleic acids comprise a sequence of DNA having an open reading frame that encodes an aldehyde tagged Ig polypeptide and, in most embodiments, is capable, under appropriate conditions, of being expressed. “Nucleic acid” encompasses DNA, cDNA, mRNA, and vectors comprising such nucleic acids.

The present disclosure provides a recombinant nucleic acid comprising a nucleotide sequence encoding an aldehyde-tagged Ig polypeptide, as described above. The recombinant nucleic acid can include:

1) a nucleotide sequence encoding an aldehyde-tagged Ig heavy chain constant region (and not an Ig heavy chain variable region, i.e., where the recombinant nucleic acid lacks a nucleotide sequence encoding an Ig VH domain);

2) a nucleotide sequence encoding an aldehyde-tagged Ig polypeptide, where the Ig polypeptide comprises an Ig VH domain and an aldehyde-tagged Ig heavy chain constant region;

3) a nucleotide sequence encoding an aldehyde-tagged Ig light chain constant region (and not an Ig light chain variable region, i.e., where the recombinant nucleic acid lacks a nucleotide sequence encoding an Ig VL domain);

4) a nucleotide sequence encoding an aldehyde-tagged Ig polypeptide, where the Ig polypeptide comprises an Ig VL domain and an aldehyde-tagged Ig light chain constant region;

5) a nucleotide sequence encoding an aldehyde-tagged Ig heavy chain constant region (and not an Ig heavy chain variable region, i.e., where the recombinant nucleic acid lacks a nucleotide sequence encoding an Ig VH domain); and a nucleotide sequence encoding an aldehyde-tagged Ig light chain constant region (and not an Ig light chain variable region, i.e., where the recombinant nucleic acid lacks a nucleotide sequence encoding an Ig VL domain);

6) a nucleotide sequence encoding an aldehyde-tagged Ig heavy chain constant region (and not an Ig heavy chain variable region, i.e., where the recombinant nucleic acid lacks a nucleotide sequence encoding an Ig VH domain); and a nucleotide sequence encoding an Ig light chain constant region (and not an Ig light chain variable region, i.e., where the recombinant nucleic acid lacks a nucleotide sequence encoding an Ig VL domain), where the Ig light chain constant region is not aldehyde tagged;

7) a nucleotide sequence encoding an Ig heavy chain constant region (and not an Ig heavy chain variable region, i.e., where the recombinant nucleic acid lacks a nucleotide sequence encoding an Ig VH domain), where the Ig heavy chain constant region is not aldehyde tagged; and a nucleotide sequence encoding an aldehyde-tagged Ig light chain constant region (and not an Ig light chain variable region, i.e., where the recombinant nucleic acid lacks a nucleotide sequence encoding an Ig VL domain);

8) a nucleotide sequence encoding a first aldehyde-tagged Ig polypeptide, where the first aldehyde-tagged Ig polypeptide comprises an Ig VH domain and an aldehyde-tagged Ig heavy chain constant region; and a nucleotide sequence encoding a second aldehyde-tagged Ig polypeptide, where the second aldehyde-tagged Ig polypeptide comprises an Ig VL domain and an aldehyde-tagged Ig light chain constant region;

9) a nucleotide sequence encoding a first Ig polypeptide, where the first Ig polypeptide is aldehyde tagged, where the first Ig polypeptide comprises an Ig VH domain and an aldehyde-tagged Ig heavy chain constant region; and a nucleotide sequence encoding a second Ig polypeptide, where the second Ig polypeptide comprises an Ig VL domain and an Ig light chain constant region, where the Ig light chain constant region is not aldehyde tagged; or 10) a nucleotide sequence encoding a first Ig polypeptide, where the first Ig polypeptide comprises an Ig VH domain and an Ig heavy chain constant region, where the Ig heavy chain constant region is not aldehyde tagged; and a nucleotide sequence encoding a second Ig polypeptide, where the second Ig polypeptide is aldehyde tagged, where the second Ig polypeptide comprising an Ig VL domain and an aldehyde-tagged Ig light chain constant region.

The present disclosure provides a recombinant expression vector comprising a nucleic acid as described above, where the nucleotide sequence encoding the Ig polypeptide(s) is operably linked to a promoter. In some embodiments, where a subject recombinant expression vector encodes both Ig heavy and light chains (with or without Ig variable regions), the heavy and light chain-encoding sequences can be operably linked to the same promoter, or to separate promoters.

Where a recombinant expression vector includes a nucleotide sequence encoding a heavy chain variable ($V_H$) region and/or a light chain variable ($V_L$) region, it will be appreciated that a large number of $V_H$ and $V_L$ amino acid sequences, and nucleotide sequences encoding same, are known in the art, and can be used. See, e.g., Kabat et al., Sequences of Proteins of Immunological Interest, 5th Ed. Public Health Service, National Institutes of Health, Bethesda, Md. (1991).

In those instances in which a recombinant expression vector comprises a nucleotide sequence encoding an Ig heavy or Ig light chain without variable region sequences, the vector can include an insertion site for an Ig variable region 5' of the Ig polypeptide-encoding nucleotide sequence. For example, a recombinant expression vector can comprise, in order from 5' to 3':

1) an insertion site for a nucleotide sequence encoding a VH domain; and a nucleotide sequence encoding an aldehyde-tagged Ig heavy chain constant region;

2) an insertion site for a nucleotide sequence encoding a VL domain; and a nucleotide sequence encoding an aldehyde-tagged Ig light chain constant region.

The present disclosure also provides a library of recombinant expression vectors, where the library can include a plurality of member recombinant expression vectors, e.g.:

1) a first recombinant expression vector comprising, in order from 5' to 3', an insertion site for a nucleotide sequence encoding a VH domain; and a nucleotide sequence encoding a first aldehyde-tagged Ig heavy chain constant region comprising an aldehyde tag in or adjacent a first surface-accessible loop region;

2) a second recombinant expression vector comprising, in order from 5' to 3', an insertion site for a nucleotide sequence encoding a VH domain; and a nucleotide sequence encoding a second aldehyde-tagged Ig heavy chain constant region comprising an aldehyde tag in or adjacent a second surface-accessible loop region;

3) a third recombinant expression vector comprising, in order from 5' to 3', an insertion site for a nucleotide sequence encoding a VH domain; and a nucleotide sequence encoding a third aldehyde-tagged Ig heavy chain constant region comprising an aldehyde tag in or adjacent a third surface-accessible loop region;

and combinations thereof, where each additional member recombinant expression vectors can include nucleotide sequences encoding aldehyde-tagged Ig polypeptides having aldehyde tags in or adjacent a different surface-accessible loop region.

In some instances, a recombinant expression vector in the library will also include a nucleotide sequence encoding an Ig light chain, which may or may not include a variable region, and which may or may not be aldehyde tagged.

The present disclosure also provides a library of recombinant expression vectors, where the library can include a plurality of member recombinant expression vectors, e.g.:

1) a first recombinant expression vector comprising, in order from 5' to 3', an insertion site for a nucleotide sequence encoding a VL domain; and a nucleotide sequence encoding a first aldehyde-tagged Ig light chain constant region comprising an aldehyde tag in or adjacent a first surface-accessible loop region;

2) a second recombinant expression vector comprising, in order from 5' to 3', an insertion site for a nucleotide sequence encoding a VL domain; and a nucleotide sequence encoding a second aldehyde-tagged Ig light chain constant region comprising an aldehyde tag in or adjacent a second surface-accessible loop region;

3) a third recombinant expression vector comprising, in order from 5' to 3', an insertion site for a nucleotide sequence encoding a VL domain; and a nucleotide sequence encoding a third aldehyde-tagged Ig light chain constant region comprising an aldehyde tag in or adjacent a third surface-accessible loop region;

and combinations thereof, where each additional member recombinant expression vectors can include nucleotide sequences encoding aldehyde-tagged Ig polypeptides having aldehyde tags in or adjacent a different surface-accessible loop region.

In some instances, a recombinant expression vector in the library will also include a nucleotide sequence encoding an Ig heavy chain, which may or may not include a variable region, and which may or may not be aldehyde tagged.

FIG. 2 depicts an example of a scheme for generating a library of aldehyde-tagged Ig polypeptides, in which each member Ig polypeptide comprises an aldehyde tag at a different location from the other members. For example, an Ig heavy chain or an Ig light chain, a "tagged cassette" is modified with aldehyde tags that can be further elaborated chemically. These cassettes can be applied to different Fvs for antibody-drug conjugate production.

Nucleic acids contemplated herein can be provided as part of a vector (also referred to as a construct), a wide variety of which are known in the art and need not be elaborated upon herein. Exemplary vectors include, but are not limited to, plasmids; cosmids; viral vectors (e.g., retroviral vectors); non-viral vectors; artificial chromosomes (yeast artificial chromosomes (YAC's), BAC's, etc.); mini-chromosomes; and the like. The choice of vector will depend upon a variety of factors such as the type of cell in which propagation is desired and the purpose of propagation.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding a polypeptide of interest (e.g., an aldehyde tagged polypeptide, an FGE, etc.), may provide for propagating the subject nucleic acids, or both.

Exemplary vectors that may be used include but are not limited to those derived from recombinant bacteriophage DNA, plasmid DNA or cosmid DNA. For example, plasmid vectors such as pBR322, pUC19/18, pUC118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Alternatively, recombinant virus vectors may be engineered, including but not limited to those derived from viruses such as herpes virus, retroviruses, vaccinia virus, poxviruses, adenoviruses, adeno-associated viruses, or bovine papilloma virus.

For expression of a protein of interest (e.g., an aldehyde-tagged Ig polypeptide or an FGE), an expression cassette may be employed. Thus, the present invention provides a recombinant expression vector comprising a subject nucleic acid. The expression vector provides a transcriptional and translational regulatory sequence, and may provide for inducible or constitutive expression, where the coding region is operably linked under the transcriptional control of the transcriptional initiation region, and a transcriptional and translational termination region. These control regions may be native to the gene encoding the polypeptide (e.g., the Ig polypeptide or the FGE), or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. In addition to constitutive and inducible promoters, strong promoters (e.g., T7, CMV, and the like) find use in the constructs described herein, particularly where high expression levels are desired in an in vivo (cell-based) or in an in vitro expression system. Further exemplary promoters include mouse mammary tumor virus (MMTV) promoters, Rous sarcoma virus (RSV) promoters, adenovirus promoters, the promoter from the immediate early gene of human CMV (Boshart et al., *Cell* 41:521-530, 1985), and the promoter from the long terminal repeat (LTR) of RSV (Gorman et al., *Proc. Natl. Acad. Sci. USA* 79:6777-6781, 1982). The promoter can also be provided by, for example, a 5'UTR of a retrovirus.

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

Expression constructs encoding aldehyde tagged Ig polypeptides can also be generated using amplification methods (e.g., a polymerase chain reaction (PCR)), where at least one amplification primer (i.e., at least one of a forward or reverse primer) includes a nucleic acid sequence encoding an aldehyde tag. For example, an amplification primer having an aldehyde tag-encoding sequence is designed to provide for amplification of a nucleic acid encoding an Ig polypeptide. The extension product that results from polymerase-mediated synthesis from the aldehyde tag-containing forward primer produces a nucleic acid amplification product encoding a fusion protein composed of an aldehyde-tagged Ig polypeptide. The amplification product is then inserted into an expression construct of choice to provide an aldehyde tagged polypeptide expression construct.

Host Cells

The present disclosure provides genetically modified host cells comprising a subject nucleic acid, including a genetically modified host cell comprising a recombinant expression vector as described above. Any of a number of suitable host cells can be used in the production of an aldehyde-tagged Ig polypeptide. The host cell used for production of an aldehyde tagged Ig polypeptide can optionally provide for FGE-mediated conversion, so that the Ig polypeptide produced contains an FGly-containing aldehyde tag following expression and modification by FGE. Alternatively the host cell can provide for production of an unconverted aldehyde tagged Ig polypeptide (e.g., due to lack of expression of an FGE that facilitates conversion of the aldehyde tag).

The aldehyde moiety of a converted aldehyde tag can be used for a variety of applications including, but not limited to, visualization using fluorescence or epitope labeling (e.g., electron microscopy using gold particles equipped with aldehyde reactive groups); protein immobilization (e.g., protein microarray production); protein dynamics and localization studies and applications; and conjugation of proteins with a moiety of interest (e.g., moieties that improve a parent protein's half-life (e.g., poly(ethylene glycol)), targeting moieties (e.g., to enhance delivery to a site of action), and biologically active moieties (e.g., a therapeutic moiety).

In general, the polypeptides described herein may be expressed in prokaryotes or eukaryotes in accordance with conventional ways, depending upon the purpose for expression. Thus, the present invention further provides a host cell, e.g., a genetically modified host cell that comprises a nucleic acid encoding an aldehyde tagged polypeptide. The host cell can further optionally comprise a recombinant FGE, which may be endogenous or heterologous to the host cell.

Host cells for production (including large scale production) of an unconverted or (where the host cell expresses a suitable FGE) converted aldehyde tagged Ig polypeptide, or for production of an FGE (e.g., for use in a cell-free method) can be selected from any of a variety of available host cells. Exemplary host cells include those of a prokaryotic or eukaryotic unicellular organism, such as bacteria (e.g., *Escherichia coli strains, Bacillus* spp. (e.g., *B. subtilis*), and the like) yeast or fungi (e.g., *S. cerevisiae, Pichia* spp., and the like), and other such host cells can be used. Exemplary host cells originally derived from a higher organism such as insects, vertebrates, particularly mammals, (e.g. CHO, HEK, and the like), may be used as the expression host cells.

Suitable mammalian cell lines include, but are not limited to, HeLa cells (e.g., American Type Culture Collection (ATCC) No. CCL-2), CHO cells (e.g., ATCC Nos. CRL9618 and CRL9096), CHO DG44 cells (Urlaub (1983) Cell 33:405), CHO-K1 cells (ATCC CCL-61), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, and the like.

Specific expression systems of interest include bacterial, yeast, insect cell and mammalian cell derived expression systems. Representative systems from each of these categories are provided below.

The product can be recovered by any appropriate means known in the art. Further, any convenient protein purification procedures may be employed, where suitable protein purification methodologies are described in Guide to Protein Purification, (Deuthser ed.) (Academic Press, 1990). For example, a lysate may prepared from a cell comprising the expression vector expressing the ald-tagged Ig polypeptide, and purified using high performance liquid chromatography (HPLC), exclusion chromatography, gel electrophoresis, affinity chromatography, and the like.

Methods for Conversion and Modification of an Aldehyde Tag

Conversion of an aldehyde tag present in an aldehyde tagged Ig polypeptide can be accomplished by cell-based (in vivo) or cell-free methods (in vitro). Similarly, modification of a converted aldehyde tag of an aldehyde tagged polypeptide can be accomplished by cell-based (in vivo) or cell-free methods (in vitro). These are described in more detail below.

"In vivo" Host Cells Conversion and Modification

Conversion of an aldehyde tag of an aldehyde tagged polypeptide can be accomplished by expression of the aldehyde tagged polypeptide in a cell that contains a suitable FGE. In this embodiment, conversion of the cysteine or serine of the aldehyde tag occurs during or following translation in the host cell. The FGE of the host cell can be endogenous to the host cell, or the host cell can be recombinant for a suitable FGE that is heterologous to the host cell. FGE expression can be provided by an expression system endogenous to the FGE gene (e.g., expression is provided by a promoter and other control elements present in the native FGE gene of the host cell), or can be provided by from a recombinant expression system in which the FGE coding sequence is operably linked to a heterologous promoter to provide for constitutive or inducible expression.

Conditions suitable for use to accomplish conjugation of a reactive partner moiety to an aldehyde tagged polypeptide are similar to those described in Mahal et al. (1997 May 16) Science 276(5315):1125-8.

In some instances, where a method is carried out in a cell, the cell is in vitro, e.g., in in vitro cell culture, e.g., where the cell is cultured in vitro in a single-cell suspension or as an adherent cell.

"In vitro" (Cell-Free) Conversion and Modification

In vitro (cell-free) conversion of an aldehyde tag of an aldehyde tagged Ig polypeptide can be accomplished by contacting an aldehyde tagged polypeptide with an FGE under conditions suitable for conversion of a cysteine or serine of a sulfatase motif of the aldehyde tag to an FGly. For example, nucleic acid encoding an aldehyde tagged Ig polypeptide can be expressed in an in vitro transcription/translation system in the presence of a suitable FGE to provide for production of converted aldehyde tagged Ig polypeptides.

Alternatively, isolated, unconverted aldehyde tagged Ig polypeptide can be isolated following recombinant production in a host cell lacking a suitable FGE or by synthetic production. The isolated aldehyde tagged Ig polypeptide is then contacted with a suitable FGE under conditions to provide for aldehyde tag conversion. The aldehyde tagged Ig polypeptide can be unfolded by methods known in the art (e.g., using heat, adjustment of pH, chaotropic agents, (e.g., urea, and the like), organic solvents (e.g., hydrocarbons: octane, benzene, chloroform), etc.) and the denatured protein contacted with a suitable FGE. The ald-tagged Ig polypeptide can then be refolded under suitable conditions.

With respect to modification of converted aldehyde tagged, modification is normally carried out in vitro. A converted aldehyde tagged Ig polypeptide is isolated from a production source (e.g., recombinant host cell production, synthetic production), and contacted with a reactive partner-containing drug or other moiety under conditions suitable to provide for conjugation of the drug or other moiety to the FGly of the aldehyde tag.

In some instances, a combination of cell-based conversion and cell-free conversion is carried out, to generate a converted aldehyde tag; followed by cell-free modification of the converted aldehyde tag. In some embodiments, a combination of cell-free conversion and cell-based conversion is carried out.

Moieties for Modification of Immunoglobulin Polypeptides

The aldehyde tagged, FGly-containing Ig polypeptides can be subjected to modification to provide for attachment of a wide variety of moieties. Exemplary molecules of interest include, but are not necessarily limited to, a drug, a detectable label, a small molecule, a water-soluble polymer, a synthetic peptide, and the like.

Thus, the present disclosure provides an Ig polypeptide conjugate (also referred to herein as an "Ig conjugate"), the Ig conjugate comprising:

an Ig polypeptide (e.g., an Ig heavy chain or an Ig light chain, or an Ig comprising both heavy and light chains) and a covalently conjugated moiety, wherein the Ig polypeptide comprises a modified sulfatase motif of the formula:

$X_1(FGly')X_2Z_2X_3Z_3$ where FGly' is of the formula:

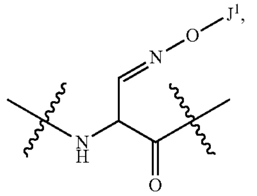

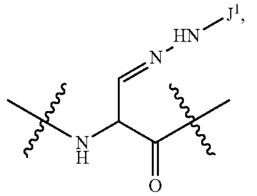

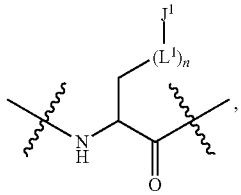

,

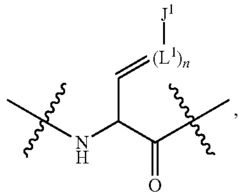

, or

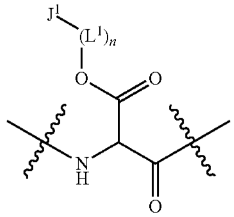

, wherein $J^1$ is the covalently bound moiety;

each $L^1$ is a divalent moiety independently selected from alkylene, substituted alkylene, alkenylene, substituted alkenylene, alkynylene, alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is a number selected from zero to 40;

$Z_2$ is a proline or alanine residue;

$X_1$ is present or absent and, when present, is any amino acid, with the proviso that when the sulfatase motif is at an N-terminus of the polypeptide, $X_1$ is present;

$X_2$ and $X_3$ are each independently any amino acid; and $Z_3$ is an aliphatic amino acid or basic amino acid; and wherein the Ig conjugate presents the covalently bound moiety on a solvent-accessible surface when in a folded state.

The present disclosure provides an antibody conjugated to a moiety of interest, where an antibody conjugated to a moiety of interest is referred to as an "antibody conjugate." An antibody conjugate of the present disclosure can include: 1) Ig heavy chain constant region conjugated to a moiety of interest; and an Ig light chain constant region conjugated to a moiety of interest; 2) an Ig heavy chain constant region conjugated to a moiety of interest; and an Ig light chain constant region that is not conjugated to a moiety of interest; or 3) an Ig heavy chain constant region that is not conjugated to a moiety of interest; and an Ig light chain constant region conjugated to a moiety of interest. A subject antibody conjugate can also include VH and/or VL domains.

The moiety of interest is provided as component of a reactive partner for reaction with an aldehyde of the FGly residue of a converted aldehyde tag of the tagged Ig polypeptide. Since the methods of tagged Ig polypeptide modification are compatible with conventional chemical processes, the methods of the present disclosure can exploit a wide range of commercially available reagents to accomplish attachment of a moiety of interest to an FGly residue of an aldehyde tagged Ig polypeptide. For example, aminooxy, hydrazide, or thiosemicarbazide derivatives of a number of moieties of interest are suitable reactive partners, and are readily available or can be generated using standard chemical methods.

For example, to attach a poly(ethylene glycol) (PEG) moiety to a tagged Ig polypeptide, an aminooxy-PEG can be generated from monoamino-PEGs and aminooxyglycine using standard protocols. The aminooxy-PEG can then be reacted with a converted (e.g., FGly-modified) aldehyde tagged Ig polypeptide to provide for attachment of the PEG moiety. Delivery of a biotin moiety to a converted aldehyde tagged polypeptide can be accomplished using aminooxy biotin, biotin hydrazide or 2,4 dinitrophenylhydrazine.

Provided the present disclosure, the ordinarily skilled artisan can readily adapt any of a variety of moieties to provide a reactive partner for conjugation to an aldehyde tagged polypeptide as contemplated herein. The ordinarily skilled artisan will appreciate that factors such as pH and steric hindrance (i.e., the accessibility of the aldehyde tag to reaction with a reactive partner of interest) are of importance. Modifying reaction conditions to provide for optimal conjugation conditions is well within the skill of the ordinary artisan, and is routine in the art. In general, it is normally desirable to conduction conjugation reactions at a pH below 7, with a pH of about 5.5, about 6, about 6.5, usually about 5.5 being optimal. Where conjugation is conducted with an aldehyde tagged polypeptide present in or on a living cell, the conditions are selected so as to be physiologically compatible. For example, the pH can be dropped temporarily for a time sufficient to allow for the reaction to occur but within a period tolerated by the cell having an aldehyde tag (e.g., from about 30 min to 1 hour). Physiological conditions for conducting modification of aldehyde tagged polypeptides on a cell surface can be similar to those used in a ketone-azide reaction in modification of cells bearing cell-surface azides (see, e.g., U.S. Pat. No. 6,570,040).

In general, the moiety or moieties can provide for one or more of a wide variety of functions or features. Exemplary moieties include detectable labels (e.g., dye labels (e.g., chromophores, fluorophores), biophysical probes (spin labels, nuclear magnetic resonance (NMR) probes), Förster Resonance Energy Transfer (FRET)-type labels (e.g., at least one member of a FRET pair, including at least one member of a fluorophore/quencher pair), Bioluminescence Resonance Energy Transfer (BRET)-type labels (e.g., at least one member of a BRET pair), immunodetectable tags (e.g., FLAG, His(6), and the like), localization tags (e.g., to identify association of a tagged polypeptide at the tissue or molecular cell level (e.g., association with a tissue type, or particular cell membrane)), and the like); light-activated dynamic moieties (e.g., azobenzene mediated pore closing, azobenzene mediated structural changes, photodecaging recognition motifs); water soluble polymers (e.g., PEGylation); purification tags (e.g., to facilitate isolation by affinity chromatography (e.g., attachment of a FLAG epitope, e.g., DYKDDDDK (SEQ ID NO:222)); membrane localization domains (e.g., lipids or glycophosphatidylinositol (GPI)-type anchors); immobilization tags (e.g., to facilitate attachment of the polypeptide to a surface, including selective attachment); drugs (e.g., to facilitate drug targeting, e.g., through attachment of the drug to an antibody); targeted delivery moieties, (e.g., ligands for binding to a target receptor (e.g., to facilitate viral attachment, attachment of a targeting protein present on a liposome, etc.)), and the like.

Specific, non-limiting examples are provided below.

Detectable Labels

The compositions and methods of the present disclosure can be used to deliver a detectable label to an aldehyde tagged Ig, e.g., where $J^1$ is a detectable label. Exemplary detectable labels include, but are not necessarily limited to, fluorescent molecules (e.g., autofluorescent molecules, molecules that fluoresce upon contact with a reagent, etc.), radioactive labels (e.g., $^{111}In$, $^{125}I$, $^{131}I$, $^{212}B$, $^{90}Y$, $^{186}Rh$, and the like); biotin (e.g., to be detected through reaction of biotin and avidin); fluorescent tags; imaging reagents, and the like. Detectable labels also include peptides or polypeptides that can be detected by antibody binding, e.g., by binding of a detectably labeled antibody or by detection of bound antibody through a sandwich-type assay.

Attachment of Target Molecules to a Support

The methods can provide for conjugation of an aldehyde tagged immunoglobulin to a moiety to facilitate attachment of the immunoglobulin to a solid substratum (e.g., to facilitate assays), or to a moiety to facilitate easy separation (e.g., a hapten recognized by an antibody bound to a magnetic bead). In one embodiment, the methods of the invention are used to provide for attachment of a protein to an array (e.g., chip) in a defined orientation. For example, a polypeptide having an aldehyde tag at a selected site (e.g., at or near the N-terminus) can be generated, and the methods and compositions of the invention used to deliver a moiety to the converted aldehyde tag. The moiety can then be used as the attachment site for affixing the polypeptide to a support (e.g., solid or semi-solid support, particularly a support suitable for use as a microchip in high-throughput assays).

Attachment of Molecules for Delivery to a Target Site

The reactive partner for the aldehyde tagged polypeptide can comprise a small molecule drug, toxin, or other molecule for delivery to the cell and which can provide for a pharmacological activity or can serve as a target for delivery of other molecules.

Also contemplated is use of a reactive partner that comprises one of a pair of binding partners (e.g., a ligand, a ligand-binding portion of a receptor, a receptor-binding portion of a ligand, etc.). For example, the reactive partner can comprise a polypeptide that serves as a viral receptor and, upon binding with a viral envelope protein or viral capsid protein, facilitates attachment of virus to the cell surface on which the modified aldehyde tagged protein is expressed. Alternatively, the reactive partner comprises an antigen that is specifically bound by an antibody (e.g., monoclonal antibody), to facilitate detection and/or separation of host cells expressing the modified aldehyde tagged polypeptide.

Water-Soluble Polymers

In some cases, an Ig conjugate comprises a covalently linked water-soluble polymer, e.g., where $J^1$ is a water-soluble polymer. A moiety of particular interest is a water-soluble polymer. A "water-soluble polymer" refers to a polymer that is soluble in water and is usually substantially non-immunogenic, and usually has an atomic molecular weight greater than about 1,000 Daltons. The methods and compositions described herein can be used to attach one or more water-soluble polymers to an aldehyde tagged polypeptide. Attachment of a water-soluble polymer (e.g., PEG) of a polypeptide, particularly a pharmaceutically active (therapeutic) polypeptide can be desirable as such modification can increase therapeutic index by increasing serum half-life as a result of increased proteolytic stability and/or decreased renal clearance. Additionally, attachment of one or more polymers (e.g., PEGylation) can reduce immunogenicity of protein pharmaceuticals.

In some embodiments, the water-soluble polymer has an effective hydrodynamic molecular weight of greater than about 10,000 Da, greater than about 20,000 to 500,000 Da, greater than about 40,000 Da to 300,000 Da, greater than about 50,000 Da to 70,000 Da, usually greater than about 60,000 Da. In some embodiments, the water-soluble polymer has an effective hydrodynamic molecular weight of from about 10 kDa to about 20 kDa, from about 20 kDa to about 25 kDa, from about 25 kDa to about 30 kDa, from about 30 kDa to about 50 kDa, or from about 50 kDa to about 100 kDa. By "effective hydrodynamic molecular weight" is intended the effective water-solvated size of a polymer chain as determined by aqueous-based size exclusion chromatography (SEC). When the water-soluble polymer contains polymer chains having polyalkylene oxide repeat units, such as ethylene oxide repeat units, each chain can have an atomic molecular weight of between about 200 Da and about 80,000 Da, or between about 1,500 Da and about 42,000 Da, with 2,000 to about 20,000 Da being of particular interest. Unless referred to specifically, molecular weight is intended to refer to atomic molecular weight. Linear, branched, and terminally charged water soluble polymers (e.g., PEG) are of particular interest.

Polymers useful as moieties to be attached to an aldehyde tagged polypeptide can have a wide range of molecular weights, and polymer subunits. These subunits may include a biological polymer, a synthetic polymer, or a combination thereof. Examples of such water-soluble polymers include: dextran and dextran derivatives, including dextran sulfate, P-amino cross linked dextrin, and carboxymethyl dextrin, cellulose and cellulose derivatives, including methylcellulose and carboxymethyl cellulose, starch and dextrines, and derivatives and hydroylactes of starch, polyalklyene glycol and derivatives thereof, including polyethylene glycol, methoxypolyethylene glycol, polyethylene glycol homopolymers, polypropylene glycol homopolymers, copolymers of ethylene glycol with propylene glycol, wherein said homopolymers and copolymers are unsubstituted or substituted at one end with an alkyl group, heparin and fragments of heparin, polyvinyl alcohol and polyvinyl ethyl ethers, polyvinylpyrrolidone, aspartamide, and polyoxyethylated polyols, with the dextran and dextran derivatives, dextrine and dextrine derivatives. It will be appreciated that various derivatives of the specifically recited water-soluble polymers are also contemplated.

Water-soluble polymers such as those described above are well known, particularly the polyalkylene oxide based polymers such as polyethylene glycol "PEG" (See. e.g., "Poly (ethylene glycol) Chemistry: Biotechnical and Biomedical Applications", J. M. Harris, Ed., Plenum Press, New York, N.Y. (1992); and "Poly(ethylene glycol) Chemistry and Biological Applications", J. M. Harris and S. Zalipsky, Eds., ACS (1997); and International Patent Applications: WO 90/13540, WO 92/00748, WO 92/16555, WO 94/04193, WO 94/14758, WO 94/17039, WO 94/18247, WO 94/28937, WO 95/11924, WO 96/00080, WO 96/23794, WO 98/07713, WO 98/41562, WO 98/48837, WO 99/30727, WO 99/32134, WO 99/33483, WO 99/53951, WO 01/26692, WO 95/13312, WO 96/21469, WO 97/03106, WO 99/45964, and U.S. Pat. Nos. 4,179,337; 5,075,046; 5,089,261; 5,100,992; 5,134,192; 5,166,309; 5,171,264; 5,213,891; 5,219,564; 5,275,838; 5,281,698; 5,298,643; 5,312,808; 5,321,095; 5,324,844; 5,349,001; 5,352,756; 5,405,877; 5,455,027; 5,446,090; 5,470,829; 5,478,805; 5,567,422; 5,605,976; 5,612,460; 5,614,549; 5,618,528; 5,672,662; 5,637,749; 5,643,575; 5,650,388; 5,681,567; 5,686,110; 5,730,990; 5,739,208; 5,756,593; 5,808,096; 5,824,778; 5,824,784; 5,840,900; 5,874,500; 5,880,131; 5,900,461; 5,902,588; 5,919,442; 5,919,455; 5,932,462; 5,965,119; 5,965,566; 5,985,263; 5,990,237; 6,011,042; 6,013,283; 6,077,939; 6,113,906; 6,127,355; 6,177,087; 6,180,095; 6,194,580; 6,214,966).

Exemplary polymers of interest include those containing a polyalkylene oxide, polyamide alkylene oxide, or derivatives thereof, including polyalkylene oxide and polyamide alkylene oxide comprising an ethylene oxide repeat unit of the formula $—(CH_2—CH_2—O)—$. Further exemplary polymers of interest include a polyamide having a molecular weight greater than about 1,000 Daltons of the formula $—[C(O)—X—C(O)—NH—Y—NH]n-$ or $—[NH—Y—NH—C(O)—X—C(O)]_n—$, where X and Y are divalent radicals that may be the same or different and may be branched or linear, and n is a discrete integer from 2-100, usually from 2 to 50, and where either or both of X and Y comprises a biocompatible, substantially non-antigenic water-soluble repeat unit that may be linear or branched. Further exemplary water-soluble repeat units comprise an ethylene oxide of the formula $—(CH_2—CH_2—O)—$ or $—(CH_2—CH_2—O)—$. The number of such water-soluble repeat units can vary significantly, with the usual number of such units being from 2 to 500, 2 to 400, 2 to 300, 2 to 200, 2 to 100, and most usually 2 to 50. An exemplary embodiment is one in which one or both of X and Y is selected from: $—((CH_2)_{n1}—(CH_2—CH_2—O)_{n2}—(CH_2)—$ or $—((CH_2)_{n1}—(O—CH_2—CH_2)_{n2}—(CH_2)_{n-1}—)$, where n1 is 1 to 6, 1 to 5, 1 to 4 and most usually 1 to 3, and where n2 is 2 to 50, 2 to 25, 2 to 15, 2 to 10, 2 to 8, and most usually 2 to 5. A further exemplary embodiment is one in which X is —($CH_2$—$CH_2$)—, and where Y is —($CH_2$—($CH_2$—$CH_2$—O)$_3$—$CH_2$—$CH_2$—$CH_2$)— or —($CH_2$—$CH_2$—$CH_2$—(O—$CH_2$—$CH_2$)$_3$—$CH_2$)—.

The polymer can include one or more spacers or linkers. Exemplary spacers or linkers include linear or branched moieties comprising one or more repeat units employed in a water-soluble polymer, diamino and or diacid units, natural or unnatural amino acids or derivatives thereof, as well as aliphatic moieties, including alkyl, aryl, heteroalkyl, heteroaryl, alkoxy, and the like, which can contain, for example, up to 18 carbon atoms or even an additional polymer chain.

The polymer moiety, or one or more of the spacers or linkers of the polymer moiety when present, may include polymer chains or units that are biostable or biodegradable. For example, Polymers with repeat linkages have varying degrees of stability under physiological conditions depending on bond lability. Polymers with such bonds can be categorized by their relative rates of hydrolysis under physiological conditions based on known hydrolysis rates of low molecular weight analogs, e.g., from less stable to more stable, e.g., polyurethanes (—NH—C(O)—O—)>polyorthoesters (—O—C((OR)(R'))—O—)>polyamides (—C(O)—NH—). Similarly, the linkage systems attaching a water-soluble polymer to a target molecule may be biostable or biodegradable, e.g., from less stable to more stable: carbonate (—O—C(O)—O—)>ester (—C(O)—O—)>urethane (—NH—C(O)—O—)>orthoester (—O—C((OR)(R'))—O—)>amide (—C(O)—NH—). In general, it may be desirable to avoid use of sulfated polysaccharide, depending on the lability of the sulfate group. In addition, it may be less desirable to use polycarbonates and polyesters. These bonds are provided by way of example, and are not intended to limit the types of bonds employable in the polymer chains or linkage systems of the water-soluble polymers useful in the modified aldehyde tagged polypeptides disclosed herein.

Synthetic Peptides

In some cases, an Ig conjugate comprises a covalently linked peptide, e.g., where $J^1$ is a peptide. Suitable peptides include, but are not limited to, cytotoxic peptides; angiogenic peptides; anti-angiogenic peptides; peptides that activate B cells; peptides that activate T cells; anti-viral peptides; peptides that inhibit viral fusion; peptides that increase production of one or more lymphocyte populations; anti-microbial peptides; growth factors; growth hormone-releasing factors; vasoactive peptides; anti-inflammatory peptides; peptides that regulate glucose metabolism; an anti-thrombotic peptide; an anti-nociceptive peptide; a vasodilator peptide; a platelet aggregation inhibitor; an analgesic; and the like.

Where $J^1$ is a peptide, the peptide can be chemically synthesized to include a group reactive with a converted FGly-containing Ig polypeptide. A suitable synthetic peptide has a length of from about 5 amino acids to about 100 amino acids, or longer than 100 amino acids; e.g., a suitable peptide has a length of from about 5 amino acids (aa) to about 10 aa, from about 10 aa to about 15 aa, from about 15 aa to about 20 aa, from about 20 aa to about 25 aa, from about 25 aa to about 30 aa, from about 30 aa to about 40 aa, from about 40 aa to about 50 aa, from about 50 aa to about 60 aa, from about 60 aa to about 70 aa, from about 70 aa to about 80 aa, from about 80 aa to about 90 aa, or from about 90 aa to about 100 aa.

A peptide can be modified to contain an α-nucleophile-containing moiety (e.g., an aminooxy or hydrazide moiety), e.g., can be reacted with the FGly-containing Ig polypeptide to yield a conjugate in which the aldehyde-tagged Ig polypeptide and peptide are linked by a hydrazone or oxime bond, respectively. Exemplary methods of synthesizing a peptide, such that the synthetic peptide comprising a reactive group reactive with a converted aldehyde tag, are described above.

Suitable peptides include, but are not limited to, hLF-11 (an 11-amino acid N-terminal fragment of lactoferrin), an anti-microbial peptide; granulysin, an anti-microbial peptide; Plectasin (NZ2114; SAR 215500), an anti-microbial peptide; viral fusion inhibitors such as Fuzeon (enfuvirtide), TRI-1249 (T-1249; see, e.g., Matos et al. (2010) *PLoS One* 5:e9830), TRI-2635 (T-2635; see, e.g., Eggink et al. (2009) *J. Biol. Chem.* 284:26941), T651, and TRI-1144; C5a receptor inhibitors such as PMX-53, JPE-1375, and JSM-7717; POT-4, a human complement factor C3 inhibitor; Pancreate (an INGAP derivative sequence, a HIP-human proislet protein); somatostatin; a somatostatin analog such as DEBIO 8609 (Sanvar), octreotide, octreotide (C2L), octreotide QLT, octreotide LAR, Sandostatin LAR, SomaLAR, Somatuline (lanreotide), see, e.g., Deghenghi et al. (2001) *Endocrine* 14:29; TH9507 (Tesamorelin, a growth hormone-releasing factor); POL7080 (a protegrin analog, an anti-microbial peptide); relaxin; a corticotropin releasing factor agonist such as urotensin, sauvagine, and the like; a heat shock protein derivative such as DiaPep277; a human immunodeficiency virus entry inhibitor; a heat shock protein-20 mimic such as AZX100; a thrombin receptor activating peptide such as TP508 (Chrysalin); a urocortin 2 mimic (e.g., a CRF2 agonist) such as urocortin-2; an immune activator such as Zadaxin (thymalfasin; thymosin-α1), see, e.g., Sjogren (2004) *J. Gastroenterol. Hepatol.* 19:S69; a hepatitis C virus (HCV) entry inhibitorE2 peptide such as HCV3; an atrial natriuretic peptide such as HANP (Sun 4936; carperitide); an annexin peptide; a defensin (anti-microbial peptide) such as hBD2-4; a defensin (anti-microbial peptide) such as hBD-3; a defensin (anti-microbial peptide) such as PMX-30063; a histatin (anti-microbial peptide) such as histatin-3, histatin-5, histatin-6, and histatin-9; a histatin (anti-microbial peptide) such as PAC-113; an indolicidin (anti-microbial peptide) such as MX-594AN (Omniganin; CLS001); an indolicidin (anti-microbial peptide) such as Omnigard (MBI-226; CPI-226); an anti-microbial peptide such as an insect cecropin; an anti-microbial peptide such as a lactoferrin (talactoferrin); an LL-37/cathelicidin derivative (an anti-microbial peptide) such as P60.4 (OP-145); a magainin (an anti-microbial peptide) such as Pexiganan (MSI-78; Suponex); a protegrin (an anti-microbial peptide) such as IB-367 (Iseganan); an agan peptide; a beta-natriuretic peptide such as Natrecor, or Noratak (Nesiritide), or ularitide; bivalarudin (Angiomax), a thrombin inhibitor; a C peptide derivative; a calcitonin such as Miacalcin (Fortical); an enkephalin derivative; an erythropoiesis-stimulating peptide such as Hematide; a gap junction modulator such as Danegaptide (ZP1609); a gastrin-releasing peptide; a ghrelin; a glucagon-like peptide; a glucagon-like peptide-2 analog such as ZP1846 or ZP1848; a glucosaminyl muramyl dipeptide such as GMDP; a glycopeptide antibiotic such as Oritavancin; a teicoplanin derivative such as Dalbavancin; a gonadotropin releasing hormone (GnRH) such as Zoladex (Lupon) or Triptorelin; a histone deacetylase (HDAC) inhibitor depsipeptide such as PM02734 (Irvalec); an integrin such as eptifibatide; an insulin analog such as Humulog; a kahalalide depsipeptide such as PM02734; a kallikrein inhibitor such as Kalbitor (ecallantide); an antibiotic such as Telavancin; a lipopeptide such as Cubicin or MX-2401; a lutenizing hormone releasing hormone (LHRH) such as goserelin; an LHRH synthetic decapeptide agonist analog such as Treistar (triptorelin pamoate); an LHRH such as Eligard; an M2 protein channel peptide inhibitor; metreleptin; a melanocortin receptor agonist peptide such as bremalanotide/PT-141; a melanocortin; a muramyl tripeptide such as Mepact (mifamurtide); a myelin basic protein peptide such as MBP 8298 (dirucotide); an N-type voltage-gated calcium channel blocker such as Ziconotide (Prialt); a parathyroid hormone peptide; a parathyroid analog such as 768974; a peptide hormone analog such as UGP281; a prostaglandin F2-α receptor inhibitor such as PDC31; a protease inhibitor such as PPL-100; surfaxin; a thrombospondin-1 (TSP-1) mimetic such as CVX-045 or ABT 510; a vasoactive intestinal peptide; vasopressin; a Y2R agonist peptide such as RG7089; obinepeptide; and TM30339.

Drugs for Conjugation to an Aldehyde-Tagged Immunoglobulin Polypeptide

Any of a number of drugs are suitable for use, or can be modified to be rendered suitable for use, as a reactive partner to conjugate to an ald-tagged-Ig polypeptide. Exemplary drugs include small molecule drugs and peptide drugs. Thus, the present disclosure provides drug-antibody conjugates.

"Small molecule drug" as used herein refers to a compound, e.g., an organic compound, which exhibits a pharmaceutical activity of interest and which is generally of a molecular weight of no greater than about 800 Da, or no greater than 2000 Da, but can encompass molecules of up to 5 kDa and can be as large as about 10 kDa. A small inorganic molecule refers to a molecule containing no carbon atoms, while a small organic molecule refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

In some cases, the drug is a cancer chemotherapeutic agent. For example, where an antibody has specificity for a tumor cell, the antibody can be modified as described herein to include an aldehyde tag, can be subsequently converted to an FGly-modified antibody, and can then be conjugated to a cancer chemotherapeutic agent. Cancer chemotherapeutic agents include non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones. Peptidic compounds can also be used.

Suitable cancer chemotherapeutic agents include dolastatin and active analogs and derivatives thereof; and auristatin and active analogs and derivatives thereof. See, e.g., WO 96/33212, WO 96/14856, and U.S. Pat. No. 6,323,315. For example, dolastatin 10 or auristatin PE can be included in an antibody-drug conjugate of the present disclosure. Suitable cancer chemotherapeutic agents also include maytansinoids and active analogs and derivatives thereof (see, e.g., EP 1391213; and Liu et al (1996) *Proc. Natl. Acad. Sci. USA* 93:8618-8623); and duocarmycins and active analogs and derivatives thereof (e.g., including the synthetic analogues, KW-2189 and CB 1-TM1).

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (CYTOXAN™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U™), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (TAXOL®), docetaxel (TAXOTERE®), deoxycoformycin, mitomycin-C,L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, PROGRAF™), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (TAXOL®), TAXOL® derivatives, docetaxel (TAXOTERE®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (DROGENIL®), Toremifene (FARESTON®), and (ZOLADEX®). Estrogens stimulate proliferation and differentiation; therefore compounds that bind to the estrogen receptor are used to block this activity. Corticosteroids may inhibit T cell proliferation.

Other suitable chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); IRESSA® (ZD 1839, 4-(3-chloro-4-fluorophenylamino)-7-methoxy-6-(3-(4-morpholinyl)propoxy)quinazoline); etc.

Taxanes are suitable for use. “Taxanes” include paclitaxel, as well as any active taxane derivative or pro-drug. “Paclitaxel” (which should be understood herein to include analogues, formulations, and derivatives such as, for example, docetaxel, TAXOLT™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., TAXOTERE™ docetaxel, as noted above) and paclitaxel conjugates (e.g., paclitaxel-PEG, paclitaxel-dextran, or paclitaxel-xylose).

Also included within the term “taxane” are a variety of known derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Biological response modifiers suitable for use include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) IFN-α; (7) IFN-γ; (8) colony-stimulating factors; and (9) inhibitors of angiogenesis.

Methods for Modification of Drugs to Contain Reactive Partner for Reaction with 2-Formylglycine Peptide drugs to be conjugated to an ald-tagged Ig polypeptide are modified to incorporate a reactive partner for reaction with an aldehyde of the FGly residue of the ald-tagged Ig polypeptide. Since the methods of ald-tagged polypeptide modification are compatible with conventional chemical processes, any of a wide variety of commercially available reagents can be used to accomplish conjugation. For example, aminooxy, hydrazide, hydrazine, or thiosemicarbazide derivatives of a number of moieties of interest are suitable reactive partners, and are readily available or can be generated using standard chemical methods.

Where the drug is a peptide drug, the reactive moiety (e.g., aminooxy or hydrazide can be positioned at an N-terminal region, the N-terminus, a C-terminal region, the C-terminus, or at a position internal to the peptide. For example, an exemplary method involves synthesizing a peptide drug having an aminooxy group. In this example, the peptide is synthesized from a Boc-protected precursor. An amino group of a peptide can react with a compound comprising a carboxylic acid group and oxy-N-Boc group. As an example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphosphate), DPPA (diphenylphosphorazidate), BOP (benzotriazol-1-yloxytris(dimethylamino)phosphonium hexafluorophosphate), HBTU (O-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). As a non-limiting example, HOBt and DIC can be used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999, John Wiley & Sons, NY and Harrison et al. Certain deprotection conditions include a hydrazine reagent, amino reagent, or sodium borohydride. Deprotection of a Boc protecting group can occur with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the aldehyde tag to reaction with a reactive partner of interest) are of importance, Modifying reaction conditions to provide for optimal conjugation conditions is well within the skill of the ordinary artisan, and is routine in the art. In general, it is normally desirable to conduction conjugation reactions at a pH below 7, with a pH of about 5.5, about 6, about 6.5, usually about 5.5 being optimal. Where conjugation is conducted with an aldehyde tagged polypeptide present in or on a living cell, the conditions are selected so as to be physiologically compatible. For example, the pH can be dropped temporarily for a time sufficient to allow for the reaction to occur but within a period tolerated by the cell having an aldehyde tag (e.g., from about 30 min to 1 hour). Physiological conditions for conducting modification of aldehyde tagged polypeptides on a cell surface can be similar to those used in a ketone-azide reaction in modification of cells bearing cell-surface azides (see, e.g., U.S. Pat. No. 6,570,040).

Small molecule compounds containing, or modified to contain, an α-nucleophilic group that serves as a reactive partner with an aldehyde of an FGly of an ald tag are also contemplated for use as drugs in the Ig-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Thus small molecules having an aminooxy or hydrazone group for reaction with an aldehyde of an FGly of an ald-tagged Ig polypeptide are available or can be readily synthesized. An aminooxy or hydrazone group can be installed onto a small molecule using standard synthetic chemistry techniques.

Ig Conjugates

In some embodiments, a subject Ig-conjugate is an antibody conjugate. For example, the present disclosure provides an antibody conjugate that comprises a subject Ig conjugate, where the antibody conjugate binds an antigen. The antibody conjugate can include a $J^1$ moiety covalently bound to an Ig heavy chain constant region only, covalently bound to an Ig light chain constant region only, or a $J^1$ moiety covalently bound to an Ig heavy chain constant region and a $J^1$ moiety covalently bound to an Ig light chain constant region.

An antibody conjugate can have any of a variety of antigen-binding specificities, as described above, including, e.g., an antigen present on a cancer cell; an antigen present on an autoimmune cell; an antigen present on a pathogenic microorganism; an antigen present on a virus-infected cell (e.g., a human immunodeficiency virus-infected cell), e.g., CD4 or gp120; an antigen present on a diseased cell; and the like. For example, an antibody conjugate can bind an antigen, as noted above, where the antigen is present on the surface of the cell.

An antibody conjugate of the present disclosure can include, as the $J^1$ moiety, any of a variety of compounds, as described above, e.g., a drug (e.g., a peptide drug, a small molecule drug, and the like), a water-soluble polymer, a detectable label, a synthetic peptide, etc.

An antibody conjugate of the present disclosure can bind antigen with a suitable binding affinity, e.g., from about $5\times10^{-6}$M to about $10^{-7}$ M, from about $10^{-7}$ M to about $5\times10^{-7}$ M, from about $5\times10^{-7}$ M to about $10^{-8}$ M, from about $10^{-8}$ M to about $5\times10^{-8}$ M, from about $5\times10^{-8}$ M to about $10^{-9}$ M, or a binding affinity greater than $10^{-9}$ M.

As non-limiting examples, a subject antibody conjugate can bind an antigen present on a cancer cell (e.g., a tumor-specific antigen; an antigen that is over-expressed on a cancer cell; etc.), and the $J^1$ moiety can be a cytotoxic compound (e.g., a cytotoxic small molecule, a cytotoxic synthetic peptide, etc.). For example, a subject antibody conjugate can be specific for CD19, where the $J^1$ moiety is a cytotoxic compound (e.g., a cytotoxic small molecule, a cytotoxic synthetic peptide, etc.). As another example, a subject antibody conjugate can be specific for CD22, where the $J^1$ moiety can be a cytotoxic compound (e.g., a cytotoxic small molecule, a cytotoxic synthetic peptide, etc.).

As further non-limiting examples, a subject antibody conjugate can bind an antigen present on a cell infected with a virus (e.g., where the antigen is encoded by the virus; where the antigen is expressed on a cell type that is infected by a virus; etc.), and the $J^1$ moiety can be a viral fusion inhibitor. For example, a subject antibody conjugate can bind CD4, and the $J^1$ moiety can be a viral fusion inhibitor. As another example, a subject antibody conjugate can bind gp120, and the $J^1$ moiety can be a viral fusion inhibitor.

Formulations

The Ig conjugates (including antibody conjugates) of the present disclosure can be formulated in a variety of different ways. In general, where the Ig conjugate is an Ig-drug conjugate, the Ig conjugate is formulated in a manner compatible with the drug conjugated to the Ig, the condition to be treated, and the route of administration to be used.

The Ig conjugate (e.g., Ig-drug conjugate) can be provided in any suitable form, e.g., in the form of a pharmaceutically acceptable salt, and can be formulated for any suitable route of administration, e.g., oral, topical or parenteral administration. Where the Ig conjugate is provided as a liquid injectable (such as in those embodiments where they are administered intravenously or directly into a tissue), the Ig conjugate can be provided as a ready-to-use dosage form, or as a reconstitutable storage-stable powder or liquid composed of pharmaceutically acceptable carriers and excipients.

Methods for formulating Ig conjugates can be adapted from those available in the art. For example, Ig conjugates can be provided in a pharmaceutical composition comprising an effective amount of a Ig conjugate and a pharmaceutically acceptable carrier (e.g., saline). The pharmaceutical composition may optionally include other additives (e.g., buffers, stabilizers, preservatives, and the like). Of particular interest in some embodiments are formulations that are suitable for administration to a mammal, particularly those that are suitable for administration to a human.

Methods of Treatment

The Ig-drug conjugates of the present disclosure find use in treatment of a condition or disease in a subject that is amenable to treatment by administration of the parent drug (i.e., the drug prior to conjugation to the Ig). By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

In the context of cancer, the term "treating" includes any or all of: reducing growth of a solid tumor, inhibiting replication of cancer cells, reducing overall tumor burden, and ameliorating one or more symptoms associated with a cancer.

The subject to be treated can be one that is in need of therapy, where the host to be treated is one amenable to treatment using the parent drug. Accordingly, a variety of subjects may be amenable to treatment using an Ig-drug conjugates disclosed herein. Generally such subjects are "mammals", with humans being of particular interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys.

The amount of Ig-drug conjugate administered can be initially determined based on guidance of a dose and/or dosage regimen of the parent drug. In general, the Ig-drug conjugates can provide for targeted delivery and/or enhanced serum half-life of the bound drug, thus providing for at least one of reduced dose or reduced administrations in a dosage regimen. Thus the Ig-drug conjugates can provide for reduced dose and/or reduced administration in a dosage regimen relative to the parent drug prior to being conjugated in an Ig-drug conjugate of the present disclosure.

Furthermore, as noted above, because the Ig-drug conjugates can provide for controlled stoichiometry of drug delivery, dosages of Ig-drug conjugates can be calculated based on the number of drug molecules provided on a per Ig-drug conjugate basis.

In some embodiments, multiple doses of an Ig-drug conjugate are administered. The frequency of administration of an Ig-drug conjugate can vary depending on any of a variety of factors, e.g., severity of the symptoms, etc. For example, in some embodiments, an Ig-drug conjugate is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

Methods of Treating Cancer

The present disclosure provides methods for delivering a cancer chemotherapeutic agent to an individual having a cancer. The methods are useful for treating a wide variety of cancers, including carcinomas, sarcomas, leukemias, and lymphomas.

Carcinomas that can be treated using a subject method include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, etc.

Sarcomas that can be treated using a subject method include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be treated using a subject method include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be treated using a subject method include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's B cell lymphoma; and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1

Cloning of CD19 and CD22 Specific Antibodies

Genes encoding the CD19 and CD22 specific variable light chain regions were synthesized and cloned into a plasmid containing the human IgG kappa light chain constant region using NcoI and BsiWI restriction sites. The light chain constant region plasmid was either wild-type or contained LCTPSR (SEQ ID NO:17) or LATPSR (SEQ ID NO:24), which were inserted into the plasmid using Quikchange mutagenesis.

Genes encoding the CD19 and CD22 specific variable heavy chain regions were synthesized and cloned into a plasmid containing the human IgG heavy chain constant region using EcoRI and NheI restriction sites. The heavy chain constant region plasmid was either wild-type or contained LCTPSR (SEQ ID NO:17) or LATPSR (SEQ ID NO:24), which were inserted into the plasmid using Quikchange mutagenesis.

FIG. 3 shows amino acid sequences of anti-CD19 light chain (upper sequence) and heavy chain (lower sequence)

constant regions, with an LCTPSR sulfatase motif in the heavy chain constant region. The signal peptide is shown in lower-case letters; the variable region is underlined; solvent-accessible loop regions in the constant regions are shown in bold and underlined. The LCTPSR sequence is shown in bold and double underlining. The initial methionine (M) present in the heavy and light chain amino acid sequences is for purposes of facilitating expression and can be optionally present in these and all heavy and light chains amino acid sequences described herein.

Wild-Type Anti-CD19 and Anti-CD22 Sequences

Amino acid sequences of wild-type (not aldehyde-tagged) anti-CD22 heavy and light chains are shown in FIGS. 6B and 19B, respectively. Nucleotide sequences encoding wild-type (not aldehyde-tagged) anti-CD22 heavy and light chains are shown in FIGS. 6A and 15A, respectively.

Amino acid sequences of wild-type (not aldehyde-tagged) anti-CD19 heavy and light chains are shown in FIGS. 19B and 31B, respectively. Nucleotide sequences encoding wild-type (not aldehyde-tagged) anti-CD19 heavy and light chains are shown in FIGS. 19A and 31A, respectively.

Sequences of Anti-CD19 and Anti-CD22 Heavy Chains Modified to Include LCTPSR

Amino acid sequences of anti-CD22 heavy chain constant regions modified to include the aldehyde tag sequence LCTPSR (which is recognized and converted by FGE) are shown in FIGS. 7B, 8B, and 9B, where the aldehyde tag is in the CH1 domain; FIGS. 11B, 12B and 13B where the aldehyde tag is in the CH2 domain; FIG. 15B, where the aldehyde tag is in the CH2/CH3 region; and FIG. 17B, where the aldehyde tag is near the C-terminus. FIGS. 7A, 8A, 9A, 11A, 12A, 13A, and 15A provide nucleotide sequences encoding the amino acid sequences shown in FIGS. 7A, 8B, 9B, 11B, 12B, 13B and 15B, respectively.

Amino acid sequences of anti-CD19 heavy chain constant regions modified to include the aldehyde tag sequence LCTPSR (which is recognized and converted by FGE) are shown in FIG. 23B, where the aldehyde tag is in the CH1 domain; FIG. 25B, where the aldehyde tag is in the CH2 domain; FIG. 27B, where the aldehyde tag is in the CH2/CH3 region; and FIG. 29B, where the aldehyde tag is near the C-terminus. FIGS. 19A, 21A, 23A, and 25A provide nucleotide sequences encoding the amino acid sequences shown in FIGS. 19B, 21B, 23B, and 25B, respectively.

Sequences of Anti-CD19 and Anti-CD22 Heavy Chains Modified to Include LATPSR

Amino acid sequences of anti-CD22 heavy chain constant regions modified to include the control sequence LATPSR (which is not recognized by FGE) are shown in FIG. 10B, where the control sequence is in the CH1 domain; FIG. 14B, where the control sequence is in the CH2 domain; FIG. 16B, where the control sequence is in the CH2/CH3 region; and FIG. 18B, where the control sequence is near the C-terminus. FIGS. 10A, 14A, 16A, and 18A provide nucleotide sequences encoding the amino acid sequences shown in FIGS. 10B, 14B, 16B, and 18B, respectively.

Amino acid sequences of anti-CD19 heavy chain constant regions modified to include the control sequence LATPSR (which is not recognized by FGE) are shown in FIG. 24B, where the control sequence is in the CH1 domain; FIG. 26B, where the control sequence is in the CH2 domain; FIG. 28B where the control sequence is in the CH2/CH3 region; and FIG. 30B, where the control sequence is near the C-terminus.

Sequences of Anti-CD19 and Anti-CD22 Light Chains Modified to Include LCTPSR

An amino acid sequence of an anti-CD22 light chain constant region modified to include the aldehyde tag sequence LCTPSR is shown in FIG. 20B. FIG. 20A provides a nucleotide sequence encoding the amino acid sequence shown in FIG. 20B. FIG. 21B provides an amino acid sequence of an anti-CD22 light chain constant region modified to include the control sequence LATPSR; FIG. 21A provides a nucleotide sequence encoding the amino acid sequence shown in FIG. 21B.

An amino acid sequence of an anti-CD19 light chain constant region modified to include the aldehyde tag sequence LCTPSR is shown in FIG. 32B. FIG. 32A provides a nucleotide sequence encoding the amino acid sequence shown in FIG. 32B. FIG. 33B provides an amino acid sequence of an anti-CD22 light chain constant region modified to include the control sequence LATPSR; FIG. 33A provides a nucleotide sequence encoding the amino acid sequence shown in FIG. 33B.

Example 2

Expressing and Purifying CD19 and CD22 Specific Antibodies

Plasmids containing genes encoding the CD19 or CD22 specific heavy and light chains were transfected into CHO-K1 cells stably expressing human FGE using Lipofectamine 2000 transfection reagent. 12 μg of the heavy and light chain plasmids were used for every 10 mL of Opti-MEM serum-free medium used. After 5 h at 37° C., the Opti-MEM was removed and Ex-Cell 325 protein-free medium was added. After 72 h at 37° C., the media was collected and cleared of debris. Cleared medium was combined with Protein A binding buffer and Protein A resin and incubated with rotation for 1 h at room temperature (RT). The mixture was added to a column to let the unbound material flow through. The resin was washed with Protein A binding buffer and then eluted 5 with Protein A elution buffer.

Anti-CD19 and anti-CD22 heavy chain constant regions were modified to include an aldehyde tag in the CH1 domain, the CH2 domain, or the CH3 domain. Anti-CD19 and anti-CD22 light chains were also modified to include an aldehyde tag. Aldehyde-tagged anti-CD19 and aldehyde-tagged anti-CD22 antibodies were subjected to protein blot analysis. The results are shown in FIG. 4.

Figure 4:
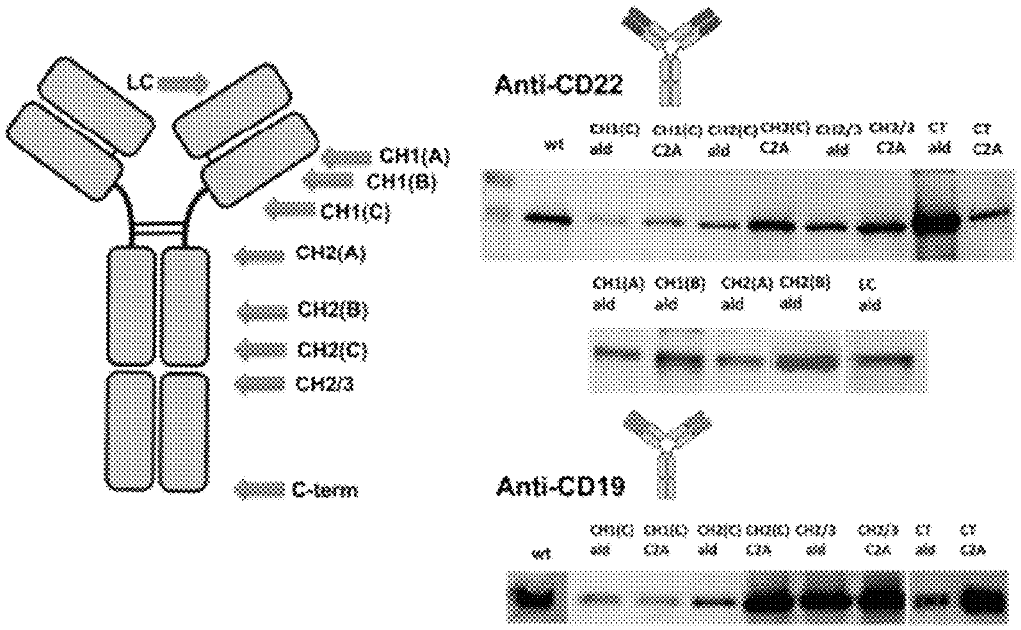
FIG. 4 depicts protein blot analysis of aldehyde-tagged anti-CD19 and aldehyde-tagged anti-CD22 antibodies. The left panel provides a schematic of an antibody and indicates the relative positions of examples of sites of aldehyde tag modification in an Ig heavy chain CH1 region ("CH1 (A)", "CH1 (B)", "CH1 (C)"), Ig heavy chain CH2 region ("CH2 (A)", "CH2 (B)", "CH2 (C)"), CH2/3 region ("CH2/CH3"), and C-terminal region ("C-terminal").

As shown in FIG. 4, inclusion of an aldehyde tag did not disrupt protein expression, folding, or secretion. “Ald” refers to modification of the constant region to include LCTPSR, a sequence that is recognized by FGE. “C2A” refers to modification of the constant region to include “LATPSR,” a sequence that is not recognized by FGE.

The aldehyde-tagged anti-CD19 and anti-CD22 antibodies include aldehyde tags in both heavy and light chains.

Example 3

Conjugation of Aminooxy Flag Peptide to Purified Aldehyde-Tagged Antibody

Purified antibodies were combined with 1 mM aminooxy FLAG peptide and 100 mM MES buffer pH 5.5 for 16 h at room temperature (RT). Samples were run on a sodium dodecyl sulfate-polyacrylamide gel electrophoresis (SDS-PAGE) gel and subjected to Western Blot analysis using an anti-FLAG antibody to detect conjugation of the FLAG peptide to the antibody.

The results are shown in FIG. 5. FIG. 5 depicts protein blot analysis of aldehyde-tagged anti-CD19 and aldehyde-tagged anti-CD22 antibodies that were chemically conjugated with aminooxy-FLAG.

FIG. 5A depicts a schematic of protein expression followed by aldehyde specific chemical conjugation. A western blot, probed with goat anti-human IgG or with anti-FLAG antibody, illustrates an example of protein conjugation. No labeling was observed with the C2A (LATPSR)-tagged antibody (lower panel).

FIG. 5B depicts labeling with aminooxy FLAG to the tagged anti-CD19 and Anti-CD22 IgGs. The protein loading and labeling was monitored by Western blot. "CtoA" refers to antibodies modified to include the LATPSR sequence.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An immunoglobulin (Ig) polypeptide comprising a sulfatase motif comprising an amino acid sequence LCTPSR (SEQ ID NO:17), the Ig polypeptide comprising:

a) an $IgG_1$ heavy chain constant region comprising an amino acid sequence selected from the group consisting of:
ASTKGLCTPSRV (SEQ ID NO: 231),
LCTPSRSKSTSGGT (SEQ ID NO: 234),
NSGALCTPSRGVHTFPAVLQSSGL (SEQ ID NO:235),
EPKSCDKTHTCPPCPLCTPSRELLGG (SEQ ID NO: 236),
NLCTPSRAP (SEQ ID NO: 206),
SKAKGLCTPSRE (SEQ ID NO: 237), and
DVSHEDLCTPSREV (SEQ ID NO: 250);

or b) an $IgG_4$ heavy chain constant region comprising an amino acid sequence selected from the group consisting of:
NSGALCTPSRGVHTFPAVLQSSGL (SEQ ID NO:235), and
SKAKGLCTPSRE (SEQ ID NO:237);

or c) an Ig kappa light chain constant region comprising the amino acid sequence:
DNALCTPSRQSGN (SEQ ID NO: 220).

2. The Ig polypeptide of claim 1, wherein the Ig polypeptide comprises:

a) an $IgG_1$ heavy chain constant region comprising an amino acid sequence selected from the group consisting of
ASTKGLCTPSRV (SEQ ID NO: 231),
LCTPSRSKSTSGGT (SEQ ID NO: 234),
NSGALCTPSRGVHTFPAVLQSSGL (SEQ ID NO: 235),
EPKSCDKTHTCPPCPLCTPSRELLGG (SEQ ID NO: 236),
NLCTPSRAP (SEQ ID NO: 206),
SKAKGLCTPSRE (SEQ ID NO: 237), and
DVSHEDLCTPSREV (SEQ ID NO: 250); or b) an $IgG_4$ heavy chain constant region comprising an amino acid sequence selected from the group consisting of
NSGALCTPSRGVHTFPAVLQSSGL (SEQ ID NO:235), and
SKAKGLCTPSRE (SEQ ID NO:237).

3. The Ig polypeptide of claim 1, wherein the Ig polypeptide comprises an Ig kappa light chain constant region comprising the amino acid sequence DNALCTPSRQSGN (SEQ ID NO: 220).

4. An antibody comprising the Ig polypeptide of claim 2.

5. An antibody comprising the Ig polypeptide of claim 3.

6. An immunoglobulin (Ig) polypeptide comprising a 2-formylglycine (FGly) moiety, comprising:

a) an $IgG_1$ heavy chain constant region comprising an amino acid sequence selected from the group consisting of:
ASTKGL(FGly)TPSRV (SEQ ID NO: 232),
L(FGly)TPSRSKSTSGGT (SEQ ID NO: 238),
NSGAL(FGly)TPSRGVHTFPAVLQSSGL (SEQ ID NO: 239),
EPKSCDKTHTCPPCPL(FGly)TPSRELLGG (SEQ ID NO: 240),
NL(FGly)TPSRAP (SEQ ID NO: 241),
SKAKGL(FGly)TPSRE (SEQ ID NO: 242), and
DVSHEDL(FGly)TPSREV (SEQ ID NO:251);

or b) an $IgG_4$ heavy chain constant region comprising an amino acid sequence selected from the group consisting of:
NSGAL(FGly)TPSRGVHTFPAVLQSSGL (SEQ ID NO:239), and
SKAKGL(CGly)TPSRE (SEQ ID NO:242);

or c) an Ig light chain constant region comprising the amino acid sequence:
DNAL(FGly)TPSRQSGN (SEQ ID NO: 248).

7. The immunoglobulin (Ig) polypeptide of claim 6, wherein the Ig polypeptide comprises:

a) an $IgG_1$ heavy chain constant region comprising an amino acid sequence selected from the group consisting of:
ASTKGL(FGly)TPSRV (SEQ ID NO: 232),
L(FGly)TPSRSKSTSGGT (SEQ ID NO: 238),
NSGAL(FGly)TPSRGVHTFPAVLQSSGL (SEQ ID NO: 239), EPKSCDKTHTCPPCPL(FGly)TPSRELLGG (SEQ ID NO: 240), NL(FGly)TPSRAP (SEQ ID NO: 241), SKAKGL(FGly)TPSRE (SEQ ID NO: 242), and DVSHEDL(FGly)TPSREV (SEQ ID NO:251); or b) an $IgG_4$ heavy chain constant region comprising an amino acid sequence selected from the group consisting of NSGAL(FGly)TPSRGVHTFPAVLQSSGL (SEQ ID NO:239), and SKAKGL(FGly)TPSRE (SEQ ID NO:242).

8. The immunoglobulin (Ig) polypeptide of claim 6, wherein the Ig polypeptide comprises an Ig kappa light chain constant region comprising the amino acid sequence DNAL(FGly)TPSRQSGN (SEQ ID NO: 248).

9. An antibody comprising a formylglycine (FGly) moiety, wherein the antibody comprises the Ig polypeptide of claim 7.

10. An antibody comprising a formylglycine (FGly) moiety, wherein the antibody comprises the Ig polypeptide of claim 8.

11. An immunoglobulin (Ig) conjugate comprising:

an Ig polypeptide and a covalently bound moiety, wherein the Ig polypeptide comprises:

a) an $IgG_1$ heavy chain constant region comprising an amino acid sequence selected from the group consisting of:

ASTKGL(FGly')TPSRV (SEQ ID NO: 233),

L(FGly')TPSRSKSTSGGT (SEQ ID NO: 243),

NSGAL(FGly')TPSRGVHTFPAVLQSSGL (SEQ ID NO: 244),

EPKSCDKTHTCPPCPL(FGly')TPSRELLGG (SEQ ID NO: 245),

NL(FGly')TPSRAP (SEQ ID NO: 246),

SKAKGL(FGly')TPSRE (SEQ ID NO: 247), and

DVSHEDL(FGly')TPSREV (SEQ ID NO:252);

or b) an $IgG_4$ heavy chain constant region comprising an amino acid sequence selected from the group consisting of:

NSGAL(FGly')TPSRGVHTFPAVLQSSGL (SEQ ID NO:244), and

SKAKGL(FGly')TPSRE (SEQ ID NO:247);

or c) an Ig light chain constant region comprising DNAL (FGly')TPSRQSGN (SEQ ID NO: 249);

and wherein FGly' is of the formula:

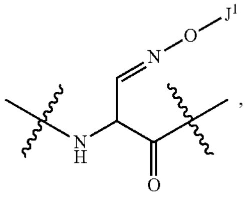
,
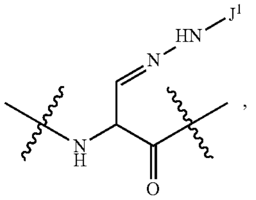
,
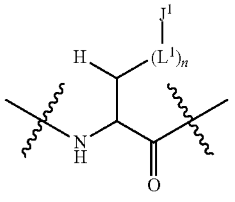
, or

-continued

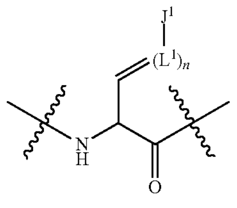
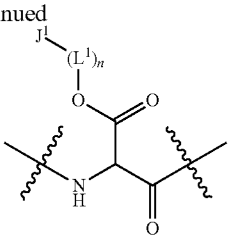

wherein $J^1$ is the covalently bound moiety;

each $L^1$ is independently selected from alkylene, substituted alkylene, alkenylene, substituted alkenylene, alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, O, S, NH, and substituted amine; and n is a number selected from zero to 40.

12. The immunoglobulin (Ig) conjugate of claim 11, wherein the Ig polypeptide comprises:

a) an $IgG_1$ heavy chain constant region comprising an amino acid sequence selected from the group consisting of:

ASTKGL(FGly')TPSRV (SEQ ID NO: 233),

L(FGly')TPSRSKSTSGGT (SEQ ID NO: 243),

NSGAL(FGly')TPSRGVHTFPAVLQSSGL (SEQ ID NO: 244),

EPKSCDKTHTCPPCPL(FGly')TPSRELLGG (SEQ ID NO: 245),

NL(FGly')TPSRAP (SEQ ID NO: 246),

SKAKGL(FGly')TPSRE (SEQ ID NO: 247), and

DVSHEDL(FGly')TPSREV (SEQ ID NO:252); or b) an $IgG_4$ heavy chain constant region comprising an amino acid sequence selected from the group consisting of:

NSGAL(FGly')TPSRGVHTFPAVLQSSGL (SEQ ID NO:244), and

SKAKGL(FGly')TPSRE (SEQ ID NO:247).

13. The immunoglobulin (Ig) conjugate of claim 11, wherein the Ig polypeptide comprises an Ig kappa light chain constant region comprising DNAL(FGly') TPSRQSGN (SEQ ID NO: 249).

14. The immunoglobulin (Ig) conjugate of claim 11, wherein the Ig polypeptide comprises an $IgG_1$ heavy chain constant region comprising the amino acid sequence ASTKGL(FGly')TPSRV (SEQ ID NO: 233).

15. The immunoglobulin (Ig) conjugate of claim 11, wherein the Ig polypeptide comprises an $IgG_1$ heavy chain constant region comprising the amino acid sequence L(FGly')TPSRSKSTSGGT (SEQ ID NO: 243).

16. The immunoglobulin (Ig) conjugate of claim 11, wherein the Ig polypeptide comprises an $IgG_1$ or $IgG_4$ heavy chain constant region comprising the amino acid sequence NSGAL(FGly')TPSRGVHTFPAVLQSSGL (SEQ ID NO: 244).

17. The immunoglobulin (Ig) conjugate of claim 11, wherein the Ig polypeptide comprises an $IgG_1$ heavy chain constant region comprising the amino acid sequence EPKSCDKTHTCPPCPL(FGly')TPSRELLGG (SEQ ID NO: 245).

18. The immunoglobulin (Ig) conjugate of claim 11, wherein the Ig polypeptide comprises an $IgG_1$ heavy chain constant region comprising the amino acid sequence NL(FGly')TPSRAP (SEQ ID NO: 246).

19. The immunoglobulin (Ig) conjugate of claim 11, wherein the Ig polypeptide comprises an $IgG_1$ or $IgG_4$ heavy chain constant region comprising the amino acid sequence SKAKGL(FGly')TPSRE (SEQ ID NO: 247).

20. The immunoglobulin (Ig) conjugate of claim 11, wherein the Ig polypeptide comprises an $IgG_1$ heavy chain constant region comprising the amino acid sequence DVSHEDL(FGly')TPSREV (SEQ ID NO:252).

21. The immunoglobulin (Ig) conjugate of claim 11, wherein the Ig polypeptide comprises an Ig light chain constant region comprising the amino acid sequence DNAL (FGly')TPSRQSGN (SEQ ID NO: 249).

22. The Ig conjugate of claim 11, wherein $J^1$ is selected from a drug, a detectable label, a water-soluble polymer, and a synthetic peptide.

23. The Ig conjugate of claim 11, wherein $J^1$ is a small molecule drug.

24. The Ig conjugate of claim 23, wherein the small molecule drug is a cancer chemotherapeutic agent.

25. The Ig conjugate of claim 24, wherein the Ig polypeptide comprises:

a) an $IgG_1$ heavy chain constant region comprising an amino acid sequence selected from the group consisting of:
- ASTKGL(FGly')TPSRV (SEQ ID NO: 233),
- L(FGly')TPSRSKSTSGGT (SEQ ID NO: 243),
- NSGAL(FGly')TPSRGVHTFPAVLQSSGL (SEQ ID NO: 244),
- EPKSCDKTHTCPPCPL(FGly')TPSRELLGG (SEQ ID NO: 245),
- NL(FGly')TPSRAP (SEQ ID NO: 246),
- SKAKGL(FGly')TPSRE (SEQ ID NO: 247), and
- DVSHEDL(FGly')TPSREV (SEQ ID NO:252); or b) an $IgG_4$ heavy chain constant region comprising an amino acid sequence selected from the group consisting of:
- NSGAL(FGly')TPSRGVHTFPAVLQSSGL (SEQ ID NO:235), and
- SKAKGL(FGly')TPSRE (SEQ ID NO:237).

26. The Ig conjugate of claim 24, wherein the Ig polypeptide comprises an Ig kappa light chain constant region comprising the amino acid sequence DNAL(FGly') TPSRQSGN (SEQ ID NO: 249).

27. The Ig conjugate of claim 11, wherein $J^1$ is a water-soluble polymer.

28. The Ig conjugate of claim 27, wherein the water-soluble polymer is poly(ethylene glycol).

29. The Ig conjugate of claim 11, wherein $J^1$ is a detectable label.

30. The Ig conjugate of claim 29, wherein the detectable label is an imaging agent.

31. An antibody conjugate comprising an immunoglobulin (Ig) conjugate of claim 12.

32. An antibody conjugate comprising an immunoglobulin (Ig) conjugate of claim 13.

33. The antibody conjugate of claim 31, wherein the antibody specifically binds a tumor antigen on a cancer cell.

34. The antibody conjugate of claim 33, wherein the $J^1$ moiety is a cytotoxic agent.

35. The antibody conjugate of claim 32, wherein the antibody specifically binds a tumor antigen on a cancer cell.

36. The Ig conjugate of claim 35, wherein the $J^1$ moiety is a cytotoxic agent.

37. The antibody conjugate of claim 31, wherein the antibody conjugate specifically binds an antigen on a cell infected by a virus.

38. The antibody conjugate of claim 37, wherein the antigen is encoded by the virus.

39. The antibody conjugate of claim 31, wherein the $J^1$ moiety is a viral fusion inhibitor.

40. A formulation comprising:

a) an Ig conjugate of claim 12; and b) a pharmaceutically acceptable excipient.

41. A formulation comprising:

a) an Ig conjugate of claim 13; and b) a pharmaceutically acceptable excipient.

42. The immunoglobulin (Ig) polypeptide of claim 1, comprising:

a) an $IgG_1$ heavy chain constant region comprising an amino acid sequence selected from the group consisting of:
- SEQ ID NO:253,
- SEQ ID NO:256,
- SEQ ID NO:259,
- SEQ ID NO:262,
- SEQ ID NO:265,
- SEQ ID NO:268, and
- SEQ ID NO:271; or b) an $IgG_4$ heavy chain constant region comprising an amino acid sequence selected from the group consisting of:
- SEQ ID NO:277, and
- SEQ ID NO:280; or c) an Ig kappa light chain constant region comprising an amino acid sequence set forth in SEQ ID NO:274.

43. The Ig polypeptide of claim 6, comprising:

a) an $IgG_1$ heavy chain constant region comprising an amino acid sequence selected from the group consisting of:
- SEQ ID NO:254,
- SEQ ID NO:257,
- SEQ ID NO:260,
- SEQ ID NO:263,
- SEQ ID NO:266,
- SEQ ID NO:269, and
- SEQ ID NO:272; or b) an $IgG_4$ heavy chain constant region comprising an amino acid sequence selected from the group consisting of:
- SEQ ID NO:278, and
- SEQ ID NO:281; or c) an Ig kappa light chain constant region comprising an amino acid sequence set forth in SEQ ID NO:275.

44. The Ig conjugate of claim 11, wherein the Ig polypeptide comprises:

a) an $IgG_1$ heavy chain constant region comprising an amino acid sequence selected from the group consisting of:
- SEQ ID NO:255,
- SEQ ID NO:258,
- SEQ ID NO:261,
- SEQ ID NO:264,
- SEQ ID NO:269,
- SEQ ID NO:270, and
- SEQ ID NO:273; or b) an $IgG_4$ heavy chain constant region comprising an amino acid sequence selected from the group consisting of:
SEQ ID NO:279, and
SEQ ID NO:282; or c) an Ig kappa light chain constant region comprising an amino acid sequence set forth in SEQ ID NO:276.

* * * * *

UNITED STATES PATENT AND TRADEMARK OFFICE

CERTIFICATE OF CORRECTION

PATENT NO. : 9,540,438 B2
APPLICATION NO. : 13/350676
DATED : January 10, 2017
INVENTOR(S) : Robyn M. Barfield et al.

It is certified that error appears in the above-identified patent and that said Letters Patent is hereby corrected as shown below:

In the Claims

Column 289, in Claim 2, Line 55, replace “of” with --of:--; Line 67, replace “of” with --of:--.

Column 290, in Claim 6, Line 54, replace “SKAKGL (CGly) TPSRE” with --SKAKGL (FGly) TPSRE--.

Column 291, in Claim 7, Line 8, replace “of” with --of:--; in Claim 11, Line 60 to Column 292, Line 10, replace:

“ 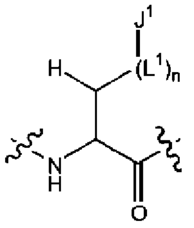 , or 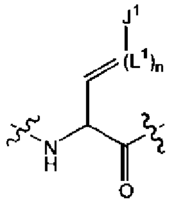 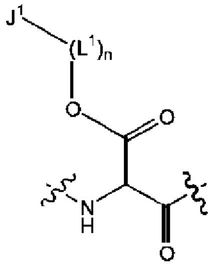 ” with

-- 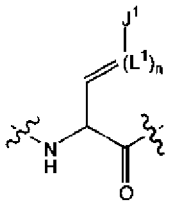 , or 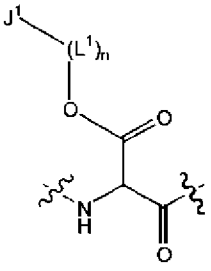 --.

Signed and Sealed this
Twenty-seventh Day of March, 2018

Andrei Iancu
*Director of the United States Patent and Trademark Office*